United States Patent
McMinn et al.

(10) Patent No.: US 9,657,057 B2
(45) Date of Patent: May 23, 2017

(54) DIPEPTIDE AND TRIPEPTIDE EPOXY KETONE PROTEASE INHIBITORS

(71) Applicant: Onyx Therapeutics, Inc., South San Francisco, CA (US)

(72) Inventors: Dustin McMinn, Pacifica, CA (US); Henry Johnson, San Bruno, CA (US); David C. Moebius, Foster City, CA (US)

(73) Assignee: Onyx Therapeutics, Inc., Thousand Oaks, CA (US)

( * ) Notice: Subject to any disclaimer, the term of this patent is extended or adjusted under 35 U.S.C. 154(b) by 0 days.

(21) Appl. No.: 14/774,231

(22) PCT Filed: Mar. 14, 2014

(86) PCT No.: PCT/US2014/026980
§ 371 (c)(1),
(2) Date: Sep. 10, 2015

(87) PCT Pub. No.: WO2014/152127
PCT Pub. Date: Sep. 25, 2014

(65) Prior Publication Data
US 2016/0031934 A1    Feb. 4, 2016

Related U.S. Application Data

(60) Provisional application No. 61/785,608, filed on Mar. 14, 2013, provisional application No. 61/786,086, filed on Mar. 14, 2013, provisional application No. 61/847,780, filed on Jul. 18, 2013, provisional application No. 61/856,847, filed on Jul. 22, 2013, provisional application No. 61/883,798, filed on Sep. 27, 2013, provisional application No. 61/883,843, filed on Sep. 27, 2013, provisional application No. 61/941,798, filed on Feb. 19, 2014.

(51) Int. Cl.
| | |
|---|---|
| A61K 38/06 | (2006.01) |
| C07K 5/083 | (2006.01) |
| C07K 5/097 | (2006.01) |
| C07K 5/02 | (2006.01) |
| C07K 5/062 | (2006.01) |
| C07K 5/06 | (2006.01) |
| C07K 5/078 | (2006.01) |
| C07K 5/065 | (2006.01) |
| C07K 5/072 | (2006.01) |
| A61K 38/00 | (2006.01) |

(52) U.S. Cl.
CPC ........... *C07K 5/0806* (2013.01); *A61K 38/06* (2013.01); *C07K 5/0202* (2013.01); *C07K 5/0205* (2013.01); *C07K 5/06026* (2013.01); *C07K 5/06069* (2013.01); *C07K 5/06078* (2013.01); *C07K 5/06121* (2013.01); *C07K 5/06139* (2013.01); *C07K 5/06147* (2013.01); *C07K 5/06173* (2013.01); *C07K 5/06191* (2013.01); *C07K 5/0821* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,522,811 A | 6/1985 | Eppstein et al. | |
| 5,340,736 A | 8/1994 | Goldberg | |
| 6,468,798 B1 | 10/2002 | Debs et al. | |
| 6,471,996 B1 | 10/2002 | Sokoll et al. | |
| 6,472,375 B1 | 10/2002 | Hoon et al. | |
| 7,232,818 B2 | 6/2007 | Smyth et al. | |
| 7,417,042 B2 | 8/2008 | Smyth et al. | |
| 7,589,066 B2 * | 9/2009 | Orlowski | C07K 5/06078 514/1.1 |
| 7,687,456 B2 | 3/2010 | Zhou et al. | |
| 7,691,852 B2 | 4/2010 | Shenk et al. | |
| 7,737,112 B2 | 6/2010 | Lewis et al. | |
| 8,088,741 B2 | 1/2012 | Smyth et al. | |
| 2003/0216325 A1 | 11/2003 | Saksena et al. | |
| 2007/0105786 A1 | 5/2007 | Zhou et al. | |
| 2008/0090785 A1* | 4/2008 | Smyth | C07K 5/06034 514/99 |
| 2013/0303482 A1 | 11/2013 | Lewis et al. | |

FOREIGN PATENT DOCUMENTS

| WO | WO-98/10779 A1 | 3/1998 |
|---|---|---|
| WO | WO-2007/149512 A2 | 12/2007 |
| WO | WO-2010/048298 A1 | 4/2010 |

OTHER PUBLICATIONS

Adams, The proteasome: a suitable antineoplastic target. *Nat. Rev. Cancer*, 4(5): 349-60 (2004).

(Continued)

*Primary Examiner* — Fred Reynolds
(74) *Attorney, Agent, or Firm* — Marshall, Gerstein & Borun LLP

(57) ABSTRACT

Provided herein are dipeptide and tripeptide epoxy ketone protease inhibitors, methods of their preparation, related pharmaceutical compositions, and methods of using the same. For example, provided herein are compounds of Formula (X): and pharmaceutically acceptable salts and compositions including the same. The compounds and compositions provided herein may be used, for example, in the treatment of proliferative diseases including cancer and autoimmune diseases.

(X)

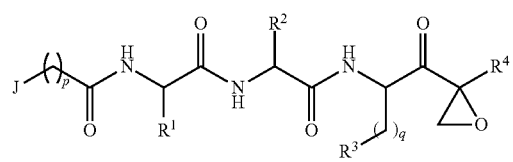

21 Claims, No Drawings

(56) References Cited

OTHER PUBLICATIONS

Berge et al., Pharmaceutical salts. *J. Pharm. Sci.* 66(1): 1-19 (1977).
Braun et al., Targeting NF-kappaB in hematologic malignancies. *Cell Death Differ.* 13(5): 748-58 (2006).
Chapatte et al., Processing of tumor-associated antigen by the proteasomes of dendritic cells controls in vivo T-cell responses. *Cancer Res.* 66(10): 5461-8 (2006).
Ciechanover, The ubiquitin-proteasome proteolytic pathway. *Cell,* 79(1): 13-21 (1994).
Cilloni et al., Nuclear factor kB as a target for new drug development in myeloid malignancies. Haematologica, 92(9): 1224-9 (2007).
Cohen, AIDS Mood Upbeat—for a Change. *Science,* 267: 959-60 (1995).
Collins, Endothelial nuclear factor-kappa B and the initiation of the atherosclerotic lesion. *Lab. Invest.* 68(5): 499-508 (1993).
Demo et al., Antitumor activity of PR-171, a novel irreversible inhibitor of the proteasome. *Cancer Res.* 67(13): 6383-91 (2007).
Garrett et al., Selective inhibitors of the osteoblast proteasome stimulate bone formation in vivo and in vitro. *J. Clin. Invest.* 111(11): 1771-82 (2003).
Gonzalez et al., Proteasome function is required for encystation of Entamoeba invadens. *Arch. Med. Res.* 28 Spec No. 139-40 (1997).
Hamajima et al., Intranasal administration of HIV-DNA vaccine formulated with a polymer, carboxymethylcellulose, augments mucosal antibody production and cell-mediated immune response. *Clin. Immunol. Immunopathol.* 88(2): 205-10 (1998).
Hardy, The secret life of the hair follicle. *Trends Genet.* 8(2): 55-61 (1992).
Harris et al., Effects of transforming growth factor beta on bone nodule formation and expression of bone morphogenetic protein 2, osteocalcin, osteopontin, alkaline phosphatase, and type I collagen mRNA in long-term cultures of fetal rat calvarial osteoblasts. *J. Bone Miner. Res.* 9(6): 855-63 (1994).
Ho et al., LMP2-specific inhibitors: chemical genetic tools for proteasome biology. *Chem. Biol.* 14(4) :419-30 (2007).
Huber et al., Immuno- and constitutive proteasome crystal structures reveal differences in substrate and inhibitor specificity. *Cell,* 148(4): 727-38 (2011).
International Search Report and Written Opinion of the International Searching Authority in Application No. PCT/US2014/026980, United States Patent Office, dated Mar. 14, 2014, Jun. 28, 2014.
Kojima et al., Two-way cleavage of beta-amyloid protein precursor by multicatalytic proteinase. *FEBS Lett.* 304(1): 57-60 (1992).
Kumatori et al., Abnormally high expression of proteasomes in human leukemic cells. *Proc. Natl. Acad. Sci. USA,* 87(18): 7071-5 (1990).
Lee et al., The immunoproteasome: an emerging therapeutic target. *Curr. Top. Med. Chem.* 11(23): 2923-30 (2011).
Muchamuel et al., A selective inhibitor of the immunoproteasome subunit LMP7 blocks cytokine production and attenuates progression of experimental arthritis. *Nat. Med.* 15(7): 781-7 (2009).
Palombella et al., The ubiquitin-proteasome pathway is required for processing the NF-kappa B1 precursor protein and the activation of NF-kappa B. *Cell,* 78(5): 773-85 (1994).
Parlati et al., Carfilzomib can induce tumor cell death through selective inhibition of the chymotrypsin-like activity of the proteasome. *Blood,* 114(16): 3439-47 (2009).
Paugam et al., Characterization and role of protozoan parasite proteasomes. *Trends Parasitol.* 19(2): 55-9 (2003).
Qureshi et al., the proteasome as a lipopolysaccharide-binding protein in macrophages: differential effects of proteasome inhibition on lipopolysaccharide-induced signaling events. *J. Immunol.* 171(3): 1515-25 (2003).
Rolfe et al., The ubiquitin-mediated proteolytic pathway as a therapeutic area. *J. Mol. Med. (Berl.),* 75(1): 5-17 (1997).
Screen et al., Nature of pharmacophore influences active site specificity of proteasome inhibitors. *J. Biol. Chem.* 285(51): 40125-34 (2010).
Shimada et al., Proteasome inhibitors improve the function of mutant lysosomal ?-glucosidase in fibroblasts from Pompe disease patient carrying c.546G>T mutation. *Biochem. Biophys. Res. Commun.* 415(2): 274-8 (2011).
Simsek et al., Hepatitis B virus large and middle glycoproteins are degraded by a proteasome pathway in glucosidase-inhibited cells but not in cells with functional glucosidase enzyme. *J. Virol.* 79(20): 12914-20 (2005).
Szalay et al., Ongoing coxsackievirus myocarditis is associated with increased formation and activity of myocardial immunoproteasomes. *Am. J. Pathol.* 168(5): 1542-52 (2006).
Thanos et al., NF-kappa B: a lesson in family values. *Cell,* 80(4): 529-32 (1995).
Traenckner et al., A proteasome inhibitor prevents activation of NF-kappa B and stabilizes a newly phosphorylated form of I kappa B-alpha that is still bound to NF-kappa B. *EMBO J.* 13(22): 5433-41 (1994).
Wehenkel et al., A selective inhibitor of the immunoproteasome subunit LMP2 induces apoptosis in PC-3 cells and suppresses tumour growth in nude mice. *Br. J. Cancer,* 107(1): 53-62 (2012).
Yu et al., the ubiquitin-proteasome system facilitates the transfer of murine coronavirus from endosome to cytoplasm during virus entry. *J. Virol.* 79(1): 644-8 (2005).

\* cited by examiner

DIPEPTIDE AND TRIPEPTIDE EPOXY KETONE PROTEASE INHIBITORS

CROSS-REFERENCE TO RELATED APPLICATIONS

This application is filed pursuant to 35 U.S.C. §371 as a U.S. National Phase Application of international application No. PCT/US2014/026980 (filed on Mar. 14, 2014), claiming the benefit of U.S. Provisional Application No. 61/941,798 (filed Feb. 19, 2014), 61/883,798 (filed on Sep. 27, 2013), 61/856,847 (filed on Jul. 22, 2013), 61/847,780 (filed on Jul. 18, 2013), 61/786,086 (filed on Mar. 14, 2013), 61/883,843 (filed on Sep. 27, 2013), and 61/785,608 (filed on Mar. 14, 2013), each of which is incorporated herein by reference in its entirety.

BACKGROUND OF THE INVENTION

Field of the Invention

This disclosure relates to dipeptide and tripeptide epoxy ketone protease inhibitors including methods of making and using the same.

Description of Related Technology

In eukaryotes, protein degradation is predominately mediated through the ubiquitin pathway in which proteins targeted for destruction are ligated to the 76 amino acid polypeptide ubiquitin. Once targeted, ubiquitinated proteins then serve as substrates for the 26S proteasome, a multicatalytic protease, which cleaves proteins into short peptides through the action of its three major proteolytic activities. While having a general function in intracellular protein turnover, proteasome-mediated degradation also plays a key role in many processes such as major histocompatibility complex (MHC) class I antigen presentation, apoptosis, cell growth regulation, NF-κB activation, antigen processing, and transduction of pro-inflammatory signals.

The 20S proteasome is a 700 kDa cylindrical-shaped multicatalytic protease complex comprised of 28 subunits organized into four rings. In yeast and other eukaryotes, 7 different α subunits form the outer rings and 7 different β subunits comprise the inner rings. The α subunits serve as binding sites for the 19S (PA700) and 11S (PA28) regulatory complexes, as well as a physical barrier for the inner proteolytic chamber formed by the two β subunit rings. Thus, in vivo, the proteasome is believed to exist as a 26S particle ("the 26S proteasome"). In vivo experiments have shown that inhibition of the 20S form of the proteasome can be readily correlated to inhibition of 26S proteasome. Cleavage of amino-terminal prosequences of β subunits during particle formation expose amino-terminal threonine residues, which serve as the catalytic nucleophiles. The subunits responsible for catalytic activity in proteasomes thus possess an amino terminal nucleophilic residue, and these subunits belong to the family of N-terminal nucleophile (Ntn) hydrolases (where the nucleophilic N-terminal residue is, for example, Cys, Ser, Thr, and other nucleophilic moieties). This family includes, for example, penicillin G acylase (PGA), penicillin V acylase (PVA), glutamine PRPP amidotransferase (GAT), and bacterial glycosylasparaginase. In addition to the ubiquitously expressed β subunits, higher vertebrates also possess three interferon-γ-inducible β subunits (LMP7, LMP2 and MECL1), which replace their normal counterparts, $\beta_5$, $\beta_1$ and $\beta_7$ respectively, thus altering the catalytic activities of the proteasome. Through the use of different peptide substrates, three major proteolytic activities have been defined for the eukaryote 20S proteasome: chymotrypsin-like activity (CT-L), which cleaves after large hydrophobic residues; trypsin-like activity (T-L), which cleaves after basic residues; and peptidylglutamyl peptide hydrolyzing activity (PGPH), which cleaves after acidic residues. Two additional less characterized activities have also been ascribed to the proteasome: BrAAP activity, which cleaves after branched-chain amino acids; and SNAAP activity, which cleaves after small neutral amino acids. The major proteasome proteolytic activities appear to be contributed by different catalytic sites, since inhibitors, point mutations in β subunits and the exchange of γ interferon-inducing β subunits alter these activities to various degrees.

New compositions and methods for preparing and formulating proteasome inhibitor(s) would be useful.

SUMMARY OF THE INVENTION

Provided herein is a compound having a structure of Formula (X) or a pharmaceutically acceptable salt thereof,

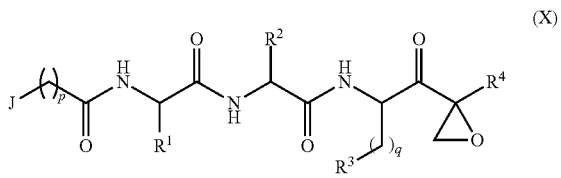

with substituents defined as discussed in detail below.

Also provided herein is a pharmaceutical composition comprising a pharmaceutically acceptable carrier or diluent and a compound provided herein, or a pharmaceutically acceptable salt thereof.

The compounds and compositions provided herein are useful in inhibiting LMP2. The compounds and compositions provided herein also are useful in the treatment of diseases or disorders, such as an immune-related disease, cancer, inflammation, infection, proliferative disease, and neurodegenerative disease. Accordingly, provided herein is a method of treating a disease or disorder in a patient, the method comprising administering a therapeutically effective amount of a compound or composition as provided herein.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the disclosure will be apparent from the following detailed description and figures, and from the claims.

DETAILED DESCRIPTION

Definitions

For the terms "for example" and "such as" and grammatical equivalences thereof, the phrase "and without limitation" is understood to follow unless explicitly stated otherwise. As used herein, the term "about" is meant to account for variations due to experimental error. All measurements reported herein are understood to be modified by the term "about," whether or not the term is explicitly used, unless explicitly stated otherwise. As used herein, the singular forms "a," "an," and "the" include plural referents unless the context clearly dictates otherwise.

As used herein, chemical structures which contain one or more stereocenters depicted with dashed and bold bonds (i.e., ⸺ and ⸺) are meant to indicate absolute stereochemistry of the stereocenter(s) present in the chemical structure. As used herein, bonds symbolized by a simple line do not indicate a stereo-preference. Unless otherwise indicated to the contrary, chemical structures that include one or more stereocenters which are illustrated herein without indicating absolute or relative stereochemistry encompass all possible stereoisomeric forms of the compound (e.g., diastereomers, enantiomers) and mixtures thereof. Structures with a single bold or dashed line, and at least one additional simple line, encompass a single enantiomeric series of all possible diastereomers.

Resolution of racemic mixtures of compounds can be carried out by any of numerous methods known in the art. An exemplary method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid, or the various optically active camphorsulfonic acids such as camphorsulfonic acid. Other resolving agents suitable for fractional crystallization methods include stereoisomerically pure forms of methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent compositions can be determined by one skilled in the art.

Compounds provided herein can also include all isotopes of atoms occurring in the intermediates or final compounds. Isotopes include those atoms having the same atomic number but different mass numbers. For example, isotopes of hydrogen include hydrogen, tritium, and deuterium.

The term, "compound," as used herein is meant to include all stereoisomers, geometric isomers, tautomers, and isotopes of the structures depicted. Compounds herein identified by name or structure as one particular tautomeric form are intended to include other tautomeric forms unless otherwise specified.

All compounds, and pharmaceutically acceptable salts thereof, can be found together with other substances such as water and solvents (e.g., hydrates and solvates).

The term "$C_{x-y}$alkyl" refers to substituted or unsubstituted saturated hydrocarbon groups, including straight-chain alkyl and branched-chain alkyl groups that contain from x to y carbons in the chain. For example, $C_{1-7}$alkyl refers to an alkyl groups having a number of carbon atoms encompassing the entire range (i.e., 1 to 7 carbon atoms), as well as all subgroups (e.g., 1-6, 2-7, 1-5, 3-6, 1, 2, 3, 4, 5, 6, and 7 carbon atoms). The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond, respectively.

The term "alkoxy" refers to an alkyl group having an oxygen attached thereto. Representative alkoxy groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxy.

The term, "$C_{x-y}$alkoxyalkyl" refers to a $C_{x-y}$alkyl group, as previously defined, substituted with an alkoxy group. For example, the term "$C_{1-6}$alkoxyalkyl" refers to a $C_{1-6}$alkyl group substituted with an alkoxy group, thereby forming an ether.

The term, "$C_{x-y}$aralkyl" refers to a $C_{x-y}$alkyl group, as previously defined, substituted with an aryl group. For example, the term "$C_{1-6}$aralkyl", as used herein, refers to a $C_{1-6}$alkyl group substituted with an aryl group.

The terms "amine" and "amino" are art-recognized and refer to both unsubstituted and substituted amines and salts thereof, e.g., a moiety that can be represented by the general formulae:

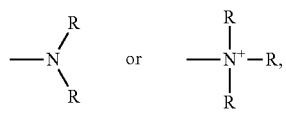

where each R group independently represents a hydrogen, an alkyl, an alkenyl, $-(CH_2)_b$-T, or two of the R groups taken together with the N atom to which they are attached complete a heterocycle having from 4 to 8 atoms in the ring structure; T represents an aryl, a cycloalkyl, a cycloalkenyl, a heterocyclyl or a polycyclyl; and b is zero or an integer from 1 to 8. In certain embodiments, an amino group is basic, meaning its protonated form has a pKa above 7.00. In some embodiments, the terms "amine" and "amino" refer to a moiety that is covalently bonded to a unsubstituted or substituted nitrogen atom.

The terms "amide" and "amido" are art-recognized as an amino-substituted carbonyl and include a moiety that can be represented by the general formula:

In some embodiments, the amide will not include imides, which may be unstable.

The term "aryl" as used herein includes 5-, 6-, and 7-membered substituted or unsubstituted single-ring aromatic groups in which each atom of the ring is carbon. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like. In some embodiments, an aryl ring can be substituted with a halogen, such as fluorine.

The terms "carbocycle" and "carbocyclyl", as used herein, refer to a 3- to 7-membered non-aromatic substituted or unsubstituted ring in which each atom of the ring is carbon. The ring may be completely saturated or may have one or more unsaturated bonds such that the ring remains non-aromatic. The terms "carbocycle" and "carbocyclyl" also include polycyclic ring systems having two or more cyclic rings in which one or more carbons are common to two adjoining rings wherein at least one of the rings is carbocyclic, e.g., the other cyclic rings can be cycloalkyls, cycloalkenyls, cycloalkynyls, aryls, heteroaryls, and/or heterocyclyls. Carbocyclyls include cyclopropyl, cyclopentyl, cyclopentenyl, cyclohexyl, cyclohexylmethyl, and 4-methylcyclohexyl. Examples of polycyclic carbocyclyls include bicyclo[2.2.1]heptanyl, spiro[2.4]heptanyl, norbornyl, and adamantyl.

The term "cycloalkyl" as used herein refers to a 3- to 7-membered saturated substituted or unsubstituted ring in which each atom of the ring is carbon. The term "cycloalkyl" also includes polycyclic ring systems having two or more cyclic rings in which one or more carbon atoms are common to two adjoining rings wherein at least one of the rings is a cycloalkyl.

The term "cycloalkenyl" as used herein refers to a 3- to 7-membered substituted or unsubstituted ring in which each atom of the ring is carbon. The ring has one or more unsaturated bonds such that the ring remains non-aromatic. The term "cycloalkenyl" also includes polycyclic ring systems having two or more cyclic rings in which one or more carbon atoms are common to two adjoining rings wherein at least one of the rings is a cycloalkenyl.

The term "carbonyl" is art-recognized and includes moieties containing a C=O group, such as, for example, those represented by the general formulae:

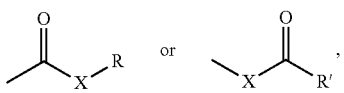

wherein X is a bond or represents an oxygen or a sulfur, and R represents a hydrogen, an alkyl, an alkenyl, —(CH$_2$)$_b$-T or a pharmaceutically acceptable salt, R' represents a hydrogen, an alkyl, an alkenyl or —(CH$_2$)$_b$-T, where m and T are as defined above. Where X is an oxygen and R or R' is not hydrogen, the formula represents an "ester". Where X is an oxygen and R is a hydrogen, the formula represents a "carboxylic acid".

The term, "C$_{x-y}$heteroaralkyl" refers to a C$_{x-y}$alkyl group, as previously defined, substituted with a heteroaryl group. For example, the term "C$_{1-6}$heteroaralkyl", as used herein, refers to a C$_{1-6}$alkyl group substituted with a heteroaryl group.

The term "heteroaryl" includes substituted or unsubstituted aromatic 5- to 7-membered ring structures, for example, 5- to 6-membered rings, whose ring structures include one to four heteroatoms. The term "heteroaryl" also includes polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, triazole, pyrazole, pyridine, pyrazine, pyridazine, and pyrimidine, and the like. In some embodiments, a heteroaryl ring can be substituted with a halogen, such as fluorine.

The term "heteroatom" as used herein means an atom of any element other than carbon or hydrogen. For example, heteroatoms include nitrogen, oxygen, phosphorus, and sulfur.

The term "heterocyclyl" or "heterocyclic group" refers to substituted or unsubstituted non-aromatic 3- to 10-membered ring structures, for example, 3- to 7-membered rings, whose ring structures include one to four heteroatoms. The ring may be completely saturated (e.g., heterocycloalkyl) or may have one or more unsaturated bonds such that the ring remains non-aromatic (e.g., heterocycloalkenyl). The term "heterocyclyl" or "heterocyclic group" also includes polycyclic ring systems having one or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term, "C$_{x-y}$hydroxyalkyl" refers to a C$_{x-y}$alkyl group, as previously defined, substituted with a hydroxy group. For example, the term "C$_{1-6}$hydroxyalkyl" refers to a C$_{1-6}$alkyl group substituted with a hydroxy group.

The term "thioether" refers to an alkyl group, as defined above, having a sulfur moiety attached thereto. In some embodiments, the "thioether" is represented by —S— alkyl. Representative thioether groups include methylthio, ethylthio, and the like.

The term "substituted," refers to moieties having substituents replacing a hydrogen on one or more non-hydrogen atoms of the molecule. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Substituents can include, for example, an alkyl, alkenyl, alkynyl, a halogen, a hydroxyl, a carbonyl (such as a carboxyl, an ester, a thioester, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a carbocyclyl (e.g., cycloalkyl, cycloalkenyl), a heterocyclyl (e.g., heterocycloalkyl), an aralkyl, a heteroaralkyl, or an aromatic (i.e., aryl) or heteroaromatic (i.e., heteroaryl) moiety. It will be understood by those skilled in the art that the moieties substituted on the hydrocarbon chain can themselves be substituted, if appropriate. In some embodiments, the substituent is a halogen, such as fluorine. When a chemical functional group includes more than one substituent, the substituents can be bound to the same carbon atom or to two or more different carbon atoms. A substituted chemical functional group can itself include one or more substituents.

In some embodiments, the compounds provided herein, or salts thereof, are substantially isolated or purified. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds, or salt thereof. Methods for isolating compounds and their salts are routine in the art.

The term "prophylactic or therapeutic" treatment is art-recognized and includes administration to the host of one or more of the subject compositions. If the subject composition is administered prior to clinical manifestation of the unwanted condition (e.g., disease or other unwanted state of the host animal) then the treatment is prophylactic, (i.e., it protects the host against developing the unwanted condition), whereas if the subject composition is administered after manifestation of the unwanted condition, the treatment is therapeutic, (i.e., it is intended to diminish, ameliorate, or stabilize the existing unwanted condition or side effects thereof).

The term "proteasome" as used herein is meant to include immuno- and constitutive proteasomes. In some embodiments, a compound of the disclosure preferentially inhibits the immunoproteasome.

The term "i20S" as used herein refers to the 20S immunoproteasome.

The term "c20S" as used herein refers to the constitutive 20S proteasome.

As used herein, the term "inhibitor" is meant to describe a compound that blocks or reduces an activity of an enzyme or system of enzymes, receptors, or other pharmacological target (for example, inhibition of proteolytic cleavage of standard fluorogenic peptide substrates such as succinyl-Leu-Leu-Val-Tyr-AMC, Boc-Leu-Leu-Arg-AMC and Z-Leu-Leu-Glu-AMC, inhibition of various catalytic activities of the 20S proteasome). An inhibitor can act with competitive, uncompetitive, or noncompetitive inhibition. An inhibitor can bind reversibly or irreversibly, and therefore, the term includes compounds that are suicide substrates of an enzyme. An inhibitor can modify one or more sites on or near the active site of the enzyme, or it can cause a conformational change elsewhere on the enzyme. The term inhibitor is used more broadly herein than scientific literature so as to also encompass other classes of pharmacologically or therapeutically useful agents, such as agonists, antagonists, stimulants, co-factors, and the like.

A "therapeutically effective amount" of a compound with respect to the subject method of treatment, refers to an amount of the compound(s) in a preparation which, when administered as part of a desired dosage regimen (to a patient, e.g., a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

As used herein, the term "treating" or "treatment" includes reversing, reducing, or arresting the symptoms, clinical signs, and underlying pathology of a condition in manner to improve or stabilize a patient's condition.

Compounds

In one aspect, the disclosure provides a compound having a structure of Formula (X), or a pharmaceutical salt thereof:

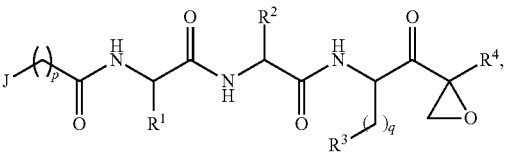

(X)

wherein:

p is 0 or 1;

q is 0, 1, or 2;

J is selected from the group consisting of $C_{1-6}$alkylene$R^5$, $C_{2-6}$alkenylene$R^5$, $OC_{1-6}$ alkylene$R^5$, $CF_3$, $C_{0-6}$alkyleneN$(R^6)_2$, aryl, heteroaryl, polyetherCH$_3$, and $C_{3-6}$cycloalkenyl, wherein J is optionally substituted with one or more substituents selected from the group consisting of $C_{1-6}$alkyl, halo, $CF_3$, $OR^6$, $SR^6$, $N(R^6)_2$, and 3-7 membered heterocycloalkyl;

$R^1$ is selected from the group consisting of H, $C_{1-2}$alkylene$R^7$, $C_{3-6}$cycloalkyl, and 3-6 membered heterocycloalkyl, wherein $R^1$ is optionally substituted with one or more substituents selected from the group consisting of halo, $OR^6$, $SR^6$, and $N(R^6)_2$;

$R^2$ is $C_{1-2}$alkylene-G; wherein G is selected from the group consisting of $C_{3-7}$cycloalkenyl, aryl, and heteroaryl, with the proviso that when $R^2$ is CH$_2$phenyl, the phenyl is substituted with one or more substituents selected from the group consisting of $OR^6$, halo, $C_{1-3}$alkyl, and $SO_2R^6$;

$R^3$ is selected from the group consisting of $C_{3-7}$cycloalkyl, $C_{3-7}$cycloalkenyl, a 3-7 membered heterocycloalkyl, a 3-7 membered heterocycloalkenyl and aryl, wherein $R^3$ is optionally substituted with one or more substituents selected from the group consisting $OR^6$ and $C_{1-6}$alkyl;

$R^4$ is H or $C_{1-3}$alkyl;

$R^5$ is selected from the group consisting of H, $CF_3$, $OR^6$, $C_{1-6}$alkoxyl, and aryl;

each $R^6$ is independently H or $C_{1-6}$alkyl; and, $R^7$ is selected from the group consisting of H, $OR^6$, $COOR^6$, CN, and 3-6 membered heterocycloalkyl.

In some embodiments, p is 0. In other embodiments, p is 1.

In some embodiments q is 0. In other embodiments, q is 1. In various embodiments, q is 2.

In some embodiments, J is $C_{1-6}$ alkylene$R^5$, $C_{2-6}$ alkenylene$R^5$, $OC_{1-6}$ alkylene$R^5$, polyetherCH$_3$, $CF_3$ or $N(R^6)_2$. In exemplary embodiments, J is selected from the group consisting of methyl, ethyl, propyl, isopropyl, butyl, difluoromethyl, 2,2-difluoroethyl, hydroxymethyl, methoxy, ethoxy, propoxy, butoxy, trifluoromethyl, hydroxyethyl, MeOCH$_2$OCH$_2$CH$_2$—, MeOCH$_2$CH$_2$OCH$_2$—, methoxyethyl, ethoxymethyl, 2-hydroxy-2-methylpropyl, 2-hydroxypropyl, 2-hydroxy-2-methylbutyl, 2-hydroxy-2-methyl-3-trifluoropropyl, 1-trifluoromethyl-2-hydroxyethyl, NH$_2$, NH(CH$_3$), NH(CH$_2$CH$_3$), N(CH$_3$)$_2$, and C(CH$_3$)$_2$NH$_2$.

In other embodiments, J is aryl, such as phenyl or indenyl. In some of these embodiments, the aryl is substituted with one or more substituent selected from the group consisting of methyl, ethyl, propyl, isopropyl, hydroxy, fluoro, chloro, methoxy, ethoxy, trifluromethyl, and amino. For example, J can include

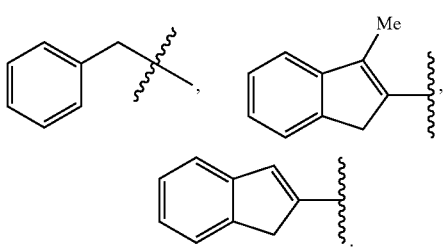

In some embodiments, J is heteroaryl. For example, J can include oxazolyl, isoxazolyl, thiazolyl, benimidazolyl, pyridyl, imidazolyl, indazolyl, tetrahydroindazolyl, pyrrolyl, or pyrazinyl. Optionally, the heteroaryl can be substituted with one or more substituents selected from the group consisting of methyl, ethyl, amino, dimethylamino, azetidinyl, and pyrolidinyl. In some exemplary embodiments, J is selected from the group consisting of

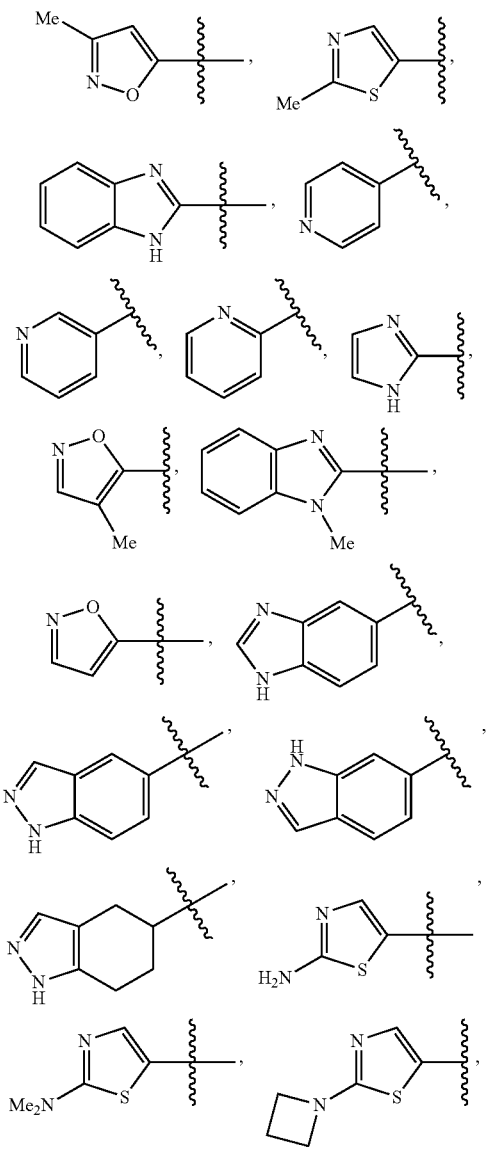

In various embodiments, J is $C_{3-6}$cycloalkenyl, such as cyclohexenyl or cyclopentenyl.

In some embodiments, $R^1$ is methyl. In other embodiments, $R^1$ is hydroxymethyl. In still other embodiments, $R^1$ is $CH_2CO_2R^6$. In various embodiments, $R^1$ is H, $CH_2$morpholinyl, oxetanyl, or 1-hydroxyl-cyclopropyl. In various embodiments, the carbon to which $R^1$ is attached is in the (S) configuration.

In some embodiments, $R^2$ is $CH_2$-G. In other embodiments, $R^2$ is $CH_2CH_2$-G. In various embodiments, G is aryl. In other embodiments, G is $C_{3-7}$cycloalkenyl. In yet other embodiments, G is a heteroaryl. In embodiments, G is selected from the group consisting of 4-methoxyphenyl, 3-hydroxy-4-methoxyphentyl, indolyl, and 4-methylsulfonylphenyl. In some exemplary embodiments, G comprises 4-methoxyphenyl. In other exemplary embodiments, G is 3-hydroxy-4-methoxyphenyl. In still other exemplary embodiments, G is indolyl. In embodiments, G can include 4-methylsulfonylphenyl.

In some embodiments, $R^3$ is $C_{3-7}$cycloalkyl. In other embodiments, $R^3$ is $C_{3-7}$cycloalkenyl. In still other embodiments, $R^3$ is a 3-7 membered heterocycloalkyl. In various embodiments, $R^3$ is a 3-7 membered heterocycloalkenyl. In embodiments, $R^3$ is aryl. In some exemplary embodiments, $R^3$ is selected from the group consisting of phenyl, cyclopentyl, 4-methylphenyl, and cyclopentenyl.

In embodiments, q is 1 and $R^3$ is $C_{3-7}$cycloalkyl. In other embodiments, q is 1 and $R^3$ is $C_{3-7}$cycloalkenyl. In various embodiments, q is 1 and $R^3$ is a 3-7 membered heterocycloalkyl. In yet other embodiments, q is 1 and $R^3$ is a 3-7 membered heterocycloalkenyl. In some embodiments, q is 1 and $R^3$ is aryl. In some exemplary embodiments, q is 1 and $R^3$ is selected from the group consisting of phenyl, cyclopentyl, 4-methylphenyl, and cyclopentenyl.

In some embodiments, $R^4$ is $C_{1-3}$alkyl, such as methyl or ethyl. In various embodiments, $R^4$ is H. In some cases, $R^4$ is methyl.

In some embodiments, q is 1; $R^1$ is H, methyl or hydroxymethyl; $R^2$ is selected from the group consisting of $CH_2$-(4-methoxyphenyl), $CH_2$— indolyl, $CH_2$-(4-methylsulfonylphenyl), and $CH_2$-(3-hydroxy-4-methoxyphenyl); $R^3$ is selected from the group consisting of phenyl, cyclopentyl, 4-methylphenyl, and cyclopentenyl; and $R^4$ is methyl.

Specifically contemplated is a compound of Formula X including J, as described in paragraphs [0047]-[0050], $R^1$ as described in paragraph [0051], $R^2$ as described in paragraph [0052], $R^3$ as described in paragraph [0053], and $R^4$ as described in paragraph [0054].

In some embodiments, a compound of Formula (X) is selected from:

11
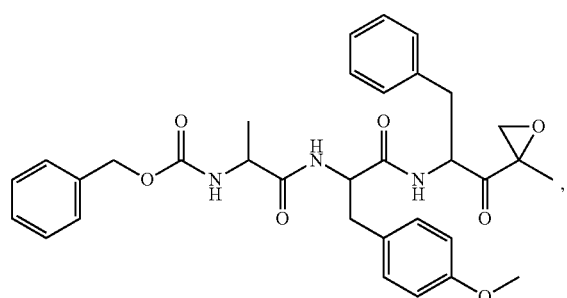
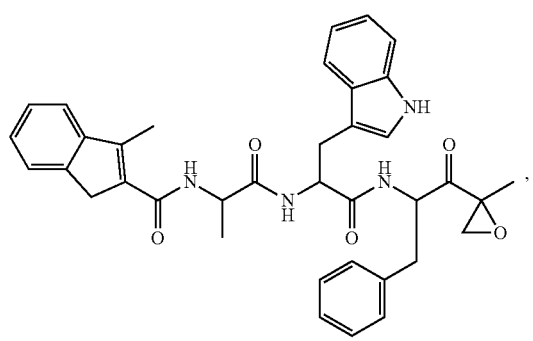
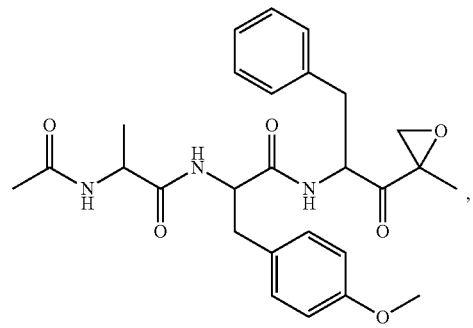
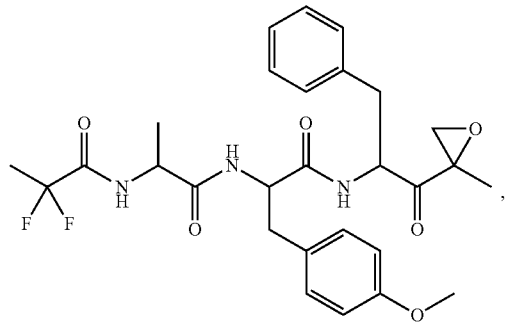
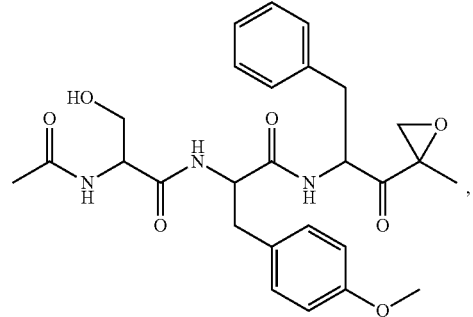
12
-continued
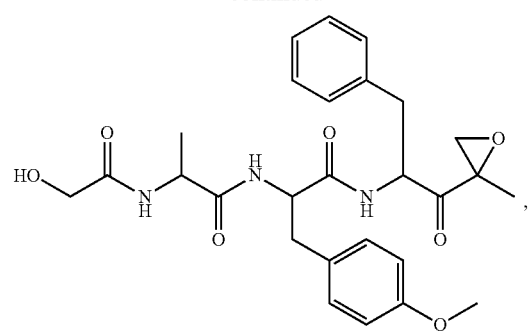
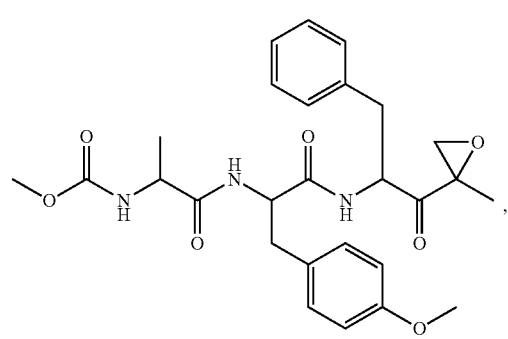
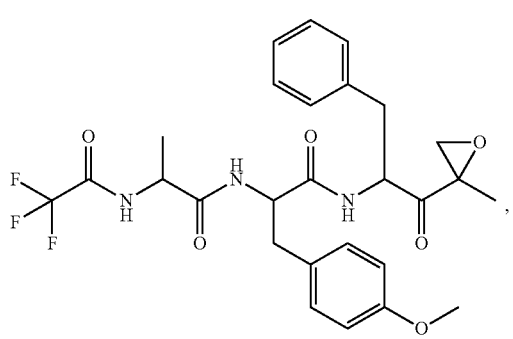
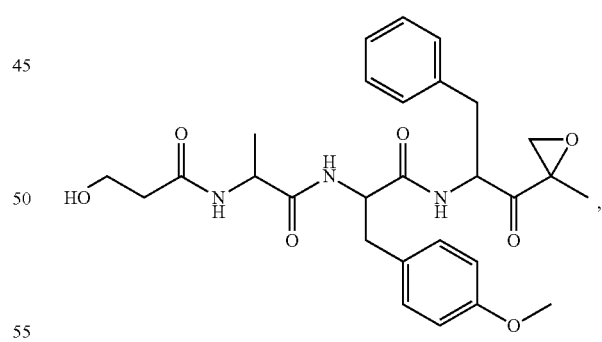
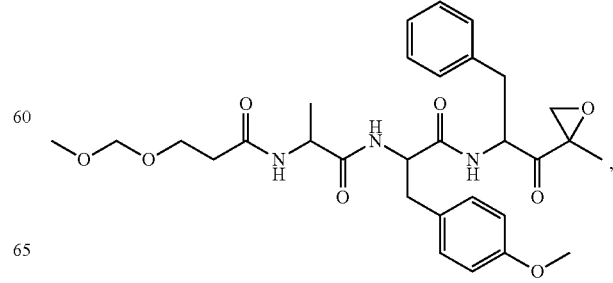

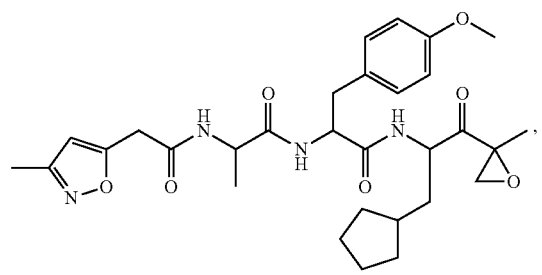
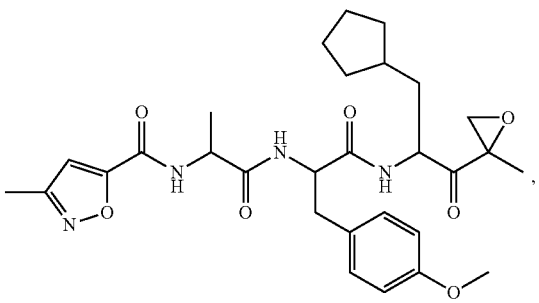
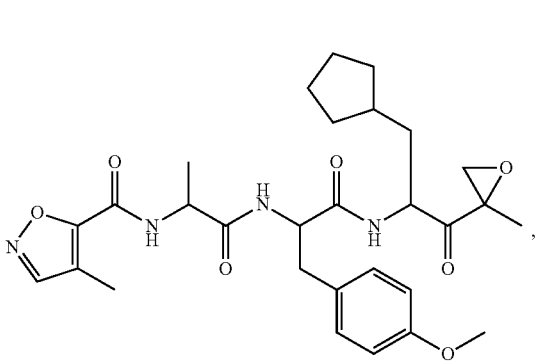
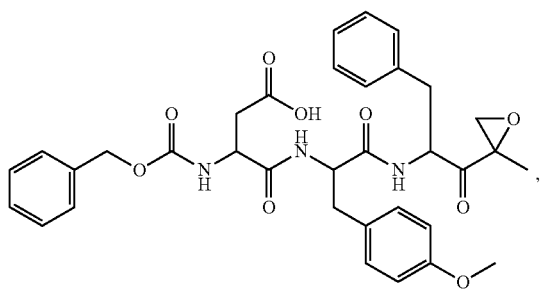
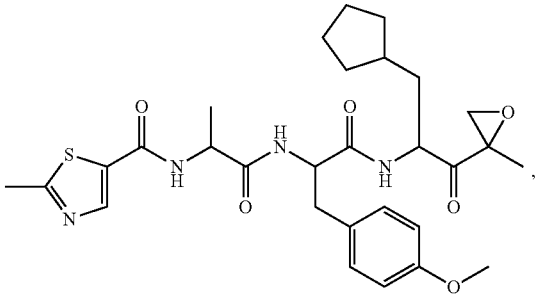
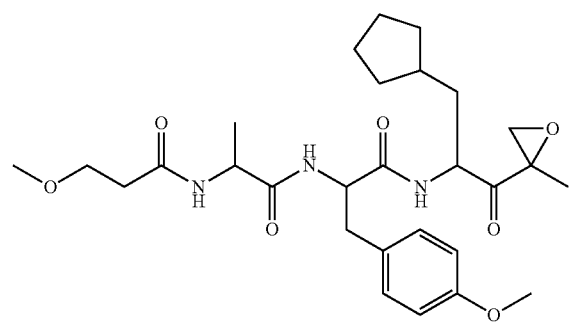
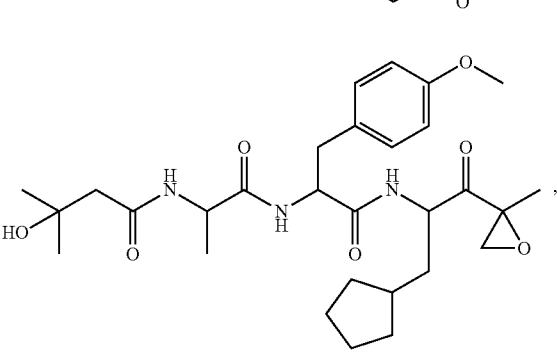
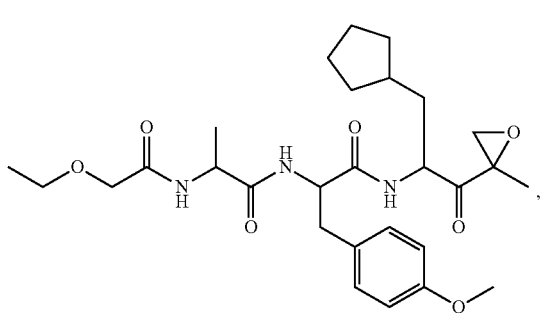
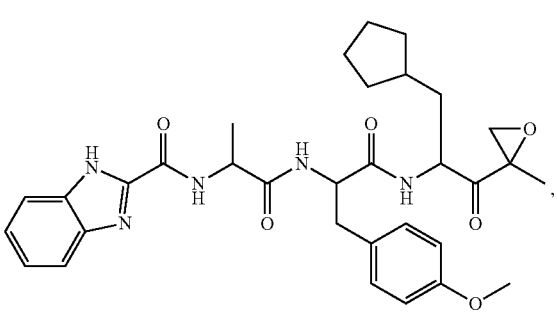

-continued
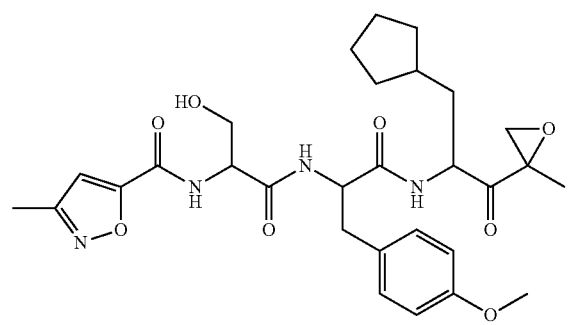
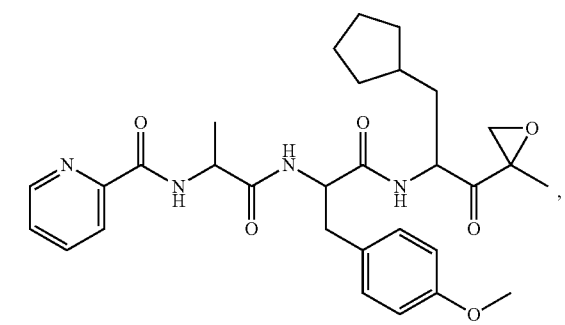
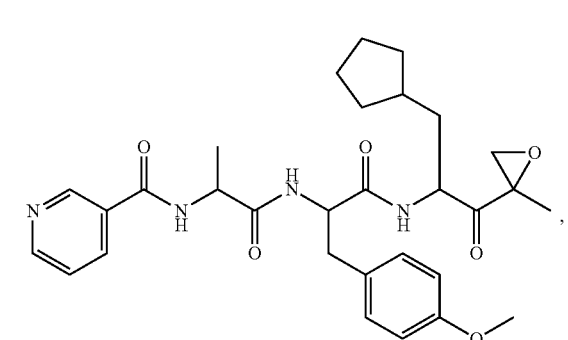
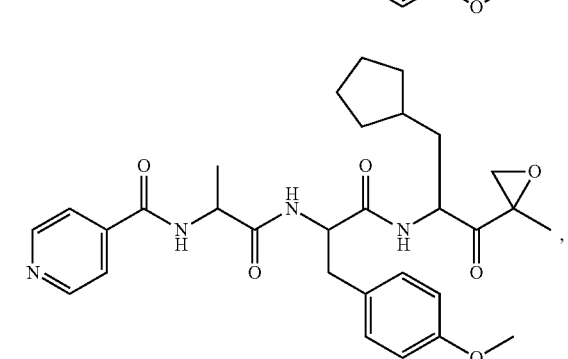
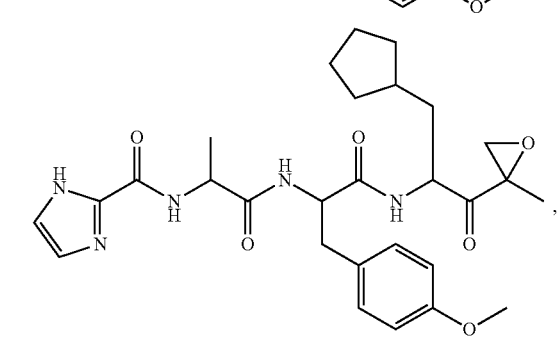
-continued
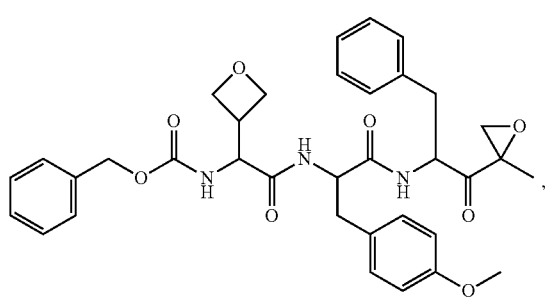
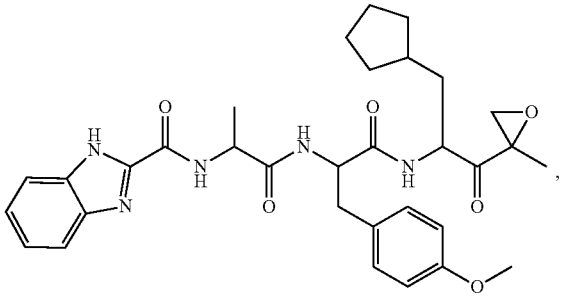
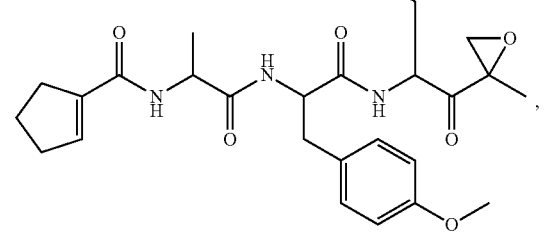
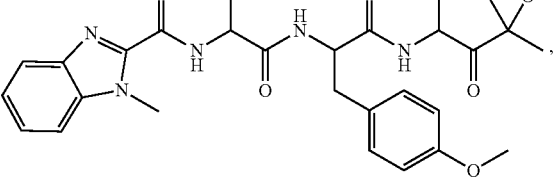
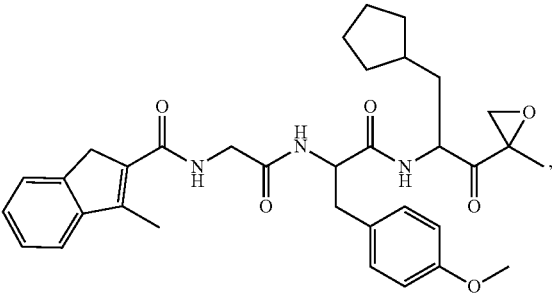

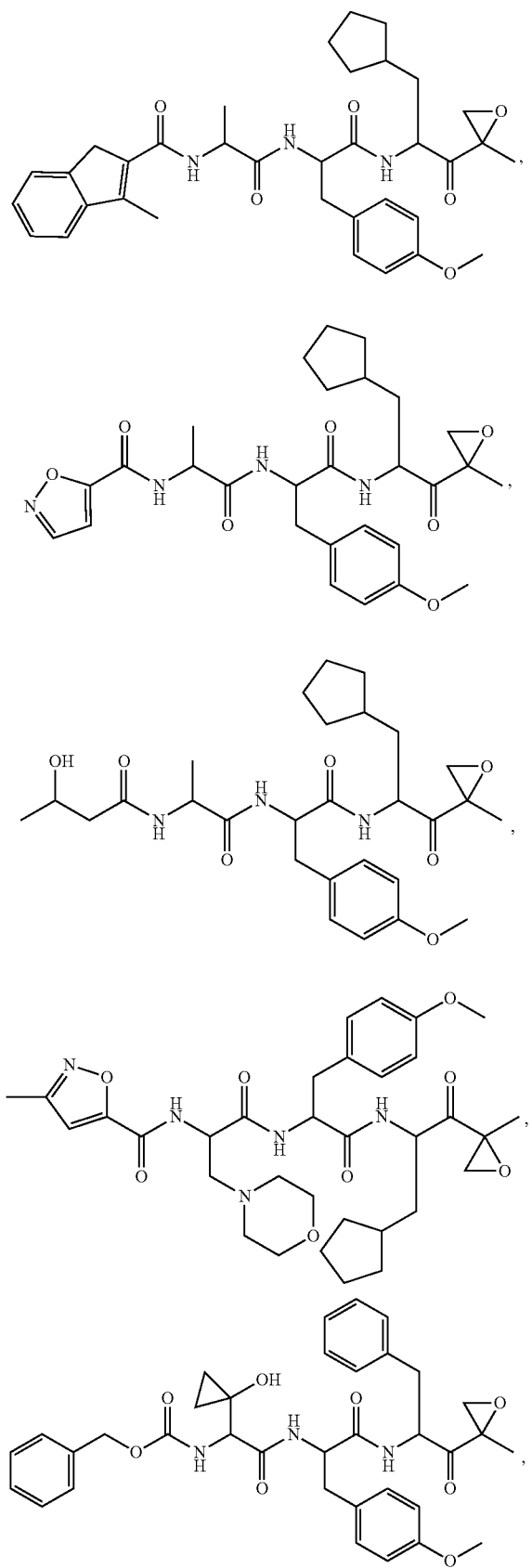
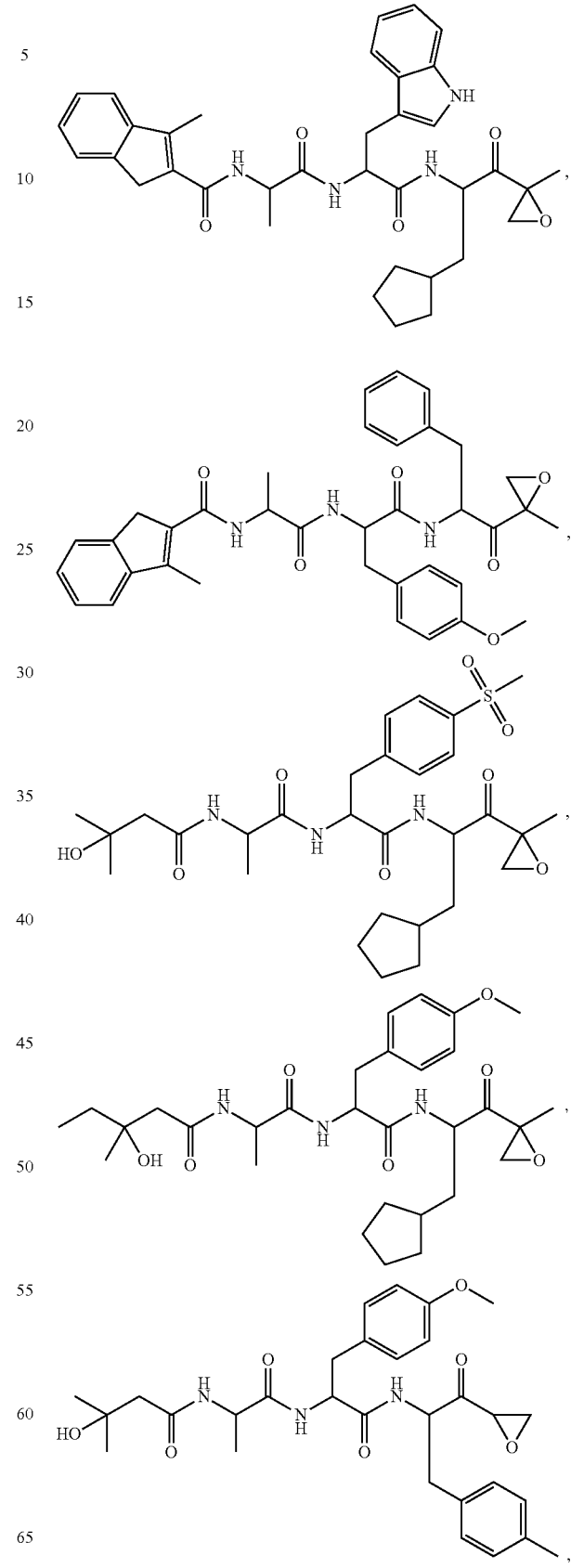

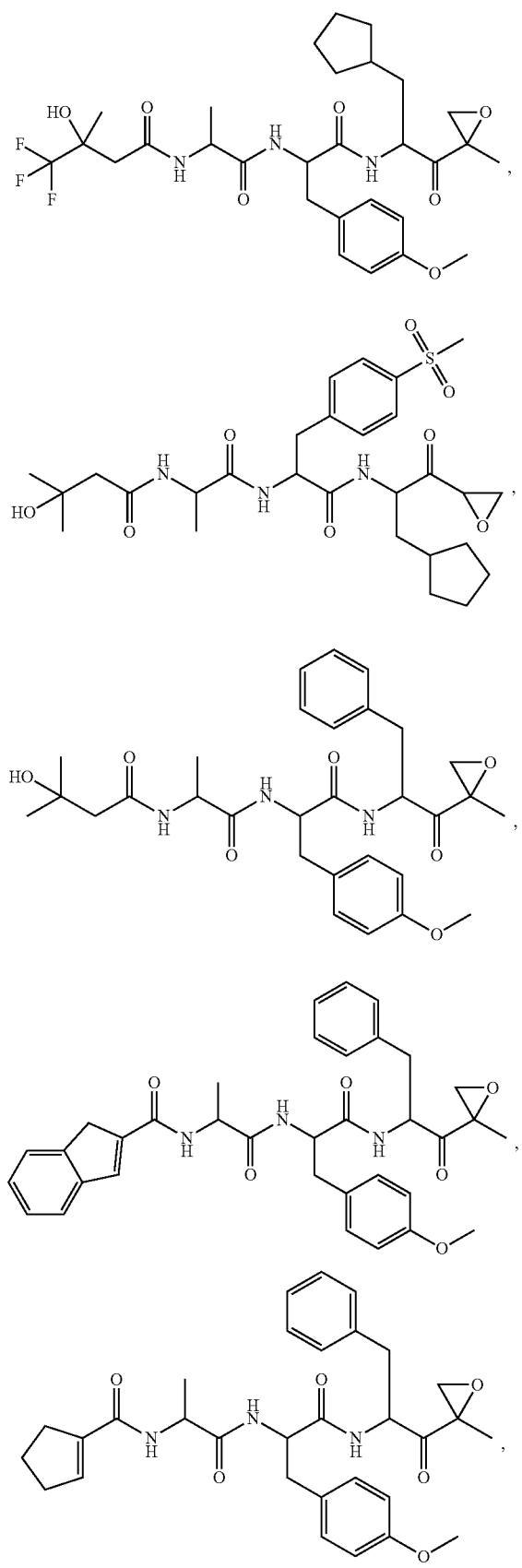
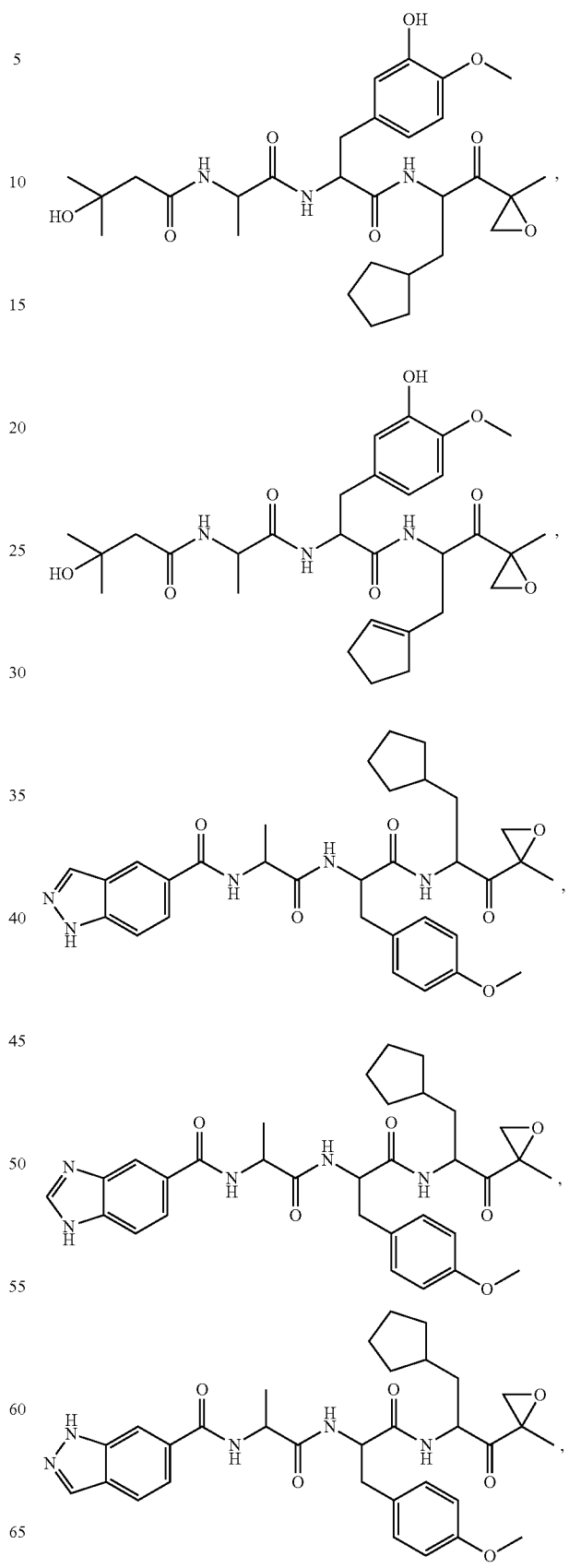

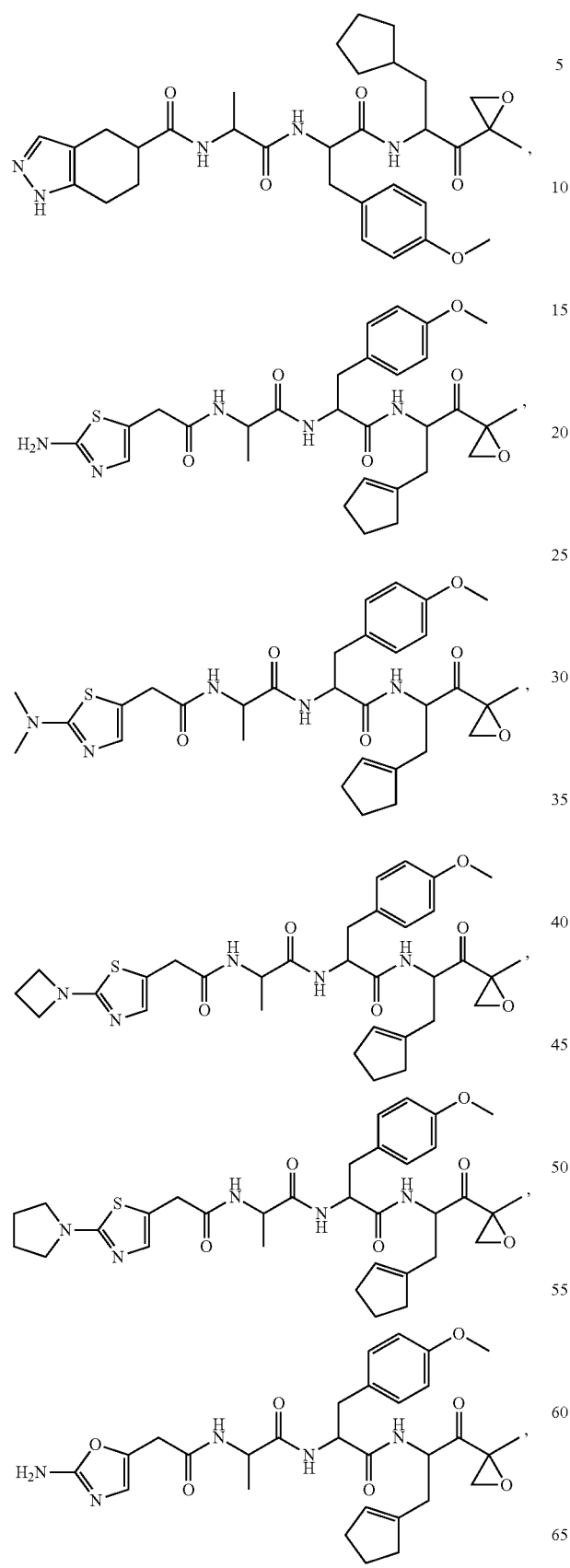
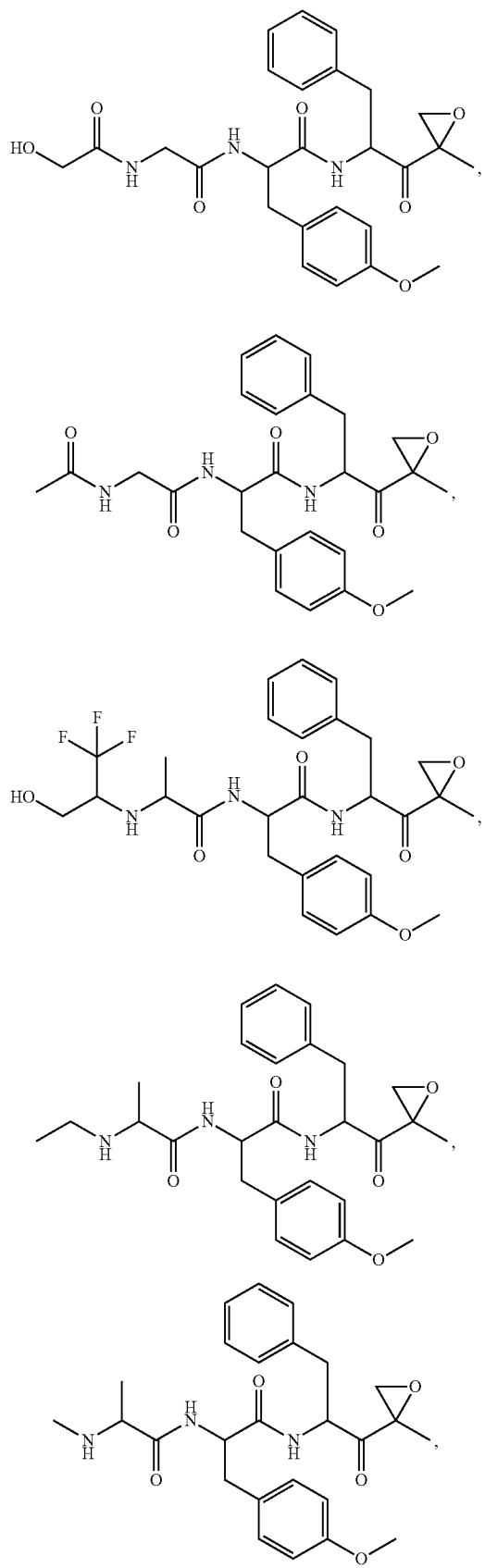

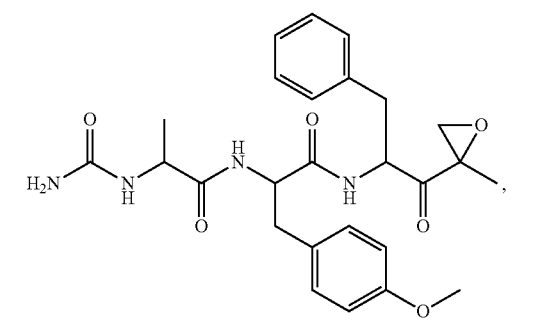
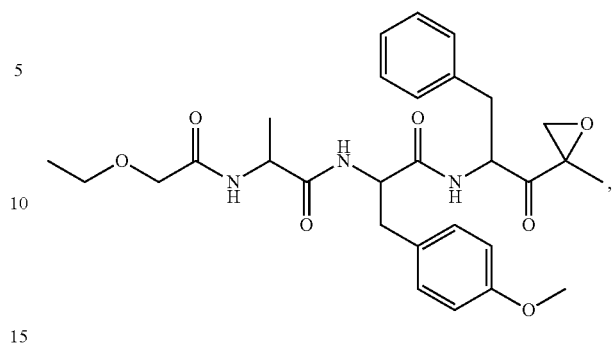
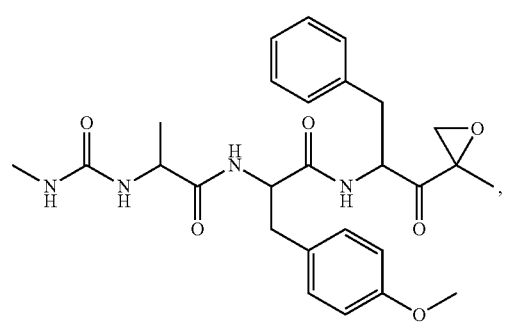
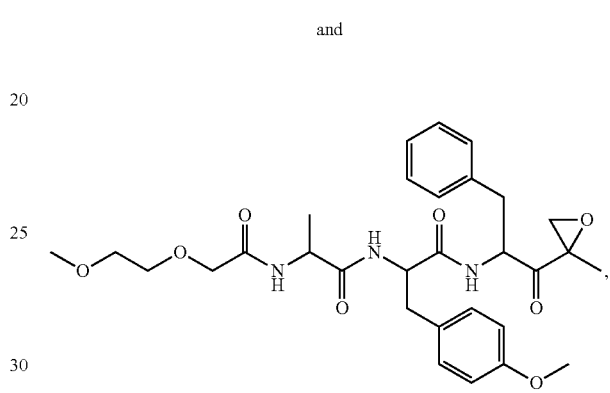
and
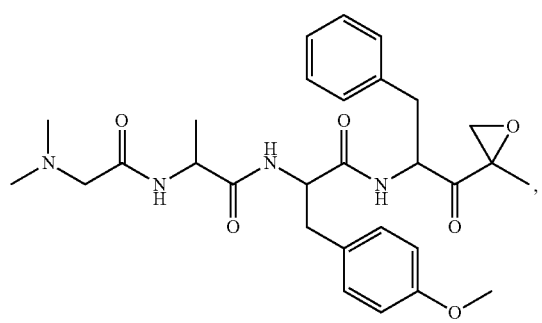
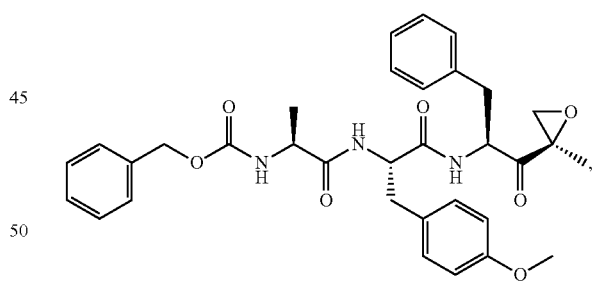
or a pharmaceutically acceptable salt thereof
In some exemplary embodiments, a compound of Formula (X) is selected from the group consisting of:
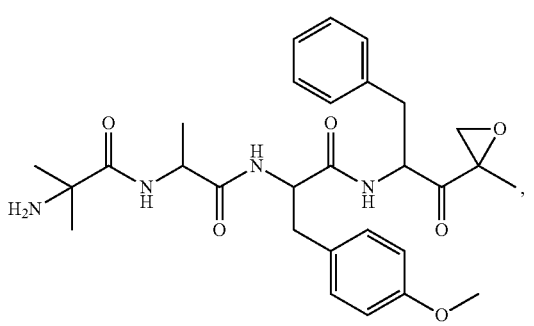
C-2001
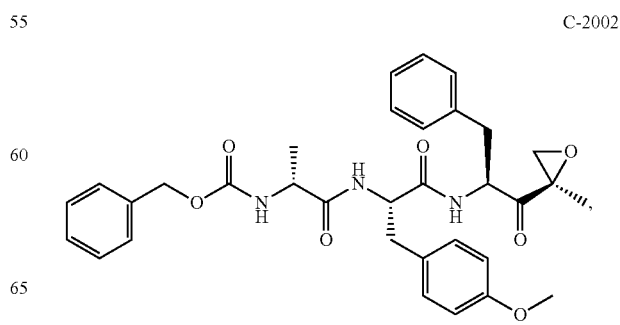
C-2002
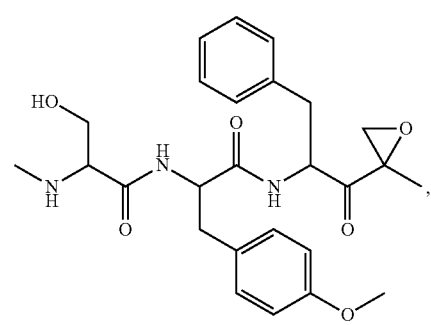

C-2003
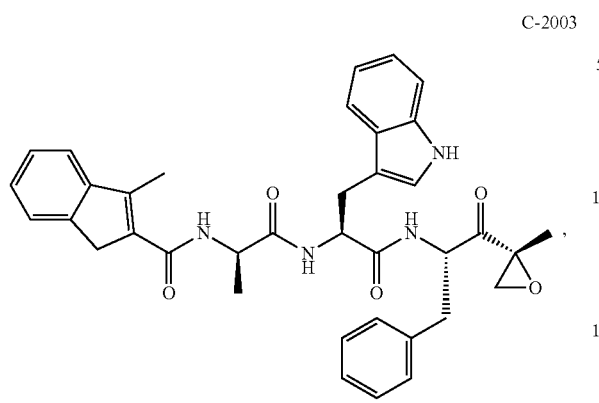
C-2004
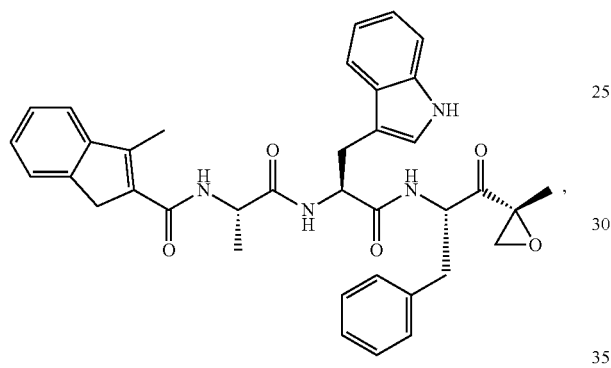
C-2005
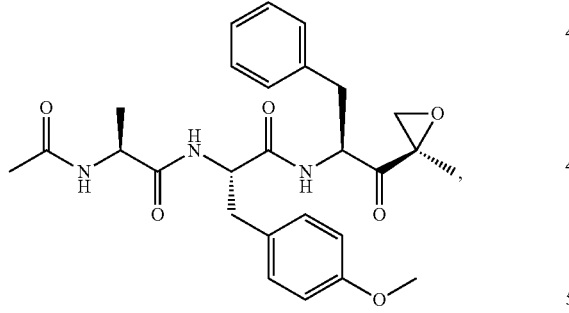
C-2006
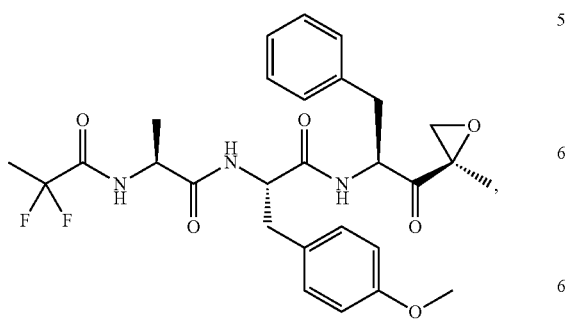
C-2007
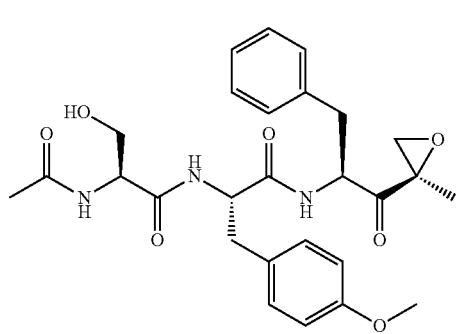
C-2008
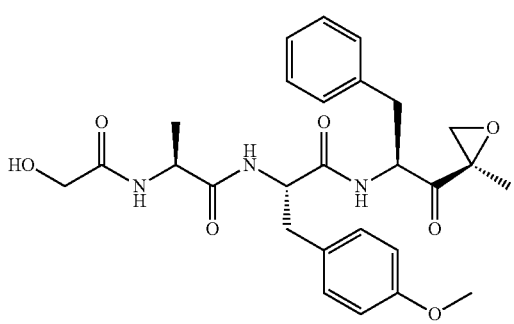
C-2009
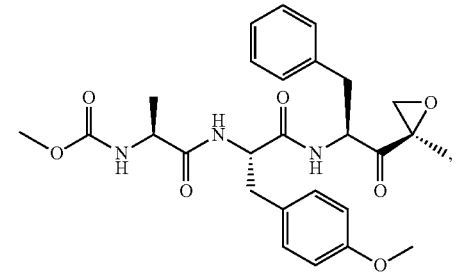
C-2010
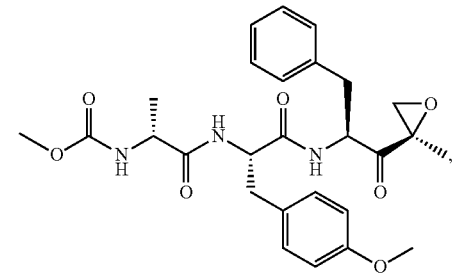
C-2011
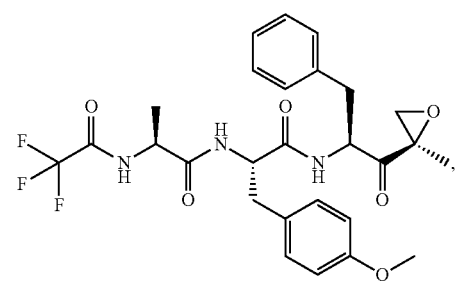

C-2012
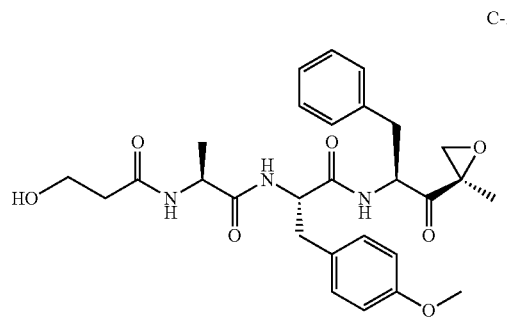
C-2017
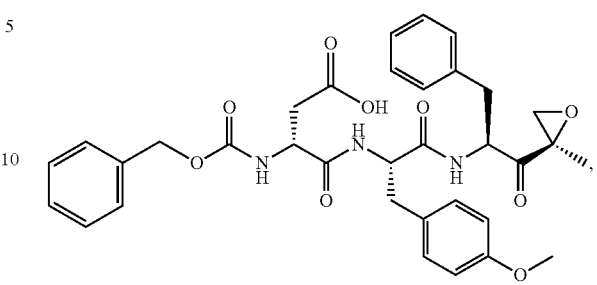
C-2013
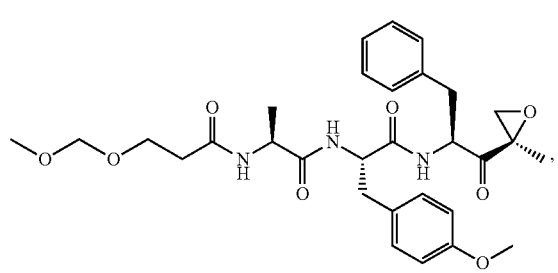
C-2018
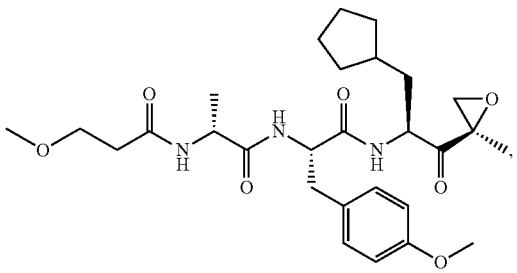
C-2014
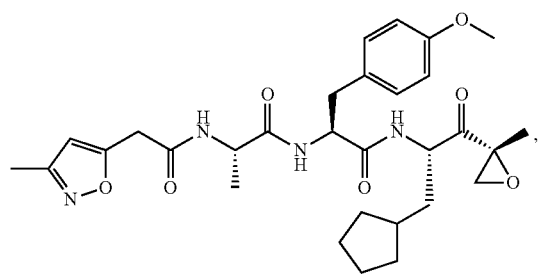
C-2019
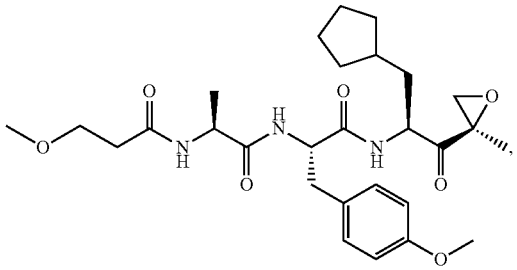
C-2015
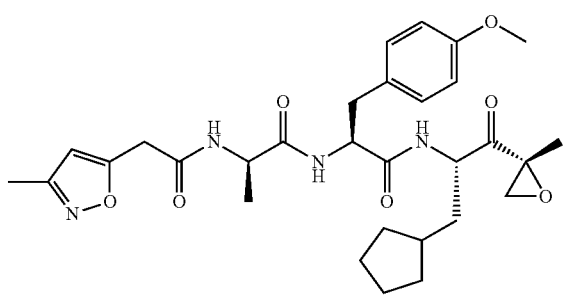
C-2020
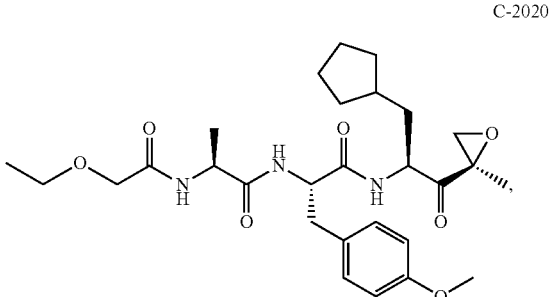
C-2016
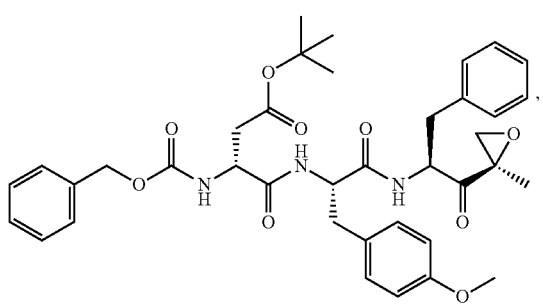
C-2021
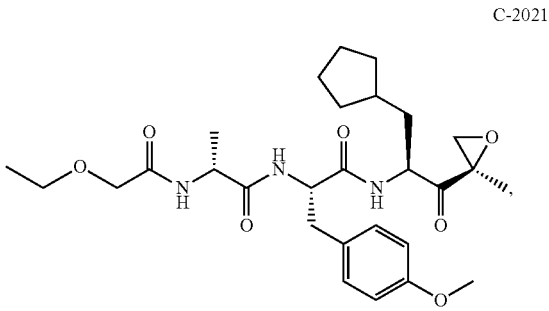

C-2022
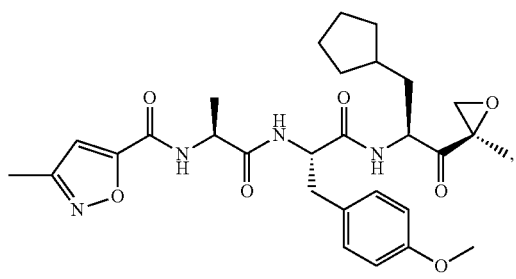
C-2023
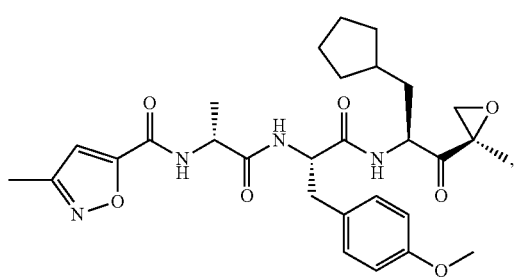
C-2024
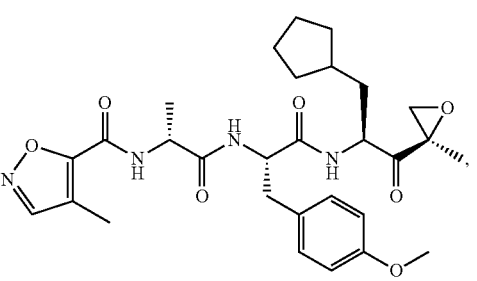
C-2025
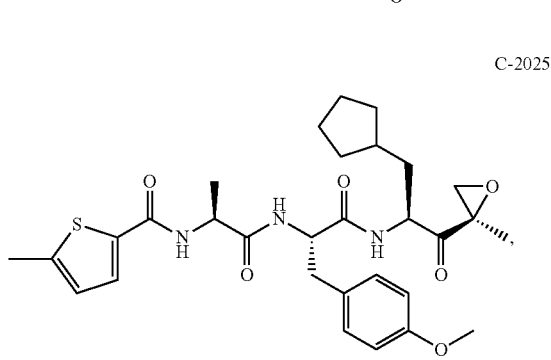
C-2026
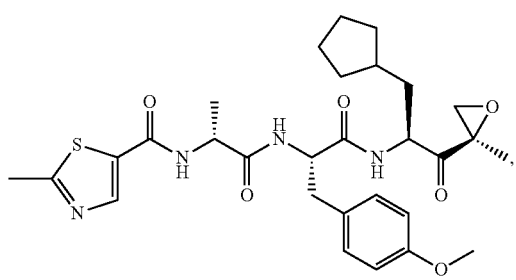
C-2027
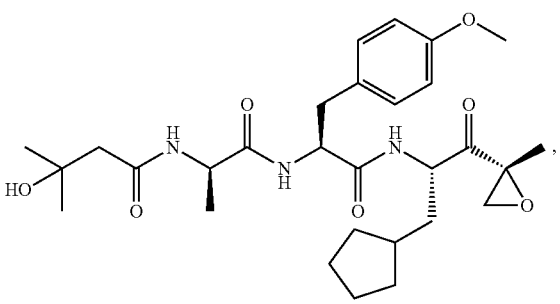
C-2028
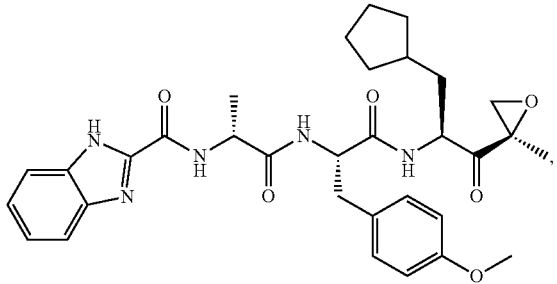
C-2029
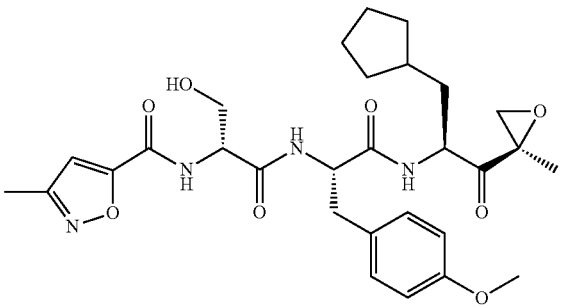
C-2030
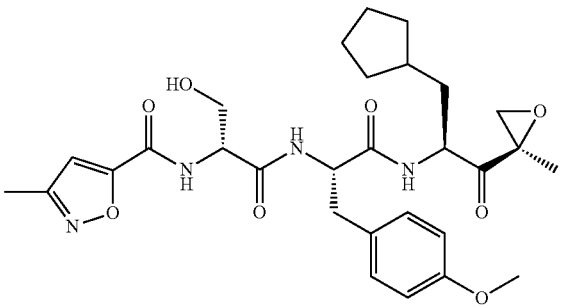
C-2031
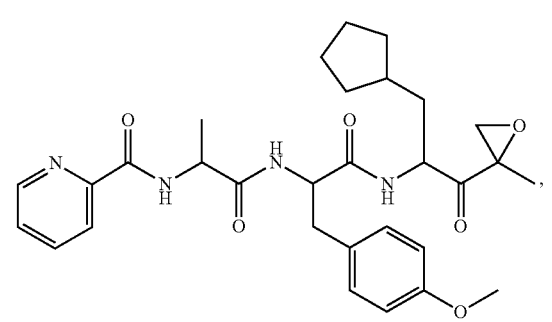

C-2032
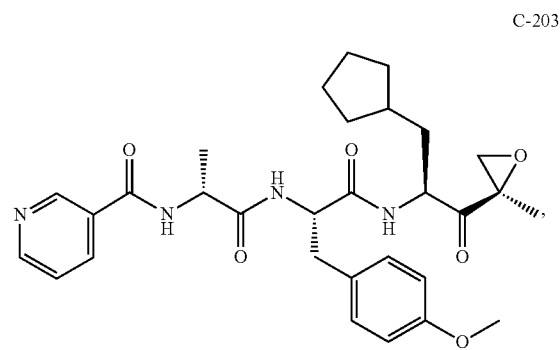
C-2033
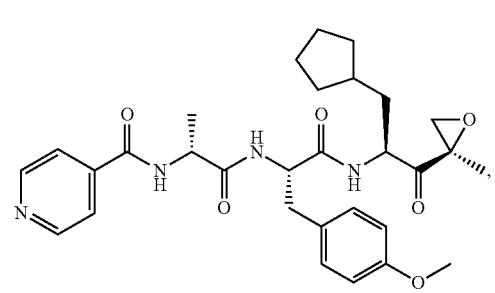
C-2034
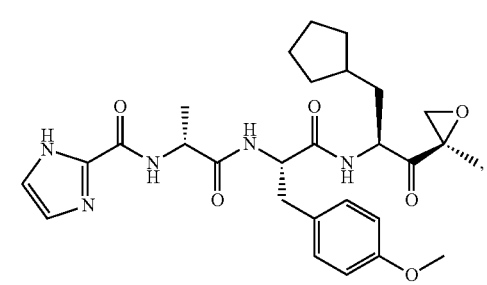
C-2035
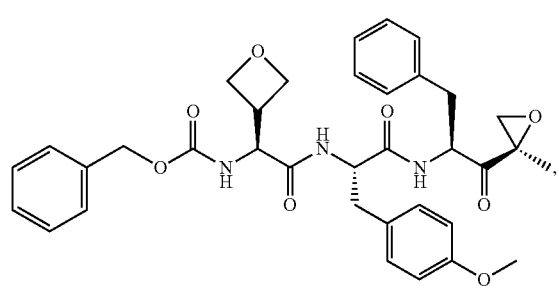
C-2036
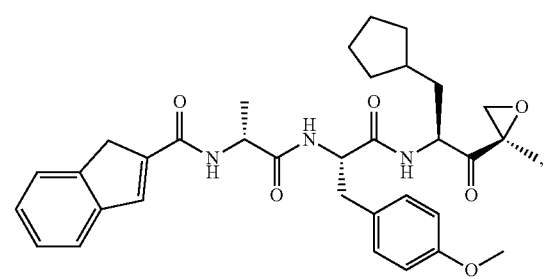
C-2037
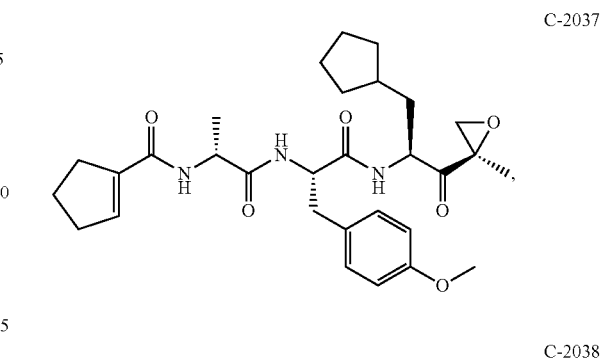
C-2038
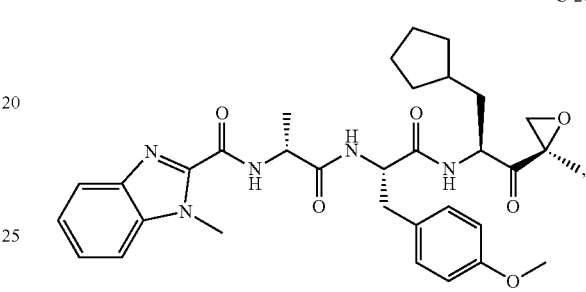
C-2039
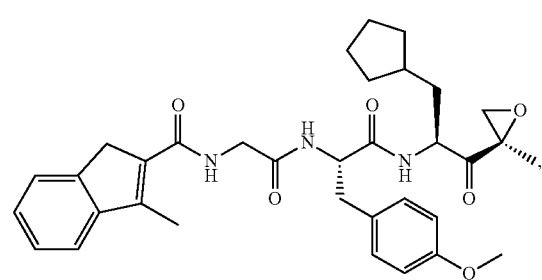
C-2040
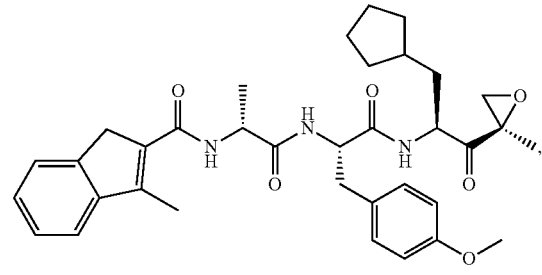
C-2041
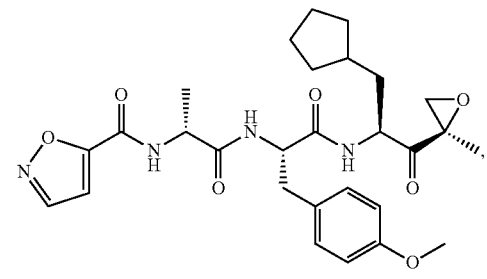

C-2042
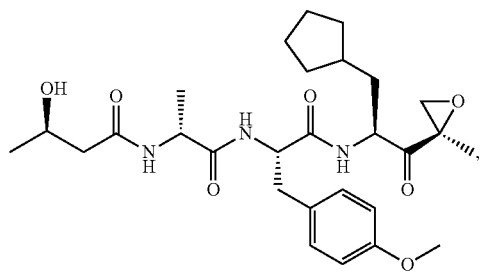
C-2043
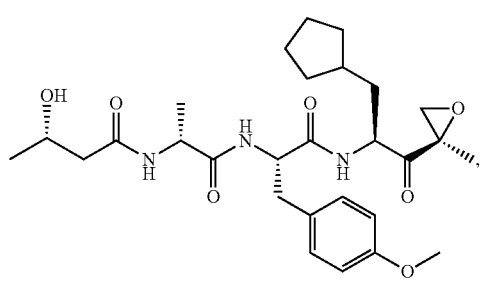
C-2044
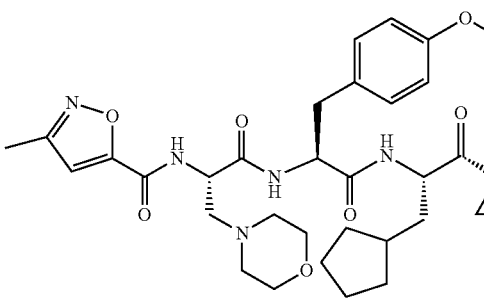
C-2045
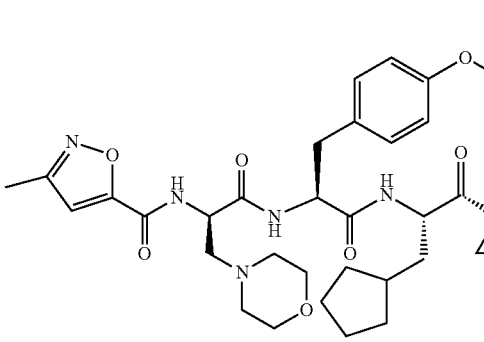
C-2046
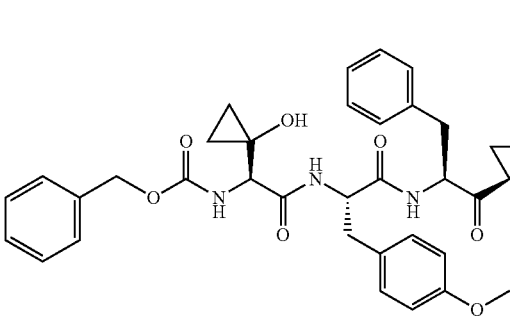
C-2047
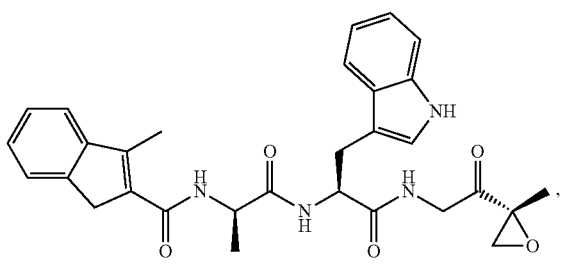
C-2048
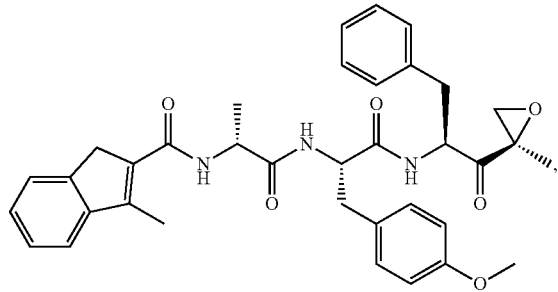
C-2049
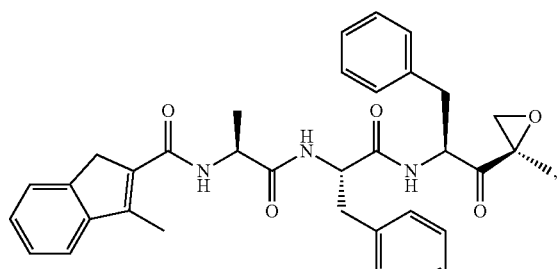
C-2050
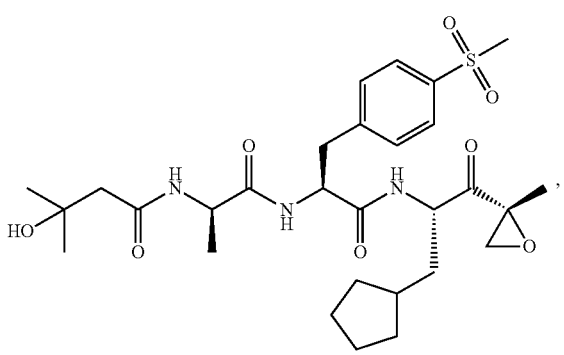
C-2051
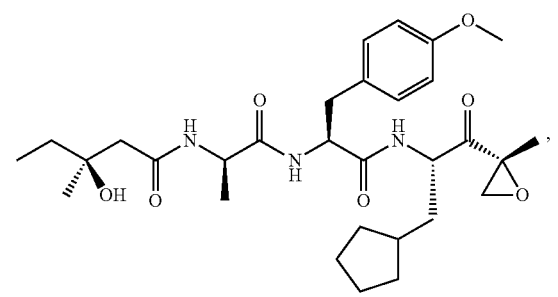

C-2052
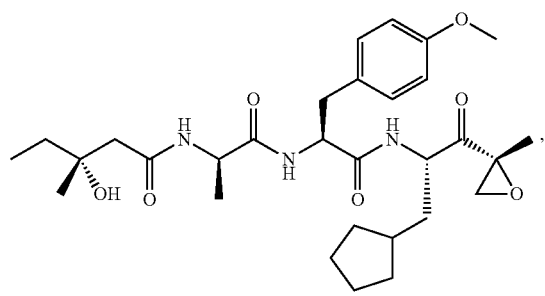
C-2053
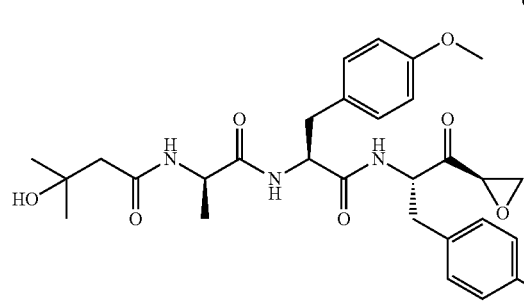
C-2054
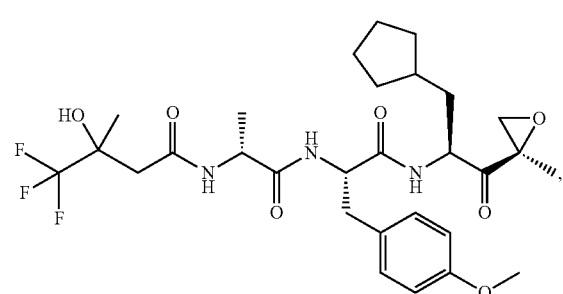
C-2055
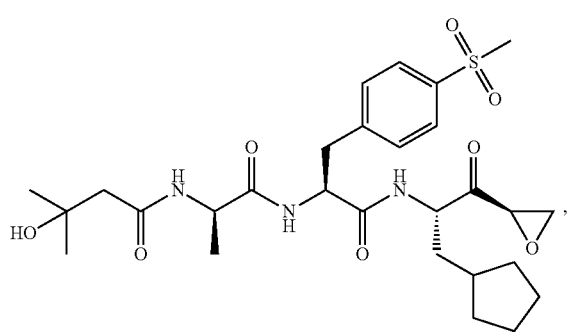
C-2056
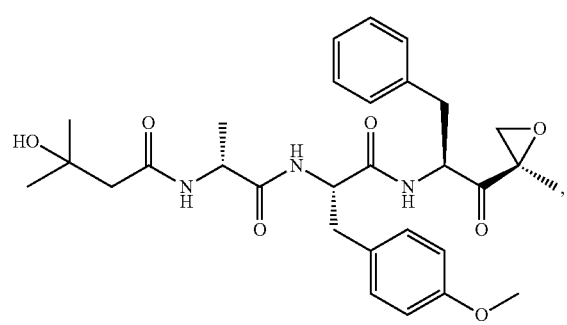
C-2057
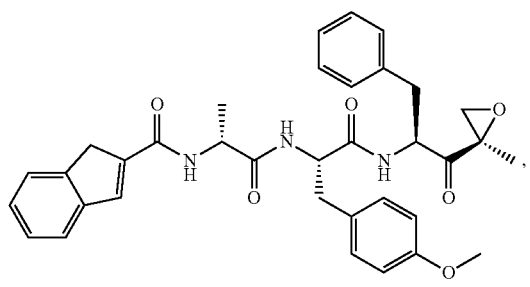
C-2058
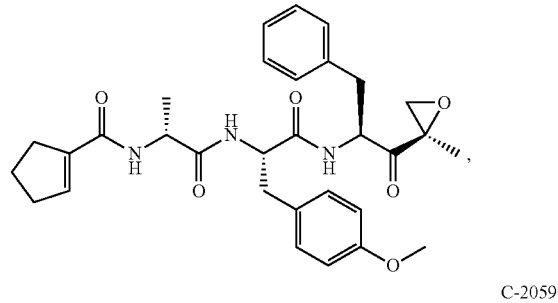
C-2059
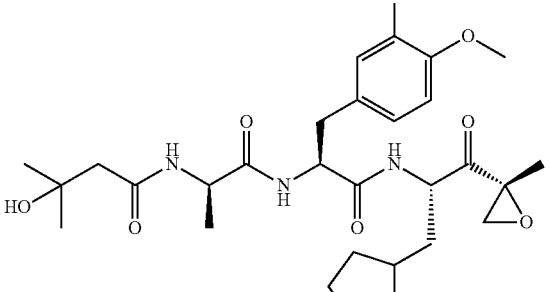
C-2060
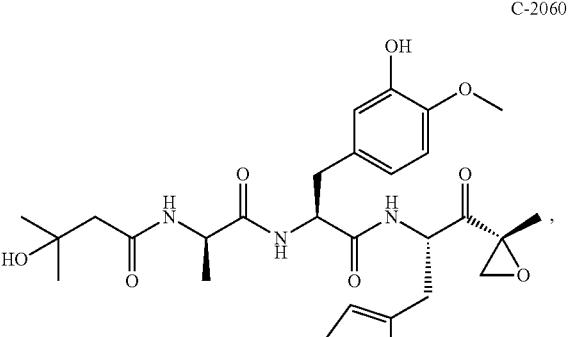
C-2061
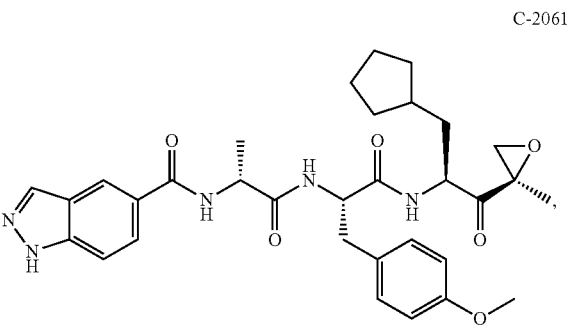

C-2062
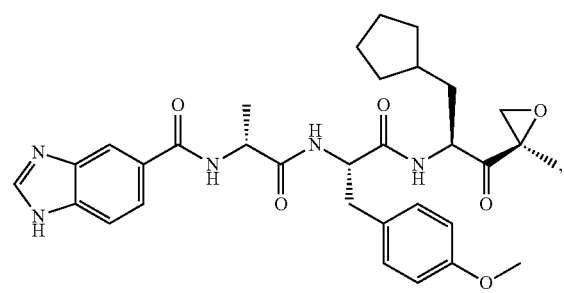
C-2067
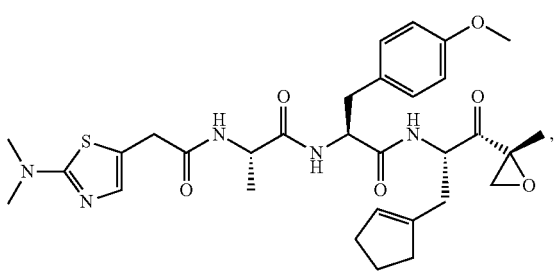
C-2063
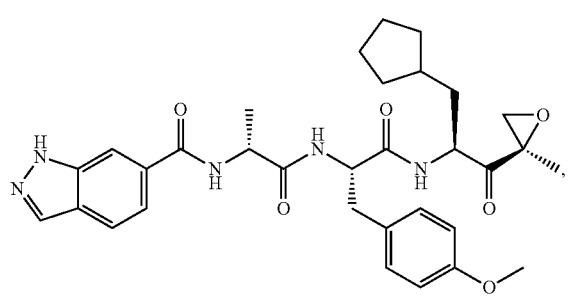
C-2068
C-2064
C-2069
C-2065
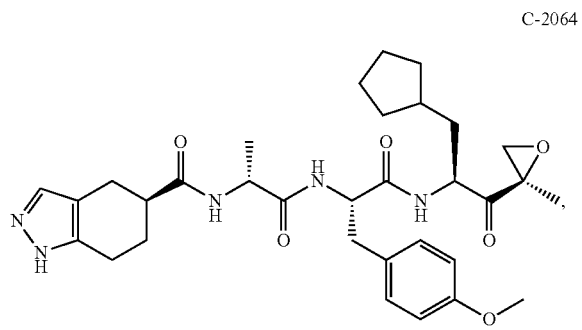
C-2070
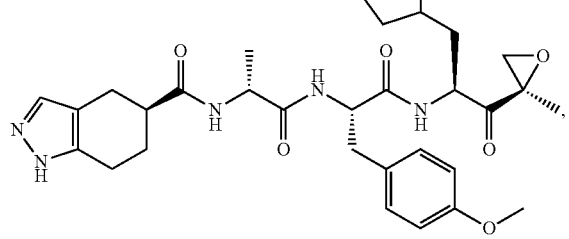
C-2066
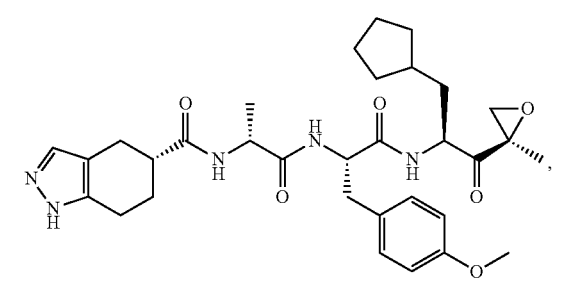
C-2071
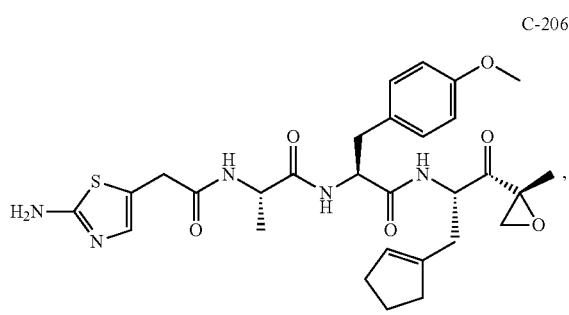
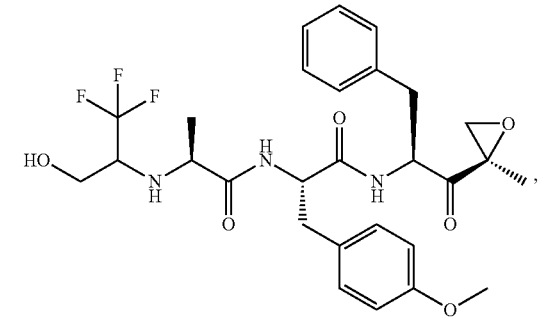

C-2072
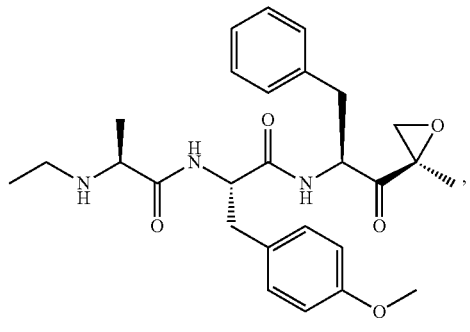
C-2073
C-2074
C-2075
C-2076
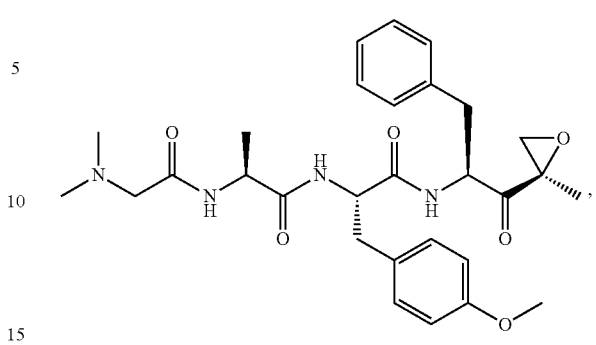
C-2077
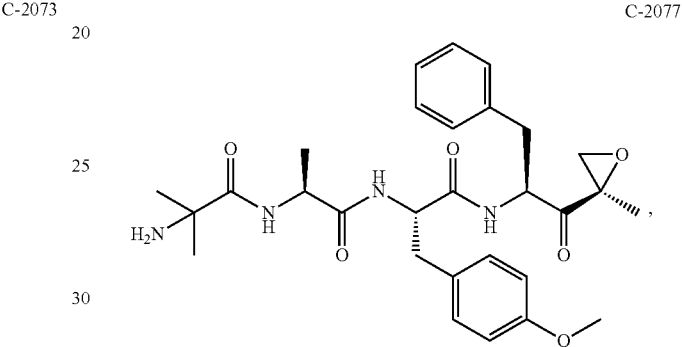
C-2078
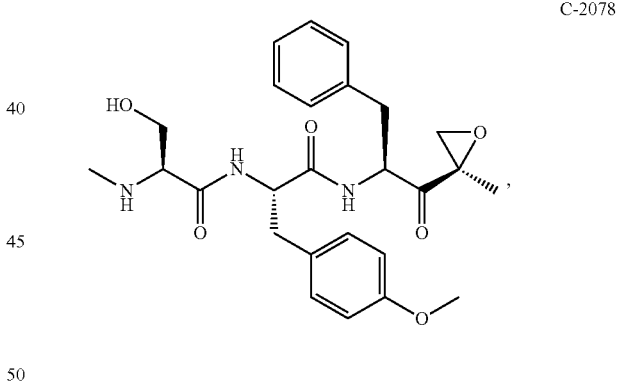
C-2079
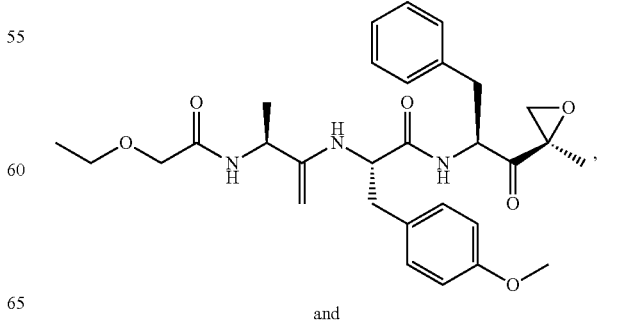
and -continued

C-2080

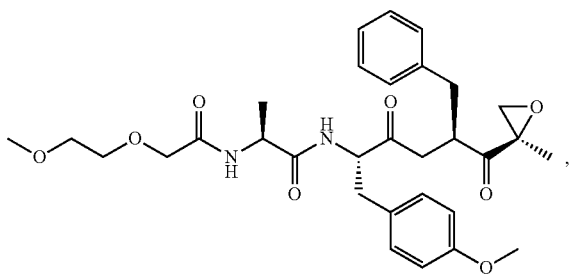

or a pharmaceutically acceptable salt thereof.

In another aspect, provided herein is a compound having a structure of Formula (I) or a pharmaceutically acceptable salt thereof,

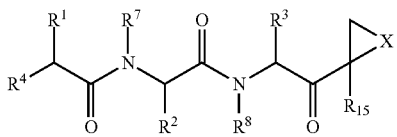

wherein:

B is absent or is $N(R^9)R^{10}$;

L is absent or is selected from C=O, C=S, and $SO_2$;

Q is absent or is selected from O, NH, and N—$C_{1-6}$alkyl;

X is selected from O, S, NH, and N—$C_{1-6}$alkyl;

M is absent or $C_{1-12}$alkyl;

each of $R^1$, $R^2$, and $R^3$ are independently selected from hydrogen, —$C_{1-6}$alkyl-B, $C_{2-6}$alkenyl, $C_{2-6}$alkynyl, $C_{1-6}$hydroxyalkyl, $C_{1-6}$ alkoxyalkyl, carbocyclyl, carbocyclylM-, heterocyclyl, heterocyclylM-, aryl, $C_{1-6}$aralkyl, heteroaryl, and $C_{1-6}$heteroaralkyl;

$R^4$ is $N(R^5)$L-Q-$R^6$;

$R^5$ is selected from hydrogen, OH, $C_{1-6}$aralkyl, and $C_{1-6}$alkyl;

$R^6$ is selected from hydrogen, and $C_{1-6}$alkyl;

$R^7$ and $R^8$ are independently selected from hydrogen, $C_{1-6}$alkyl, and $C_{1-6}$aralkyl;

$R^9$ is selected from hydrogen, OH, and $C_{1-6}$alkyl; and $R^{10}$ is an N-terminal protecting group; and $R^{15}$ is selected from hydrogen, $C_{1-6}$ alkyl, $C_{1-6}$hydroxyalkyl, $C_{1-6}$ alkoxy, —C(O)O$C_{1-6}$ alkyl, —C(O)NH$C_{1-6}$ alkyl, and $C_{1-6}$ aralkyl.

In some embodiments, $R^7$ and $R^8$ are independently selected from hydrogen and $C_{1-6}$alkyl. For example, $R^7$ and $R^8$ can both be hydrogen.

In some embodiments, $R^{15}$ is selected from hydrogen, $C_{1-6}$alkyl and $C_{1-6}$hydroxyalkyl. For example, $R^{15}$ can be selected from hydrogen, methyl, ethyl, hydroxymethyl, and 2-hydroxyethyl.

In some embodiments, $R^5$ is hydrogen.

In some embodiments, $R^2$ is selected from $C_{1-6}$aralkyl and $C_{1-6}$heteroaralkyl. For example, $R^2$ can be selected from $C_{1-6}$ alkyl-phenyl, $C_{1-6}$ alkyl-indolyl, $C_{1-6}$ alkyl-thienyl, $C_{1-6}$alkyl-thiazolyl, and $C_{1-6}$alkyl-isothiazolyl. In some embodiments, $R^2$ is selected from

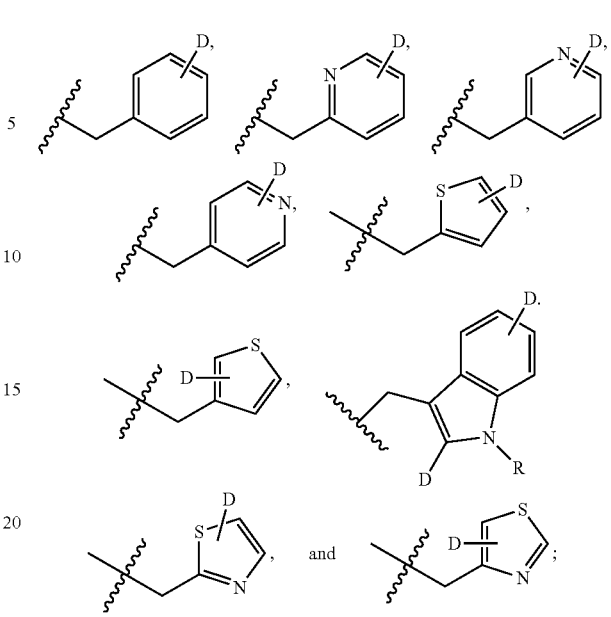

wherein D is selected from hydrogen, methoxy, t-butoxy, hydroxy, halogen, cyano, trifluoromethyl, and $C_{1-4}$alkyl; and R is hydrogen or a suitable protecting group.

In some embodiments, $R^3$ is selected from carbocyclylM-, $C_{1-6}$aralkyl and $C_{1-6}$heteroaralkyl. For example, $R^3$ can be selected from $C_{1-6}$alkyl-cyclopentyl, $C_{1-6}$alkyl-cyclopentenyl, $C_{1-6}$alkyl-phenyl and $C_{1-6}$alkyl-indolyl. In some embodiments, $R^3$ is selected from

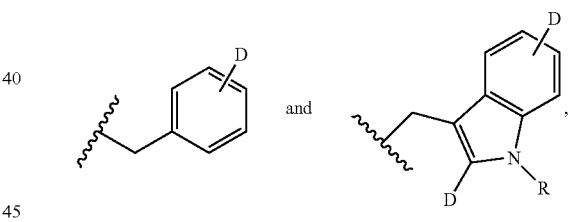

wherein D is selected from hydrogen, methoxy, t-butoxy, hydroxy, halogen, cyano, trifluoromethyl, and $C_{1-6}$alkyl; and R is hydrogen or a suitable protecting group.

In some embodiments, $R^6$ is $C_{1-6}$alkyl. In some embodiments, $R^1$ is substituted with one or more halogens, such as fluorine.

In some embodiments, $R^1$ is selected from hydrogen, —$C_{1-6}$alkyl-B, $C_{1-6}$hydroxyalkyl, $C_{1-6}$alkoxyalkyl, aryl, and $C_{1-6}$aralkyl. For example, $R^1$ can be selected from —$C_{1-6}$alkylB and $C_{1-6}$aralkyl. Non-limiting examples of $R^1$ include methyl, ethyl, isopropyl, carboxymethyl, and benzyl. In some embodiments, $R^1$ is substituted with one or more halogens, such as fluorine.

In some embodiments, L is C=O, Q is absent, and $R^6$ is —$C_{1-6}$alkyl. In some embodiments, $R^6$ is substituted with one or more halogens, such as fluorine. In other embodiments, L is C=O, Q is absent, and $R^6$ is hydrogen.

Also provided herein is a compound of Formula (II) or a pharmaceutically acceptable salt thereof,

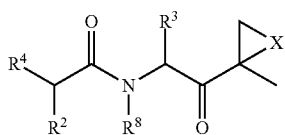

(II)

L is absent or is selected from C=O, C=S, and SO$_2$;
M is absent or is C$_{1-12}$alkyl;
Q is absent or is selected from O, NH, and N—C$_{1-6}$alkyl;
X is selected from O, S, NH, and N—C$_{1-6}$alkyl;
each Z is independently selected from O, S, NH, and N—C$_{1-6}$alkyl; or
Z is optionally a covalent bond when adjacent to an occurrence of A;
R$^2$ and R$^3$ are each independently selected from aryl, C$_{1-6}$aralkyl, heteroaryl, and C$_{1-6}$heteroaralkyl;
R$^4$ is N(R$^5$)L-Q-R$^6$;
R$^5$ is selected from hydrogen, OH, C$_{1-6}$aralkyl, and C$_{1-6}$alkyl;
R$^6$ is selected from C$_{1-6}$alkyl, heterocyclyl, heteroaryl, C$_{1-6}$heteroaralkyl, heterocyclylM-, carbocyclylM; and
R$^8$ is selected from hydrogen, C$_{1-6}$alkyl, and C$_{1-6}$aralkyl.

In some embodiments, R$^8$ is selected from hydrogen and C$_{1-6}$alkyl. For example, R$^8$ can be hydrogen.

In some embodiments, R$^5$ is hydrogen.

In some embodiments, R$^2$ is selected from C$_{1-6}$aralkyl and C$_{1-6}$heteroaralkyl. For example, R$^2$ can be selected from C$_{1-6}$ alkyl-phenyl, C$_{1-6}$ alkyl-indolyl, C$_{1-6}$alkyl-thienyl, C$_{1-6}$alkyl-thiazolyl, and C$_{1-6}$alkyl-isothiazolyl. In some embodiments, R$^2$ is selected from

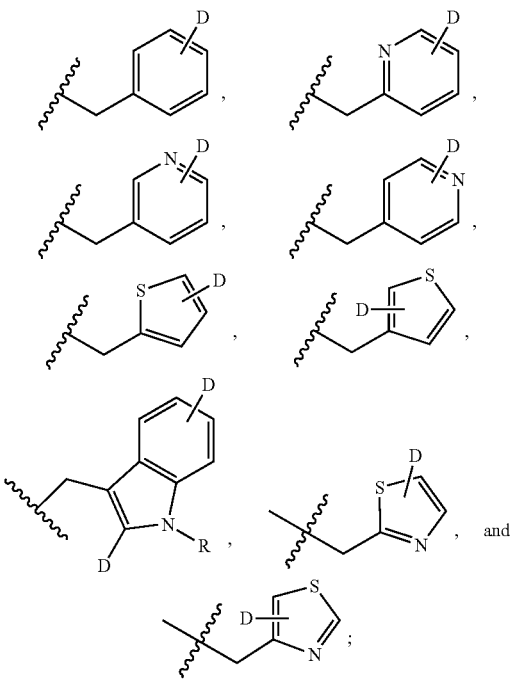

wherein D is selected from hydrogen, methoxy, t-butoxy, hydroxy, halogen, cyano, trifluoromethyl, and C$_{1-4}$alkyl; and
R is hydrogen or a suitable protecting group.

In some embodiments, R$^3$ is selected from C$_{1-6}$aralkyl and C$_{1-6}$heteroaralkyl. For example, R$^3$ can be selected from C$_{1-6}$alkyl-phenyl and C$_{1-6}$alkyl-indolyl. In some embodiments, R$^3$ is selected from

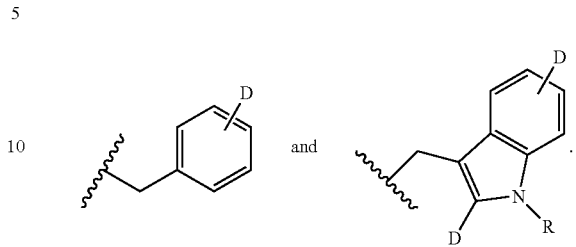

wherein D is selected from hydrogen, methoxy, t-butoxy, hydroxy, cyano, trifluoromethyl, and C$_{1-4}$alkyl; and
R is hydrogen or a suitable protecting group.

In some embodiments, R$^6$ is selected from heterocyclyl, heteroaryl, and heterocyclylM-.

In some embodiments, L is C=O, Q is absent, and R$^6$ is heterocyclyl. In other embodiments, L is C=O, Q is absent, and R$^6$ is heteroaryl. In certain embodiments, L is C=O, Q is absent, and R$^6$ is heterocyclylM-.

Non-limiting examples of a compound of Formula (II) include:

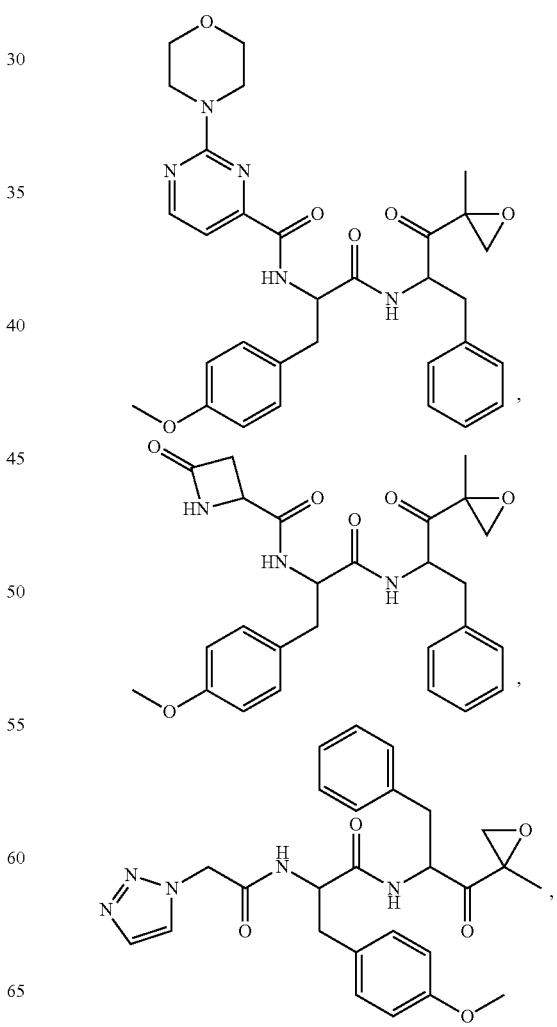

-continued
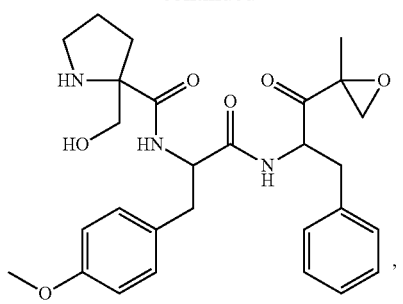
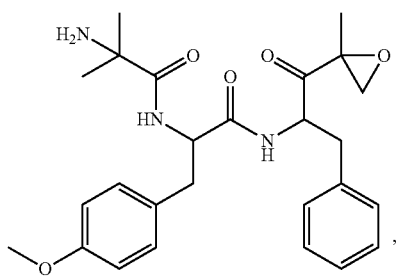
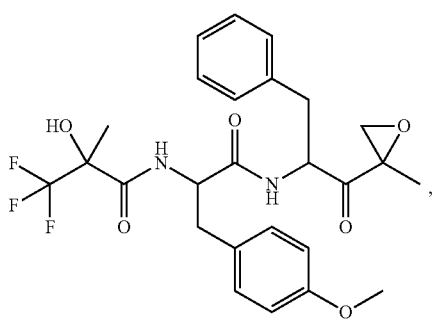
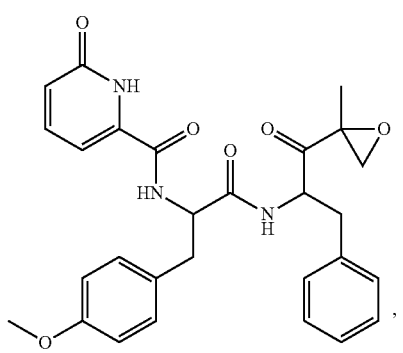
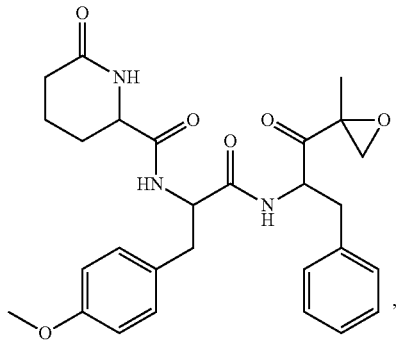
-continued
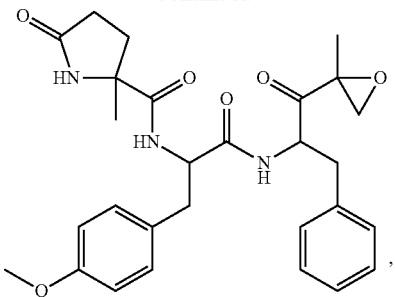
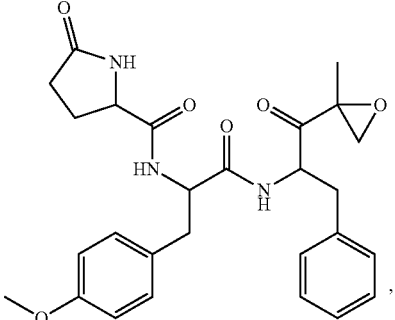
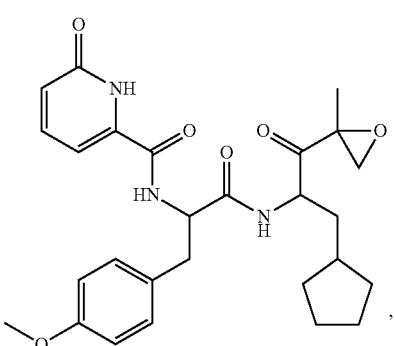
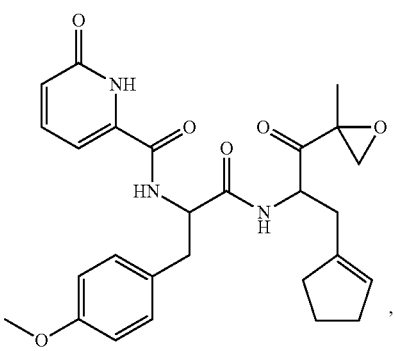
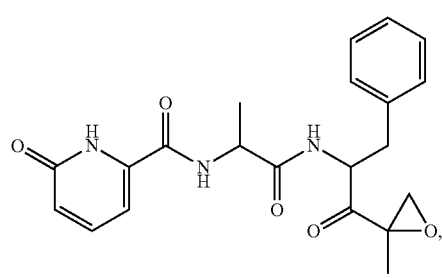

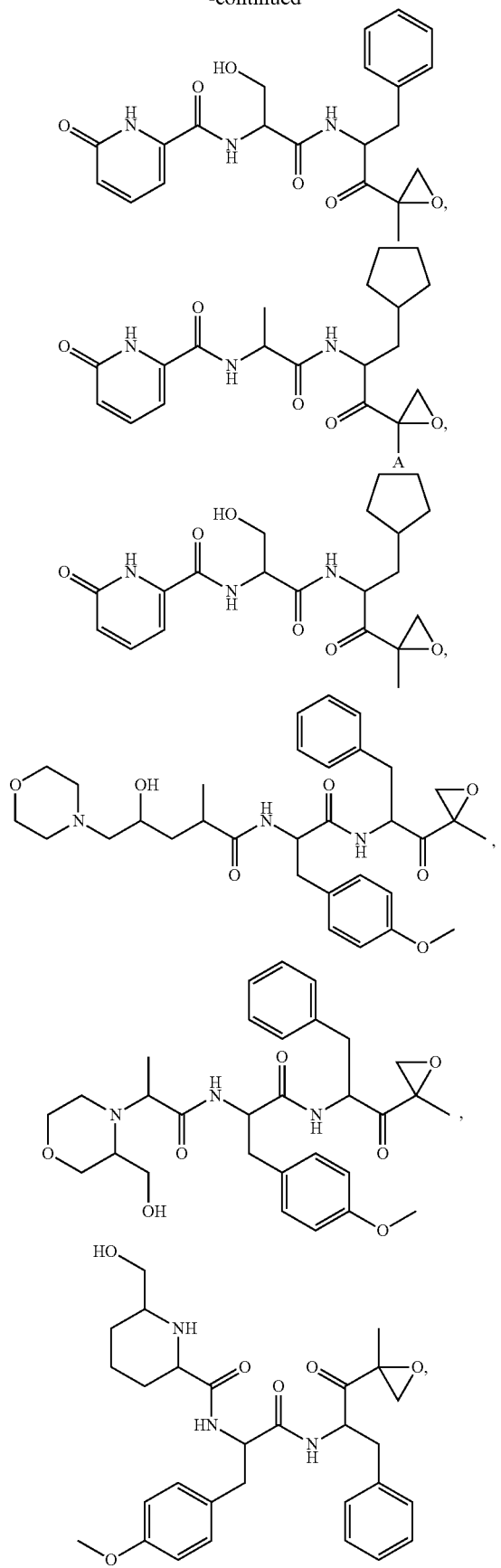
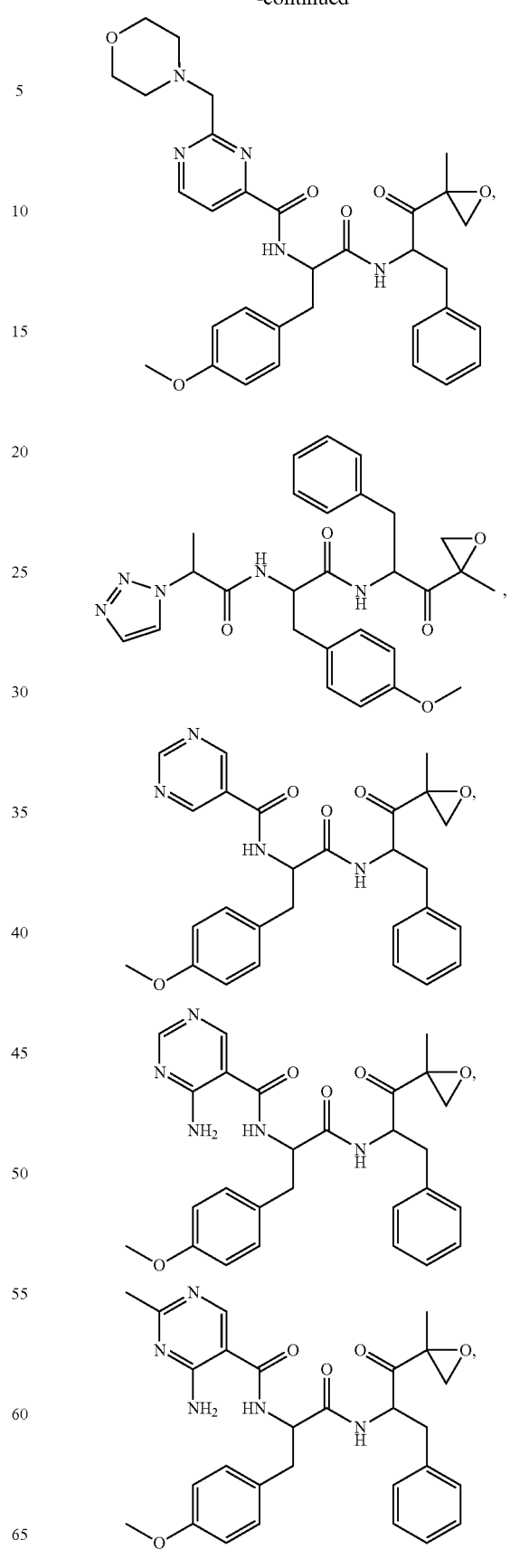

49
-continued
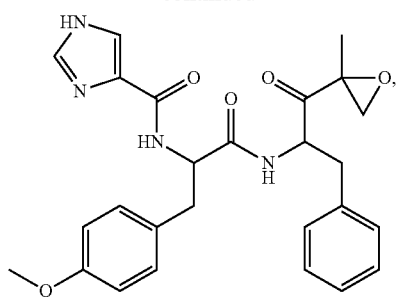
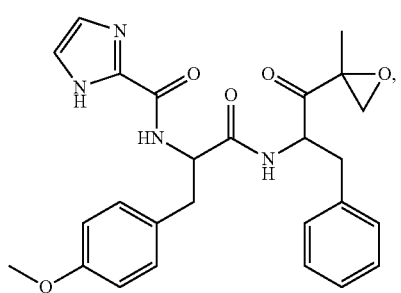
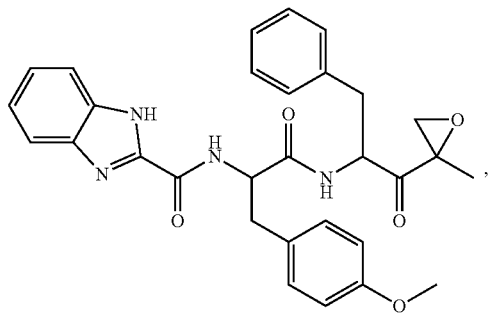
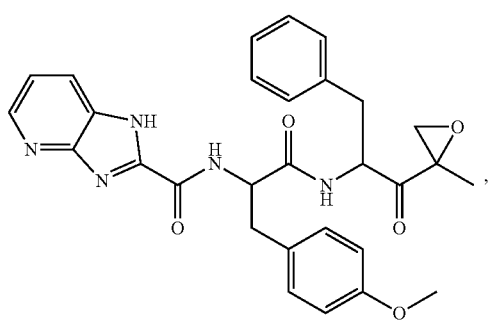
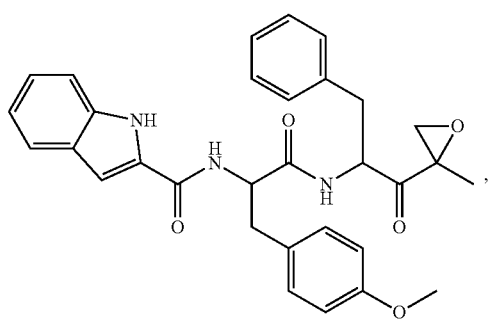
50
-continued
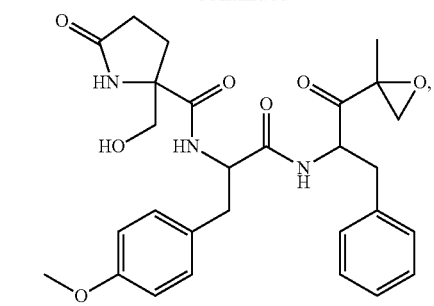
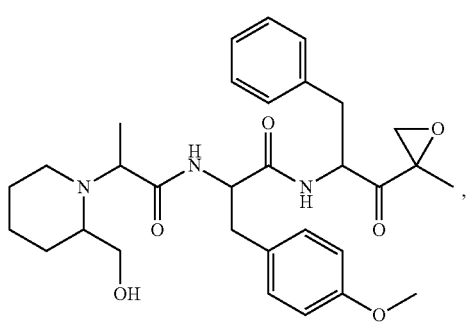
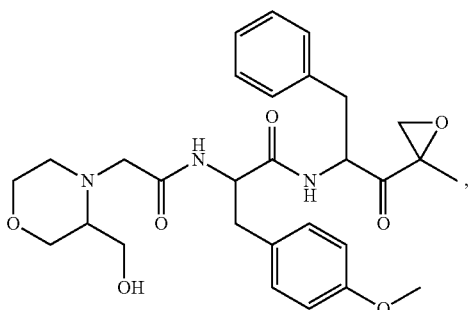
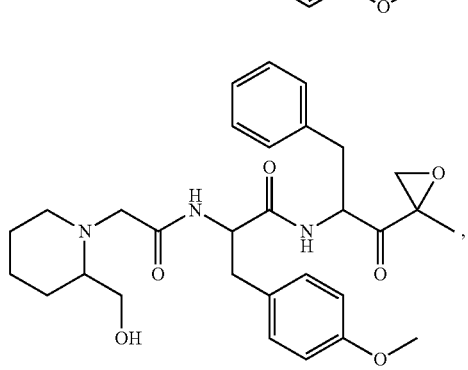
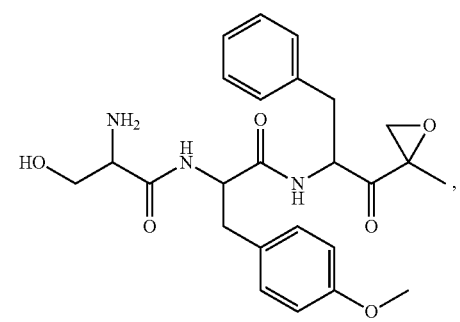

51
-continued
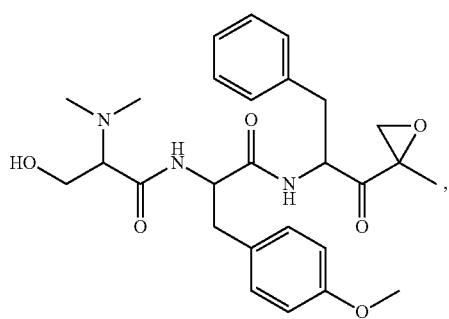
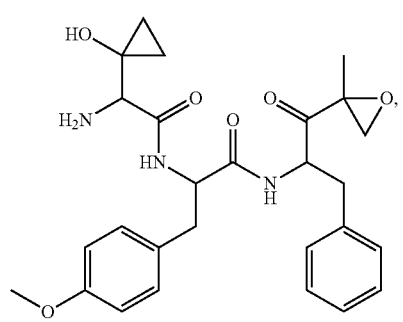
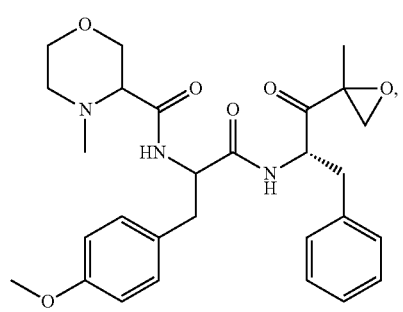
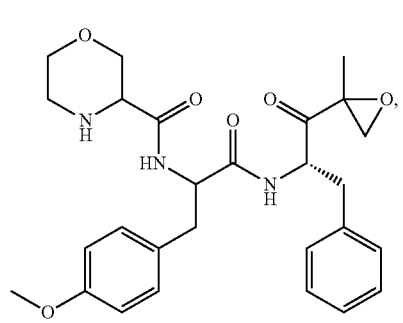
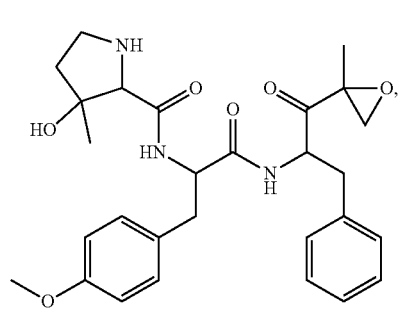
52
-continued
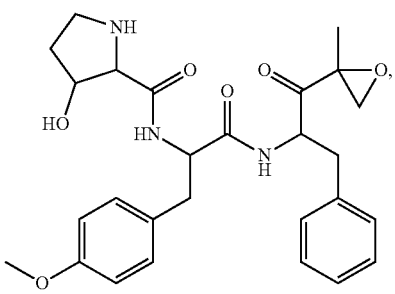
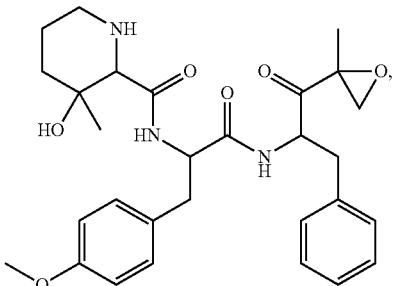
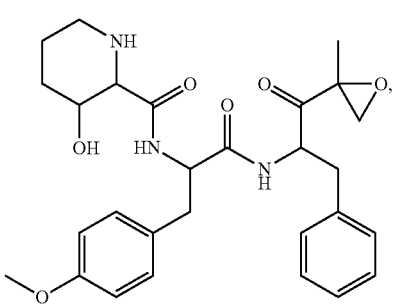
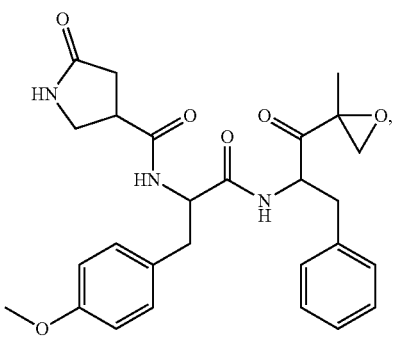
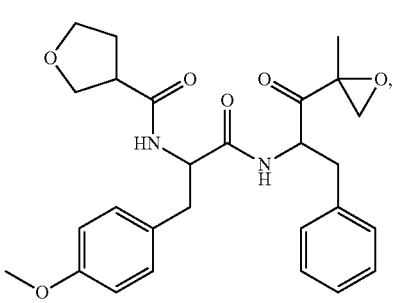

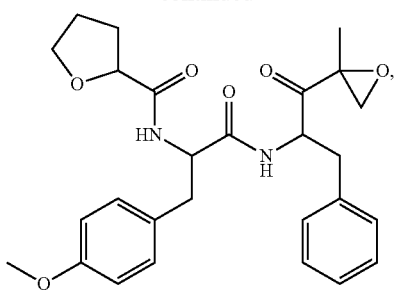
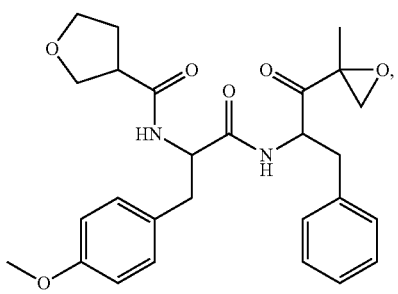
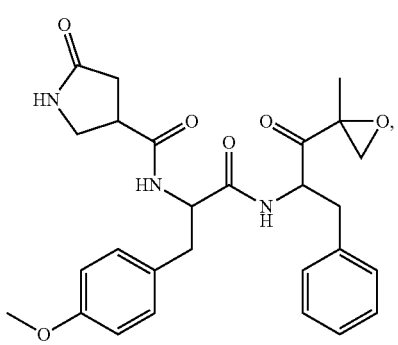
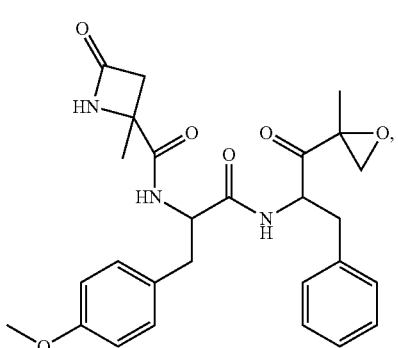
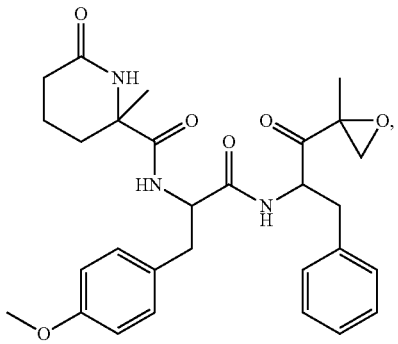
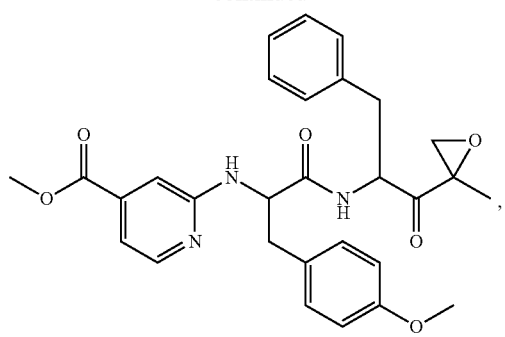
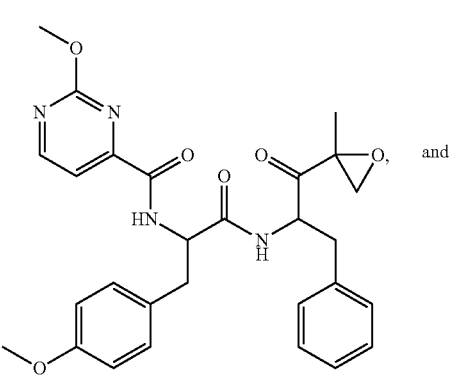
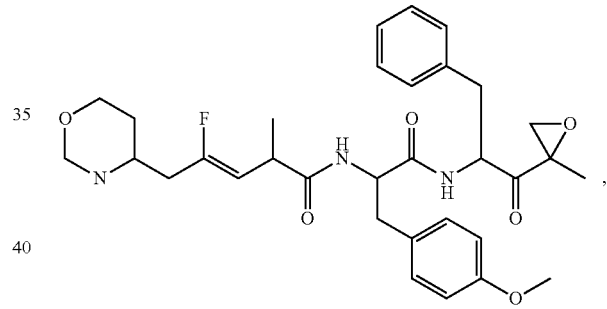
or a pharmaceutically acceptable salt form thereof.
For example, a compound of Formula (II) can be selected from the group consisting of:
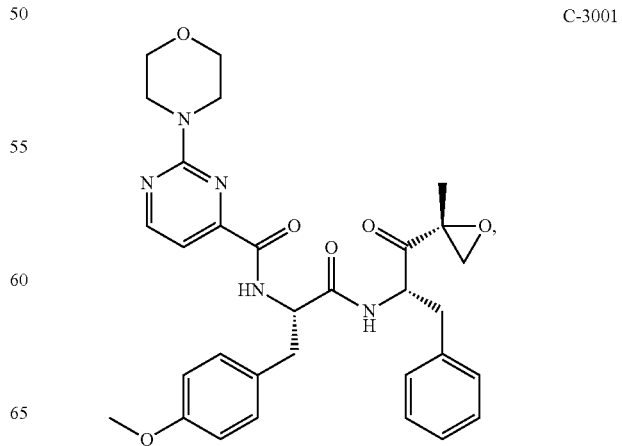
C-3001

-continued
C-3002
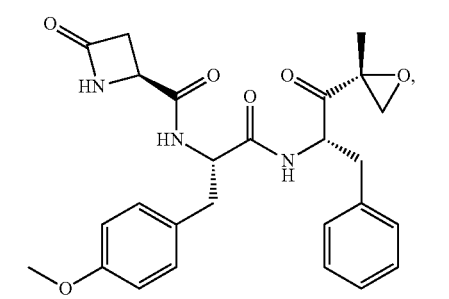
C-3003
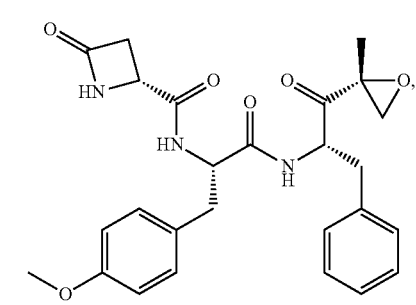
C-3004
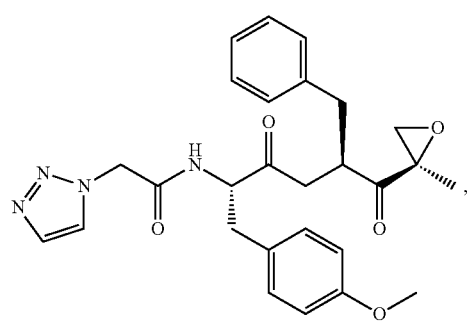
C-3005
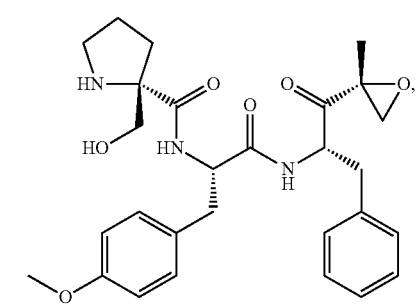
C-3006
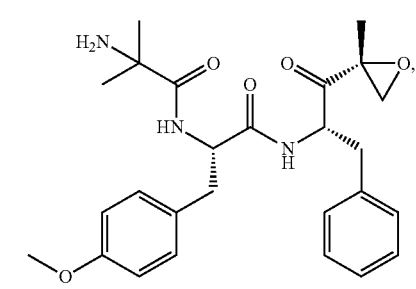
C-3007
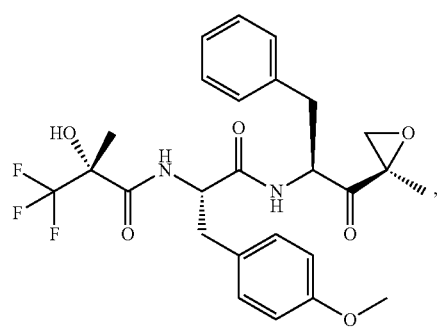
C-3008
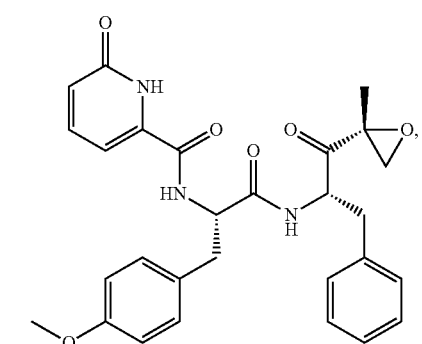
C-3009
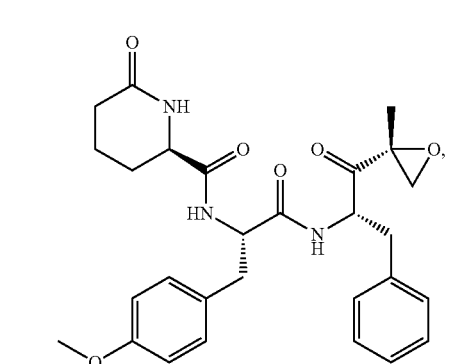
C-3010
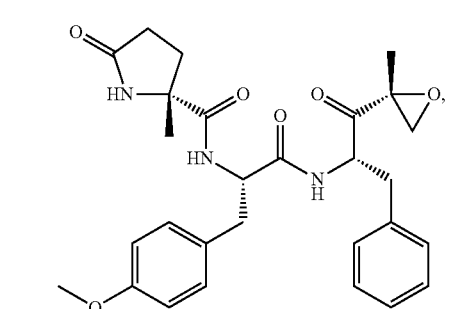
C-3011
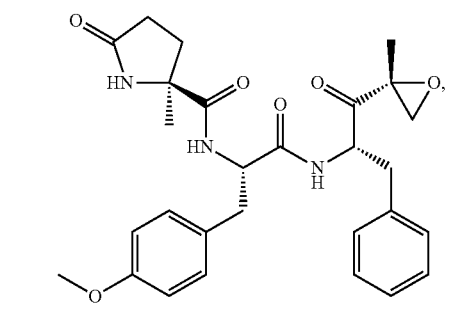

C-3012
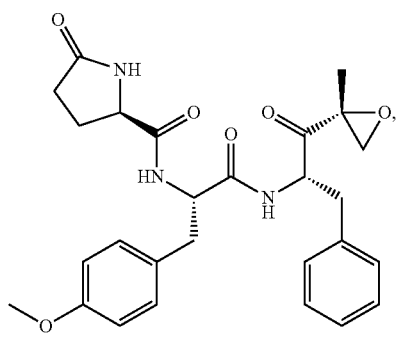
C-3013
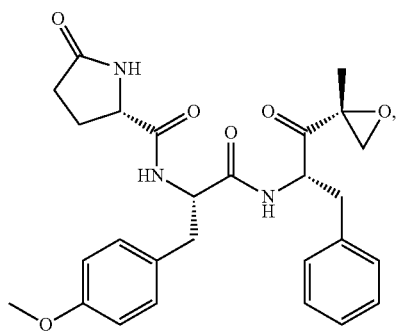
C-3014
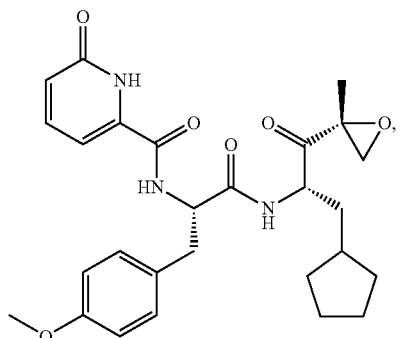
C-3015
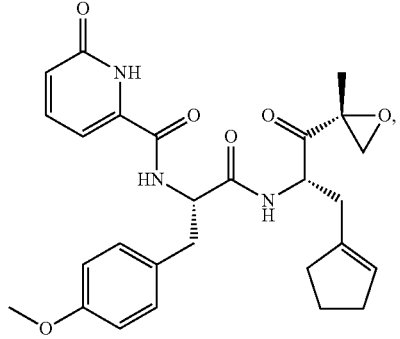
C-3016
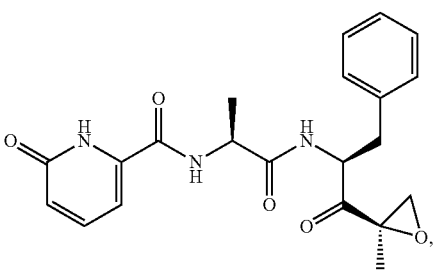
C-3017
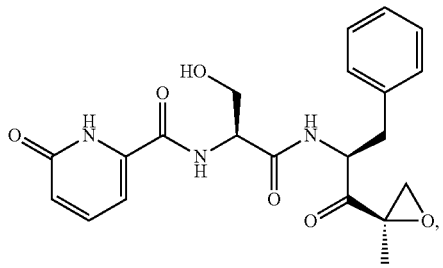
C-3018
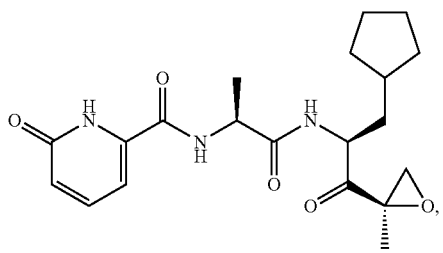
C-3019
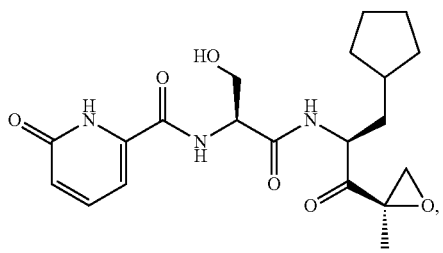
C-3020
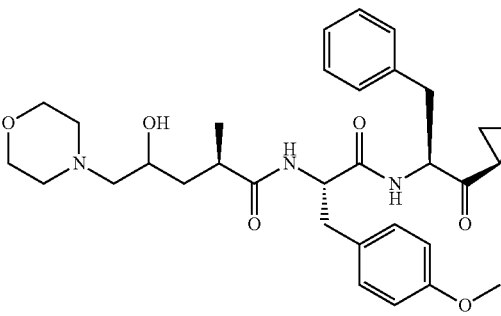
C-3021
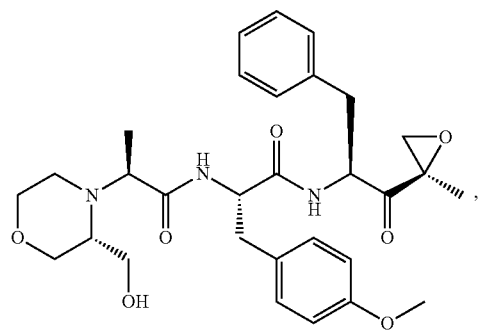

C-3022
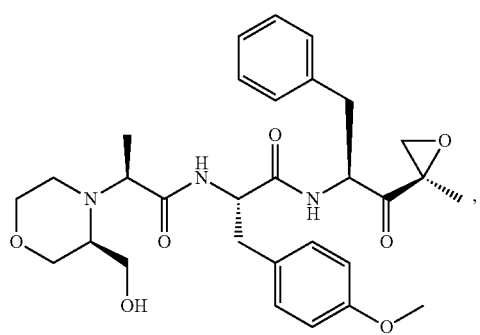
C-3023
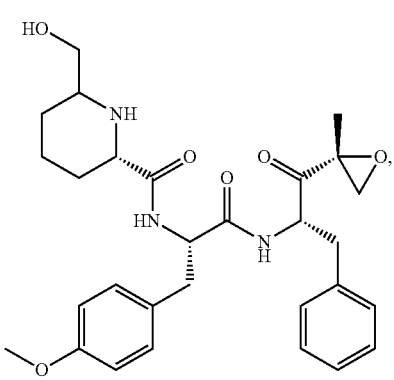
C-3024
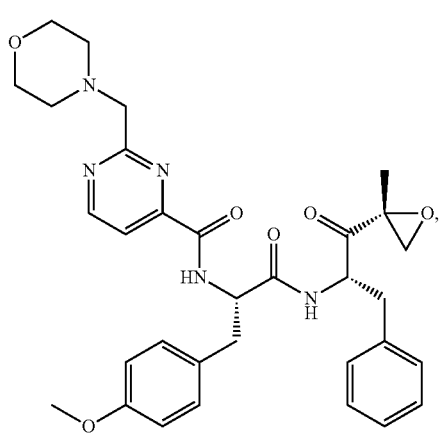
C-3025
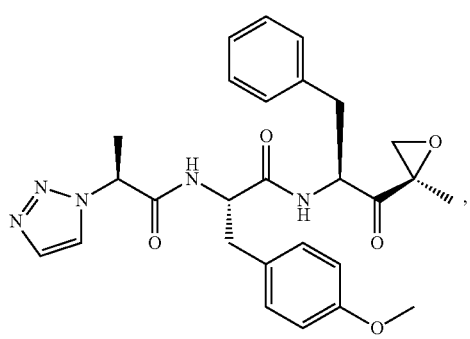
C-3026
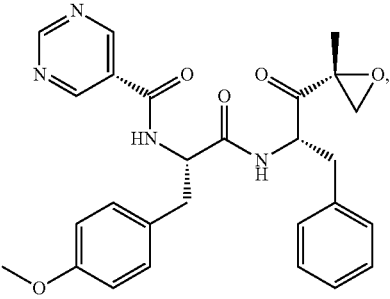
C-3027
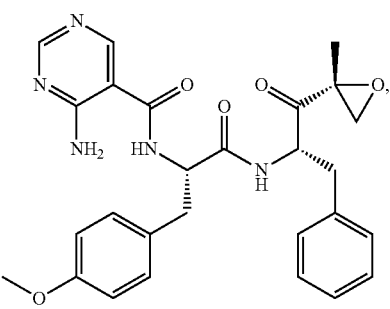
C-3028
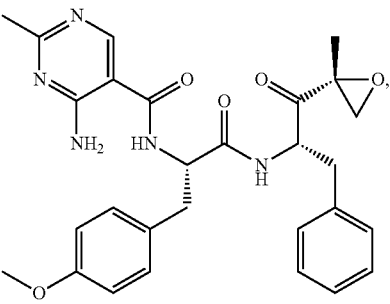
C-3029
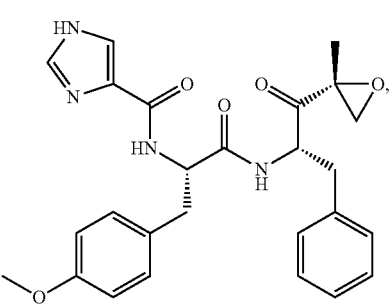
C-3030
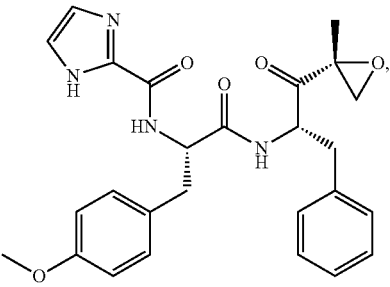

C-3031
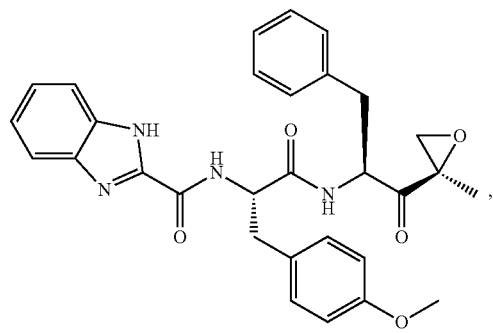
C-3032
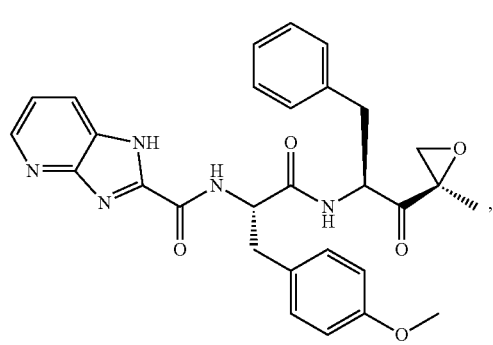
C-3033
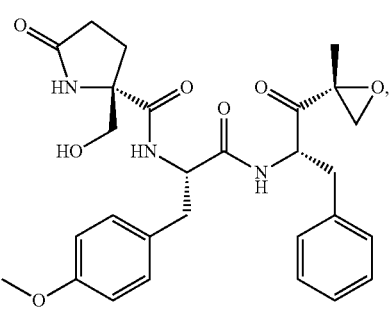
C-3034
C-3035
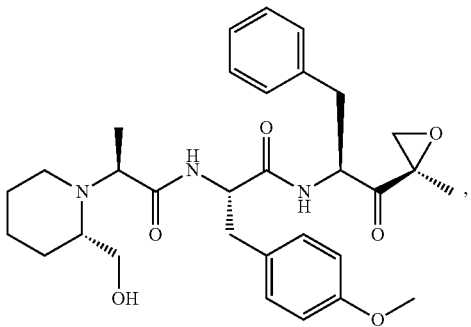
C-3036
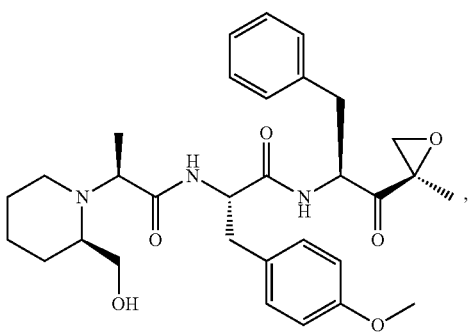
C-3037
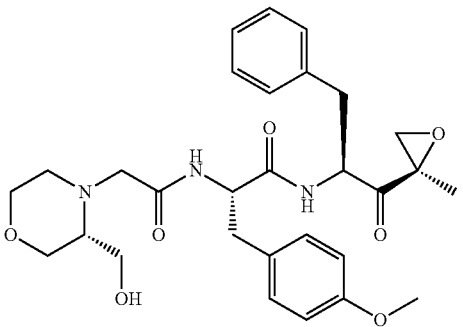
C-3038
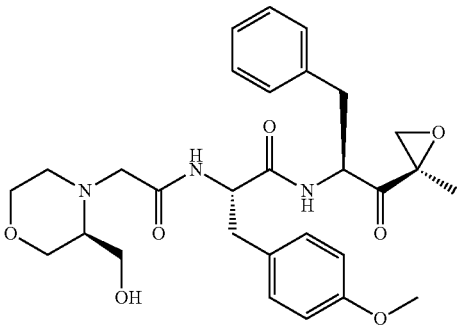

C-3039
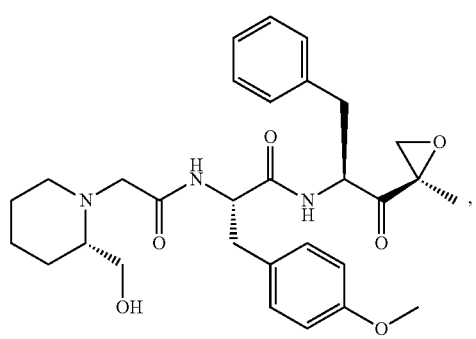
C-3040
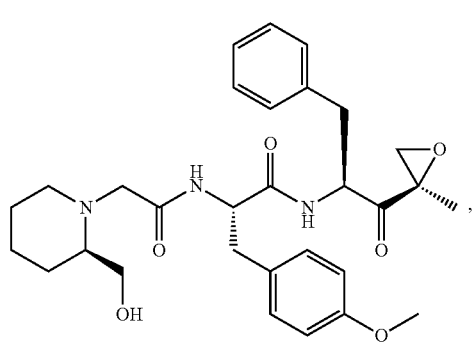
C-3041
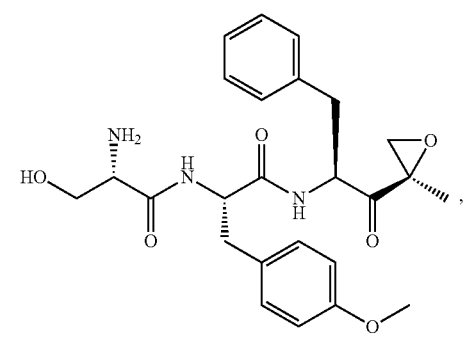
C-3042
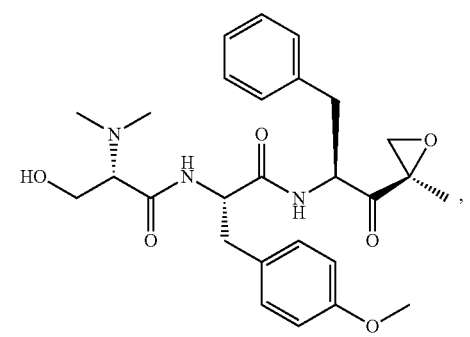
C-3043
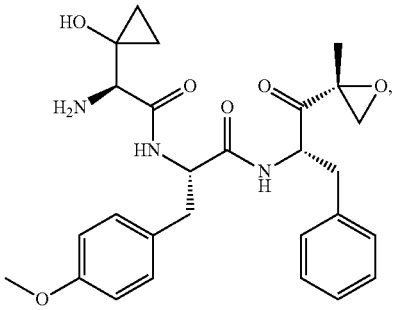
C-3044
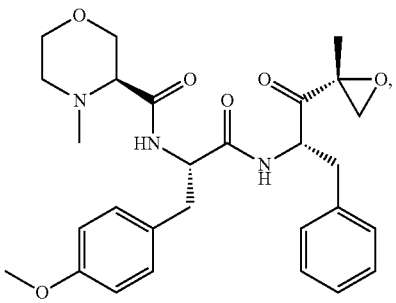
C-3045
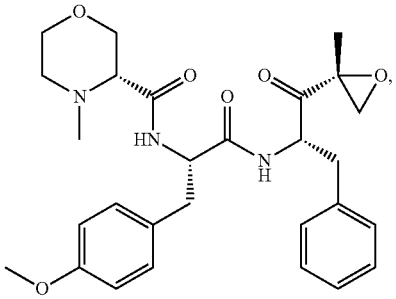
C-3046
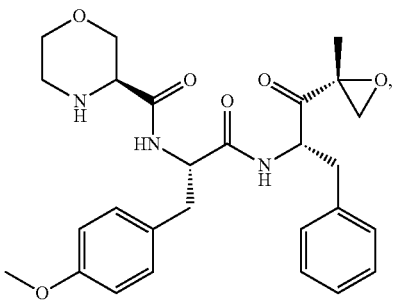
C-3047
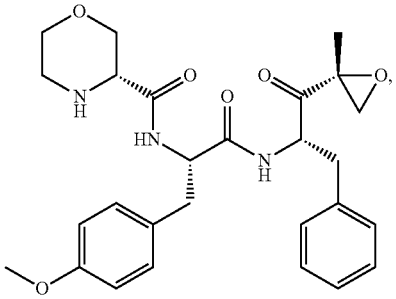

C-3048
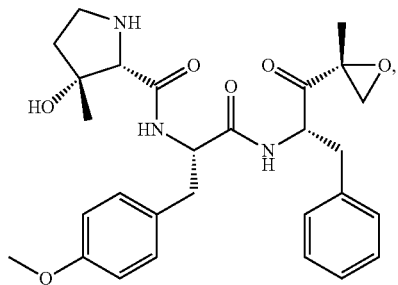
C-3049
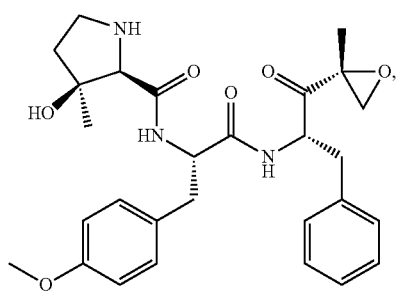
C-3050
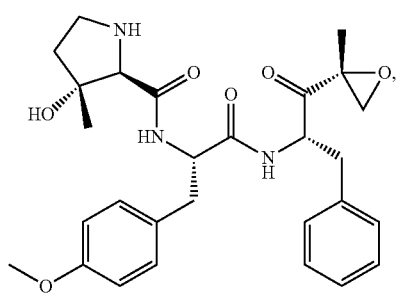
C-3051
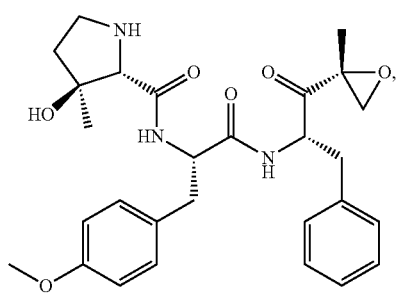
C-3052
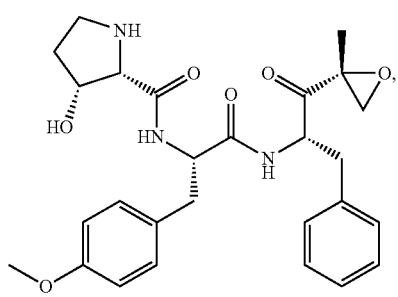
C-3053
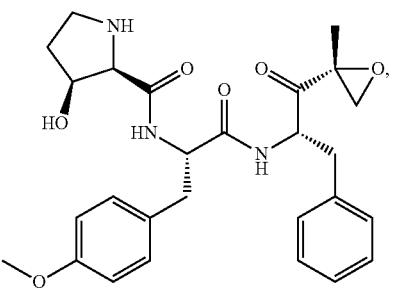
C-3054
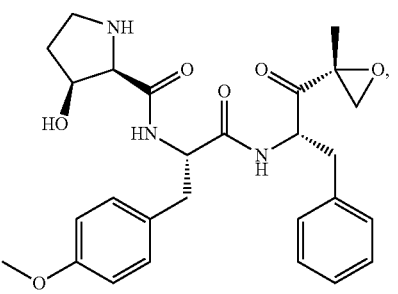
C-3055
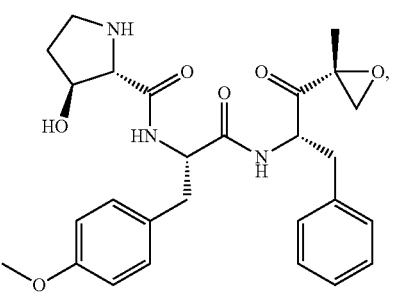
C-3056
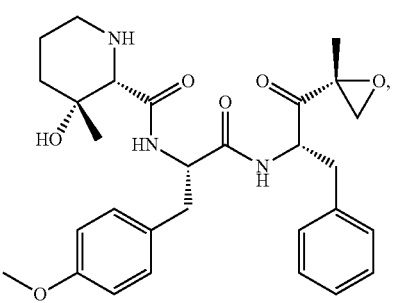
C-3057
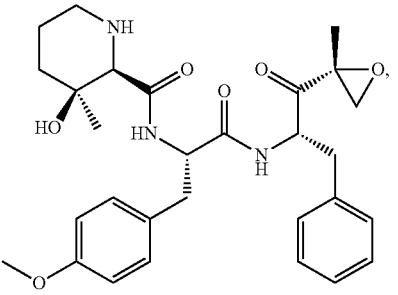

C-3058
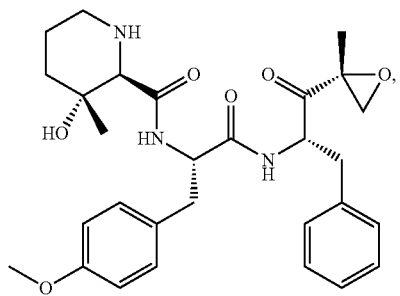
C-3059
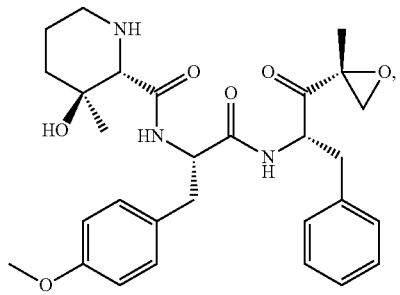
C-3060
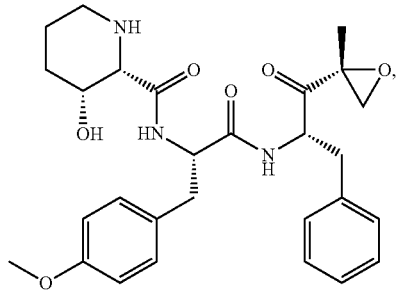
C-3061
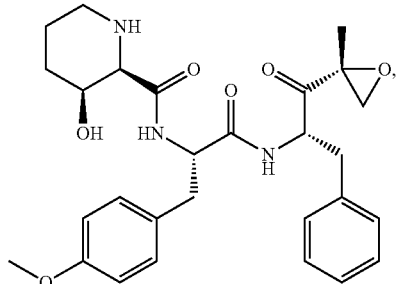
C-3062
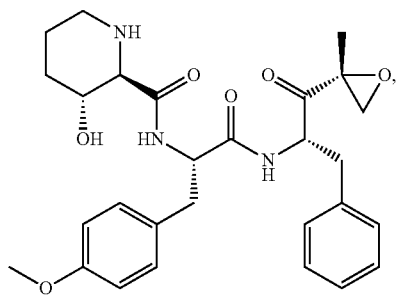
C-3063
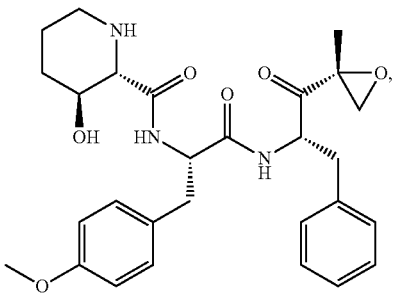
C-3064
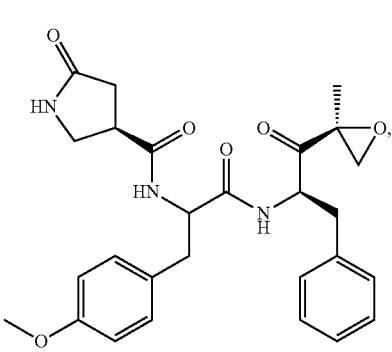
C-3065
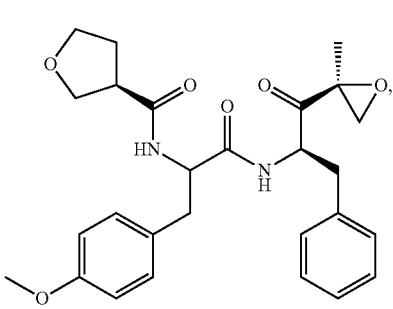
C-3066
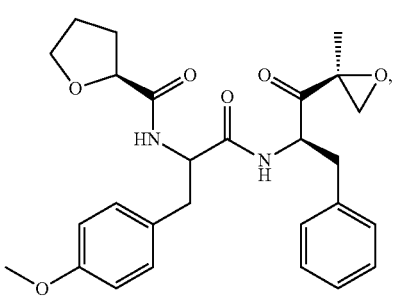
C-3067
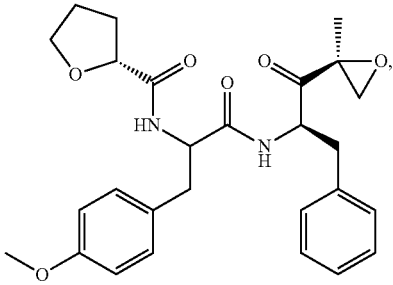

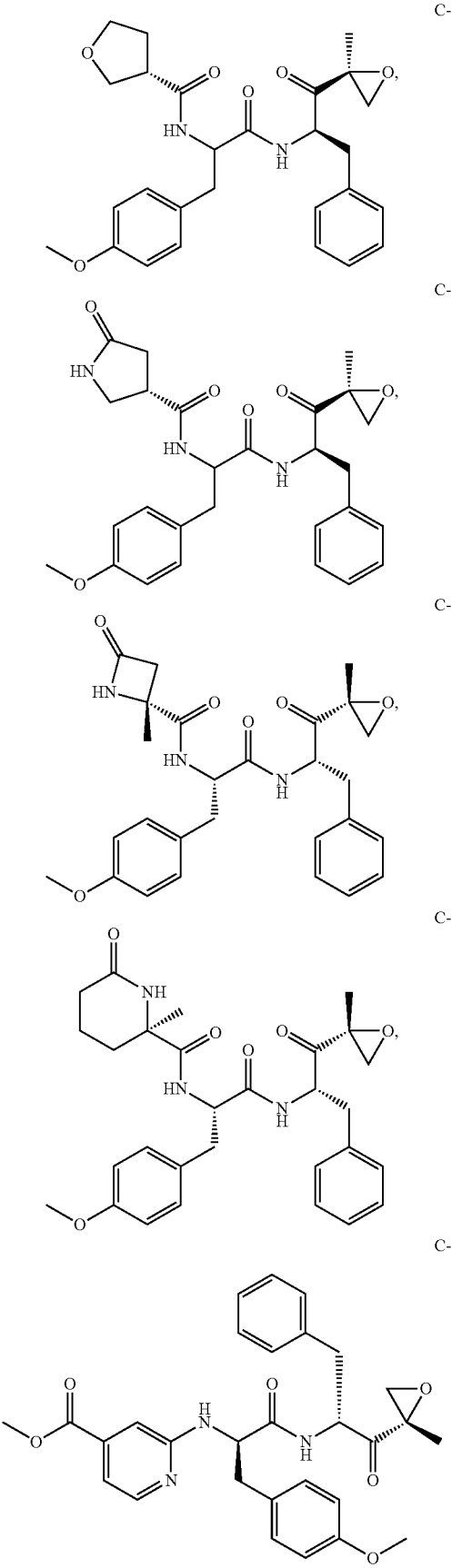

or a pharmaceutically acceptable salt form thereof.

The compounds provided herein can be synthesized using conventional techniques using readily available starting materials. In general, the compounds provided herein are conveniently obtained via standard organic chemistry synthesis methods. For example, the compounds provided herein may be prepared using the methods described herein or using the synthetic methods described in U.S. Pat. Nos. 7,232,818; 7,417,042; 7,687,456; 7,691,852; and 8,088,741, each of which is incorporated by reference in its entirety.

Methods of Use

The compounds disclosed herein can be used to inhibit the immunoproteasome (iP). In some cases, the compounds disclosed herein inhibit LMP2 of the iP. LMP2 has been implicated in regulating cell growth of various tumors, and may be implicated in prostate cancer. See Wehenkel et al., Brit. J. Cancer, 107:53-62 (2012) and Ho et al., Chem. & Biol., 14:419-430 (2007).

The biological consequences of proteasome inhibition are numerous. Proteasome inhibition has been suggested as a prevention and/or treatment of a multitude of diseases including, but not limited to, proliferative diseases, neurotoxic/degenerative diseases, Alzheimer's, ischemic conditions, inflammation, auto-immune diseases, HIV, cancers, organ graft rejection, septic shock, inhibition of antigen presentation, decreasing viral gene expression, parasitic infections, conditions associated with acidosis, macular degeneration, pulmonary conditions, muscle wasting diseases, fibrotic diseases, and bone and hair growth diseases. Therefore, pharmaceutical formulations for proteasome-specific compounds, such as the epoxy ketone class of molecules, provide a means of administering a drug to a patient and treating these conditions.

At the cellular level, the accumulation of polyubiquitinated proteins, cell morphological changes, and apoptosis have been reported upon treatment of cells with various proteasome inhibitors. Proteasome inhibition has also been suggested as a possible antitumor therapeutic strategy. The fact that epoxomicin was initially identified in a screen for antitumor compounds validates the proteasome as an antitumor chemotherapeutic target. Accordingly, these compositions are useful for treating cancer.

Both in vitro and in vivo models have shown that malignant cells, in general, are susceptible to proteasome inhibition. In fact, proteasome inhibition has already been validated as a therapeutic strategy for the treatment of multiple myeloma. This could be due, in part, to the highly proliferative malignant cell's dependency on the proteasome system to rapidly remove proteins (Rolfe et al., *J. Mol. Med.* (1997) 75:5-17; Adams, *Nature* (2004) 4: 349-360). Therefore, provided herein is a method of treating a cancer comprising administering to a patient in need of such treatment a therapeutically effective amount of a compound or composition as provided herein.

As used herein, the term "cancer" includes, but is not limited to, blood born and solid tumors. Cancer refers to disease of blood, bone, organs, skin tissue, and the vascular system, including, but not limited to, cancers of the bladder, blood, bone, brain, breast, cervix, chest, colon, endometrium, esophagus, eye, head, kidney, liver, lung, lymph nodes, mouth, neck, ovaries, pancreas, prostate, rectum, renal, skin, stomach, testis, throat, and uterus. Specific cancers include, but are not limited to, leukemia (acute lymphocytic leukemia (ALL), acute lyelogenous leukemia (AML), chronic lymphocytic leukemia (CLL), chronic myelogenous leukemia (CML), hairy cell leukemia), mature B cell neoplasms (small lymphocytic lymphoma, B cell prolymphocytic leukemia, lymphoplasmacytic lymphoma (such as Waldenstrom's macroglobulinemia), splenic marginal zone lymphoma, plasma cell myeloma, plasmacytoma, monoclonal immunoglobulin deposition diseases, heavy chain diseases, extranodal marginal zone B cell lymphoma (MALT lymphoma), nodal marginal zone B cell lymphoma (NMZL), follicular lymphoma, mantle cell lymphoma, diffuse B cell lymphoma, diffuse large B cell lymphoma (DLBCL), mediastinal (thymic) large B cell lymphoma, intravascular large B cell lymphoma, primary effusion lymphoma and Burkitt lymphoma/leukemia), mature T cell and natural killer (NK) cell neoplasms (T cell prolymphocytic leukemia, T cell large granular lymphocytic leukemia, aggressive NK cell leukemia, adult T cell leukemia/lymphoma, extranodal NK/T cell lymphoma, enteropathy-type T cell lymphoma, hepatosplenic T cell lymphoma, blastic NK cell lymphoma, mycosis fungoides (Sezary syndrome), primary cutaneous anaplastic large cell lymphoma, lymphomatoid papulosis, angioimmunoblastic T cell lymphoma, unspecified peripheral T cell lymphoma and anaplastic large cell lymphoma), Hodgkin lymphoma (nodular sclerosis, mixed celluarity, lymphocyte-rich, lymphocyte depleted or not depleted, nodular lymphocyte-predominant), myeloma (multiple myeloma, indolent myeloma, smoldering myeloma), chronic myeloproliferative disease, myelodysplastic/myeloproliferative disease, myelodysplastic syndromes, immunodeficiency-associated lymphoproliferative disorders, histiocytic and dendritic cell neoplasms, mastocytosis, chondrosarcoma, Ewing sarcoma, fibrosarcoma, malignant giant cell tumor, myeloma bone disease, osteosarcoma, breast cancer (hormone dependent, hormone independent), gynecological cancers (cervical, endometrial, fallopian tube, gestational trophoblastic disease, ovarian, peritoneal, uterine, vaginal and vulvar), basal cell carcinoma (BCC), squamous cell carcinoma (SCC), malignant melanoma, dermatofibrosarcoma protuberans, Merkel cell carcinoma, Kaposi's sarcoma, astrocytoma, pilocytic astrocytoma, dysembryoplastic neuroepithelial tumor, oligodendrogliomas, ependymoma, glioblastoma multiforme, mixed gliomas, oligoastrocytomas, medulloblastoma, retinoblastoma, neuroblastoma, germinoma, teratoma, malignant mesothelioma (peritoneal mesothelioma, pericardial mesothelioma, pleural mesothelioma), gastro-enteropancreatic or gastroenteropancreatic neuroendocrine tumor (GEP-NET), carcinoid, pancreatic endocrine tumor (PET), pancreatic adenocarcinoma, colorectal adenocarcinoma, colorectal carcinoma, aggressive neuroendocrine tumor, leiomyosarcomamucinous adenocarcinoma, Signet Ring cell adenocarcinoma, hepatocellular carcinoma, cholangiocarcinoma, hepatoblastoma, hemangioma, hepatic adenoma, focal nodular hyperplasia (nodular regenerative hyperplasia, hamartoma), non-small cell lung carcinoma (NSCLC) (squamous cell lung carcinoma, adenocarcinoma, large cell lung carcinoma), small cell lung carcinoma, lung cancer, thyroid carcinoma, prostate cancer (hormone refractory, androgen independent, androgen dependent, hormone-insensitive), and soft tissue sarcomas (fibrosarcoma, malignant fibrous hystiocytoma, dermatofibrosarcoma, liposarcoma, rhabdomyosarcoma leiomyosarcoma, hemangiosarcoma, synovial sarcoma, malignant peripheral nerve sheath tumor/neurofibrosarcoma, extraskeletal osteosarcoma).

In some embodiments, a compound provided herein, or a pharmaceutical composition comprising the same, can be administered to treat multiple myeloma in a patient. For example, multiple myeloma can include relapsed and/or refractory multiple myeloma.

Many tumors of the hematopoietic and lymphoid tissues are characterized by an increase in cell proliferation, or a particular type of cell. The chronic myeloproliferative diseases (CMPDs) are clonal hematopoietic stem cell disorders characterized by proliferation in the bone marrow of one or more of the myeloid lineages, resulting in increased numbers of granulocytes, red blood cells and/or platelets in the peripheral blood. As such, use of a compound provided herein for the treatment of such diseases is attractive and being examined (Cilloni et al., *Haematologica* (2007) 92: 1124-1229). CMPD can include chronic myelogenous leukemia, chronic neutrophilic leukemia, chronic eosinophilic leukemia, polycythaemia vera, chronic idiopathic myelofibrosis, essential thrombocythaemia and unclassifiable chronic myeloproliferative disease. Provided herein is a method of treating CMPD comprising administering to a patient in need of such treatment a therapeutically effective amount of a compound provided herein.

Myelodisplastic/myeloproliferative diseases, such as chronic myelomonocytic leukemia, atypical chronic myeloid leukemia, juvenile myelomonocytic leukemia and unclassifiable myelodysplastic/myeloproliferative disease, are characterized by hypercellularity of the bone marrow due to proliferation in one or more of the myeloid lineages Inhibiting the proteasome with a composition described herein, can serve to treat these myelodisplatic/myeloproliferative diseases by providing a patient in need of such treatment a therapeutically effective amount of the composition.

Myelodysplastic syndromes (MDS) refer to a group of hematopoietic stem cell disorders characterized by dysplasia and ineffective hematopoiesis in one or more of the major myeloid cell lines. Targeting NF-kB with a proteasome inhibitor in these hematologic malignancies induces apoptosis, thereby killing the malignant cell (Braun et al. *Cell Death and Differentiation* (2006) 13:748-758). Further provided herein is a method to treat MDS comprising administering to a patient in need of such treatment a therapeutically effective amount of a compound provided herein. MDS includes refractory anemia, refractory anemia with ringed sideroblasts, refractory cytopenia with multilineage dysplasia, refractory anemia with excess blasts, unclassifiable myelodysplastic syndrome and myelodysplastic syndrome associated with isolated del (5q) chromosome abnormality.

Mastocytosis is a proliferation of mast cells and their subsequent accumulation in one or more organ systems. Mastocytosis includes, but is not limited to, cutaneous mastocytosis, indolent systemic mastocytosis (ISM), systemic mastocytosis with associated clonal hematological non-mast-cell-lineage disease (SM-AHNMD), aggressive systemic mastocytosis (ASM), mast cell leukemia (MCL), mast cell sarcoma (MCS) and extracutaneous mastocytoma. Further provided herein is a method to treat mastocytosis comprising administering an effect amount of the compound disclosed herein to a patient diagnosed with mastocytosis.

The proteasome regulates NF-κB, which in turn regulates genes involved in the immune and inflammatory response. For example, NF-κB is required for the expression of the immunoglobulin light chain κ gene, the IL-2 receptor α-chain gene, the class I major histocompatibility complex gene, and a number of cytokine genes encoding, for example, IL-2, IL-6, granulocyte colony-stimulating factor, and IFN-β (Palombella et al., Cell (1994) 78:773-785). Thus, provided herein are methods of affecting the level of expression of IL-2, MHC-I, IL-6, TNFα, IFN-β or any of the other previously-mentioned proteins, each method comprising administering to a patient a therapeutically effective amount of a compound or composition disclosed herein.

Also provided herein is a method of treating an autoimmune disease in a patient comprising administering a therapeutically effective amount of the compound described herein. An "autoimmune disease" as used herein is a disease or disorder arising from and directed against an individual's own tissues. Examples of autoimmune diseases include, but are not limited to, inflammatory responses such as inflammatory skin diseases including psoriasis and dermatitis (e.g., atopic dermatitis); systemic scleroderma and sclerosis; responses associated with inflammatory bowel disease (such as Crohn's disease and ulcerative colitis); respiratory distress syndrome (including adult respiratory distress syndrome (ARDS)); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); diabetes mellitus (e.g., Type I diabetes mellitus or insulin dependent diabetes mellitus); multiple sclerosis; Reynaud's syndrome; autoimmune thyroiditis; allergic encephalomyelitis; Sjorgen's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Beheet disease; giant cell arteritis; immune complex nephritis; IgA nephropathy; IgM polyneuropathies; immune thrombocytopenic purpura (ITP) or autoimmune thrombocytopenia.

The immune system screens for autologous cells that are virally infected, have undergone oncogenic transformation or present unfamiliar peptides on their surface. Intracellular proteolysis generate small peptides for presentation to T-lymphocytes to induce MHC class I-mediated immune responses. Thus, provided herein is a method of using a compound or composition provided herein as an immunomodulatory agent for inhibiting or altering antigen presentation in a cell, comprising exposing the cell (or administering to a patient) to the compound described herein. Specific embodiments include a method of treating graft or transplant-related diseases, such as graft-versus-host disease or host versus-graft disease in a patient, comprising administering a therapeutically effective amount of the compound described herein. The term "graft" as used herein refers to biological material derived from a donor for transplantation into a recipient. Grafts include such diverse material as, for example, isolated cells such as islet cells; tissue such as the amniotic membrane of a newborn; bone marrow; hematopoietic precursor cells; ocular tissue, such as corneal tissue; and organs such as skin, heart, liver, spleen, pancreas, thyroid lobe, lung, kidney, and tubular organs (e.g., intestine, blood vessels, or esophagus). The tubular organs can be used to replace damaged portions of esophagus, blood vessels, or bile duct. The skin grafts can be used not only for burns, but also as a dressing to damaged intestine or to close certain defects such as diaphragmatic hernia. The graft is derived from any mammalian source, including human, whether from cadavers or living donors. In some cases, the donor and recipient is the same patient. In some embodiments, the graft is bone marrow or an organ such as heart and the donor of the graft and the host are matched for HLA class II antigens.

Histiocytic and dendritic cell neoplasms are derived from phagocytes and accessory cells, which have major roles in the processing and presentation of antigens to lymphocytes. Depleting the proteasome content in dendritic cells has been shown to alter their antigen-induced responses (Chapatte et al. Cancer Res. (2006) 66:5461-5468). In some embodiments, a composition provided herein can be administered to a patient with histiocytic or dendritic cell neoplasm. Histiocytic and dendritic cell neoplasms include histiocytic sarcoma, Langerhans cell histiocytosis, Langerhans cell sarcoma, interdigitating dendritic cell sarcoma/tumor, follicular dendritic cell sarcoma/tumor, and non-specified dendritic cell sarcoma.

Inhibition of the proteasome has been shown to be beneficial to treat diseases whereby a cell type is proliferating and immune disorders; thus, in some embodiments, the treatment of lymphoproliferative diseases (LPD) associated with primary immune disorders (PID) is provided comprising administering a therapeutically effective amount of the disclosed compound to a patient in need thereof. The most common clinical settings of immunodeficiency associated with an increased incidence of lymphoproliferative disorders, including B-cell and T-cell neoplasms and lymphomas, are primary immunodeficiency syndromes and other primary immune disorders, infection with the human immunodeficiency virus (HIV), iatrogenic immunosuppression in patients who have received solid organ or bone marrow allografts, and iatrogenis immunosuppression associated with methotrexate treatment. Other PIDs commonly associated with LPDs, but not limited to, are ataxia telangiectasia (AT), Wiskott-Aldrich syndrome (WAS), common variable immunodeficiency (CVID), severe combined immunodeficiency (SCID), X-linked lymphoproliferative disorder (XLP), Nijmegen breakage syndrome (NBS), hyper-IgM syndrome, and autoimmune lymphoproliferative syndrome (ALPS).

Proteasome inhibition has also been associated with inhibition of NF-κB activation and stabilization of p53 levels. Thus, compositions provided herein may also be used to inhibit NF-κB activation, and stabilize p53 levels in cell culture. Since NF-κB is a key regulator of inflammation, it is an attractive target for anti-inflammatory therapeutic intervention. Thus, compositions provided herein may be useful for the treatment of conditions associated with inflammation, including, but not limited to COPD, psoriasis, asthma, bronchitis, emphysema, and cystic fibrosis.

The disclosed compositions can be used to treat conditions mediated directly by the proteolytic function of the proteasome such as muscle wasting, or mediated indirectly via proteins which are processed by the proteasome such as NF-κB. The proteasome participates in the rapid elimination and post-translational processing of proteins (e.g., enzymes) involved in cellular regulation (e.g., cell cycle, gene transcription, and metabolic pathways), intercellular communication, and the immune response (e.g., antigen presentation). Specific examples discussed below include β-amyloid protein and regulatory proteins such as cyclins and transcription factor NF-κB.

In some embodiments, a composition provided herein is useful for the treatment of neurodegenerative diseases and conditions, including, but not limited to, stroke, ischemic damage to the nervous system, neural trauma (e.g., percussive brain damage, spinal cord injury, and traumatic damage to the nervous system), multiple sclerosis, and other immune-mediated neuropathies (e.g., Guillain-Barre syndrome and its variants, acute motor axonal neuropathy, acute inflammatory demyelinating polyneuropathy, and Fisher Syndrome), HIV/AIDS dementia complex, axonomy, diabetic neuropathy, Parkinson's disease, Huntington's disease, bacterial, parasitic, fungal, and viral meningitis, encephalitis, vascular dementia, multi-infarct dementia, Lewy body dementia, frontal lobe dementia such as Pick's disease, subcortical dementias (such as Huntington or progressive supranuclear palsy), focal cortical atrophy syndromes (such as primary aphasia), metabolic-toxic dementias (such as chronic hypothyroidism or B12 deficiency), and dementias caused by infections (such as syphilis or chronic meningitis).

Alzheimer's disease is characterized by extracellular deposits of β-amyloid protein (β-AP) in senile plaques and cerebral vessels. β-AP is a peptide fragment of 39 to 42 amino acids derived from an amyloid protein precursor (APP). At least three isoforms of APP are known (695, 751, and 770 amino acids). Alternative splicing of mRNA generates the isoforms; normal processing affects a portion of the β-AP sequence, thereby preventing the generation of β-AP. It is believed that abnormal protein processing by the proteasome contributes to the abundance of β-AP in the Alzheimer brain. The APP-processing enzyme in rats contains about ten different subunits (22 kDa-32 kDa). The 25 kDa subunit has an N-terminal sequence of X-Gln-Asn-Pro-Met-X-Thr-Gly-Thr-Ser, which is identical to the β-subunit of human macropain (Kojima, S. et al., Fed. Eur. Biochem. Soc., (1992) 304:57-60). The APP-processing enzyme cleaves at the Gln15-Lys16 bond; in the presence of calcium ion, the enzyme also cleaves at the Met-1-Asp1 bond, and the Asp1-Ala2 bonds to release the extracellular domain of β-AP.

One embodiment, therefore, is a method of treating Alzheimer's disease, including administering to a patient a therapeutically effective amount of a composition provided herein. Such treatment includes reducing the rate of β-AP processing, reducing the rate of β-AP plaque formation, reducing the rate of β-AP generation, and reducing the clinical signs of Alzheimer's disease.

Also provided herein are methods of treating cachexia and muscle-wasting diseases. The proteasome degrades many proteins in maturing reticulocytes and growing fibroblasts. In cells deprived of insulin or serum, the rate of proteolysis nearly doubles. Inhibiting the proteasome reduces proteolysis, thereby reducing both muscle protein loss and the nitrogenous load on kidneys or liver. Peptide proteasome inhibitors (e.g., a compound or composition provided herein) are useful for treating conditions such as cancer, chronic infectious diseases, fever, muscle disuse (atrophy) and denervation, nerve injury, fasting, renal failure associated with acidosis, kidney disease, and hepatic failure. See, e.g., Goldberg, U.S. Pat. No. 5,340,736. Methods of treatment include: reducing the rate of muscle protein degradation in a cell; reducing the rate of intracellular protein degradation; reducing the rate of degradation of p53 protein in a cell; and inhibiting the growth of p53-related cancers. Each of these methods includes contacting a cell (in vivo or in vitro, e.g., a muscle in a patient) with an effective amount of a pharmaceutical composition disclosed herein to reduce the rate of muscle protein degradation in the cell; reduce the rate of intracellular protein degradation in the cell; and/or reduce the rate of degradation of p53 protein in the cell. In some embodiments, the methods include administering to a patient a therapeutically effective amount of a pharmaceutical composition disclosed herein.

Fibrosis is the excessive and persistent formation of scar tissue resulting from the hyperproliferative growth of fibroblasts and is associated with activation of the TGF-β signaling pathway. Fibrosis involves extensive deposition of extracellular matrix and can occur within virtually any tissue or across several different tissues. Normally, the level of intracellular signaling protein (Smad) that activates transcription of target genes upon TGF-β stimulation is regulated by proteasome activity. However, accelerated degradation of the TGF-β signaling components has been observed in cancers and other hyperproliferative conditions. Thus, in certain embodiments, a method for treating hyperproliferative conditions such as diabetic retinopathy, macular degeneration, diabetic nephropathy, glomerulosclerosis, IgA nephropathy, cirrhosis, biliary atresia, congestive heart failure, scleroderma, radiation-induced fibrosis, and lung fibrosis (idiopathic pulmonary fibrosis, collagen vascular disease, sarcoidosis, interstitial lung diseases, and extrinsic lung disorders) is provided. The treatment of burn victims is often hampered by fibrosis, thus, in some embodiments a compound provided herein may be administered by topical or systemic administration to treat burns. Wound closure following surgery is often associated with disfiguring scars, which may be prevented by inhibition of fibrosis. Thus, in certain embodiments, a method for the prevention or reduction of scarring is provided herein.

Another protein processed by the proteasome is NF-κB, a member of the Rel protein family. The Rel family of transcriptional activator proteins can be divided into two groups. The first group requires proteolytic processing, and includes p50 (NF-κB1, 105 kDa) and p52 (NF-κ2, 100 kDa). The second group does not require proteolytic processing, and includes p65 (RelA, Rel (c-Rel), and RelB). Both homo- and heterodimers can be formed by Rel family members;

NF-κB, for example, is a p50-p65 heterodimer. After phosphorylation and ubiquitination of IκB and p105, the two proteins are degraded and processed, respectively, to produce active NF-κB which translocates from the cytoplasm to the nucleus. Ubiquitinated p105 is also processed by purified proteasomes (Palombella et al., Cell (1994) 78:773-785). Active NF-κB forms a stereospecific enhancer complex with other transcriptional activators and, e.g., HMG I(Y), inducing selective expression of a particular gene.

NF-κB regulates genes involved in the immune and inflammatory response, and mitotic events. For example, NF-κB is required for the expression of the immunoglobulin light chain κ gene, the IL-2 receptor α-chain gene, the class I major histocompatibility complex gene, and a number of cytokine genes encoding, for example, IL-2, IL-6, granulocyte colony-stimulating factor, and IFN-β (Palombella et al., Cell (1994) 78:773-785). Some embodiments include methods of affecting the level of expression of IL-2, MHC-I, IL-6, TNFα, IFN-β, or any of the other previously-mentioned proteins, each method including administering to a patient a therapeutically effective amount of a composition disclosed herein. Complexes including p50 are rapid mediators of acute inflammatory and immune responses (Thanos, D. and Maniatis, T., Cell (1995) 80:529-532).

NF-κB also participates in the expression of the cell adhesion genes that encode E-selectin, P-selectin, ICAM, and VCAM-1 (Collins, T., Lab. Invest. (1993) 68:499-508). In some embodiments, a method for inhibiting cell adhesion (e.g., cell adhesion mediated by E-selectin, P-selectin, ICAM, or VCAM-1) is provided, including contacting a cell with an effective amount of a pharmaceutical composition disclosed herein. In some embodiments, a method for inhibiting cell adhesion (e.g., cell adhesion mediated by E-selectin, P-selectin, ICAM, or VCAM-1) is provided, including administering to a patient a therapeutically effective amount of a pharmaceutical composition disclosed herein.

Ischemia and reperfusion injury results in hypoxia, a condition in which there is a deficiency of oxygen reaching the tissues of the body. This condition causes increased degradation of Iκ-Bα, thereby resulting in the activation of NF-κB. It has been demonstrated that the severity of injury resulting in hypoxia can be reduced with the administration of a proteasome inhibitor. Thus, provided herein is a method of treating an ischemic condition or reperfusion injury comprising administering to a patient in need of such treatment a therapeutically effective amount of a compound provided herein. Examples of such conditions or injuries include, but are not limited to, acute coronary syndrome (vulnerable plaques), arterial occlusive disease (cardiac, cerebral, peripheral arterial, and vascular occlusions), atherosclerosis (coronary sclerosis, coronary artery disease), infarctions, heart failure, pancreatitis, myocardial hypertrophy, stenosis, and restenosis.

NF-κB also binds specifically to the HIV-enhancer/promoter. When compared to the Nef of mac239, the HIV regulatory protein Nef of pbj14 differs by two amino acids in the region which controls protein kinase binding. It is believed that the protein kinase signals the phosphorylation of IκB, triggering IκB degradation through the ubiquitin-proteasome pathway. After degradation, NF-κB is released into the nucleus, thus enhancing the transcription of HIV (Cohen, J., Science, (1995) 267:960). Provided herein is a method for inhibiting or reducing HIV infection in a patient, and a method for decreasing the level of viral gene expression, each method including administering to the patient a therapeutically effective amount of a composition disclosed herein.

Viral infections contribute to the pathology of many diseases. Heart conditions such as ongoing myocarditis and dilated cardiomyopathy have been linked to the coxsackievirus B3. In a comparative whole-genome microarray analyses of infected mouse hearts, specific proteasome subunits were uniformly up-regulated in hearts of mice which developed chronic myocarditis (Szalay et al, Am J Pathol 168:1542-52, 2006). Some viruses utilize the ubiquitin-proteasome system in the viral entry step where the virus is released from the endosome into the cytosol. The mouse hepatitis virus (MHV) belongs to the Coronaviridae family, which also includes the severe acute respiratory syndrome (SARS) coronvirus. Yu and Lai (J Virol 79:644-648, 2005) demonstrated that treatment of cells infected with MHV with a proteasome inhibitor resulted in a decrease in viral replication, correlating with reduced viral titer as compared to that of untreated cells. The human hepatitis B virus (HBV), a member of the Hepadnaviridae virus family, likewise requires virally encoded envelop proteins to propagate Inhibiting the proteasome degradation pathway causes a significant reduction in the amount of secreted envelope proteins (Simsek et al, J Virol 79:12914-12920, 2005). In addition to HBV, other hepatitis viruses (A, C, D and E) may also utilize the ubiquitin-proteasome degradation pathway for secretion, morphogenesis and pathogenesis. Accordingly, in certain embodiments, a method for treating viral infection, such as SARS or hepatitis A, B, C, D and E, is provided comprising contacting a cell with an effective amount of the compound disclosed herein. In some embodiments, a method for treating viral infection, such as SARS or hepatitis A, B, C, D and E, is provided comprising administering to a patient a therapeutically effective amount of the compound disclosed herein.

Overproduction of lipopolysaccharide (LPS)-induced cytokines such as TNFα is considered to be central to the processes associated with septic shock. Furthermore, it is generally accepted that the first step in the activation of cells by LPS is the binding of LPS to specific membrane receptors. The α- and β-subunits of the 20S proteasome complex have been identified as LPS-binding proteins, suggesting that the LPS-induced signal transduction may be an important therapeutic target in the treatment or prevention of sepsis (Qureshi, N. et al., J. Immun. (2003) 171: 1515-1525). Therefore, in certain embodiments, compositions as provided herein may be used for the inhibition of TNFα to prevent and/or treat septic shock.

Intracellular proteolysis generates small peptides for presentation to T-lymphocytes to induce MHC class I-mediated immune responses. The immune system screens for autologous cells that are virally infected or have undergone oncogenic transformation. One embodiment is a method for inhibiting antigen presentation in a cell, including exposing the cell to a composition described herein. In some embodiments, the cell is contacted with an effective amount of a compound or composition provided herein to inhibit antigen presentation in the cell. A further embodiment is a method for suppressing the immune system of a patient (e g., inhibiting transplant rejection, allergy, asthma), including administering to the patient a therapeutically effective amount of a composition described herein. Compositions provided herein can also be used to treat autoimmune diseases such as lupus, rheumatoid arthritis, multiple sclerosis, and inflammatory bowel diseases such as ulcerative colitis and Crohn's disease.

Another embodiment is a method for altering the repertoire of antigenic peptides produced by the proteasome or other Ntn with multicatalytic activity. For example, if the PGPH activity of 20S proteasome is selectively inhibited, a different set of antigenic peptides will be produced by the proteasome and presented in MHC molecules on the surfaces of cells than would be produced and presented either without any enzyme inhibition, or with, for example, selective inhibition of chymotrypsin-like activity of the proteasome.

Certain proteasome inhibitors block both degradation and processing of ubiquitinated NF-κB in vitro and in vivo. Proteasome inhibitors also block IκB-α degradation and NF-κB activation (Palombella, et al. *Cell* (1994) 78:773-785; and Traenckner, et al., *EMBO J.* (1994) 13:5433-5441). In some embodiments, a method for inhibiting IκB-α degradation is provided, including contacting a cell with a composition described herein. In some embodiments, a cell is contacted with an effective amount of the composition to inhibit IκB-α degradation. A further embodiment is a method for reducing the cellular content of NF-κB in a cell, muscle, organ, or patient, including contacting the cell, muscle, organ, or patient with a composition described herein. In some embodiments, a cell is contacted with an effective amount of the composition to reduce the cellular content of NF-κB in a cell.

Other eukaryotic transcription factors that require proteolytic processing include the general transcription factor TFIIA, herpes simplex virus VP16 accessory protein (host cell factor), virus-inducible IFN regulatory factor 2 protein, and the membrane-bound sterol regulatory element-binding protein 1.

Further provided herein are methods for affecting cyclin-dependent eukaryotic cell cycles, including exposing a cell (in vitro or in vivo) to a composition disclosed herein. Cyclins are proteins involved in cell cycle control. The proteasome participates in the degradation of cyclins. Examples of cyclins include mitotic cyclins, G1 cyclins, and cyclin B. Degradation of cyclins enables a cell to exit one cell cycle stage (e.g., mitosis) and enter another (e.g., division). It is believed all cyclins are associated with p34cdc2 protein kinase or related kinases. The proteolysis targeting signal is localized to amino acids 42-RAAL-GNISEN-50 (destruction box). There is evidence that cyclin is converted to a form vulnerable to a ubiquitin ligase or that a cyclin-specific ligase is activated during mitosis (Ciechanover, A., *Cell*, (1994) 79:13-21) Inhibition of the proteasome inhibits cyclin degradation, and therefore inhibits cell proliferation, for example, in cyclin-related cancers (Kumatori et al., *Proc. Natl. Acad. Sci. USA* (1990) 87:7071-7075). Provided herein is a method for treating a proliferative disease in a patient (e.g., cancer, psoriasis, or restenosis), including administering to the patient a therapeutically effective amount of a composition disclosed herein. Also provided herein is a method for treating cyclin-related inflammation in a patient, including administering to a patient a therapeutically effective amount of a composition described herein.

Additional embodiments include methods for affecting the proteasome-dependent regulation of oncoproteins and methods of treating or inhibiting cancer growth, each method including exposing a cell (in vivo, e.g., in a patient, or in vitro) to a composition disclosed herein. HPV-16 and HPV-18-derived E6 proteins stimulate ATP- and ubiquitin-dependent conjugation and degradation of p53 in crude reticulocyte lysates. The recessive oncogene p53 has been shown to accumulate at the nonpermissive temperature in a cell line with a mutated thermolabile E1. Elevated levels of p53 may lead to apoptosis. Examples of proto-oncoproteins degraded by the ubiquitin system include c-Mos, c-Fos, and c-Jun. One embodiment is a method for treating p53-related apoptosis, including administering to a patient a therapeutically effective amount of a composition disclosed herein.

In another embodiment, the disclosed compositions are useful for the treatment of a parasitic infection, such as infections caused by protozoan parasites. The proteasome of these parasites is considered to be involved primarily in cell differentiation and replication activities (Paugam et al., *Trends Parasitol.* 2003, 19(2): 55-59). Furthermore, entamoeba species have been shown to lose encystation capacity when exposed to proteasome inhibitors (Gonzales, et al., *Arch. Med. Res.* 1997, 28, Spec No: 139-140). In certain such embodiments, the disclosed compositions are useful for the treatment of parasitic infections in humans caused by a protozoan parasite selected from *Plasmodium* sps. (including *P. falciparum, P. vivax, P. malariae*, and *P. ovale*, which cause malaria), *Trypanosoma* sps. (including *T. cruzi*, which causes Chagas' disease, and *T. brucei* which causes African sleeping sickness), *Leishmania* sps. (including *L. amazonesis, L. donovani, L. infantum, L. mexicana*, etc.), *Pneumocystis carinii* (a protozoan known to cause pneumonia in AIDS and other immunosuppressed patients), *Toxoplasma gondii, Entamoeba histolytica, Entamoeba invadens,* and *Giardia lamblia*. In certain embodiments, the disclosed compositions are useful for the treatment of parasitic infections in animals and livestock caused by a protozoan parasite selected from *Plasmodium hermani, Cryptosporidium* sps., *Echinococcus granulosus, Eimeria tenella, Sarcocystis neurona*, and *Neurospora crassa*. Other compounds useful as proteasome inhibitors in the treatment of parasitic diseases are described in WO 98/10779, which is incorporated herein in its entirety.

In certain embodiments, the disclosed compositions inhibit proteasome activity irreversibly in a parasite. Such irreversible inhibition has been shown to induce shutdown in enzyme activity without recovery in red blood cells and white blood cells. In certain such embodiments, the long half-life of blood cells may provide prolonged protection with regard to therapy against recurring exposures to parasites. In certain embodiments, the long half-life of blood cells may provide prolonged protection with regard to chemoprophylaxis against future infection.

Prokaryotes have what is equivalent to the eukaryote 20S proteasome particle. Albeit, the subunit composition of the prokaryote 20S particle is simpler than that of eukaryotes, it has the ability to hydrolyze peptide bonds in a similar manner. For example, the nucleophilic attack on the peptide bond occurs through the threonine residue on the N-terminus of the β-subunits. In some embodiments, a method of treating prokaryotic infections is provided, comprising administering to a patient a therapeutically effective amount of a compound or composition provided herein. Prokaryotic infections may include diseases caused by either mycobacteria (such as tuberculosis, leprosy or Buruli Ulcer) or archaebacteria.

It has also been demonstrated that inhibitors that bind to the 20S proteasome stimulate bone formation in bone organ cultures. Furthermore, when such inhibitors have been administered systemically to mice, certain proteasome inhibitors increased bone volume and bone formation rates over 70% (Garrett, I. R. et al., *J. Clin. Invest.* (2003) 111: 1771-1782), therefore suggesting that the ubiquitin-proteasome machinery regulates osteoblast differentiation and bone formation. Therefore, the disclosed compositions may be useful in the treatment and/or prevention of diseases associated with bone loss, such as osteoporosis.

Provided herein is a method for treating a disease or condition selected from cancer, autoimmune disease, graft or transplant-related condition, neurodegenerative disease, fibrotic-associated condition, ischemic-related conditions, infection (viral, parasitic or prokaryotic), and diseases associated with bone loss, comprising administering a compound as provided herein.

Bone tissue is an excellent source for factors which have the capacity for stimulating bone cells. Thus, extracts of bovine bone tissue contain not only structural proteins which are responsible for maintaining the structural integrity of bone, but also biologically active bone growth factors which can stimulate bone cells to proliferate. Among these latter factors are a recently described family of proteins called bone morphogenetic proteins (BMPs). All of these growth factors have effects on other types of cells, as well as on bone cells, including Hardy, M. H., et al., *Trans Genet* (1992) 8:55-61 describes evidence that bone morphogenetic proteins (BMPs), are differentially expressed in hair follicles during development. Harris, S. E., et al., *J Bone Miner Res* (1994) 9:855-863 describes the effects of TGF-β on expression of BMP-2 and other substances in bone cells. BMP-2 expression in mature follicles also occurs during maturation and after the period of cell proliferation (Hardy, et al. (1992, supra). Thus, compounds provided herein may also be useful for hair follicle growth stimulation.

Also provided herein is a method for treating a lysosomal storage disorder. Lysosomal storage disorders are a group of diseases resulting from the abnormal metabolism of various substrates, including glycosphingolipids, glycogen, mucopolysaccharides, and glycoproteins. The metabolism of exo- and endogenous high molecular weight compounds normally occurs in the lysosomes, and the process is normally regulated in a stepwise process by degradation enzymes. Therefore, a deficient activity in one enzyme may impair the process, resulting in an accumulation of particular substrates. It has been shown that inhibition of the proteasome can improve the function of certain substrates in patients suffering from a lysosomal storage disorder (Y. Shimada et al. *Biochem. Biophys. Res. Commun.* (2011) 415(2):274-8). Most of these diseases can be clinically classified into subtypes: i) infantile-onset; ii) juvenile-onset; or iii) late-onset. The infantile-onset forms are often the most severe usually with no residual enzyme activity. The later-onset forms are often milder with low, but often detectable residual enzyme activity. The severity of the juvenile-onset forms are in between the infantile-onset and late-onset forms. Non-limiting examples of such disorders include: Pompe disease, Gaucher disease, Fabry disease, GM1-gangliosidosis, Tay-Sachs disease, Sandhoff disease, Niemann-Pick disease, Krabbe disease, Farber disease, Metachromatic leukodystrophy, Hurler-Scheie disease, Hunter disease, Sanfilippo disease A, Sanfilippo disease B, Sanfilippo disease C, Sanfilippo disease D, Morquio disease A, Morquio disease B, Maroteaux-Lamy disease, Sly disease, α-mannosidosis, β-mannosidosis, fucosidosis, sialidosis, and Schindler-Kanzaki disease. One embodiment, therefore, is a method of treating Pompe disease, including administering to a patient a therapeutically effective amount of a composition provided herein.

The disclosed compositions are also useful as diagnostic agents (e.g., in diagnostic kits or for use in clinical laboratories) for screening for proteins (e.g., enzymes, transcription factors) processed by Ntn hydrolases, including the proteasome. The disclosed compositions are also useful as research reagents for specifically binding the X/MB1 subunit or α-chain and inhibiting the proteolytic activities associated with it. For example, the activity of (and specific inhibitors of) other subunits of the proteasome can be determined.

Most cellular proteins are subject to proteolytic processing during maturation or activation. Enzyme inhibitors disclosed herein can be used to determine whether a cellular, developmental, or physiological process or output is regulated by the proteolytic activity of a particular Ntn hydrolase. One such method includes obtaining an organism, an intact cell preparation, or a cell extract; exposing the organism, cell preparation, or cell extract to a composition disclosed herein; exposing the compound-exposed organism, cell preparation, or cell extract to a signal; and monitoring the process or output. The high selectivity of the compounds disclosed herein permits rapid and accurate elimination or implication of the Ntn (for example, the 20S proteasome) in a given cellular, developmental, or physiological process.

Pharmaceutical Compositions and Administration

The methods provided herein include the manufacture and use of pharmaceutical compositions, which include one or more of the compounds provided herein. Also included are the pharmaceutical compositions themselves.

In some embodiments, the compounds provided herein can be formulated as described in U.S. Pat. No. 7,737,112 and U.S. application Ser. No. 13/614,829, each of which is incorporated herein by reference in its entirety. Pharmaceutical compositions typically include a pharmaceutically acceptable carrier.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent or encapsulating material. As used herein the language "pharmaceutically acceptable carrier" includes buffer, sterile water for injection, solvents, dispersion media, coatings, antibacterial and antifungal agents, isotonic and absorption delaying agents, and the like, compatible with pharmaceutical administration. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other nontoxic compatible substances employed in pharmaceutical formulations. In certain embodiments, pharmaceutical compositions provided herein are non-pyrogenic, i.e., do not induce significant temperature elevations when administered to a patient.

The term "pharmaceutically acceptable salt" refers to the relatively non-toxic, inorganic and organic acid addition salts of a compound provided herein. These salts can be prepared in situ during the final isolation and purification of a compound provided herein, or by separately reacting the compound in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", J. Pharm. Sci. 66: 1-19.)

In some embodiments, a compound provided herein may contain one or more acidic functional groups and, thus, is capable of forming pharmaceutically acceptable salts with pharmaceutically acceptable bases. The term "pharmaceutically acceptable salts" in these instances refers to the relatively non-toxic inorganic and organic base addition salts of a compound provided herein. These salts can likewise be prepared in situ during the final isolation and purification of the compound, or by separately reacting the purified compound in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

Wetting agents, emulsifiers, and lubricants, such as sodium lauryl sulfate and magnesium stearate, as well as coloring agents, release agents, coating agents, sweetening, flavoring, and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

A pharmaceutical composition may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include tonicity-adjusting agents, such as sugars and the like into the compositions. In addition, prolonged absorption of the injectable pharmaceutical form may be brought about by the inclusion of agents which delay absorption such as aluminum monostearate and gelatin.

In some cases, in order to prolong the effect of one or more compounds provided herein, it is desirable to slow the absorption of the compound from subcutaneous or intramuscular injection. For example, delayed absorption of a parenterally administered compound can be accomplished by dissolving or suspending the compound in an oil vehicle.

Compositions prepared as described herein can be administered in various forms, depending on the disorder to be treated and the age, condition, and body weight of the patient, as is well known in the art. For example, where the compositions are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These formulations can be prepared by conventional means in conjunction with the methods described herein, and, if desired, the active ingredient may be mixed with any conventional additive or excipient, such as a binder, a disintegrating agent, a lubricant, a corrigent, a solubilizing agent, a suspension aid, an emulsifying agent, or a coating agent.

Formulations suitable for oral administration may be in the form of capsules (e.g., gelatin capsules), cachets, pills, tablets, lozenges (using a flavored basis, usually sucrose and acacia or tragacanth), powders, troches, granules, or as a solution or a suspension in an aqueous or non-aqueous liquid, or as an oil-in-water or water-in-oil liquid emulsion, or as an elixir or syrup, or as pastilles (using an inert matrix, such as gelatin and glycerin, or sucrose and acacia) and/or as mouthwashes, and the like, each containing a predetermined amount of a compound provided herein as an active ingredient. A composition may also be administered as a bolus, electuary, or paste. Oral compositions generally include an inert diluent or an edible carrier.

Pharmaceutically compatible binding agents, and/or adjuvant materials can be included as part of an oral composition. In solid dosage forms for oral administration (capsules, tablets, pills, dragees, powders, granules, and the like), the active ingredient can be mixed with one or more pharmaceutically acceptable carriers, such as sodium citrate or dicalcium phosphate, and/or any of the following: (1) fillers or extenders, such as starches, cyclodextrins, lactose, sucrose, saccharin, glucose, mannitol, and/or silicic acid; (2) binders, such as, for example, carboxymethylcellulose, microcrystalline cellulose, gum tragacanth, alginates, gelatin, polyvinyl pyrrolidone, sucrose, and/or acacia; (3) humectants, such as glycerol; (4) disintegrating agents, such as agar-agar, calcium carbonate, potato, corn, or tapioca starch, alginic acid, Primogel, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, Sterotes, solid polyethylene glycols, sodium lauryl sulfate, and mixtures thereof; (10) a glidant, such as colloidal silicon dioxide; (11) coloring agents; and (12) a flavoring agent such as peppermint, methyl salicylate, or orange flavoring. In the case of capsules, tablets, and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols, and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of a powdered compound moistened with an inert liquid diluent.

Tablets, and other solid dosage forms, such as dragees, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, microspheres, and/or nanoparticles. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active compound(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions suitable for parenteral administration can include one or more compounds provided herein in combination with one or more pharmaceutically acceptable sterile aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions provided herein include water for injection (e.g., sterile water for injection), bacteriostatic water, ethanol, polyols (such as glycerol, propylene glycol, polyethylene glycol such as liquid polyethylene glycol, and the like), sterile buffer (such as citrate buffer), and suitable mixtures thereof, vegetable oils, such as olive oil, injectable organic esters, such as ethyl oleate, and Cremophor EL™ (BASF, Parsippany, N.J.). In all cases, the composition must be sterile and should be fluid to the extent that easy syringability exists. Proper fluidity can be maintained, for example, by the use of coating materials, such as lecithin, by the maintenance of the required particle size in the case of dispersions, and by the use of surfactants.

The composition should be stable under the conditions of manufacture and storage and must be preserved against the contaminating action of microorganisms such as bacteria and fungi. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation is freeze-drying (lyophilization), which yields a powder of the active ingredient plus any additional desired ingredient from a previously sterile-filtered solution thereof.

Injectable depot forms can be made by forming microencapsule or nanoencapsule matrices of a compound provided herein in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes, microemulsions or nanoemulsions, which are compatible with body tissue.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798, which is incorporated herein by reference in its entirety. Additionally, intranasal delivery can be accomplished, as described in, inter alia, Hamajima et al., *Clin. Immunol. Immunopathol.*, 88(2), 205-10 (1998). Liposomes (e.g., as described in U.S. Pat. No. 6,472,375, which is incorporated herein by reference in its entirety), microencapsulation and nanoencapsulation can also be used. Biodegradable targetable microparticle delivery systems or biodegradable targetable nanoparticle delivery systems can also be used (e.g., as described in U.S. Pat. No. 6,471,996, which is incorporated herein by reference in its entirety).

Systemic administration of a therapeutic compound as described herein can also be by transmucosal or transdermal means. Dosage forms for the topical or transdermal administration of a compound provided herein include powders, sprays, ointments, pastes, creams, lotions, gels, solutions, patches, and inhalants. The active component may be mixed under sterile conditions with a pharmaceutically acceptable carrier, and with any preservatives, buffers, or propellants which may be required. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The ointments, pastes, creams, and gels may contain, in addition to one or more compounds provided herein, excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to a compound provided herein, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

A compound provided herein can be administered by aerosol. This is accomplished by preparing an aqueous aerosol, liposomal preparation, or solid particles containing a compound or composition provided herein. A nonaqueous (e.g., fluorocarbon propellant) suspension could be used. In some embodiments, sonic nebulizers are preferred because they minimize exposing the agent to shear, which can result in degradation of the compound.

Ordinarily, an aqueous aerosol can be made by formulating an aqueous solution or suspension of the agent together with conventional pharmaceutically acceptable carriers and stabilizers. The carriers and stabilizers vary with the requirements of the particular composition, but typically include nonionic surfactants (TWEEN® (polysorbates), PLURONIC® (poloxamers), sorbitan esters, lecithin, CREMOPHOR® (polyethoxylates)), pharmaceutically acceptable co-solvents such as polyethylene glycol, innocuous proteins like serum albumin, sorbitan esters, oleic acid, lecithin, amino acids such as glycine, buffers, salts, sugars, or sugar alcohols. Aerosols generally are prepared from isotonic solutions.

Transdermal patches have the added advantage of providing controlled delivery of a compound provided herein to the body. Such dosage forms can be made by dissolving or dispersing the agent in the proper medium. Absorption enhancers can also be used to increase the flux of the compound across the skin. The rate of such flux can be controlled by either providing a rate controlling membrane or dispersing the compound in a polymer matrix or gel.

The pharmaceutical compositions can also be prepared in the form of suppositories or retention enemas for rectal and/or vaginal delivery. Formulations presented as a suppository can be prepared by mixing one or more compounds provided herein with one or more suitable nonirritating excipients or carriers comprising, for example, cocoa butter, glycerides, polyethylene glycol, a suppository wax or a salicylate, which is solid at room temperature, but liquid at body temperature and, therefore, will melt in the rectum or vaginal cavity and release the active agent. Formulations which are suitable for vaginal administration also include pessaries, tampons, creams, gels, pastes, foams, or spray formulations containing such carriers as are known in the art to be appropriate.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

As described above, the preparations of one or more compounds provided herein may be given orally, parenterally, topically, or rectally. They are, of course, given by forms suitable for each administration route. For example, they are administered in tablets or capsule form, by injection, inhalation, eye lotion, ointment, suppository, infusion; topically by lotion or ointment; and rectally by suppositories. In some embodiments, administration is oral.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection, and infusion.

The phrases "systemic administration", "administered systemically", "peripheral administration", and "administered peripherally" as used herein mean the administration of a ligand, drug, or other material via route other than directly into the central nervous system, such that it enters the patient's system and thus, is subject to metabolism and other like processes, for example, subcutaneous administration.

A compound provided herein may be administered to humans and other animals for therapy by any suitable route of administration, including orally, nasally, as by, for example, a spray, rectally, intravaginally, parenterally, intracisternally, and topically, as by powders, ointments or drops, including buccally and sublingually. Regardless of the route of administration selected, a compound provided herein, which may be used in a suitable hydrated form, and/or the pharmaceutical compositions provided herein, is formulated into a pharmaceutically acceptable dosage form by conventional methods known to those of skill in the art. In another embodiment, the pharmaceutical composition is an oral solution or a parenteral solution. Another embodiment is a freeze-dried preparation that can be reconstituted prior to administration. As a solid, this formulation may also include tablets, capsules or powders.

Actual dosage levels of the active ingredients in the pharmaceutical compositions provided herein may be varied so as to obtain an amount of the active ingredient which is effective to achieve the desired therapeutic response for a particular patient, composition, and mode of administration, without being toxic to the patient.

The concentration of a compound provided herein in a pharmaceutically acceptable mixture will vary depending on several factors, including the dosage of the compound to be administered, the pharmacokinetic characteristics of the compound(s) employed, and the route of administration. In some embodiments, the compositions provided herein can be provided in an aqueous solution containing about 0.1-10% w/v of a compound disclosed herein, among other substances, for parenteral administration. Typical dose ranges can include from about 0.01 to about 50 mg/kg of body weight per day, given in 1-4 divided doses. Each divided dose may contain the same or different compounds. The dosage will be a therapeutically effective amount depending on several factors including the overall health of a patient, and the formulation and route of administration of the selected compound(s).

Dosage forms or compositions containing a compound as described herein in the range of 0.005% to 100% with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%. Although the dosage will vary depending on the symptoms, age and body weight of the patient, the nature and severity of the disorder to be treated or prevented, the route of administration and the form of the drug, in general, a daily dosage of from 0.01 to 2000 mg of the compound is recommended for an adult human patient, and this may be administered in a single dose or in divided doses. The amount of active ingredient which can be combined with a carrier material to produce a single dosage form will generally be that amount of the compound which produces a therapeutic effect.

The pharmaceutical composition may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the patient and adjusting the dosage and/or timing.

The pharmaceutical compositions can be included in a container, pack, or dispenser together with instructions for administration.

Also provided herein is a conjoint therapy wherein one or more other therapeutic agents are administered with a compound or a pharmaceutical composition comprising a compound provided herein. Such conjoint treatment may be achieved by way of the simultaneous, sequential, or separate dosing of the individual components of the treatment. Non-limiting examples of conjoint therapies include those provided in WO 2010/048298.

In certain embodiments, a composition provided herein is conjointly administered with one or more other proteasome inhibitor(s) (see, e.g., U.S. Pat. Nos. 7,232,818 and 8,088,741, each of which is incorporated herein by reference in its entirety). Additional examples of proteasome inhibitors include bortezomib, MLN9708, marizomib, carfilzomib (see, e.g., U.S. Pat. No. 7,417,042, which is incorporated herein by reference in its entirety), and those compounds disclosed in U.S. Pat. No. 7,687,456 and U.S. Pat. No. 7,691,852, each of which is incorporated herein by reference in its entirety.

In certain embodiments, a composition provided herein is conjointly administered with a chemotherapeutic. Suitable chemotherapeutics may include, natural products such as vinca alkaloids (e.g., vinblastine, vincristine, and vinorelbine), paclitaxel, epidipodophyllotoxins (e.g., etoposide and teniposide), antibiotics (e.g., dactinomycin (actinomycin D), daunorubicin, doxorubicin, and idarubicin), anthracyclines, mitoxantrone, bleomycins, plicamycin (mithramycin), mitomycin, enzymes (e.g., L-asparaginase which systemically metabolizes L-asparagine and deprives cells which do not have the capacity to synthesize their own asparagine), anti-platelet agents, antiproliferative/antimitotic alkylating agents such as nitrogen mustards (e.g., mechlorethamine, cyclophosphamide and analogs, melphalan, and chlorambucil), ethylenimines and methylmelamines (e.g., hexaamethylmelaamine and thiotepa), CDK inhibitors (e.g., seliciclib, UCN-01, P1446A-05, PD-0332991, dinaciclib, P27-00, AT-7519, RGB286638, and SCH727965), alkyl sulfonates (e.g., busulfan), nitrosoureas (e.g., carmustine (BCNU) and analogs, and streptozocin), trazenes-dacarbazinine (DTIC), antiproliferative/antimitotic antimetabolites such as folic acid analogs (e.g., methotrexate), pyrimidine analogs (e.g., fluorouracil, floxuridine, and cytarabine), purine analogs and related inhibitors (e.g., mercaptopurine, thioguanine, pentostatin and 2-chlorodeoxyadenosine), aromatase inhibitors (e.g., anastrozole, exemestane, and letrozole), and platinum coordination complexes (e.g., cisplatin and carboplatin), procarbazine, hydroxyurea, mitotane, aminoglutethimide, histone deacetylase (HDAC) inhibitors (e.g., trichostatin, sodium butyrate, apicidan, suberoyl anilide hydroamic acid, vorinostat, LBH 589, romidepsin, ACY-1215, and panobinostat), mTor inhibitors (e.g., temsirolimus, everolimus, ridaforolimus, and sirolimus), KSP(Eg5) inhibitors (e.g., Array 520), DNA binding agents (e.g., Zalypsis), PI3K delta inhibitor (e.g., GS-1101 and TGR-1202), PI3K delta and gamma inhibitor (e.g., CAL-130), multi-kinase inhibitor (e.g., TGO2 and sorafenib), hormones (e.g., estrogen) and hormone agonists such as leutinizing hormone releasing hormone (LHRH) agonists (e.g., goserelin, leuprolide and triptorelin), BAFF-neutralizing antibody (e.g., LY2127399), IKK inhibitors, p38MAPK inhibitors, anti-IL-6 (e.g., CNT0328), telomerase inhibitors (e.g., GRN 163L), aurora kinase inhibitors (e.g., MLN8237), cell surface monoclonal antibodies (e.g., anti-CD38 (HUMAX-CD38), anti-CS1 (e.g., elotuzumab), HSP90 inhibitors (e.g., 17 AAG and KOS 953), P13K/Akt inhibitors (e.g., perifosine), Akt inhibitor (e.g., GSK-2141795), PKC inhibitors (e.g., enzastaurin), FTIs (e.g., Zarnestra™), anti-CD138 (e.g., BT062), Torcl/2 specific kinase inhibitor (e.g., INK128), kinase inhibitor (e.g., GS-1101), ER/UPR targeting agent (e.g., MKC-3946), cFMS inhibitor (e.g., ARRY-382), JAK1/2 inhibitor (e.g., CYT387), PARP inhibitor (e.g., olaparib and veliparib (ABT-888)), BCL-2 antagonist. Other chemotherapeutic agents may include mechlorethamine, camptothecin, ifosfamide, tamoxifen, raloxifene, gemcitabine, navelbine, sorafenib, or any analog or derivative variant of the foregoing.

In certain embodiments, a pharmaceutical composition as provided herein is conjointly administered with a cytokine Cytokines include, but are not limited to, Interferon-γ, -α, and -β, Interleukins 1-8, 10 and 12, Granulocyte Monocyte Colony-Stimulating factor (GM-CSF), TNF-α and -β, and TGF-β.

In certain embodiments, a pharmaceutical composition provided herein is conjointly administered with a steroid. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts and/or derivatives thereof.

In some embodiments, a pharmaceutical composition provided herein is conjointly administered with an immunotherapeutic agent. Suitable immunotherapeutic agents may include, but are not limited to, MDR modulators (e.g., verapamil, valspordar, biricodar, tariquidar, laniquidar), cyclosporine, thalidomide, lenalidomide (REVLIMID®), pomalidomide, and monoclonal antibodies. The monoclonal antibodies can be either naked or conjugated such as rituximab, tositumomab, alemtuzumab, epratuzumab, ibritumomab tiuxetan, gemtuzumab ozogamicin, bevacizumab, cetuximab, erlotinib, and trastuzumab.

EXAMPLES

General Experimental Methods

Nuclear Magnetic Resonance (NMR) spectra were recorded at 400 MHz for ¹H. Chemical shifts (δ) are given in ppm downfield from tetramethylsilane, an internal standard, and coupling constants (J-values) are in hertz (Hz). Mass spectrometry (MS) was used to confirm the mass of the compounds by ionizing the compounds to generate charged molecules or molecule fragments and measuring their mass-to-charge ratios (m/z). As the ionization method, EI (electron impact) ionization was used.

Synthetic Procedures—Dipeptide and Tripeptide Epoxy Ketone Compounds

Example 1

Type A

Preparation of (R)—N—((S)-3-(4-methoxyphenyl)-1-(((S)-1-((R)-2-methyloxiran-2-yl)-1-oxo-3-phenylpropan-2-yl)amino)-1-oxopropan-2-yl)-2-methyl-5-oxopyrrolidine-2-carboxamide (C-3010)

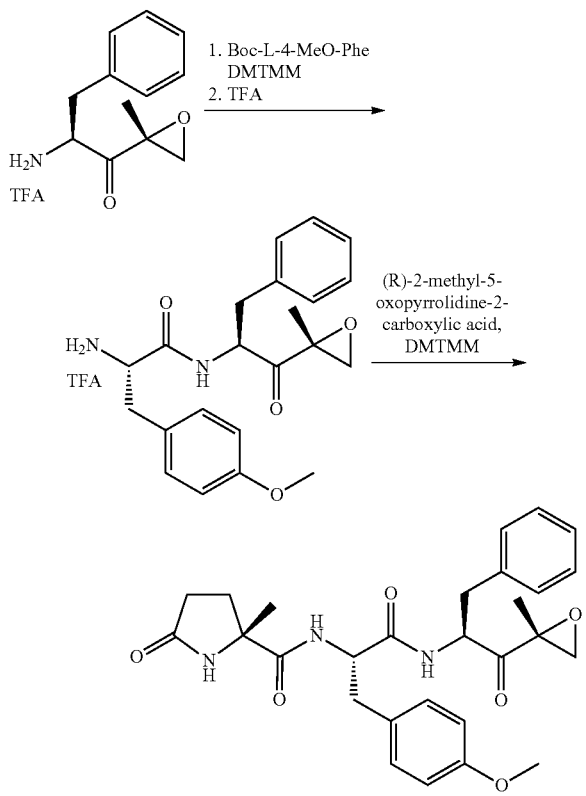

Preparation of Boc-(S)-2-amino-3-(4-methoxyphenyl)-N—((S)-1-((R)-2-methyloxiran-2-yl)-1-oxo-3-phenylpropan-2-yl)propanamide using 4-(4,6-Dimethoxy-1,3,5-triazin-2-yl)-4-methylmorpholinium chloride (DMTMM)

DMTMM (8.65 g, 31.3 mmol) and N-methylmorpholine (4.0 mg, 39 mmol) were added to a solution of Boc-L-4-MeO-phenylalanine (4.6 g, 15.7 mmol) and (S)-2-amino-1-((R)-2-methyloxiran-2-yl)-3-phenylpropan-1-one (trifluoroacetic acid (TFA) salt, 5.0 g, 15.7 mmol) in methylene chloride (100 mL) and dimethylformamide (DMF, 10 mL) at 0° C. with stirring. The suspension was stirred for 1 h at room temperature. The mixture was concentrated and the residue was purified by flash column chromatography on silica gel (methylene chloride/methanol=20:1) to afford Boc-(S)-2-amino-3-(4-methoxyphenyl)-N—((S)-1-((R)-2-methyloxiran-2-yl)-1-oxo-3-phenylpropan-2-yl)propanamide (6.9 g, 91% yield).

Preparation of Boc-(S)-2-amino-3-(4-methoxyphenyl)-N—((S)-1-((R)-2-methyloxiran-2-yl)-1-oxo-3-phenylpropan-2-yl)propanamide using 1-[Bis(dimethylamino)methylene]-1H-1,2,3-triazolo[4,5-b]pyridinium 3-oxid hexafluorophosphate (HATU)

To a flask charged with Boc-L-4-MeO-phenylalanine (3.1 g, 10.3 mmol), (S)-2-amino-1-((R)-2-methyloxiran-2-yl)-3-phenylpropan-1-one (TFA salt, 3.0 g, 9.4 mmol) and HATU (3.2 g, 10.3 mmol) was added dichloromethane (DCM, 20 mL). The mixture was cooled to 0° C. and basified with N,N-Diisopropylethylamine (DIPEA) to pH=8. The reaction mixture was stirred at room temperature for 30 min and then quenched with water (30 mL). The resulting mixture was extracted with methyl tertiary butyl ether (MTBE; 30 mL×3). The organics were combined, dried over anhydrous sodium sulfate and concentrated. The residue was purified by flash column chromatography on silica gel (petroleum ether/ethyl acetate=5:1 to 4:1) to afford Boc-(S)-2-amino-3-(4-methoxyphenyl)-N—((S)-1-((R)-2-methyloxiran-2-yl)-1-oxo-3-phenylpropan-2-yl)propanamide as a white solid (4.5 g, 88% yield).

TFA (2 mL) was added to a solution of Boc-(S)-2-amino-3-(4-methoxyphenyl)-N—((S)-1-((R)-2-methyloxiran-2-yl)-1-oxo-3-phenylpropan-2-yl)propanamide (800 mg, 1.66 mmol) in $CH_2Cl_2$ (5 mL) at 0° C. with stirring. The reaction mixture was stirred for 1 h and then concentrated to dryness. The residue was azeotroped three times with EtOAc (5 mL×3) to remove residual TFA to afford (S)-2-amino-3-(4-methoxyphenyl)-N—((S)-1-((R)-2-methyloxiran-2-yl)-1-oxo-3-phenylpropan-2-yl)propanamide (1.66 mmol) as its TFA salt, which was used in the next step without further purification. DMTMM (916 mg, 3.3 mmol) and N-methylmorpholine (500 mg, 5 mmol) were added to a solution of (S)-2-amino-3-(4-methoxyphenyl)-N—((S)-1-((R)-2-methyloxiran-2-yl)-1-oxo-3-phenylpropan-2-yl)propanamide (1.66 mmol) and (R)-2-methyl-5-oxopyrrolidine-2-carboxylic (500 mg, 4 mmol) in $CH_2Cl_2$ (20 mL) and DMF (5 mL) at 0° C. with stirring. The suspension was stirred for 1 h at room temperature and EtOAc (100 mL) and water (100 mL) were added. The resulting two phases were separated and the aqueous phase was extracted with EtOAc (50 mL×3). The combined organic phases were washed with brine (50 mL×3), dried over $Na_2SO_4$ and concentrated. The residue was purified by flash column chromatography on silica gel ($CH_2Cl_2$/MeOH=20:1) to afford (R)—N—((S)-3-(4-methoxyphenyl)-1-(((S)-1-((R)-2-methyloxiran-2-yl)-1-oxo-3-phenylpropan-2-yl)amino)-1-oxopropan-2-yl)-2-methyl-5-oxopyrrolidine-2-carboxamide (150 mg, 17% yield) as a yellow solid.

$^1$H NMR (300 MHz, $CDCl_3$): δ 7.20~7.30 (m, 4H), 7.15 (d, J=8.7 Hz, 2H), 6.9~7.10 (m, 3H), 6.85 (d, J=8.7 Hz, 2H), 6.65 (m, 1H), 6.25 (m, 1H), 4.75 (m, 1H), 4.45 (m, 1H), 3.80 (s, 3H), 3.25 (d, J=4.8 Hz, 1H), 3.10 (m, 1H), 2.80~2.99 (m, 3H), 2.70 (m, 1H), 2.10~2.35 (m, 3H), 1.95 (m, 1H), 1.49 (s, 3H), 1.40 (s, 3H). MS (EI) for $C_{28}H_{33}N_3O_6$. found 506.1 [M−H]−.

The following compounds were synthesized in a similar manner:

(S)—N—((S)-3-(4-methoxyphenyl)-1-(((S)-1-((R)-2-methyloxiran-2-yl)-1-oxo-3-phenylpropan-2-yl)amino)-1-oxopropan-2-yl)-2-methyl-5-oxopyrrolidine-2-carboxamide (C-3011): 1H NMR (300 MHz, CDCl3): δ 7.20~7.30 (m, 4H), 7.10~7.20 (m, 5H), 6.85 (d, J=8.7 Hz, 2H), 6.80 (m, 1H), 6.50 (m, 1H), 4.75 (m, 1H), 4.56 (m, 1H), 3.80 (s, 3H), 3.28 (d, J=4.8 Hz, 1H), 3.10 (m, 1H), 2.80~2.99 (m, 3H), 2.70 (m, 1H), 2.00~2.30 (m, 3H), 1.90 (m, 1H), 1.47 (s, 3H), 1.41 (s, 3H). MS (EI) for $C_{28}H_{33}N_3O_6$. found 508.1 [M+H]+.

(S)—N—((S)-3-(4-methoxyphenyl)-1-(((S)-1-((R)-2-methyloxiran-2-yl)-1-oxo-3-phenylpropan-2-yl)amino)-1-oxopropan-2-yl)-4-oxoazetidine-2-carboxamide (C-3002): $^1$H NMR (400 MHz, $CDCl_3$): δ 7.26-7.21 (m, 2H), 7.10 (d, J=8.8 Hz, 2H), 7.03-7.01 (m, 2H), 6.83-6.78 (m, 3H), 6.22-6.18 (m, 2H), 4.73-4.70 (m, 1H), 4.56 (q, J=8.0 Hz, 1H), 3.99-3.97 (m, 1H), 3.78 (s, 3H), 3.27-3.21 (m, 2H), 3.12-3.08 (m, 1H), 2.94-2.92 (m, 3H), 2.71-2.61 (M, 2H), 1.50 (s, 3H). MS (EI) for $C_{26}H_{29}N_3O_6$. found 480.2 [M+H]+.

(R)—N—((S)-3-(4-methoxyphenyl)-1-(((S)-1-((R)-2-methyloxiran-2-yl)-1-oxo-3-phenylpropan-2-yl)amino)-1-oxopropan-2-yl)-4-oxoazetidine-2-carboxamide (C-3003): $^1$H NMR (400 MHz, $CDCl_3$): δ 7.26-7.20 (m, 3H), 7.09 (d, J=6.8 Hz, 2H), 7.02-7.01 (m, 2H), 6.93 (d, J=7.6 Hz, 1H), 6.81 (d, J=8.8 Hz, 2H), 6.38 (s, 1H), 6.33 (d, J=6.8 Hz, 1H), 4.71-4.69 (m, 1H), 4.55 (q, J=7.6 Hz, 1H), 3.98 (q, J=2.8 Hz, 1H), 3.78 (s, 3H), 3.26-3.20 (m, 2H), 3.08 (dd, J=12.0, 4.8 Hz, 1H), 2.95-2.91 (m, 3H), 2.81-2.77 (m, 1H), 2.62 (dd, J=13.8, 8.6 Hz, 1H), 1.72 (s, 1H), 1.48 (s, 3H). MS (EI) for $C_{26}H_{29}N_3O_6$. found 480.2 [M+H]+

Methyl ((S)-1-(((S)-3-(4-methoxyphenyl)-1-(((S)-1-((R)-2-methyloxiran-2-yl)-1-oxo-3-phenylpropan-2-yl)amino)-1-oxopropan-2-yl)amino)-1-oxopropan-2-yl)carbamate (C-2009): $^1$H NMR (400 MHz, $CDCl_3$): δ 8.41 (d, J=7.2 Hz, 1H), 7.75 (d, J=8.0, 1H), 7.31-7.19 (m, 6H), 4.61-4.55 (m, 1H), 4.45-4.35 (m, 1H), 3.97-3.86 (m, 1H0, 3.70 (s, 3H), 3.50 (s, 3H), 3.20-3.14 (m, 1H), 2.98-2.80 (m, 3H), 2.75-2.6 (m, 2H), 1.35 (s, 3H), 1.14 (d, J=8.4 Hz, 1H0, 1.08-1.05 (m, 3H). LC-MS for $C_{27}H_{33}N_3O_7$. found 512.38 [M+H]$^+$.

Methyl ((R)-1-(((S)-3-(4-methoxyphenyl)-1-(((S)-1-((R)-2-methyloxiran-2-yl)-1-oxo-3-phenylpropan-2-yl)amino)-1-oxopropan-2-yl)amino)-1-oxopropan-2-yl)carbamate (C-2010): $^1$H NMR (400 MHz, DMSO-$d_6$): δ 8.42 (d, J=7.2 Hz, 1H), 7.95 (d, J=8.8 Hz, 1H), 7.31-7.21 (m, 5H), 7.07 (d, J=8.4 Hz, 2H), 6.767 (d, J=8.8 Hz, 2H), 4.60-4.44 (m, 2H), 3.98-3.94 (m, 1H), 3.69 (s, 3H), 3.50 (s, 3H), 3.22 (d, J=5.6 Hz, 1H), 3.00-2.89 (m, 3H), 2.76-2.70 (m, 1H), 2.61-2.55 (1H), 1.35 (s, 3H), 0.93 (s, 3H). MS (EI) for $C_{27}H_{33}N_3O_7$. found 512.3 [M+H]$^+$.

(S)-3-(4-Methoxyphenyl)-N—((S)-1-((R)-2-methyloxiran-2-yl)-1-oxo-3-phenylpropan-2-yl)-2-((S)-2-(2,2,2-trifluoroacetamido)propanamido)propanamide (C-2011): $^1$H NMR (400 MHz, DMSO-$d_6$): δ 9.43 (d, J=7.6 Hz, 1H), 8.45 (d, J=7.2 Hz, 1H), 8.06 (d, J=8.4 Hz, 1H), 7.34-7.15 (m, 5H), 7.08 (d, J=8.4 Hz, 2H), 6.76 (d, J=8.4 Hz, 2H), 4.70-4.50 (m, 1H), 4.48-4.40 (m, 1H), 4.36-4.31 (m, 1H), 3.70 (s, 3H), 3.18-3.16 (m, 1H), 2.99-2.85 (m, 3H0, 2.73-2.68 (m, 2H), 1.35 (s, 3H0, 1.23-1.05 (m, 3H). MS (EI) for $C_{26}H_{29}N_5O_5$. found 492.48 [M+H]$^+$.

(S)-2-(2-(1H-1,2,3-Triazol-1-yl)acetamido)-3-(4-methoxyphenyl)-N—((S)-1-((R)-2-methyloxiran-2-yl)-1-oxo-3-phenylpropan-2-yl)propanamide (C-3004): $^1$H NMR (400 MHz, DMSO-$d_6$): δ 8.61 (d, J=7.2 Hz, 1H), 8.42 (d, J=8.0 Hz, 1H), 8.36 (s, 1H), 7.91 (s, 1H), 7.34-7.22 (m, 5H), 7.09 (d, J=8.4 Hz, 2H), 6.80 (d, J=8.4 Hz, 2H), 4.88-4.78 (m, 2H), 3.72 (s, 3H), 3.20-3.19 (m, 1H), 3.00-2.87 (m, 3H), 2.72-2.62 (m, 3H), 1.36 (s, 3H). MS (EI) for $C_{27}H_{30}F_3N_3O_6$. found 550.51 [M+H]$^+$.

2-Amino-N—((S)-3-(4-methoxyphenyl)-1-(((S)-1-((R)-2-methyloxiran-2-yl)-1-oxo-3-phenylpropan-2-yl)amino)-1-oxopropan-2-yl)-2-methylpropanamide (C-3006): $^1$H NMR (400 MHz, $CDCl_3$): δ 7.97 (d, J=8.1 Hz, 1H), 7.26-7.19 (m, 3H), 7.13 (d, J=8.7 Hz, 2H), 6.98 (dd, J=7.5, 1.8 Hz, 2H), 6.85-6.79 (m, 2H), 6.36 (d, J=7.2 Hz, 1H), 4.74 (td, J=7.6, 5.1 Hz, 1H), 4.50-4.39 (m, 1H), 3.78 (s, 3H), 3.27 (d, J=4.9 Hz, 1H), 3.05 (dd, J=14.0, 5.0 Hz, 1H), 2.97 (dd, J=6.9, 2.0 Hz, 2H), 2.90 (d, J=4.9 Hz, 1H), 2.71 (dd, J=14.0, 7.8 Hz, 1H), 1.22 (d, J=13.6 Hz, 6H). MS (EI) for $C_{26}H_{33}N_3O_5$. found 468.3 [M+H]+.

(R)-3,3,3-Trifluoro-2-hydroxy-N—((S)-3-(4-methoxyphenyl)-1-(((S)-1-((R)-2-methyloxiran-2-yl)-1-oxo-3-phenylpropan-2-yl)amino)-1-oxopropan-2-yl)-2-methylpropanamide (C-3007): $^1$H NMR (400 MHz, CDCl3) δ 7.23 (dd, J=5.1, 2.0 Hz, 3H), 7.15 (d, J=8.6 Hz, 2H), 6.94 (dd, J=7.1, 2.3 Hz, 2H), 6.84 (d, J=8.6 Hz, 2H), 5.80 (d, J=7.0 Hz, 1H), 4.72-4.62 (m, 1H), 4.55-4.46 (m, 1H), 4.11 (s, 1H), 3.80 (s, 3H), 3.24 (d, J=4.9 Hz, 1H), 3.06 (td, J=14.4, 5.3 Hz, 2H), 2.96 (s, 2H), 2.95-2.81 (m, 2H), 2.60 (dd, J=13.9, 8.2 Hz, 1H), 1.51 (s, 3H), 1.47 (s, 3H). MS (EI) for $C_{26}H_{29}F_3N_2O_6$. found 523.0 [M+H]+.

N—((S)-3-(4-Methoxyphenyl)-1-(((S)-1-((R)-2-methyloxiran-2-yl)-1-oxo-3-phenylpropan-2-yl)amino)-1-oxopropan-2-yl)-6-oxo-1,6-dihydropyridine-2-carboxamide (C-3008): $^1$H NMR (400 MHz, DMSO-d$_6$): δ 11.13 (s, OH), 8.76 (s, 1H), 8.17 (s, 1H), 7.74 (s, 1H), 7.44 (s, 1H), 7.33-7.11 (m, 7H), 7.02 (s, 2H), 6.84-6.72 (m, 4H), 4.72 (s, 1H), 4.62 (ddd, J=9.3, 7.6, 4.4 Hz, 1H), 3.68 (s, 3H), 3.17 (d, J=5.0 Hz, 2H), 3.06-2.91 (m, 4H), 2.86-2.76 (m, 2H), 2.75-2.65 (m, 7H), 1.38 (s, 3H). MS (EI) for $C_{28}H_{29}N_3O_6$. found 504.0 [M+H]+.

(R)—N—((S)-3-(4-Methoxyphenyl)-1-(((S)-1-((R)-2-methyloxiran-2-yl)-1-oxo-3-phenylpropan-2-yl)amino)-1-oxopropan-2-yl)-6-oxopiperidine-2-carboxamide (C-3009): $^1$H NMR (400 MHz, CDCl3) δ 7.26-7.20 (m, 3H), 7.15-7.11 (m, 2H), 6.99 (dd, J=7.6, 1.8 Hz, 2H), 6.89-6.80 (m, 2H), 6.55 (d, J=7.6 Hz, 1H), 6.08-5.97 (m, 2H), 4.74-4.65 (m, 1H), 4.49 (q, J=7.4 Hz, 1H), 3.89 (td, J=7.2, 6.1, 2.4 Hz, 1H), 3.80 (s, 3H), 3.24 (d, J=4.9 Hz, 1H), 3.08 (dd, J=14.0, 4.8 Hz, 1H), 3.02-2.86 (m, 3H), 2.62 (dd, J=14.0, 8.3 Hz, 1H), 2.33 (td, J=6.4, 2.1 Hz, 2H), 1.99-1.90 (m, 1H), 1.79-1.64 (m, 3H), 1.59 (s, 3H), 1.50 (s, 3H). MS (EI) for $C_{28}H_{33}N_3O_6$. found 508.0 [M+H]+.

(R)-tert-Butyl 3-(((benzyloxy)carbonyl)amino)-4-(((S)-3-(4-methoxyphenyl)-1-(((S)-1-((R)-2-methyloxiran-2-yl)-1-oxo-3-phenylpropan-2-yl)amino)-1-oxopropan-2-yl)amino)-4-oxobutanoate (C-2016): $^1$H NMR (400 MHz, Chloroform-d) δ 7.44-7.32 (m, 5H), 7.23-7.10 (m, 4H), 7.09-6.96 (m, 6H), 6.78-6.68 (m, 4H), 6.38 (d, J=7.3 Hz, 1H), 3.09-2.92 (m, 4H), 2.89 (d, J=5.0 Hz, 1H), 2.84 (dd, J=14.0, 6.6 Hz, 1H), 2.65 (dd, J=13.8, 8.9 Hz, 1H), 2.55 (dd, J=17.3, 5.7 Hz, 1H), 1.62 (s, 2H), 1.45 (s, 3H), 1.42 (s, 8H). MS (EI) for $C_{38}H_{45}N_3O_9$. found 688.0 [M+H]+.

N—((S)-1-(((S)-3-Cyclopentyl-1-((R)-2-methyloxiran-2-yl)-1-oxopropan-2-yl)amino)-3-(4-methoxyphenyl)-1-oxopropan-2-yl)-6-oxo-1,6-dihydropyridine-2-carboxamide (C-3014): $^1$H NMR (400 MHz, CDCl$_3$) δ 7.61 (d, J=6.6 Hz, 1H), 7.50 (dd, J=9.0, 6.9 Hz, 1H), 7.18 (d, J=8.7 Hz, 2H), 6.87-6.79 (m, 5H), 6.75 (d, J=9.1 Hz, 1H), 6.21-6.09 (m, 1H), 4.77 (q, J=7.0, 6.5 Hz, 1H), 4.51-4.43 (m, 1H), 3.78 (s, 3H), 3.22 (d, J=4.7 Hz, 1H), 3.15 (dd, J=13.9, 6.1 Hz, 1H), 3.03 (dd, J=13.9, 7.5 Hz, 1H), 2.90 (d, J=5.0 Hz, 1H), 1.78-1.30 (m, 12H), 1.19-0.89 (m, 2H). LC-MS for $C_{27}H_{33}N_3O_6$. found 496.0 [M+H]$^+$.

N—((S)-1-(((S)-3-(Cyclopent-1-en-1-yl)-1-((R)-2-methyloxiran-2-yl)-1-oxopropan-2-yl)amino)-3-(4-methoxyphenyl)-1-oxopropan-2-yl)-6-oxo-1,6-dihydropyridine-2-carboxamide (C-3015): $^1$H NMR (400 MHz, CDCl$_3$): δ 7.50 (dd, J=9.2, 6.8 Hz, 1H), 7.23 (d, J=8.4 Hz, 2H), 6.87-6.76 (m, 4H), 5.85 (d, J=6.4 Hz, 1H), 5.25 (app s, 1H), 4.72-4.69 (m, 1H), 4.52-4.48 (m, 1H), 3.79 (s 3H), 3.26 (d, J=4.8 Hz, 1H), 3.15 (dd, J=13.6, 5.2 Hz, 1H), 2.99 (dd, J=13.6, 8.4 Hz, 1H), 2.91 (d, J=5.2 Hz, 1H), 2.55-2.45 (m, 2H), 2.19-2.11 (m, 6H), 1.82-1.76 (m, 4H), 1.52 (s, 3H), 1.49-1.42 (m, 1H). MS (EI) for $C_{27}H_{33}N_3O_6$. found 494.2 [M+H]$^+$.

N—((S)-1-(((S)-1-((R)-2-Methyloxiran-2-yl)-1-oxo-3-phenylpropan-2-yl)amino)-1-oxopropan-2-yl)-6-oxo-1,6-dihydropyridine-2-carboxamide (C-3016): $^1$H NMR (400 MHz, DMSO-d$_6$): δ 11.19 (br s, 1H), 8.62 (br s, 1H), 8.32 (br s, 1H), 7.75 (br s, 1H), 7.29-7.17 (m, 8H), 6.78 (br s, 1H), 4.58-4.74 (m, 2H), 3.22 (d, J=5.2 Hz, 1H), 3.03 (d, J=5.2 Hz, 1H), 2.96 (dd, J=14.4, 4.0 Hz, 1H), 2.69-2.63 (m, 1H), 1.38 (s, 3H), 1.26 (d, 6.8 Hz, 3H). MS (EI) for $C_{21}H_{23}N_3O_5$. found 398.0 [M+H]$^+$.

N—((S)-3-Hydroxy-1-(((S)-1-((R)-2-methyloxiran-2-yl)-1-oxo-3-phenylpropan-2-yl)amino)-1-oxopropan-2-yl)-6-oxo-1,6-dihydropyridine-2-carboxamide (C-3017): $^1$H NMR (400 MHz, DMSO-d$_6$): δ 11.23 (s, 1H), 8.58-8.56 (m, 1H), 8.31-8.29 (m, 1H), 7.79 (br s, 1H), 7.50 (br s, 1H), 7.27-7.16 (m, 5H), 6.84 (br s, 1H), 5.10-4.90 (m, 1H), 4.65-4.60 (m, 1H), 4.53-4.48 (m, 1H), 3.63-3.61 (m, 2H), 3.20 (d, J=5.2 Hz, 1H), 3.00 (d, J=5.2 Hz, 1H), 2.93 (dd, J=14.0, 4.8 Hz, 1H), 2.70 (dd, J=14.0, 9.6 Hz, 1H), 1.36 (s, 3H). MS (EI) for $C_{21}H_{23}N_3O_6$. found 414.0 [M+H]$^+$.

N—((S)-1-(((S)-3-Cyclopentyl-1-((R)-2-methyloxiran-2-yl)-1-oxopropan-2-yl)amino)-1-oxopropan-2-yl)-6-oxo-1,6-dihydropyridine-2-carboxamide (C-3018): $^1$H NMR (400 MHz, DMSO-d$_6$): δ 11.19 (s, 1H), 8.51-8.20 (m, 2H), 7.80-7.25 (m, 2H), 6.83 (br s, 1H), 4.60-4.55 (m, 1H), 4.34-4.28 (m, 1H), 3.18 (d, J=5.2 Hz, 1H), 3.02 (d, J=5.2 Hz, 1H), 1.82-1.41 (m, 12H), 1.29 (d, J=7.2 Hz, 3H), 1.39-1.10 (m, 2H). MS (EI) for $C_{20}H_{27}N_3O_5$. found 390.0 [M+H]$^+$.

N—((S)-1-(((S)-3-Cyclopentyl-1-((R)-2-methyloxiran-2-yl)-1-oxopropan-2-yl)amino)-3-hydroxy-1-oxopropan-2-yl)-6-oxo-1,6-dihydropyridine-2-carboxamide (C-3019): $^1$H NMR (400 MHz, DMSO-d$_6$): δ 11.25 (s, 1H), 8.45-8.25 (m, 2H), 8.80 (br s, 1H), 8.50 (br s, 1H), 7.80 (br s, 1H), 5.00-4.97 (m, 1H), 4.58-4.53 (m, 1H), 4.38-4.35 (m, 1H), 3.66-6.63 (m, 2H), 3.18 (d, J=4.8 Hz, 1H), 3.01 (d, J=4.8 Hz, 1H), 1.90-1.40 (m, 11H), 1.15-1.05 (m, 4H). MS (EI) for $C_{20}H_{27}N_3O_6$. found 406.0 [M+H]+.

(R)-3-(((Benzyloxy)carbonyl)amino)-4-(((S)-3-(4-methoxyphenyl)-1-(((S)-1-((R)-2-methyloxiran-2-yl)-1-oxo-3-phenylpropan-2-yl)amino)-1-oxopropan-2-yl)amino)-4-oxobutanoic acid (C-2017): $^1$H NMR (400 MHz, DMSO-d$_6$) δ 8.54 (d, J=7.1 Hz, 1H), 8.47 (d, J=7.6 Hz, 1H), 7.44-7.09 (m, 15H), 7.04 (d, J=8.6 Hz, 2H), 6.71 (d, J=8.5 Hz, 2H), 5.01 (s, 2H), 4.54 (ddd, J=8.9, 7.1, 4.9 Hz, 1H), 4.38 (td, J=9.2, 4.0 Hz, 1H), 4.13 (q, J=6.4 Hz, 1H), 3.67 (s, 3H), 3.44-3.19 (m, 3H), 2.87 (ddt, J=33.0, 22.8, 7.1 Hz, 6H), 2.61 (dd, J=13.8, 9.5 Hz, 1H), 2.25 (dd, J=16.0, 5.6 Hz, 1H), 2.14 (dd, J=16.0, 6.5 Hz, 1H), 1.34 (s, 3H). MS (EI) for $C_{34}H_{37}N_3O_9$. found 630.2 [M−H]−.

Benzyl ((S)-1-(1-hydroxycyclopropyl)-2-(((S)-3-(4-methoxyphenyl)-1-(((S)-1-((R)-2-methyloxiran-2-yl)-1-oxo-3-phenylpropan-2-yl)amino)-1-oxopropan-2-yl)amino)-2-oxoethyl)carbamate (C-2046): $^1$H NMR (300 MHz, DMSO-d$_6$): δ 8.45 (d, J=6.9 Hz, 1H), 7.75 (d, J=8.4 Hz, 1H), 7.20~7.60 (m, 9H), 7.00~7.15 (m, 3H), 6.75 (d, J=8.4 Hz, 2H), 5.48 (s, 1H), 5.03 (s, 2H), 4.65 (m, 1H), 4.55 (m, 1H), 3.95 (d, J=9.0 Hz, 1H), 3.70 (s, 3H), 3.18 (m, 1H), 2.85~3.00 (m, 3H), 2.65~2.80 (m, 1H), 1.34 (s, 3H), 0.50~0.80 (m, 4H). LC-MS for $C_{35}H_{39}N_3O_8$. found 630.3 [M+H]$^+$.

(S)-2-(((benzyloxy)carbonyl)amino)-2-(1-((triethylsilyl)oxy)cyclopropyl)acetic acid was used in the final coupling followed by standard TBAF deprotection. $^1$H NMR (300 MHz, DMSO-d$_6$): δ 8.45 (d, J=6.9 Hz, 1H), 7.75 (d, J=8.4 Hz, 1H), 7.20~7.60 (m, 9H), 7.00~7.15 (m, 3H), 6.75 (d, J=8.4 Hz, 2H), 5.48 (s, 1H), 5.03 (s, 2H), 4.65 (m, 1H), 4.55 (m, 1H), 3.95 (d, J=9.0 Hz, 1H), 3.70 (s, 3H), 3.18 (m, 1H), 2.85~3.00 (m, 3H), 2.65~2.80 (m, 1H), 1.34 (s, 3H), 0.50~0.80 (m, 4H). LC-MS for $C_{35}H_{39}N_3O_8$. found 630.3 [M+H]$^+$.

Example 2

Type A2

Preparation of benzyl ((S)-2-(((S)-3-(4-methoxyphenyl)-1-(((S)-1-((R)-2-methyloxiran-2-yl)-1-oxo-3-phenylpropan-2-yl)amino)-1-oxopropan-2-yl)amino)-1-(oxetan-3-yl)-2-oxoethyl)carbamate (C-2035)

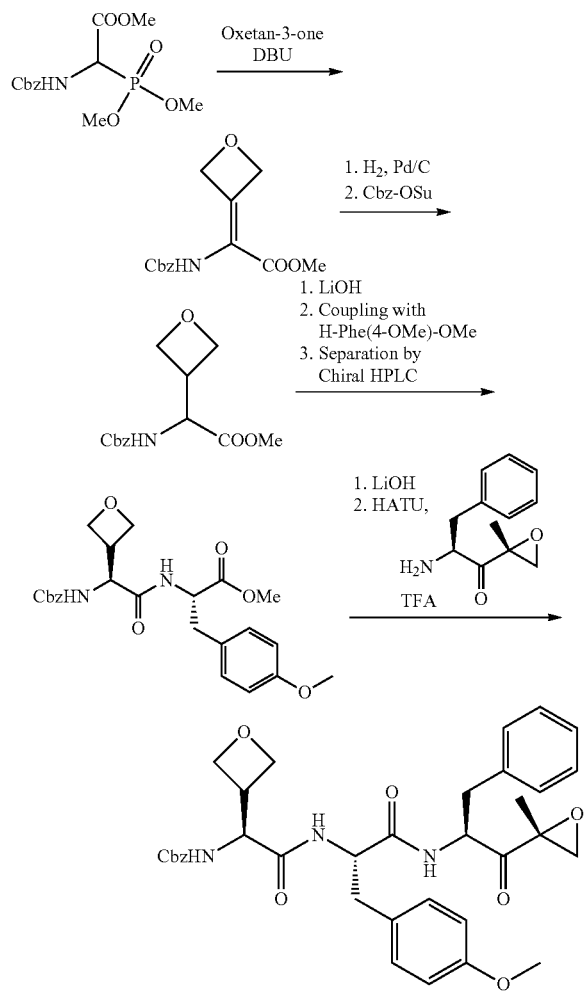

Methyl 2-(benzyloxycarbonylamino)-2-(oxetan-3-ylidene)acetate 1,8-Diazabicycloundec-7-ene (DBU; 16.25 g, 95 mmol) was added dropwise to a solution of N-benzyloxy carbonyl-(phosphono glycine trimethylester) (23.0 g, 70 mmol) and oxetan-3-one (5.0 g, 70 mmol) in methylene chloride (200 mL) at room temperature under $N_2$. The reaction mixture was stirred for 48 h at room temperature. The solvent was removed and the residue was dissolved in EtOAc (500 mL). The resulting solution was washed with 5% aqueous $KHSO_4$ (300 mL×2), saturated aqueous $NaHCO_3$ (300 mL×3) and brine (200 mL×1), respectively. The organic phase was dried over anhydrous sodium sulfate and concentrated. The residue was purified by flash column chromatography on silica gel (Hexane/EtOAc=5:1) to afford methyl 2-(benzyloxycarbonylamino)-2-(oxetan-3-ylidene)acetate (13.5 g, 69% yield).

Methyl 2-(benzyloxycarbonylamino)-2-(oxetan-3-yl)acetate

Pd/C (10%, 5.0 g) was added to a solution of compound methyl 2-(benzyloxycarbonylamino)-2-(oxetan-3-ylidene)acetate (10.0 g, 36 mmol) in MeOH (100 mL). The suspension was stirred under hydrogen atmosphere at room temperature for 12 h. The catalyst was filtered off and washed with MeOH (100 mL). The filtrate and washings were combined followed by addition of Cbz-OSu (10.0 g, 40 mmol) and triethylamine (15.2 mL, 108 mmol). The reaction mixture was stirred for 12 h at room temperature and then concentrated. The residue was purified by flash column chromatography on silica gel (Hexane/EtOAc=5:1) to afford methyl 2-(benzyloxycarbonylamino)-2-(oxetan-3-yl)acetate (4.3 g, 41% yield) as a yellow solid.

(S)-Methyl 2-((S)-2-(benzyloxycarbonylamino)-2-(oxetan-3-yl)acetamido)-3-(4-methoxyphenyl)propanoate A solution of LiOH (650 mg, 27 mmol) in water (10 mL) was added to a solution of methyl 2-(benzyloxycarbonylamino)-2-(oxetan-3-yl)acetate (2.5 g, 9.0 mmol) in THF (50 mL) at 0° C. with stirring. The reaction mixture was stirred for 12 h and then acidified with 2 N aqueous HCl to pH=3. Most of the solvent was removed and the remaining mixture was extracted with EtOAc (50 mL×3). The combined organic phases were washed with brine (50 mL×1), dried over anhydrous sodium sulfate and concentrated to afford the corresponding acid (2.0 g), which was used directly without further purification.

DMTMM (4.4 g, 16 mmol) and N-methylmorpholine (3.2 g, 32 mmol) were added to a solution of the acid (2.0 g, 8.0 mmol) and L-4-methoxylphenylalanine methyl ester hydrochloride (2.0 g, 8.2 mmol) in methylene chloride (100 mL) at 0° C. with stirring. The suspension was stirred for 1 h at room temperature and then washed with 5% aqueous $KHSO_4$ (100 mL×2), saturated aqueous $NaHCO_3$ (100 mL×3) and brine (50 mL×1), respectively. The organic phase was dried over anhydrous sodium sulfate and concentrated. The residue was purified by flash column chromatography on silica gel (Hexane/EtOAc=3:1) to afford a mixture of two diastereomers (2.5 g), which was further separated by chiral prep-HPLC to give (S)-Methyl 2-((S)-2-(benzyloxycarbonylamino)-2-(oxetan-3-yl)acetamido)-3-(4-methoxyphenyl)propanoate (1.1 g, 26% yield) as a white solid.

Benzyl ((S)-2-(((S)-3-(4-methoxyphenyl)-1-(((S)-1-((R)-2-methyloxiran-2-yl)-1-oxo-3-phenylpropan-2-yl)amino)-1-oxopropan-2-yl)amino)-1-(oxetan-3-yl)-2-oxoethyl)carbamate A solution of LiOH (70 mg, 2.8 mmol) in water (10 mL) was added to a solution of (S)-Methyl 2-((S)-2-(benzyloxycarbonylamino)-2-(oxetan-3-yl)acetamido)-3-(4-methoxyphenyl)propanoate (0.50 g, 0.94 mmol) in tetrahydrofuran (THF; 50 mL) at 0° C. with stirring. The reaction mixture was stirred for 3 h and then acidified with 2 N aqueous HCl to pH=3. Most of the solvent was removed and the remaining mixture was extracted with EtOAc (50 mL×3). The combined organic phases were washed with brine (50 mL×1), dried over anhydrous sodium sulfate and concentrated to afford the corresponding acid (0.50 g), which was used directly without further purification. HATU (380 mg, 1.0 mmol) and DIPEA (0.62 mL, 3.6 mmol) were added to a solution of the acid (0.5 g, 0.9 mmol) and (S)-2-amino-1-((R)-2-methyloxiran-2-yl)-3-phenylpropan-1-one (TFA salt, 290 mg, 0.9 mmol) in DMF (20 mL) at 0° C. with stirring. The suspension was stirred for 1 h at room temperature and then diluted with EtOAc (100 mL). The resulting mixture was washed with 5% aqueous $KHSO_4$ (50 mL×3), saturated aqueous $NaHCO_3$ (50 mL×3) and brine (50 mL×1), respectively. The organic phase was dried over anhydrous sodium sulfate and concentrated. The residue was purified by flash column chromatography on silica gel (Hexane/EtOAc=3:1) to afford Benzyl ((S)-2-((S)-3-(4-methoxyphenyl)-1-(((S)-1-((R)-2-methyloxiran-2-yl)-1-oxo-3-phenylpropan-2-yl)amino)-1-oxopropan-2-yl) amino)-1-(oxetan-3-yl)-2-oxoethyl)carbamate (200 mg, 35% yield) as a white solid.

$^1$H NMR (300 MHz, $CDCl_3$): δ 7.30~7.50 (m, 5H), 7.20~7.30 (m, 2H), 7.08 (d, J=8.4 Hz, 2H), 6.95~7.05 (m, 2H), 6.80 (d, J=8.4 Hz, 2H), 6.70 (m, 1H), 6.15 (m, 1H), 5.40 (m, 1H), 5.15 (2d, 2H), 4.60~4.80 (m, 3H), 4.30~4.50 (m, 4H), 3.78 (s, 3H), 3.28 (m, 2H), 3.10 (m, 1H), 2.90~3.00 (m, 2H), 2.70 (m, 1H), 1.60~1.70 (m, 4H), 1.51 (s, 3H). LC-MS for $C_{35}H_{39}N_3O_8$. found 630.4 [M+H]+.

Example 3

Type A3

(R)—N—((S)-3-(4-methoxyphenyl)-1-(((S)-1-((R)-2-methyloxiran-2-yl)-1-oxo-3-phenylpropan-2-yl) amino)-1-oxopropan-2-yl)-5-oxopyrrolidine-2-carboxamide

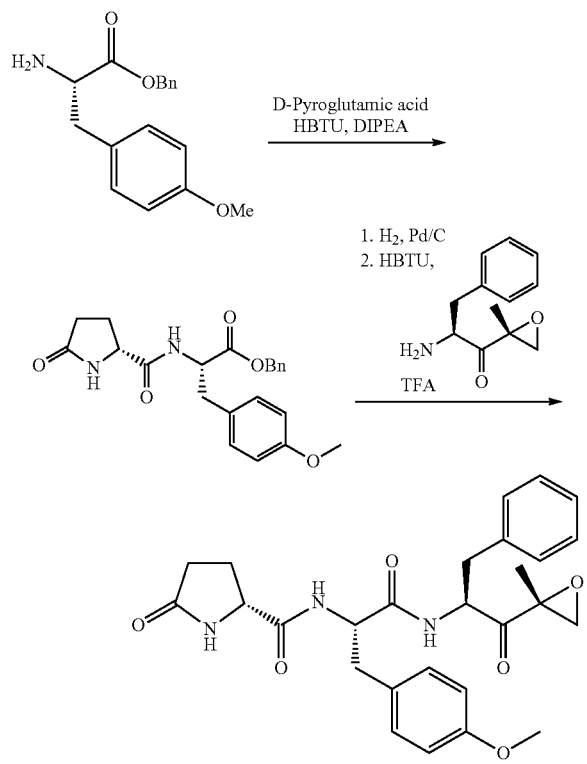

(S)-Benzyl 3-(4-methoxyphenyl)-2-((R)-5-oxopyrrolidine-2-carboxamido) propanoate To a solution of (S)-benzyl 2-amino-3-(4-methoxyphenyl) propanoate (1.0 g, 2.26 mmol) in DMF (10 mL) at 0° C. were added HBTU (1.02 g, 2.7 mmol) and HOBt (457 mg, 3.39 mmol). The mixture was stirred for 5 min and D-pyroglutamic acid (321 mg, 2.5 mmol) and DIPEA (1.58 mL, 9.04 mmol) were added. The reaction mixture was stirred at room temperature for 30 min and saturated sodium bicarbonate (50 mL) was added. The resulting mixture was extracted with ethyl acetate (50 mL×2) and the combined extracts were washed with brine (50 mL), dried over anhydrous $Na_2SO_4$ and concentrated. The residue was purified by flash column chromatography on silica gel (Heptane to Heptane/EtOAc=2:3) to afford (S)-benzyl 3-(4-methoxyphenyl)-2-((R)-5-oxopyrrolidine-2-carboxamido) propanoate (800 mg, 89% yield) as a white solid.

(R)—N—((S)-3-(4-methoxyphenyl)-1-(((S)-1-((R)-2-methyloxiran-2-yl)-1-oxo-3-phenylpropan-2-yl) amino)-1-oxopropan-2-yl)-5-oxopyrrolidine-2-carboxamide To a solution of (S)-benzyl 3-(4-methoxyphenyl)-2-((R)-5-oxopyrrolidine-2-carboxamido) propanoate (800 mg, 2.02 mmol) in THF (10 mL) was added Pd/C (10%, 500 mg). The suspension was stirred under hydrogen atmosphere at room temperature for 4 h. The catalyst was filtered off and washed with MeOH (5 mL). The filtrate and washings were combined and concentrated to dryness to afford the corresponding acid (700 mg, quantitative), which was used directly without further purification.

To a solution of the acid (700 mg, 2.29 mmol) in DMF (7 mL) at 0° C. was added HBTU (1.3 g, 3.44 mmol). The mixture was stirred for 5 min and compound (S)-2-amino-1-((R)-2-methyloxiran-2-yl)-3-phenylpropan-1-one (469 mg, 2.29 mmol) and DIPEA (1.59 mL, 9.16 mmol) were added. The reaction mixture was stirred at room temperature for 30 min and saturated sodium bicarbonate (50 mL) was added. The resulting mixture was extracted with ethyl acetate (50 mL×2) and the combined extracts were washed with brine (50 mL), dried over anhydrous $Na_2SO_4$ and concentrated. The residue was purified by flash column chromatography on silica gel (DCM/MeOH=50:1 to 10:1) to afford (R)—N—((S)-3-(4-methoxyphenyl)-1-(((S)-1-((R)-2-methyloxiran-2-yl)-1-oxo-3-phenylpropan-2-yl)amino)-1-oxopropan-2-yl)-5-oxopyrrolidine-2-carboxamide (220 mg, 22% yield over two steps) as a white solid.

$^1$H NMR (300 MHz, $CDCl_3$): δ 7.28~7.23 (m, 5H), 7.19-7.08 (m, 5H), 7.05 (q, J=3.7 Hz, 2H), 7.00 (dd, J=7.4, 2.0 Hz, 2H), 6.81 (d, J=8.4 Hz, 1H), 6.70 (br s, 1H), 6.55 (d, J=7.2 Hz, 1H), 4.74 (m, 1H), 4.65~4.62 (m, 1H), 4.03 (m, 1H), 3.79 (s, 3H), 3.27 (d, J=4.8 Hz, 1H), 3.11 (d, J=4.5 Hz, 1H), 3.07 (d, J=4.8 Hz, 1H), 2.98 (m, 2H), 2.68 (dd, J=13.8, 8.1 Hz, 1H), 2.30 (m, 1H), 2.22 (m, 2H), 2.20 (m, 3H), 1.48 (s, 3H). MS (EI) for $C_{27}H_{31}N_3O_6$. found 494.2 [M+H]+.

The following compounds were synthesized in a similar manner:

(S)—N—((S)-3-(4-methoxyphenyl)-1-(((S)-1-((R)-2-methyloxiran-2-yl)-1-oxo-3-phenylpropan-2-yl)amino)-1-oxopropan-2-yl)-5-oxopyrrolidine-2-carboxamide (C-3013): $^1$H NMR (300 MHz, $CDCl_3$): δ 7.28~7.23 (m, 5H), 7.19-7.08 (m, 5H), 7.07 (m, 2H), 7.00 (dd, J=7.4, 2.0 Hz, 2H), 6.82 (d, J=8.4 Hz, 1H), 6.70 (br s, 1H), 6.55 (d, J=7.2 Hz, 1H), 4.74 (m, 1H), 4.65-4.62 (m, 1H), 4.03 (m, 1H), 3.79 (s, 3H), 3.27 (d, J=4.8 Hz, 1H), 3.11 (d, J=4.5 Hz, 1H), 3.07 (d, J=4.8 Hz, 1H), 2.98 (m, 2H), 2.68 (dd, J=13.8, 8.1 Hz, 1H), 2.30 (m, 1H), 2.22 (m, 2H), 2.20 (m, 3H), 1.48 (s, 3H). MS (EI) for C27H31N3O6. found 494.1 [M+H]+.

Example 4

Type D

Preparation of (S)-2-((S)-2-(2-(2-aminothiazol-5-yl)acetamido)propanamido)-N—((S)-3-(cyclopent-1-en-1-yl)-1-((R)-2-methyloxiran-2-yl)-1-oxopropan-2-yl)-3-(4-methoxyphenyl)propanamide (C-2066)

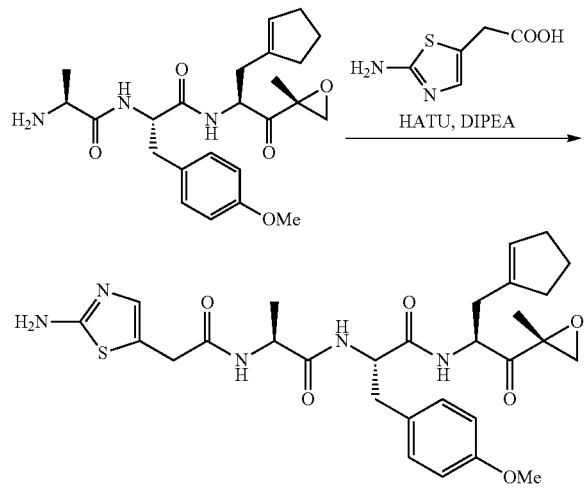

HATU (635 mg, 1.68 mmol) and DIPEA (0.78 mL, 4.48 mmol) were added to a solution of (S)-2-((S)-2-aminopropanamido)-N—((S)-3-(cyclopent-1-en-1-yl)-1-((R)-2-methyloxiran-2-yl)-1-oxopropan-2-yl)-3-(4-methoxyphenyl)propanamide (TFA salt, 600 mg, 1.11 mmol) and 2-(2-aminothiazol-5-yl)acetic acid (175 mg, 1.11 mmol) in DMF (10 mL) at 0° C. The reaction mixture was allowed to warm to room temperature and stirred for 1 h. The mixture was concentrated and the residue was purified by flash column chromatography on silica gel (CH2Cl2/MeOH=50:1) to afford the title compound (150 mg, 23% yield) as a white solid.

$^1$H NMR (300 MHz, DMSO-d6): δ 8.31 (d, J=7.2 Hz, 1H), 8.11 (d, J=7.5 Hz, 1H), 7.93 (d, J=8.1 Hz, 1H), 7.09 (d, J=8.4 Hz, 1H), 6.79-6.64 (m, 5H), 5.39 (br s, 2H), 4.49 (m, 2H), 4.42 (m, 1H), 3.70 (s, 3H), 3.42 (m, 2H), 3.17 (d, J=4.8 Hz, 1H), 2.98 (d, J=4.8 Hz, 1H), 2.86 (m, 1H), 2.66 (m, 1H), 2.41 (m, 1H), 2.23 (m, 5H), 1.81 (m, 2H), 1.37 (s, 3H), 1.11 (d, J=4.8 Hz, 3H). LC-MS for $C_{29}H_{37}N_5O_6S$. found 584.91 [M+H]+.

The following compounds were synthesized in a similar manner:

(S)—N—((S)-3-(cyclopent-1-en-1-yl)-1-((R)-2-methyloxiran-2-yl)-1-oxopropan-2-yl)-2-((S)-2-(2-(2-(dimethylamino)thiazol-5-yl)acetamido)propanamido)-3-(4-methoxyphenyl)propanamide (C-2067): $^1$H NMR (300 MHz, DMSO-d6): δ 8.23 (d, J=7.2 Hz, 1H), 8.18 (d, J=6.9 Hz, 1H), 7.93 (d, J=7.8 Hz, 1H), 7.08 (d, J=8.4 Hz, 2H), 6.85 (s, 1H), 6.78 (d, J=8.4 Hz, 2H), 5.38 (s, 1H), 4.40~4.60 (m, 2H), 4.20 (m, 1H), 3.69 (s, 3H), 3.48 (m, 2H), 3.18 (m, 1H), 2.80~3.10 (m, 8H), 2.65 (m, 1H), 2.40 (m, 1H), 2.10~2.30 (m, 5H), 1.70~1.90 (m, 2H), 1.37 (s, 3H), 1.12 (d, J=6.9 Hz, 3H). LC-MS for $C_{31}H_{41}N_5O_6S$. found 610.33 [M–H]−.

(S)-2-((S)-2-(2-(azetidin-1-yl)thiazol-5-yl)acetamido)propanamido)-N—((S)-3-(cyclopent-1-en-1-yl)-1-((R)-2-methyloxiran-2-yl)-1-oxopropan-2-yl)-3-(4-methoxyphenyl)propanamide (C-2068): $^1$H NMR (300 MHz, DMSO-d6): δ 8.25 (d, J=6.6 Hz, 1H), 8.18 (d, J=6.9 Hz, 1H), 7.93 (d, J=7.5 Hz, 1H), 7.08 (d, J=8.4 Hz, 2H), 6.84 (s, 1H), 6.78 (d, J=8.4 Hz, 2H), 5.38 (m, 1H), 4.40~4.60 (m, 2H), 4.20 (m, 1H), 3.95 (m, 4H), 3.69 (s, 3H), 3.48 (m, 2H), 3.18 (m, 1H), 3.00 (m, 1H), 2.90 (m, 1H), 2.50~2.80 (m, 2H), 2.30~2.50 (m, 4H), 2.10~2.30 (m, 5H), 1.70~1.90 (m, 2H), 1.37 (s, 3H), 1.12 (d, J=6.9 Hz, 3H). LC-MS for $C_{32}H_{41}N_5O_6S$. found 623.72 [M+H]+.

(S)—N—((S)-3-(cyclopent-1-en-1-yl)-1-((R)-2-methyloxiran-2-yl)-1-oxopropan-2-yl)-3-(4-methoxyphenyl)-2-((S)-2-(2-(2-(pyrrolidin-1-yl)thiazol-5-yl)acetamido)propanamido)propanamide (C-2069): $^1$H NMR (300 MHz, DMSO-d6): δ 8.25 (d, J=6.9 Hz, 1H), 8.15 (d, J=7.2 Hz, 1H), 7.93 (d, J=7.2 Hz, 1H), 7.08 (d, J=8.4 Hz, 2H), 6.84 (s, 1H), 6.78 (d, J=8.4 Hz, 2H), 5.38 (s, 1H), 4.40~4.60 (m, 2H), 4.20 (m, 1H), 3.69 (s, 3H), 3.50 (m, 2H), 3.30 (m, 4H), 3.18 (m, 1H), 3.00 (m, 1H), 2.90 (m, 1H), 2.65 (m, 1H), 2.40 (m, 1H), 2.10~2.30 (m, 5H), 1.90~2.00 (m, 4H), 1.85 (m, 2H), 1.37 (s, 3H), 1.12 (d, J=6.9 Hz, 3H). LC-MS for $C_{33}H_{43}N_5O_6S$. found 638.64 [M+H]+.

(S)-2-((S)-2-(2-(2-aminooxazol-5-yl)acetamido)propanamido)-N—((S)-3-(cyclopent-1-en-1-yl)-1-((R)-2-methyloxiran-2-yl)-1-oxopropan-2-yl)-3-(4-methoxyphenyl)propanamide (C-2070): $^1$H NMR (300 MHz, DMSO-d6): δ 8.29 (d, J=7.2 Hz, 1H), 8.11 (d, J=7.5 Hz, 1H), 7.98 (d, J=8.4 Hz, 1H), 7.11 (d, J=8.4 Hz, 2H), 6.79 (d, J=8.4 Hz, 2H), 6.38 (m, 3H), 5.39 (br s, 1H), 4.49 (m, 2H), 4.42 (m, 1H), 3.70 (s, 3H), 3.17 (d, J=7.6 Hz, 1H), 2.98 (d, J=5.1 Hz, 1H), 2.86 (m, 1H), 2.66 (m, 1H), 2.37 (m, 1H), 2.21 (m, 5H), 1.81 (m, 2H), 1.37 (s, 3H), 1.11 (d, J=4.8 Hz, 3H). LC-MS for $C_{29}H_{37}N_5O_7$. found 568.76 [M+H]+.

(S)-2-acetamido-3-hydroxy-N—((S)-3-(4-methoxyphenyl)-1-(((S)-1-((R)-2-methyloxiran-2-yl)-1-oxo-3-phenylpropan-2-yl)amino)-1-oxopropan-2-yl)propanamide utilizing (S)-2-amino-3-hydroxy-N—((S)-3-(4-methoxyphenyl)-1-(((S)-1-((R)-2-methyloxiran-2-yl)-1-oxo-3-phenylpropan-2-yl)amino)-1-oxopropan-2-yl)propanamide and corresponding activated acid (C-2007): $^{1H}$ NMR (400 MHz, CDCl3): δ 7.43 (d, J=8.2 Hz, 1H), 7.14 (d, J=8.4 Hz, 1H), 7.07 (d, J=8.7 Hz, 2H), 6.86 (d, J=8.6 Hz, 2H), 6.78 (d, J=8.7 Hz, 2H), 6.70 (d, J=8.6 Hz, 2H), 6.57 (d, J=7.7 Hz, 1H), 6.22 (d, J=7.6 Hz, 1H), 6.11 (s, 1H), 4.69 (td, J=8.1, 4.7 Hz, 1H), 4.48 (q, J=7.2 Hz, 1H), 4.38 (p, J=6.9 Hz, 1H), 3.77 (s, 3H), 3.73-3.65 (m, 5H), 3.22 (d, J=4.9 Hz, 1H), 3.09-2.79 (m, 8H), 2.58 (dd, J=14.1, 8.3 Hz, 1H), 2.53-2.39 (m, 4H), 1.63 (s, 3H), 1.51 (s, 3H), 1.30 (s, 3H). MS (EI) for $C_{27}H_{33}N_3O_7$. found 512.3 [M+H]+.

(S)-2-((S)-2-(3-hydroxypropanamido)propanamido)-3-(4-methoxyphenyl)-N—((S)-1-((R)-2-methyloxiran-2-yl)-1-oxo-3-phenylpropan-2-yl)propanamide utilizing (S)-2-((S)-2-aminopropanamido)-3-(4-methoxyphenyl)-N—((S)-1-((R)-2-methyloxiran-2-yl)-1-oxo-3-phenylpropan-2-yl)propanamide and corresponding activated acid (C-2012): $^1$H NMR (400 MHz, DMSO-d6): δ 8.34 (d, J=7.2 Hz, 1H), 7.96 (d, J=7.2 Hz, 1H), 7.78 (d, J=8.4 Hz, 1H), 7.31-7.22 (m, 5H), 7.06 (d, J=8.4 Hz, 1H), 6.77 (d, J=8.4 Hz, 1H), 4.64-4.57 (m, 2H), 4.39-4.38 (m, 1H), 4.21-4.19 (m, 1H), 3.70 (s, 3H), 3.58-3.56 (m, 2H), 3.17 (d, J=4.8 Hz, 1H), 2.98-2.91 (m, 3H), 2.74-2.64 (m, 2H), 2.25-2.22 (m, 2H), 1.34 (s, 3H), 1.07 (d, J=7.2 Hz, 3H). MS (EI) for $C_{28}H_{35}N_3O_7$. found 526.3 [M+H]+.

(S)-2-((S)-2-(3-(methoxymethoxy)propanamido)propanamido)-3-(4-methoxyphenyl)-N—((S)-1-((R)-2-methyloxiran-2-yl)-1-oxo-3-phenylpropan-2-yl)propanamide utilizing (S)-2-((S)-2-aminopropanamido)-3-(4-methoxyphenyl)-N—((S)-1-((R)-2-methyloxiran-2-yl)-1- oxo-3-phenylpropan-2-yl)propanamide and corresponding activated acid (C-2013): $^1$H NMR (400 MHz, DMSO-d$_6$): δ 8.38 (d, J=7.2 Hz, 1H), 7.98 (d, J=7.2 Hz, 1H), 7.78 (d, 8.0 Hz, 1H), 7.31-7.20 (m, 5H), 7.06 (d, J=8.4 Hz, 2H), 6.77 (d, J=8.4 Hz, 2H), 4.58-4.57 (m, 1H), 4.48 (s, 2H), 4.41-4.40 (m, 2H), 4.23-4.19 (m, 1H), 3.70 (s, 3H), 3.63-3.58 (m, 2H), 3.19-3.16 (m, 4H), 2.98-2.86 (m, 3H), 2.74-2.65 (m, 2H), 2.37-2.30 (m, 2H), 1.45 (s, 3H), 1.07 (d, J=6.8 Hz, 3H). MS (EI) for $C_{30}H_{39}N_3O_8$. found 570.57 [M+H]+.

N—((S)-1-(((S)-3-(4-methoxyphenyl)-1-(((S)-1-((R)-2-methyloxiran-2-yl)-1-oxo-3-phenylpropan-2-yl)amino)-1-oxopropan-2-yl)amino)-1-oxopropan-2-yl)-3-methyl-1H-indene-2-carboxamide utilizing (S)-2-((S)-2-aminopropanamido)-3-(4-methoxyphenyl)-N—((S)-1-((R)-2-methyloxiran-2-yl)-1-oxo-3-phenylpropan-2-yl) propanamide and corresponding activated acid (C-2049): $^1$H NMR (400 MHz, CD$_3$OD) δ 7.49 (t, J=5.7, 5.7 Hz, 2H), 7.44-7.28 (m, 2H), 7.28-7.09 (m, 5H), 7.03 (d, J=8.6 Hz, 2H), 6.65 (d, J=8.6 Hz, 2H), 4.75 (dd, J=9.1, 4.6 Hz, 1H), 4.54 (d, J=14.0 Hz, 1H), 4.48 (d, J=24.2 Hz, 1H), 3.66-3.47 (m, 5H), 3.21 (d, J=5.0 Hz, 1H), 3.06 (d, J=14.0 Hz, 1H), 2.98 (dd, J=13.9, 5.8 Hz, 1H), 2.91 (d, J=5.0 Hz, 1H), 2.81 (dd, J=13.9, 8.2 Hz, 1H), 2.72 (dd, J=13.8, 9.2 Hz, 1H), 2.43 (t, J=2.2, 2.2 Hz, 3H), 1.41 (s, 3H), 1.33 (d, J=7.1 Hz, 3H). LC-MS for $C_{32}H_{39}N_5O_6$. found 610.0 [M+H]+.

3-hydroxy-N—((R)-1-(((S)-3-(4-methoxyphenyl)-1-(((S)-1-((R)-2-methyloxiran-2-yl)-1-oxo-3-phenylpropan-2-yl)amino)-1-oxopropan-2-yl)amino)-1-oxopropan-2-yl)-3-methylbutanamide utilizing (S)-2-((R)-2-aminopropanamido)-3-(4-methoxyphenyl)-N—((S)-1-((R)-2-methyloxiran-2-yl)-1-oxo-3-phenylpropan-2-yl) propanamide and corresponding activated acid (C-2056): $^1$H NMR (400 MHz, DMSO-d6) δ 8.41 (d, J=7.3 Hz, 1H), 8.07 (d, J=8.7 Hz, 1H), 7.95 (d, J=7.4 Hz, 1H), 7.34-7.17 (m, 5H), 7.09 (d, J=8.7 Hz, 2H), 6.78 (d, J=8.8 Hz, 2H), 4.76 (s, 1H), 4.58 (ddd, J=9.2, 7.6, 4.6 Hz, 1H), 4.50-4.40 (m, 1H), 4.22 (p, J=7.4 Hz, 1H), 3.69 (s, 3H), 3.67-3.57 (m, 1H), 3.22 (d, J=5.1 Hz, 1H), 3.18-3.10 (m, 1H), 3.01-2.89 (m, 3H), 2.79-2.67 (m, 1H), 2.61-2.53 (m, 1H), 2.19 (s, 1H), 2.07 (s, 1H), 1.34 (s, 3H), 1.28-1.19 (m, 6H), 1.11 (d, J=4.7 Hz, 5H), 0.94 (d, J=7.0 Hz, 3H). LC-MS for $C_{30}H_{39}N_3O_7$. found 554.2 [M+H]+

N—((R)-1-(((S)-3-(4-methoxyphenyl)-1-(((S)-1-((R)-2-methyloxiran-2-yl)-1-oxo-3-phenylpropan-2-yl)amino)-1-oxopropan-2-yl)amino)-1-oxopropan-2-yl)-1H-indene-2-carboxamide utilizing (S)-2-((R)-2-aminopropanamido)-3-(4-methoxyphenyl)-N—((S)-1-((R)-2-methyloxiran-2-yl)-1-oxo-3-phenylpropan-2-yl)propanamide and corresponding activated acid (C-2057): $^1$H NMR (400 MHz, DMSO-d6) δ 8.44 (d, J=7.3 Hz, 1H), 8.15 (d, J=7.2 Hz, 1H), 8.03 (d, J=8.7 Hz, 1H), 7.95 (s, 1H), 7.63 (s, OH), 7.57-7.49 (m, 1H), 7.37-7.25 (m, 6H), 7.24-7.16 (m, 1H), 7.07 (d, J=8.7 Hz, 2H), 6.72 (d, J=8.7 Hz, 2H), 4.65-4.52 (m, 1H), 4.51-4.41 (m, 1H), 4.40-4.30 (m, 1H), 3.63 (s, 3H), 3.22 (d, J=5.3 Hz, 1H), 3.00-2.90 (m, 3H), 2.89 (s, 2H), 2.78 (dd, J=13.9, 9.3 Hz, 1H), 2.73 (s, 1H), 2.61 (dd, J=13.8, 10.1 Hz, 1H), 1.34 (s, 3H), 1.09 (d, J=7.2 Hz, 3H). LC-MS for $C_{30}H_{39}N_3O_7$. found 594.2 [M−H]−

N—((R)-1-(((S)-3-(4-methoxyphenyl)-1-(((S)-1-((R)-2-methyloxiran-2-yl)-1-oxo-3-phenylpropan-2-yl)amino)-1-oxopropan-2-yl)amino)-1-oxopropan-2-yl)cyclopent-1-enecarboxamide utilizing (S)-2-((R)-2-aminopropanamido)-3-(4-methoxyphenyl)-N—((S)-1-((R)-2-methyloxiran-2-yl)-1-oxo-3-phenylpropan-2-yl)propanamide and corresponding activated acid (C-2058): $^1$H NMR (400 MHz,) δ 8.40 (d, J=7.3 Hz, 1H), 8.28-8.03 (m, 2H), 7.99 (d, J=8.7 Hz, 1H), 7.95 (s, 1H), 7.71 (d, J=7.2 Hz, 1H), 7.33-7.24 (m, 3H), 7.24-7.17 (m, 1H), 7.07 (d, J=8.7 Hz, 2H), 6.76 (d, J=8.7 Hz, 2H), 6.53 (t, J=1.9 Hz, 1H), 4.58 (ddd, J=9.2, 7.3, 4.6 Hz, 2H), 4.42 (td, J=10.1, 4.0 Hz, 1H), 4.24 (t, J=7.2 Hz, 1H), 3.69 (s, 3H), 3.62 (pd, J=6.6, 4.0 Hz, 3H), 3.22 (d, J=5.4 Hz, 1H), 3.14 (qd, J=7.4, 4.3 Hz, 4H), 3.02-2.90 (m, 3H), 2.89 (s, 3H), 2.73 (s, 3H), 2.69 (s, 4H), 2.58 (dd, J=13.7, 10.2 Hz, 1H), 2.47-2.37 (m, 4H), 1.85 (p, J=7.7 Hz, 2H), 1.35 (s, 3H), 1.31-1.19 (m, 31H), 1.02 (d, J=7.1 Hz, 3H). LC-MS for $C_{32}H_{39}N_5O_6$. found 548.0 [M+H]+.

Example 5

Type E

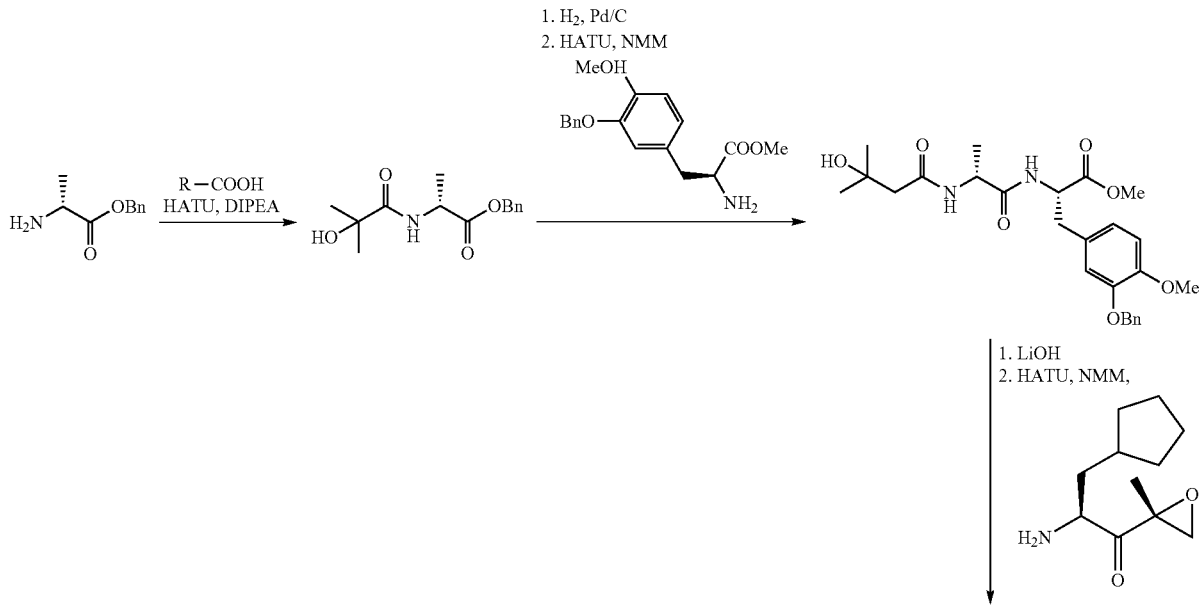

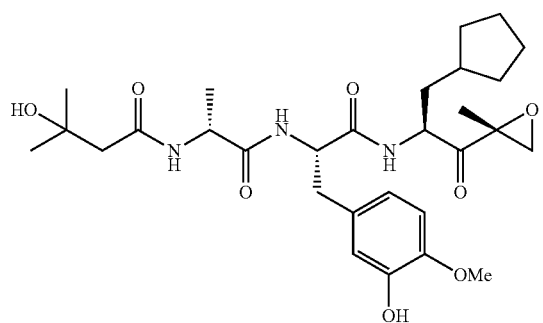 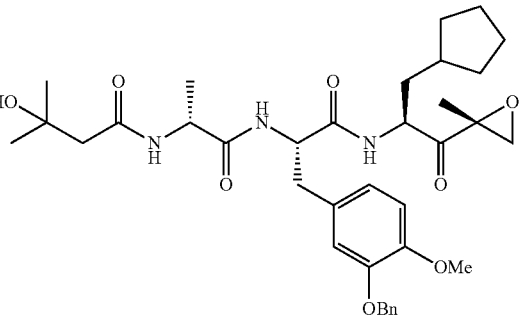

Preparation of N—((R)-1-(((S)-1-(((S)-3-cyclopentyl-1-((R)-2-methyloxiran-2-yl)-1-oxopropan-2-yl)amino)-3-(3-hydroxy-4-methoxyphenyl)-1-oxopropan-2-yl)amino)-1-oxopropan-2-yl)-3-hydroxy-3-methylbutanamide (C-2059)

(R)-Benzyl 2-(3-hydroxy-3-methylbutanamido)propanoate

DIPEA (8.9 mL, 77 mmol) was added to a mixture of 3-hydroxy-3-methylbutanoic acid (2.2 g, 18.6 mmol), (R)-benzyl 2-aminopropanoate hydrochloride (3.7 g, 17.1 mmol) and HATU (7.2 g, 18.9 mmol) in dichloromethane (50 mL) at 0° C. The reaction mixture was stirred for 1 h at room temperature. Water (100 mL) was added and the two layers were separated. The aqueous layer was extracted with dichloromethane (100 mL×3). The organic phases were combined, dried over anhydrous sodium sulfate and concentrated. The residue was purified by flash column chromatography on silica gel (petroleum ether/ethyl acetate=10:1 to 3:1) to give (R)-benzyl 2-(3-hydroxy-3-methylbutanamido)propanoate (4.7 g, 98% yield).

(S)-Methyl 3-(3-(benzyloxy)-4-methoxyphenyl)-2-((R)-2-(3-hydroxy-3-methyl butanamido)propanamido)propanoate (R)-Benzyl 2-(3-hydroxy-3-methylbutanamido)propanoate (4.7 g, 16.8 mmol) was hydrogenated in the presence of Pd/C (0.5 g) in methanol (20 mL) for 1 h at room temperature. Pd/C was filtered off and the filtrate was concentrated to give the corresponding acid (3.0 g) as an off-white solid.

The acid (1.5 g, 7.9 mmol) was dissolved in dichloromethane (30 mL) and (S)-methyl 2-amino-3-(3-(benzyloxy)-4-methoxyphenyl)propanoate (TFA salt, 3.4 g, 7.9 mmol) and HATU (3.3 g, 8.7 mmol) were added. Then N-methylmorpholine (2.4 g, 23.7 mmol) was added to the resulting solution at 0° C. The reaction mixture was stirred for 1 h at room temperature and water (100 mL) was added. The two layers were separated and the aqueous layer was extracted with dichloromethane (100 mL×3). The organic phases were combined, dried over anhydrous sodium sulfate and concentrated. The residue was purified by flash column chromatography on silica gel (dichloromethane/methanol=200:1 to 100:1) to give (S)-methyl 3-(3-(benzyloxy)-4-methoxyphenyl)-2-((R)-2-(3-hydroxy-3-methyl butanamido)propanamido)propanoate (1.5 g, 39% yield).

N—((R)-1-((S)-3-(3-(Benzyloxy)-4-methoxyphenyl)-1-((S)-3-cyclopentyl-1-((R)-2-methyloxiran-2-yl)-1-oxopropan-2-ylamino)-1-oxopropan-2-ylamino)-1-oxopropan-2-yl)-3-hydroxy-3-methylbutanamide (S)-Methyl 3-(3-(benzyloxy)-4-methoxyphenyl)-2-((R)-2-(3-hydroxy-3-methyl butanamido)propanamido)propanoate (1.5 g, 3.1 mmol) was treated with a solution of lithium hydroxide-H2O (0.26 g, 6.2 mmol) in water/THF (10 mL/4 mL) for 30 min. THF was removed and the aqueous phase was acidified to pH=3-4 with 10% aqueous KHSO4. The resulting mixture was extracted with ethyl acetate (50 mL×3). The organic extracts were combined, dried over anhydrous sodium sulfate and concentrated to give the corresponding acid (1.2 g) as a yellow solid. The acid (0.63 g, 1.3 mmol) was dissolved in dichloromethane (30 mL) and (S)-2-amino-3-cyclopentyl-1-((R)-2-methyloxiran-2-yl)propan-1-one (TFA salt, 0.4 g, 1.3 mmol) and HATU (0.56 g, 1.4 mmol) were added. N-Methylmorpholine (0.33 g, 3.2 mmol) was added to the resulting solution at 0° C. The reaction mixture was stirred for 1 h at room temperature and water (100 mL) was added. The two layers were separated and the aqueous layer was extracted with dichloromethane (100 mL×3). The organic phases were combined, dried over anhydrous sodium sulfate and concentrated. The residue was purified by flash column chromatography on silica gel (dichloromethane/methanol=200:1 to 100:1) to give N—((R)-1-(((S)-3-(3-(benzyloxy)-4-methoxyphenyl)-1-((S)-3-cyclopentyl-1-((R)-2-methyloxiran-2-yl)-1-oxopropan-2-ylamino)-1-oxopropan-2-ylamino)-1-oxopropan-2-yl)-3-hydroxy-3-methylbutanamide (0.3 g, 35% yield).

N—((R)-1-(((S)-1-(((S)-3-cyclopentyl-1-((R)-2-methyloxiran-2-yl)-1-oxopropan-2-yl)amino)-3-(3-hydroxy-4-methoxyphenyl)-1-oxopropan-2-yl)amino)-1-oxopropan-2-yl)-3-hydroxy-3-methylbutanamide N—((R)-1-((S)-3-(3-(Benzyloxy)-4-methoxyphenyl)-1-((S)-3-cyclopentyl-1-((R)-2-methyloxiran-2-yl)-1-oxopropan-2-ylamino)-1-oxopropan-2-ylamino)-1-oxopropan-2-yl)-3-hydroxy-3-methylbutanamide (0.3 g, 0.46 mmol) was hydrogenated in the presence of Pd/C (0.1 g) in methanol (20 mL) for 2 h at 0° C. Pd/C was filtered off and the filtrate was concentrated. The residue was purified by flash column chromatography on silica gel (dichloromethane/methanol=100:1 to 50:1) to afford N—((R)-1-(((S)-1-(((S)-3-cyclopentyl-1-((R)-2-methyloxiran-2-yl)-1-oxopropan-2-yl)amino)-3-(3-hydroxy-4-methoxyphenyl)-1-oxopropan-2-yl)

amino)-1-oxopropan-2-yl)-3-hydroxy-3-methylbutanamide (162 mg, 62% yield) as a white solid.

$^1$H NMR (300 MHz, DMSO-d6): δ 8.70 (s, 1H), 8.21 (d, J=7.2 Hz, 1H), 8.11 (d, J=8.7 Hz, 1H), 7.99 (d, J=7.2 Hz, 1H), 6.76 (d, J=8.4 Hz, 1H), 6.65 (d, J=1.8 Hz, 1H), 6.59 (dd, J=1.8, 8.4 Hz, 1H), 4.77 (s, 1H), 4.31 (m, 1H), 4.26 (m, 2H), 3.72 (s, 3H), 3.23 (d, J=5.4 Hz, 1H), 3.01 (d, J=5.4 Hz, 1H), 2.86 (m, 1H), 2.50 (m, 1H), 2.20 (s, 2H), 1.41-1.93 (m, 11H), 1.41 (s, 3H), 1.12 (s, 6H), 0.98 (d, J=6.9 Hz, 3H). LC-MS for $C_{29}H_{43}N_3O_8$. found 562.3 [M+H]+.

The following compounds were synthesized in a similar manner:

N—((R)-1-(((S)-1-(((S)-3-cyclopentyl-1-((R)-oxiran-2-yl)-1-oxopropan-2-yl)amino)-3-(4-(methylsulfonyl)phenyl)-1-oxopropan-2-yl)amino)-1-oxopropan-2-yl)-3-hydroxy-3-methylbutanamide (C-2055): $^1$H NMR (300 MHz, DMSO-d$_6$): δ 8.39 (d, J=6.9 Hz, 1H), 8.34 (d, J=8.7 Hz, 1H), 8.03 (d, J=6.6 Hz, 1H), 7.84 (d, J=8.1 Hz, 2H), 7.50 (d, J=8.1 Hz, 2H), 4.65 (m, 1H), 4.30 (m, 1H), 4.25 (m, 1H), 3.70 (s, 1H), 3.20 (m, 1H), 3.17 (s, 3H), 3.05 (m, 1H), 2.80~2.90 (m, 2H), 2.20 (s, 2H), 1.40~1.90 (m, 10H), 1.00~1.30 (m, 8H), 0.94 (d, J=7.2 Hz, 3H). LC-MS for $C_{28}H_{41}N_3O_8S$. found 580.3 [M+H]+.

N—((R)-1-(((S)-1-(((S)-3-cyclopentyl-1-((R)-2-methyloxiran-2-yl)-1-oxopropan-2-yl)amino)-3-(4-(methylsulfonyl)phenyl)-1-oxopropan-2-yl)amino)-1-oxopropan-2-yl)-3-hydroxy-3-methylbutanamide (C-2050): $^1$H NMR (300 MHz, DMSO-d$_6$): δ 8.32 (d, J=7.2 Hz, 1H), 8.22 (d, J=9.0 Hz, 1H), 8.00 (d, J=6.9 Hz, 1H), 7.81 (d, J=8.4 Hz, 2H), 7.47 (d, J=8.4 Hz, 2H), 4.65 (m, 1H), 4.30 (m, 1H), 4.25 (m, 1H), 3.20 (m, 2H), 3.17 (s, 3H), 3.10 (m, 1H), 3.00 (m, 1H), 2.80 (m, 1H), 1.40~1.90 (m, 13H), 1.40 (s, 3H), 1.00~1.30 (m, 9H), 0.94 (d, J=6.9 Hz, 3H). LC-MS for $C_{29}H_{43}N_3O_8S$. found 594.3 [M+H]$^+$ N—((R)-1-(((S)-1-(((S)-3-(cyclopent-1-en-1-yl)-1-((R)-2-methyloxiran-2-yl)-1-oxopropan-2-yl)amino)-3-(3-hydroxy-4-methoxyphenyl)-1-oxopropan-2-yl)amino)-1-oxopropan-2-yl)-3-hydroxy-3-methylbutanamide with order final coupling and deprotection of the benzyl acid switched (C-2060): $^1$H NMR (300 MHz, DMSO-d$_6$): δ 8.71 (s, 1H), 8.25 (d, J=7.5 Hz, 1H), 8.09 (d, J=8.4 Hz, 1H), 7.97 (d, J=6.6 Hz, 1H), 6.75 (d, J=8.1 Hz, 1H), 6.66 (m, 1H), 6.58 (d, J=7.8 Hz, 1H), 5.41 (s, 1H), 4.78 (s, 1H), 4.51 (m, 2H), 4.27 (m, 1H), 3.71 (s, 3H), 3.23 (d, J=4.2 Hz, 1H), 2.99 (d, J=4.8 Hz, 1H), 2.84 (m, 1H), 2.40 (m, 1H), 2.24 (m, 6H), 1.81 (m, 2H), 1.38 (s, 3H), 1.12 (s, 6H), 0.90 (d, J=6.9 Hz, 3H). LC-MS for $C_{29}H_{41}N_3O_8$. found 582.4 [M+Na]$^+$.

Example 6

Type F

Preparation of N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)-4,4,4-trifluoro-3-hydroxy-3-methylbutanamide (C-2054)

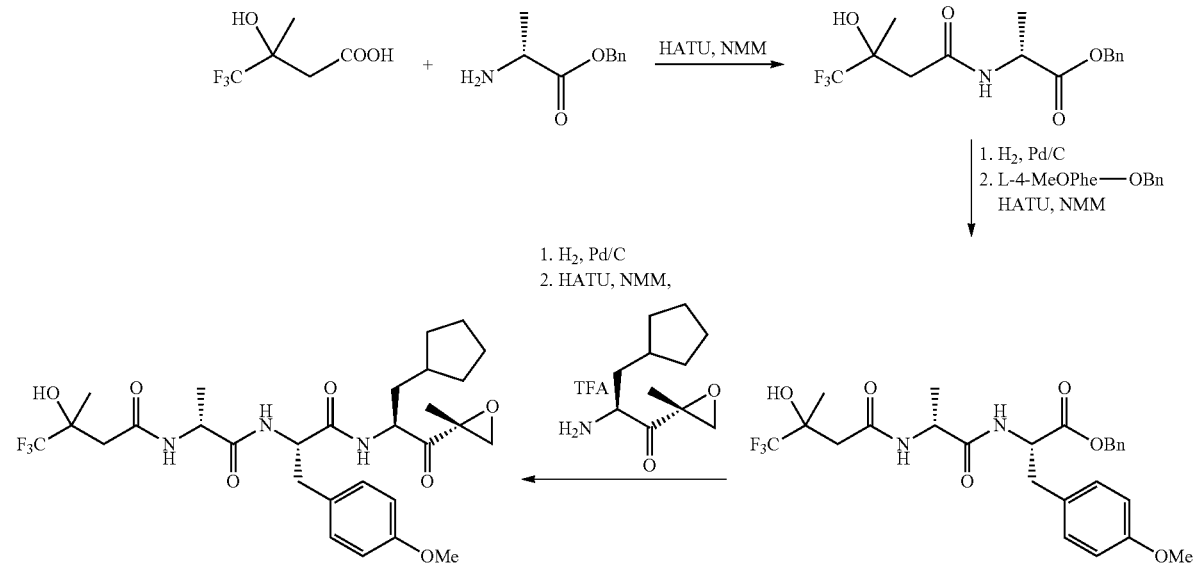

(2R)-Benzyl 2-(4,4,4-trifluoro-3-hydroxy-3-methylbutanamido)propanoate

N-Methylmorpholine (1.17 g, 11.6 mmol) was added to a mixture of 4,4,4-trifluoro-3-hydroxy-3-methylbutanoic acid (1.0 g, 5.8 mmol), (R)-benzyl 2-aminopropanoate hydrochloride (1.25 g, 5.8 mmol) and HATU (2.42 g, 6.4 mmol) in dichloromethane (50 mL) at 0° C. The reaction mixture was stirred for 1 h at room temperature and water (50 mL) was added. The resulting mixture was extracted with dichloromethane (50 mL×3). The organic extracts were combined, dried over anhydrous Na2SO4 and concentrated. The residue was purified by flash column chromatography on silica gel (petroleum ether/ethyl acetate=10:1 to 5:1) to give (2R)-benzyl 2-(4,4,4-trifluoro-3-hydroxy-3-methylbutanamido)propanoate (1.4 g, 72% yield).

(2S)-Benzyl 3-(4-methoxyphenyl)-2-((2R)-2-(4,4,4-trifluoro-3-hydroxy-3-methyl butanamido)propanamido)propanoate (2R)-Benzyl 2-(4,4,4-trifluoro-3-hydroxy-3-methylbutanamido)propanoate (0.63 g, 1.8 mmol) was hydrogenated in the presence of Pd/C (0.1 g) in methanol (20 mL) for 1 h at room temperature. The catalyst was filtered off and the filtrate was concentrated. The residue was dissolved in dichloromethane (30 mL) followed by addition of L-4-MeOPhe-OBn (HCl salt, 0.67 g, 2.0 mmol) and HATU (0.79 g, 2.0 mmol). N-Methylmorpholine (1.1 g, 10.8 mmol) was added to the solution at 0° C. The reaction mixture was stirred for 1 h at room temperature and water (30 mL) was added. The resulting mixture was extracted with dichloromethane (30 mL×3). The organic extracts were combined, dried over anhydrous Na2SO4 and concentrated. The residue was purified by flash column chromatography on silica gel (petroleum ether/ethyl acetate=10:1 to 1:1) to give compound (2S)-Benzyl 3-(4-methoxyphenyl)-2-((2R)-2-(4,4,4-trifluoro-3-hydroxy-3-methyl butanamido)propanamido)propanoate (0.7 g, 76% yield).

N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)-4,4,4-trifluoro-3-hydroxy-3-methylbutanamide (2S)-Benzyl 3-(4-methoxyphenyl)-2-((2R)-2-(4,4,4-trifluoro-3-hydroxy-3-methyl butanamido)propanamido)propanoate (0.7 g, 1.3 mmol) was hydrogenated in the presence of Pd/C (0.1 g) in methanol (20 mL) for 1 h at room temperature. The catalyst was filtered off and the filtrate was concentrated. The residue was dissolved in dichloromethane (30 mL) followed by addition of (S)-2-amino-3-cyclopentyl-1-((R)-2-methyloxiran-2-yl)propan-1-one (0.44 g, 1.3 mmol) and HATU (0.53 g, 1.3 mmol). N-Methylmorpholine (0.8 g, 7.9 mmol) was added to the solution at 0° C. The reaction mixture was stirred for 1 h at room temperature followed by addition of water (30 mL). The resulting mixture was extracted with dichloromethane (30 mL×3). The organic extracts were combined, dried over anhydrous Na2SO4 and concentrated. The residue was purified by flash column chromatography on silica gel (petroleum ether/ethyl acetate=10:1 to 1:1) to afford a mixture of N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)-4,4,4-trifluoro-3-hydroxy-3-methylbutanamide isomers (140 mg, 18% yield).

$^1$H NMR (300 MHz, DMSO-d6): δ 8.27 (m, 1H), 8.17 (m, 2H), 7.13 (d, J=7.8 Hz, 2H), 6.80 (d, J=8.4 Hz, 2H), 6.27 (m, 1H), 4.51 (m, 1H), 4.29 (m, 2H), 3.71 (s, 3H), 3.22 (d, J=4.5 Hz, 1H), 3.02 (d, J=5.1 Hz, 1H), 2.95 (m, 1H), 2.21-2.65 (m, 3H), 1.42 (s, 3H), 1.28 (m, 3H), 1.07-1.93 (m, 11H), 0.96 (d, J=6.6 Hz, 3H). LC-MS for $C_{30}H_{45}N_3O_7$. found 600.2 [M+H]$^+$ The following compounds were synthesized in a similar manner, with the exception that deprotection of benzyl esters was performed with 1.2 eq of LiOH in 2:1 mixture of MeOH:H$_2$O followed by acidification to pH 3 and filtration:

N-(2-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-2-oxoethyl)-3-methyl-1H-indene-2-carboxamide (C-2039): $^1$H NMR (300 MHz, DMSO-d$_6$): δ 7.49 (m, 2H), 7.39 (m, 2H), 7.11 (d, J=8.7 Hz, 2H), 6.80 (m, 1H), 6.72 (d, J=8.7 Hz, 2H), 6.70 (m, 1H), 6.52 (m, 1H), 6.49 (m, 3H), 4.66 (m, 1H), 4.52 (m, 1H), 4.05 (d, J=5.7 Hz, 1H), 3.62 (s, 3H), 3.59 (m, 2H), 3.27 (d, J=5.1 Hz, 1H), 3.10 (m, 1H), 3.06 (m, 1H), 2.88 (d, J=4.8 Hz, 1H), 2.53 (s, 3H), 2.06-1.83 (m, 2H), 1.71-1.70 (m, 3H), 1.68 (m, 3H), 1.48 (s, 3H), 1.28 (m, 1H), 1.11 (m, 1H), 1.06 (m, 1H), 0.90 (m, 1H). LC-MS for $C_{34}H_{41}N_3O_6$. found 588.8 [M+H]$^+$.

N—((R)-1-(((S)-1-(((S)-3-cyclopentyl-1-((R)-2-methyloxiran-2-yl)-1-oxopropan-2-yl)amino)-3-(1H-indol-3-yl)-1-oxopropan-2-yl)amino)-1-oxopropan-2-yl)-3-methyl-1H-indene-2-carboxamide (C-2047): $^1$H NMR (300 MHz, DMSO-d$_6$): δ 10.81 (br s, 1H), 8.25 (d, J=6.9 Hz, 1H), 8.11 (d, J=8.4 Hz, 1H), 7.76 (d, J=6.9 Hz, 1H), 7.58 (d, J=8.1 Hz, 1H), 7.47 (m, 2H), 7.29 (m, 3H), 7.11-6.94 (m, 3H), 4.39 (m, 1H), 4.37 (m, 2H), 3.65 (m, 2H), 3.15 (m, 3H), 3.01 (m, 2H), 2.96 (m, 2H), 2.51 (s, 3H), 1.98 (m, 1H), 1.70 (m, 5H), 1.42 (s, 3H), 1.40 (m, 6H), 1.24 (d, J=6.9 Hz, 3H), 0.80 (m, 2H). LC-MS for $C_{36}H_{42}N_4O_5$. found 611.3 [M+H]$^+$ N—((R)-1-(((S)-3-(4-methoxyphenyl)-1-(((S)-1-((R)-2-methyloxiran-2-yl)-1-oxo-3-phenylpropan-2-yl)amino)-1-oxopropan-2-yl)amino)-1-oxopropan-2-yl)-3-methyl-1H-indene-2-carboxamide (C-2048): $^1$H NMR (300 MHz, DMSO-d$_6$): δ 8.44 (d, J=8.4 Hz, 1H), 8.04 (d, J=8.7 Hz, 1H), 7.74 (d, J=6.9 Hz, 1H), 7.50 (d, J=6.9 Hz, 2H), 7.36-7.23 (m, 7H), 7.10 (d, J=8.1 Hz, 2H), 6.72 (d, J=8.4 Hz, 2H), 4.61 (m, 1H), 4.50 (m, 1H), 4.37 (m, 1H), 3.71 (m, 2H), 3.61 (s, 3H), 3.23 (m, 1H), 3.01 (m, 2H), 2.80~2.52 (m, 4H), 2.40 (s, 3H), 1.42 (s, 3H), 1.10 (d, J=6.9 Hz, 3H). LC-MS for $C_{36}H_{39}N_3O_6$. found 610.3 [M+H]$^+$ Example 7

Type H

Preparation of (R)—N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)-4,5,6,7-tetrahydro-1H-indazole-5-carboxamide (C-2064) and (S)—N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)-4,5,6,7-tetrahydro-1H-indazole-5-carboxamide (C-2065)

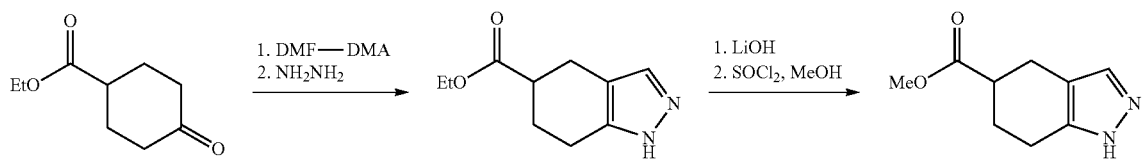

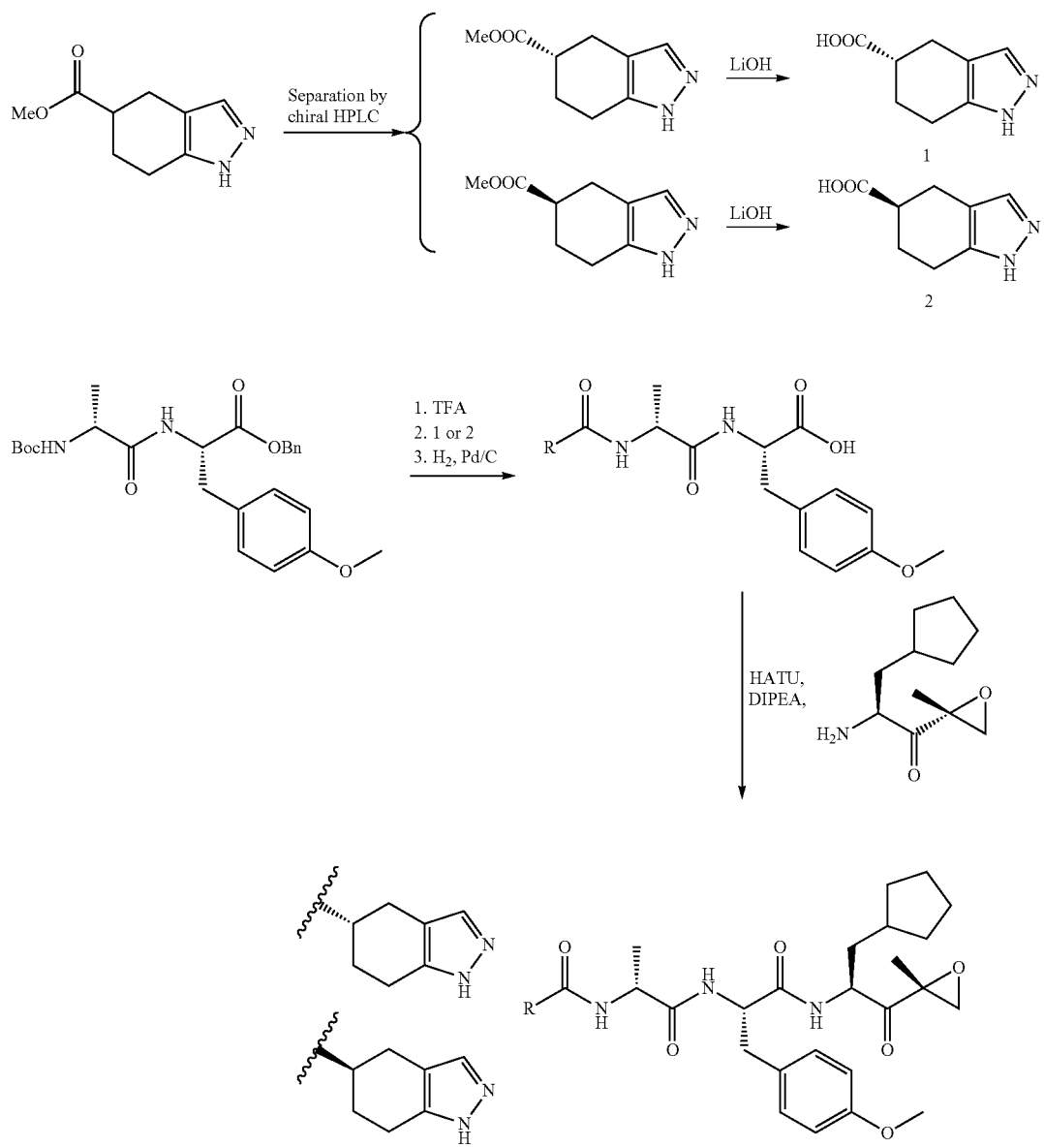

Ethyl 4,5,6,7-tetrahydro-1H-indazole-5-carboxylate

A solution of ethyl 4-oxocyclohexanecarboxylate (50 g, 0.29 mol) in DMF-DMA (275 mL) was heated at 110° C. for 12 h. The mixture was concentrated to afford the desired intermediate, which was used directly without further purification.

A mixture of the intermediate (66.1 g, 0.29 mol) and hydrazine hydrate (73.5 g, 1.47 mol) in ethanol (1000 mL) was heated under reflex overnight. Most of ethanol was removed and the remaining mixture was treated with water (400 mL). The resulting mixture was extracted with EtOAc (400 ml×2). The combined organic layers were washed with brine (400 mL) and concentrated. The residue was purified by flash column chromatography on silica gel (DCM/MeOH=30:1) to afford crude ethyl 4,5,6,7-tetrahydro-1H-indazole-5-carboxylate (18 g) as a white solid.

Methyl 4,5,6,7-tetrahydro-1H-indazole-5-carboxylate

To a solution of ethyl 4,5,6,7-tetrahydro-1H-indazole-5-carboxylate (3.0 g, 15.5 mmol) in methanol (10 mL) were added water (10 mL) and lithium hydroxide hydrate (780 mg, 5.9 mmol). The reaction mixture was stirred at room temperature overnight and then concentrated to remove most of methanol. The remaining mixture was acidified with diluted aqueous HCl to pH=4 and then concentrated. The residue was dried under vacuum to afford the corresponding acid (1.7 g, 66% yield) as a white solid, which was used directly without further purification. A mixture of the acid (1.7 g, 10 mmol) and $SOCl_2$ (2.5 g, 21 mmol) in methanol (20 mL) was heated under reflux for 2 h. The mixture was cooled to room temperature and then concentrated. The residue was purified by flash column chromatography on silica gel (DCM/MeOH=30:1) to afford compound 10 (1.0 g, 55% yield) as a light yellow solid, which was further separated by preparative chiral-HPLC to afford (S)- and (R)-methyl 4,5,6,7-tetrahydro-1H-indazole-5-carboxylate (0.2 g), (0.2 g), respectively.

(S)-4,5,6,7-Tetrahydro-1H-indazole-5-carboxylic acid

To a solution of (S)-methyl 4,5,6,7-tetrahydro-1H-indazole-5-carboxylate (500 mg, 2.8 mmol) in methanol (20 mL) were added water (10 mL) and lithium hydroxide hydrate (234 mg, 5.57 mmol) at 0° C. The reaction mixture was stirred at room temperature for 2 h and then concentrated to remove most of methanol. The remaining mixture was acidified with diluted aqueous HCl to pH=4 and then concentrated. The residue was dried under vacuum to afford (S)-4,5,6,7-tetrahydro-1H-indazole-5-carboxylic acid (380 mg, 81% yield) as a white solid, which was used directly without further purification.

(R)-4,5,6,7-Tetrahydro-1H-indazole-5-carboxylic acid

Prepared from (R)-methyl 4,5,6,7-tetrahydro-1H-indazole-5-carboxylate following the same procedure for (S)-4,5,6,7-Tetrahydro-1H-indazole-5-carboxylic acid.

(S)-3-(4-Methoxyphenyl)-2-((R)-2-((S)-4,5,6,7-tetrahydro-1H-indazole-5-carboxamido)propanamido)propanoic acid To a solution of (S)-benzyl 2-((R)-2-((tert-butoxycarbonyl)amino)propanamido)-3-(4-methoxyphenyl)propanoate (1.0 g, 2.2 mmol) in DCM (6 mL) was added TFA (6 mL). The reaction mixture was stirred for 15 min at room temperature and then concentrated to dryness to afford (S)-benzyl 2-((R)-2-aminopropanamido)-3-(4-methoxyphenyl)propanoate as its TFA salt.

To a solution of (S)-4,5,6,7-tetrahydro-1H-indazole-5-carboxylic acid (300 mg, 1.81 mmol) in DMF (20 mL) at 0° C. was added HATU (826 mg, 2.17 mmol). The mixture was stirred for 5 min followed by addition of (S)-benzyl 2-((R)-2-aminopropanamido)-3-(4-methoxyphenyl)propanoate (TFA salt, 819 mg, 1.81 mmol) and DIPEA (1.26 mL, 7.24 mmol). The reaction mixture was allowed to warm to room temperature and stirred for 30 min. Saturated aqueous sodium bicarbonate (50 mL) was added and the resulting mixture was extracted with ethyl acetate (50 mL×2). The combined extracts were dried over anhydrous sodium sulfate and concentrated to afford (S)-benzyl 3-(4-methoxyphenyl)-2-((R)-2-((R)-4,5,6,7-tetrahydro-1H-indazole-5-carboxamido)propanamido)propanoate (970 mg, 94% yield) as a white solid. To a solution of (S)-benzyl 3-(4-methoxyphenyl)-2-((R)-2-((R)-4,5,6,7-tetrahydro-1H-indazole-5-carboxamido)propanamido)propanoate (300 mg, 0.6 mol) in methanol (10 mL) was added Pd/C (100 mg, 10%). The mixture was stirred under hydrogen atmosphere (1 atm) at room temperature overnight and then filtered through a pad of celite. The filtrate was concentrated to dryness to (S)-3-(4-methoxyphenyl)-2-((R)-2-(2-((R)-4,5,6,7-tetrahydro-1H-indazol-5-yl)acetamido)propanamido)propanoic acid (250 mg, quantitative) as a white solid.

(S)—N—((S)-3-cyclopentyl-1-((R)-2-methyloxiran-2-yl)-1-oxopropan-2-yl)-3-(4-methoxyphenyl)-2-((R)-2-(2-((R)-4,5,6,7-tetrahydro-1H-indazol-5-yl)acetamido)propanamido)propanamide A mixture of (S)-2-amino-3-cyclopentyl-1-((R)-2-methyloxiran-2-yl)propan-1-one (TFA salt, 180 mg, 0.61 mmol), (S)-3-(4-methoxyphenyl)-2-((R)-2-(2-((R)-4,5,6,7-tetrahydro-1H-indazol-5-yl)acetamido)propanamido)propanoic acid (250 mg, 0.61 mmol) and HATU (278 mg, 0.73 mmol) in DMF (10 mL) was cooled to 0° C. and DIPEA (0.43 mL, 2.44 mmol) was added. The reaction mixture was allowed to warm to room temperature and stirred for 15 min. Saturated aqueous sodium bicarbonate (50 mL) was added and the resulting mixture was extracted with ethyl acetate (50 mL×2). The combined extracts were dried over anhydrous sodium sulfate and concentrated. The residue was purified by flash column chromatography on silica gel (DCM/MeOH=50:1 to 20:1) to afford (S)—N—((S)-3-cyclopentyl-1-((R)-2-methyloxiran-2-yl)-1-oxopropan-2-yl)-3-(4-methoxyphenyl)-2-((R)-2-(2-((R)-4,5,6,7-tetrahydro-1H-indazol-5-yl)acetamido)propanamido)propanamide (103 mg, 28% yield) as a white solid.

$_1$H NMR (300 MHz, DMSO-d6): δ 12.27 (br s, 1H), 8.25 (d, J=6.0 Hz, 1H), 8.05 (d, J=8.1 Hz, 1H), 8.00 (d, J=6.6 Hz, 1H), 7.11 (d, J=8.1 Hz, 2H), 6.80 (d, J=7.8 Hz, 2H), 4.45 (m, 1H), 4.23 (m, 2H), 3.69 (s, 3H), 3.22 (m, 2H), 3.01 (m, 2H), 2.77 (m, 2H), 2.09 (m, 2H), 1.90 (m, 3H), 1.69-1.67 (m, 6H), 1.50 (s, 3H), 1.28 (m, 1H), 1.04 (d, J=6.3 Hz, 3H), 0.96 (d, J=7.2 Hz, 3H). LC-MS for $C_{32}H_{43}N_5O_6$. found 594.31 [M+H]+.

(S)—N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)-4,5,6,7-tetrahydro-1H-indazole-5-carboxamide (S)—N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)-4,5,6,7-tetrahydro-1H-indazole-5-carboxamide was prepared from (R)-4,5,6,7-tetrahydro-1H-indazole-5-carboxylic acid following the same procedure for (S)—N—((S)-3-cyclopentyl-1-((R)-2-methyloxiran-2-yl)-1-oxopropan-2-yl)-3-(4-methoxyphenyl)-2-((R)-2-(2-((R)-4,5,6,7-tetrahydro-1H-indazol-5-yl)acetamido)propanamido)propanamide.

$^1$H NMR (300 MHz, DMSO-d6): δ 12.28 (br s, 1H), 8.26 (d, J=7.2 Hz, 1H), 8.08 (d, J=7.5 Hz, 1H), 8.05 (d, J=6.6 Hz, 1H), 7.12 (d, J=8.7 Hz, 2H), 6.80 (d, J=8.1 Hz, 2H), 4.45 (m, 1H), 4.23 (m, 2H), 3.70 (s, 3H), 3.22 (m, 1H), 3.01 (m, 2H), 2.65 (m, 2H), 2.09 (m, 2H), 1.90 (m, 3H), 1.69-1.67 (m, 6H), 1.50 (s, 3H), 1.28 (m, 1H), 1.04 (d, J=6.3 Hz, 3H), 0.97 (d, J=7.2 Hz, 3H). LC-MS for $C_{32}H_{43}N_5O_6$. found 594.31 [M+H]+.

The following compounds were synthesized in a similar manner:

3-hydroxy-N—((R)-1-(((S)-3-(4-methoxyphenyl)-1-(((S)-1-((R)-oxiran-2-yl)-1-oxo-3-(p-tolyl)propan-2-yl)amino)-1-oxopropan-2-yl)amino)-1-oxopropan-2-yl)-3-methylbutanamide (C-2053): $^1$H NMR (300 MHz, DMSO-d$_6$): δ 8.46 (d, J=6.3 Hz, 1H), 8.20 (d, J=8.7 Hz, 1H), 8.00 (d, J=7.2 Hz, 1H), 7.10-7.30 (m, 6H), 6.80 (d, J=8.4 Hz, 2H), 4.78 (s, 1H), 4.40~4.60 (m, 2H), 4.25 (m, 1H), 3.75 (s, 3H), 3.70 (m, 1H), 3.45 (m, 1H), 2.70~3.10 (m, 5H), 2.60 (m, 1H), 2.25 (s, 3H), 2.18 (m, 2H), 1.10 (s, 6H), 0.98 (d, J=6.9 Hz, 3H). LC-MS for $C_{30}H_{39}N_3O_7$. found 552.2 [M–H]−

Example 8

Type H2

Preparation of (S)—N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)-3-hydroxy-3-methylpentanamide (C-2051)

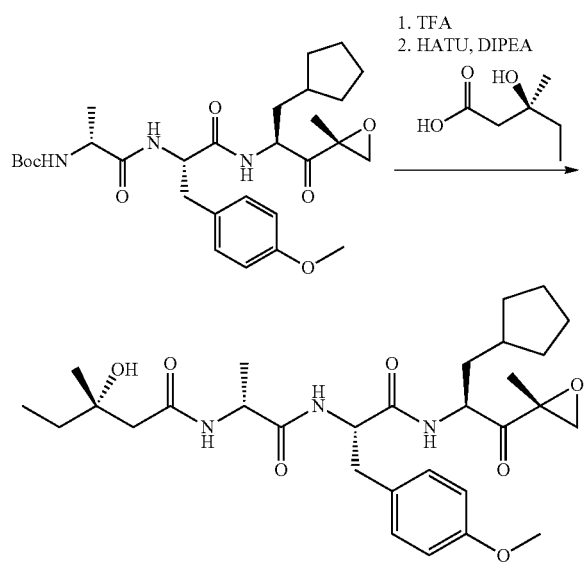

TFA (4 mL) was added to a solution of 0.1 M tert-butyl ((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)carbamate in CH2Cl2 at 0° C. with stirring. The reaction mixture was stirred for 1 h and then concentrated to dryness. The residue was azeotroped three times with EtOAc (5 mL for each portion) to remove residual TFA. The crude product and (S)-3-hydroxy-3-methylpentanoic acid (1.3 eq) was dissolved in DMF to 0.05 M in starting material and HATU (1.8 eq) and DIPEA were added at 0° C. with stirring. The resulting suspension was stirred for 1 h at room temperature. EtOAc (100 mL) and water (100 mL) were added. The two layers were separated and the aqueous phase was extracted with EtOAc (50 mL×3). The combined organic phases were washed with brine (50 mL×3), dried over anhydrous Na2SO4 and concentrated. The residue was purified by flash column chromatography on silica gel to afford (S)—N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)-3-hydroxy-3-methylpentanamide. $^1$H NMR (300 MHz, DMSO-d6): δ 8.25 (d, J=7.5 Hz, 1H), 8.11 (d, J=8.7 Hz, 1H), 8.02 (d, J=7.2 Hz, 2H), 7.12 (d, J=8.4 Hz, 2H), 6.79 (d, J=8.4 Hz, 2H), 4.67 (s, 1H), 4.60 (m, 1H), 4.20~4.40 (m, 2H), 3.71 (s, 3H), 3.22 (d, J=5.4 Hz, 1H), 2.90~3.10 (m, 2H), 2.65 (m, 1H), 2.15 (s, 2H), 1.50~2.00 (m, 8H), 1.42 (s, 3H), 1.10~1.30 (m, 4H), 1.10 (s, 3H), 0.96 (d, J=6.6 Hz, 3H), 0.80 (t, J=7.5 Hz, 3H). LC-MS for $C_{30}H_{45}N_3O_7$. found 558.4 [M−H]$^-$ The following compounds were synthesized in a similar manner:

(R)—N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)-3-hydroxy-3-methylpentanamide (C-2052): $^1$H NMR (300 MHz, DMSO-d$_6$): δ 8.24 (d, J=7.2 Hz, 1H), 8.11 (d, J=8.1 Hz, 1H), 8.00 (d, J=7.2 Hz, 2H), 7.12 (d, J=8.4 Hz, 2H), 6.79 (d, J=8.4 Hz, 2H), 4.67 (s, 1H), 4.50 (m, 1H), 4.20~4.40 (m, 2H), 3.71 (s, 3H), 3.22 (d, J=5.4 Hz, 1H), 2.90~3.10 (m, 2H), 2.65 (m, 1H), 2.15 (2d, 2H), 1.90 (m, 1H), 1.50~1.85 (m, 8H), 1.45 (s, 3H), 1.10~1.40 (m, 3H), 1.10 (s, 3H), 0.96 (d, J=6.6 Hz, 3H), 0.80 (t, J=7.5 Hz, 3H). LC-MS for $C_{30}H_{45}N_3O_7$. found 558.2 [M−H]$^-$ N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)-1H-indazole-5-carboxamide (C-2061): $^1$H NMR (300 MHz, DMSO-d$_6$): δ 13.29 (s, 1H), 8.48 (d, J=6.6 Hz, 1H), 8.38 (s, 1H), 8.27 (d, J=6.9 Hz, 1H), 8.21 (s, 1H), 8.09 (d, J=8.4 Hz, 1H), 7.87 (d, J=8.7 Hz, 1H), 7.56 (d, J=8.7 Hz, 1H), 7.10 (d, J=8.4 Hz, 2H), 6.70 (d, J=8.4 Hz, 2H), 4.40~4.60 (m, 2H), 4.30 (m, 1H), 3.64 (s, 3H), 3.22 (m, 1H), 2.90~3.10 (m, 2H), 2.70 (m, 1H), 1.95 (m, 1H), 1.40~1.80 (m, 6H), 1.41 (s, 3H), 1.16 (d, J=6.9 Hz, 3H). LC-MS for $C_{32}H_{39}N_5O_6$. found 590.24 [M+H]$^+$.

N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)-1H-benzo[d]imidazole-5-carboxamide (C-2062): $^1$H NMR (300 MHz, DMSO-d6): δ 12.53 (br s, 1H), 8.30~8.40 (m, 3H), 8.10 (m, 1H), 7.94 (d, J=6.6 Hz, 1H), 7.60~7.90 (m, 3H), 7.06 (d, J=8.4 Hz, 2H), 6.68 (d, J=8.4 Hz, 2H), 4.30~4.60 (m, 3H), 3.64 (s, 3H), 3.22 (m, 1H), 2.90~3.10 (m, 2H), 2.75 (m, 1H), 1.95 (m, 1H), 1.40~1.80 (m, 6H), 1.41 (s, 3H), 1.16 (d, J=6.9 Hz, 3H). LC-MS for $C_{32}H_{39}N_5O_6$. found 590.18 [M+H]+.

N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)-1H-indazole-6-carboxamide (C-2063): $^1$H NMR (300 MHz, DMSO-d$_6$): δ 13.39 (s, 1H), 8.61 (d, J=7.2 Hz, 1H), 8.27 (d, J=6.9 Hz, 1H), 8.10~8.20 (m, 3H), 7.82 (d, J=7.2 Hz, 1H), 7.62 (d, J=8.4 Hz, 1H), 7.10 (d, J=8.4 Hz, 2H), 6.70 (d, J=8.4 Hz, 2H), 4.40~4.60 (m, 2H), 4.30 (m, 1H), 3.64 (s, 3H), 3.22 (m, 1H), 2.90~3.10 (m, 2H), 2.70 (m, 1H), 1.95 (m, 1H), 1.40~1.80 (m, 6H), 1.41 (s, 3H), 1.16 (d, J=6.9 Hz, 3H). LC-MS for $C_{32}H_{39}N_5O_6$. found 590.24 [M+H]$^+$.

N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)-2-methylthiazole-5-carboxamide (C-2026): $^1$H NMR (300 MHz, DMSO-d$_6$): δ 8.64 (d, J=7.2 Hz, 1H), 8.28 (s, 1H), 8.26 (d, J=6.6 Hz, 1H), 8.18 (d, J=9.0 Hz, 1H), 7.12 (d, J=8.7 Hz, 2H), 6.75 (d, J=8.9 Hz, 2H), 4.60 (m, 1H), 4.25~4.50 (m, 2H), 3.69 (s, 3H), 3.50 (s, 3H), 3.22 (d, J=5.4 Hz, 1H), 3.02 (d, J=5.4 Hz, 1H), 2.70 (s, 3H), 2.65 (m, 1H), 1.95 (m, 1H), 1.50~1.85 (m, 7H), 1.40 (s, 3H), 1.00~1.20 (m, 2H), 1.26 (d, J=6.6 Hz, 3H). MS (EI) for $C_{29}H_{38}N_4O_6S$. found 571.7 [M+H]+.

N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-3-hydroxy-1-oxopropan-2-yl)-3-methylisoxazole-5-carboxamide (C-2030): $^1$H NMR (300 MHz, CDCl$_3$): δ 7.63 (d, J=7.2 Hz, 1H), 7.06 (d, J=8.7 Hz, 2H), 6.99 (d, J=7.8 Hz, 1H), 6.81 (s, 1H), 6.73 (d, J=8.7 Hz, 2H), 6.54 (d, J=7.8 Hz, 1H), 4.66 (m, 3H), 4.12 (m, 1H), 3.76 (s, 3H), 3.75 (m, 1H), 3.26 (d, J=4.8 Hz, 1H), 3.08 (m, 1H), 3.00 (m, 1H), 2.90 (d, J=4.8 Hz, 1H), 2.47 (s, 3H), 1.50 (s, 3H), 1.27-1.71 (m, 11H). LC-MS for $C_{29}H_{38}N_4O_8$. found 571.4 [M+H]+.

N—((S)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-3-morpholino-1-oxopropan-2-yl)-3-methylisoxazole-5-carboxamide (C-2044): $^1$H NMR (300 MHz, DMSO-$d_6$): δ 8.75 (d, J=8.4 Hz, 1H), 8.52 (d, J=8.4 Hz, 1H), 8.35 (d, J=6.9 Hz, 1H), 7.10 (d, J=8.4 Hz, 2H), 6.99 (s, 1H), 6.77 (d, J=8.4 Hz, 2H), 4.57 (m, 2H), 4.33 (m, 1H), 3.70 (s, 3H), 3.44 (m 4H), 3.20 (d, J=4.8 Hz, 1H), 3.03 (d, J=5.4 Hz, 1H), 2.94 (m, 1H), 2.67 (m, 1H), 2.30-2.45 (m, 5H), 2.31 (m, 4H), 1.42 (s, 3H), 1.03-1.93 (m, 11H). LC-MS for $C_{33}H_{45}N_5O_8$. found 639.9 [M+H]$^+$.

N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-3-morpholino-1-oxopropan-2-yl)-3-methylisoxazole-5-carboxamide (C-2045): $^1$H NMR (300 MHz, DMSO-$d_6$): δ 8.73 (d, J=8.1 Hz, 1H), 8.39 (d, J=8.1 Hz, 1H), 8.33 (d, J=7.5 Hz, 1H), 7.08 (d, J=8.7 Hz, 2H), 6.98 (s, 1H), 6.75 (d, J=8.7 Hz, 2H), 4.56 (m, 2H), 4.35 (m, 1H), 3.68 (s, 3H), 3.43 (m 4H), 3.16 (d, J=5.7 Hz, 1H), 3.02 (d, J=5.1 Hz, 1H), 2.91 (m, 1H), 2.68 (m, 1H), 2.36 (m, 4H), 2.31 (s, 3H), 1.42 (s, 3H), 1.07-1.93 (m, 11H). LC-MS for $C_{33}H_{45}N_5O_8$. found 640.7 [M+H]$^+$.

Example 9

Type H3)

Preparation of N—((S)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)-3-methylisoxazole-5-carboxamide (C-2022)

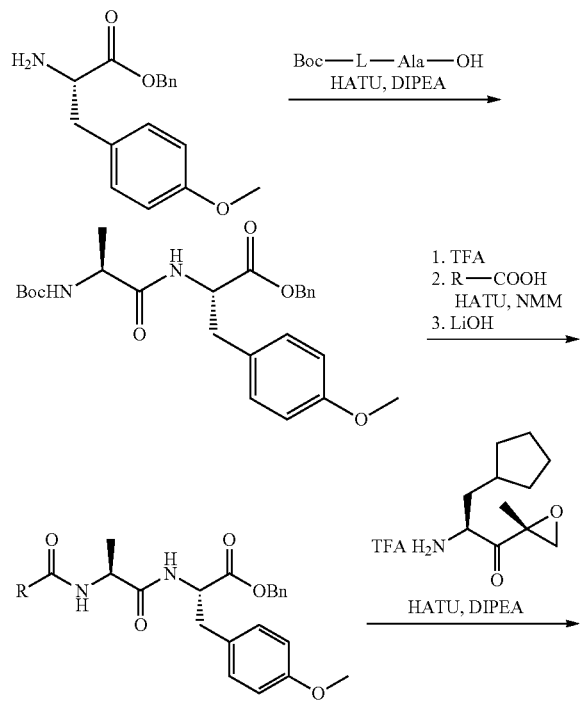

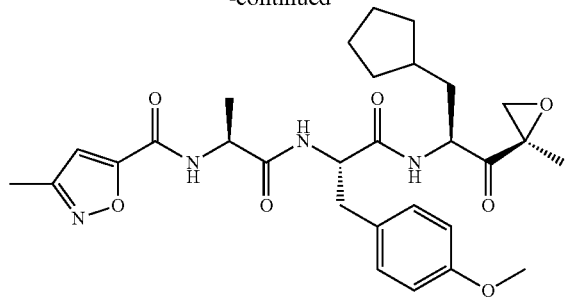

(S)-Benzyl 2-((R)-2-((tert-butoxycarbonyl)amino)propanamido)-3-(4-methoxyphenyl)propanoate HATU (19.3 g, 51 mmol) and DIPEA (29.6 mL, 170 mmol) were added to a solution of Boc-L-alanine (7.7 g, 40.7 mmol) and L-4-MeO-phenylalanine benzyl ester p-toluenesulfonate salt (15.0 g, 34 mmol) in DMF (200 mL) at 0° C. with stirring. The reaction mixture was allowed to warm to room temperature and stirred for 12 h. The mixture was concentrated and the residue was purified by flash column chromatography on silica gel (Hexane/EtOAc=3:1) to afford (S)-benzyl 2-((R)-2-((tert-butoxycarbonyl)amino)propanamido)-3-(4-methoxyphenyl)propanoate (13.7 g, 88% yield).

(S)-3-(4-Methoxyphenyl)-2-((S)-2-(3-methylisoxazole-5-carboxamido) propanamido)propanoic acid TFA (10 mL) was added to a solution of (S)-benzyl 2-((R)-2-((tert-butoxycarbonyl)amino)propanamido)-3-(4-methoxyphenyl)propanoate (1.02 g, 2.2 mmol) in CH2Cl2 (20 mL) at 0° C. with stirring. The reaction mixture was stirred for 1 h and then concentrated to dryness. The residue was azeotroped three times with EtOAc (5 mL for each portion) to remove residual TFA. The crude product and 3-methylisoxazole-5-carboxylic acid (280 mg, 2.2 mmol) were dissolved in DMF (10 mL) and the solution was cooled to 0° C. HATU (1.25 g, 3.3 mmol) and NMM (0.72 mL, 6.0 mmol) were added. The reaction mixture was stirred for 12 h at room temperature. The mixture was concentrated and the residue was purified by flash column chromatography on silica gel (Hexane/EtOAc=2:1) to afford benzyl ester of 3a (0.81 g, 78% yield over two steps). The benzyl ester (650 mg, 1.4 mmol) was dissolved in MeOH (20 mL) and a solution of LiOH (400 mg, 9.6 mmol) in water (10 mL) was added at 0° C. with stirring. The reaction mixture was stirred for 3 h and then acidified with 2 N aqueous HCl to pH=3. Removal of the volatiles gave compound 3a (0.61 g, quantitative), which was used in the next step without further purification.

N—((S)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)-3-methylisoxazole-5-carboxamide HATU (604 mg, 1.6 mmol) and DIPEA (0.89 mL, 6.0 mmol) were added to a solution of compound (S)-3-(4-Methoxyphenyl)-2-((S)-2-(3-methylisoxazole-5-carboxamido) propanamido)propanoic acid (375 mg, 1.1 mmol) and (S)-2-amino-3-cyclopentyl-1-((R)-2-methyloxiran-2-yl)propan-1-one (TFA salt, 314 mg, 1.1 mmol) in DMF (30 mL) at 0° C. The reaction mixture was stirred for 1 h at room temperature. The mixture was concentrated and the residue was purified by flash column chromatography on silica gel (EtOAc/CH2Cl2/MeOH=1:2:0.01) to afford N—((S)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)-3-methylisoxazole-5-carboxamide (150 mg, 25% yield).

$^1$H NMR (300 MHz, DMSO-d6): δ 8.85 (d, J=7.5 Hz, 1H), 8.22 (d, J=7.2 Hz, 1H), 7.97 (d, J=8.7 Hz, 1H), 7.10 (d, J=8.7 Hz, 2H), 6.98 (s, 1H), 6.75 (d, J=8.1 Hz, 2H), 4.30~4.60 (m, 3H), 3.68 (s, 3H), 3.17 (d, J=5.4 Hz, 1H), 3.02 (d, J=5.4 Hz, 1H), 2.96 (m, 1H), 2.70 (m, 1H), 2.30 (s, 3H), 1.90 (m, 1H), 1.50~1.85 (m, 7H), 1.40 (s, 3H), 1.00~1.20 (m, 2H), 1.26 (d, J=6.6 Hz, 3H). MS (EI) for $C_{29}H_{38}N_4O_7$. found 555.2 [M+H]+.

The following compounds were synthesized in a similar manner:

N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)picolinamide (C-2031): $^1$H NMR (300 MHz, DMSO-d6): δ 8.60~8.70 (m, 1H), 8.30~8.40 (m, 2H), 7.95~8.10 (m, 2H), 7.65 (m, 1H), 7.13 (d, J=8.4 Hz, 2H), 6.77 (d, J=8.4 Hz, 2H), 4.50~4.60 (m, 2H), 4.30 (m, 1H), 3.69 (s, 3H), 3.20 (d, J=5.1 Hz, 1H), 2.95~3.05 (m, 2H), 2.65 (m, 1H), 1.95 (m, 1H), 1.50~1.85 (m, 7H), 1.40 (s, 3H), 1.26 (d, J=6.6 Hz, 3H). LC-MS for $C_{30}H_{38}N_4O_6$. found 551.4 [M+H]+.

N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)nicotinamide (C-2032): $^1$H NMR (300 MHz, DMSO-d6): δ 9.02 (s, 1H), 8.70~8.80 (m, 2H), 8.10~8.30 (m, 3H), 7.53 (m, 1H), 7.13 (d, J=8.4 Hz, 2H), 6.77 (d, J=8.4 Hz, 2H), 4.30~4.60 (m, 2H), 4.30 (m, 1H), 3.69 (s, 3H), 3.20 (d, J=5.1 Hz, 1H), 2.95~3.05 (m, 2H), 2.65 (m, 1H), 1.95 (m, 1H), 1.50~1.85 (m, 7H), 1.40 (s, 3H), 1.26 (d, J=6.6 Hz, 3H). LC-MS for $C_{30}H_{38}N_4O_6$. found 551.7 [M+H]+.

(S)—N—((S)-3-cyclopentyl-1-((R)-2-methyloxiran-2-yl)-1-oxopropan-2-yl)-3-(4-methoxyphenyl)-2-((R)-2-(3-methoxypropanamido)propanamido)propanamide (C-2018): $^1$H NMR (300 MHz, CDCl$_3$): δ 7.12 (d, J=8.4 Hz, 2H), 6.83 (d, J=8.7 Hz, 2H), 6.72 (m, 2H), 6.55 (d, J=8.1 Hz, 1H), 4.60 (m, 1H), 4.53 (m, 1H), 4.37 (m, 1H), 3.79 (s, 3H), 3.65 (m, 2H), 3.38 (s, 3H), 3.30 (d, J=4.8 Hz, 1H), 3.03 (m, 2H), 2.89 (d, J=4.8 Hz, 1H), 2.49 (t, J=5.7 Hz, 2H), 1.50 (s, 3H), 1.31 (d, J=6.9 Hz, 3H), 0.85-1.83 (m, 11H). MS (EI) for $C_{28}H_{41}N_3O_7$. found 532.9 [M+H]+.

(S)—N—((S)-3-cyclopentyl-1-((R)-2-methyloxiran-2-yl)-1-oxopropan-2-yl)-2-((S)-2-(2-ethoxyacetamido)propanamido)-3-(4-methoxyphenyl)propanamide (C-2020): $^1$H NMR (CDCl3, 300 MHz): □ 7.12 (d, J=8.4 Hz, 2H), 6.83 (d, J=7.2 Hz, 1H), 6.78 (d, J=8.4 Hz, 2H), 6.77 (d, J=7.2 Hz, 1H), 6.36 (d, J=7.2 Hz, 1H), 4.47~4.61 (m, 3H), 3.92 (d, J=15.3 Hz, 1H), 3.80 (d, J=15.3 Hz, 1H), 3.79 (s, 3H), 3.56 (q, J=6.9 Hz, 2H), 3.27 (d, J=4.8 Hz, 1H), 2.99~3.04 (m, 2H), 2.90 (d, J=4.8 Hz, 1H), 1.53~1.90 (m, 9H), 1.52 (s, 3H), 1.39 (d, J=7.2 Hz, 3H), 1.26 (t, J=6.9 Hz, 3H), 1.10~1.20 (m, 2H). LC-MS for C28H41N3O7. found 532.1 [M+H]+.

(S)—N—((S)-3-cyclopentyl-1-((R)-2-methyloxiran-2-yl)-1-oxopropan-2-yl)-2-((R)-2-(2-ethoxyacetamido)propanamido)-3-(4-methoxyphenyl)propanamide (C-2021): $^1$H NMR (300 MHz, CDCl3): δ 7.13 (d, J=8.4 Hz, 2H), 7.04 (d, J=7.2 Hz, 1H), 6.82 (d, J=8.7 Hz, 2H), 6.68 (d, J=8.1 Hz, 1H), 6.47 (d, J=8.1 Hz, 1H), 4.62 (m, 1H), 4.50 (m, 1H), 4.39 (m, 1H), 3.94 (s, 2H), 3.79 (s, 3H), 3.57 (m, 2H), 3.29 (d, J=5.1 Hz, 1H), 3.03 (m, 2H), 2.89 (d, J=4.8 Hz, 1H), 2.83 (s, 3H), 2.49 (t, J=5.7 Hz, 2H), 1.51 (s, 3H), 1.34 (d, J=6.9 Hz, 3H), 1.27 (t, J=3.5 Hz, 3H), 0.95-1.78 (m, 6H). MS (EI) for $C_{28}H_{41}N_3O_7$. found 532.2 [M+H]+.

(S)—N—((S)-3-cyclopentyl-1-((R)-2-methyloxiran-2-yl)-1-oxopropan-2-yl)-3-(4-methoxyphenyl)-2-((R)-2-(2-(3-methylisoxazol-5-yl)acetamido)propanamido)propanamide (C-2015): $^1$H NMR (300 MHz, DMSO-d6): δ 8.35 (d, J=7.5 Hz, 1H), 8.28 (d, J=6.9 Hz, 1H), 8.18 (d, J=9.0 Hz, 1H), 7.12 (d, J=8.7 Hz, 2H), 6.75 (d, J=8.7 Hz, 2H), 4.55 (m, 1H), 4.25~4.40 (m, 2H), 3.70 (s, 3H), 3.65 (s, 2H), 3.22 (d, J=5.4 Hz, 1H), 3.02 (d, J=5.4 Hz, 1H), 2.70 (m, 1H), 2.15 (s, 3H), 1.95 (m, 1H), 1.50~1.85 (m, 7H), 1.40 (s, 3H), 1.00~1.20 (m, 2H), 1.26 (d, J=6.6 Hz, 3H). MS (EI) for $C_{30}H_{40}N_4O_7$. found 569.7 [M+H]+.

N—((S)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)-2-methylthiazole-5-carboxamide (C-2025): $^1$H NMR (300 MHz, DMSO-d$_6$): δ 8.65 (d, J=7.8 Hz, 1H), 8.29 (s, 1H), 8.20 (d, J=7.5 Hz, 1H), 7.90 (d, J=8.1 Hz, 1H), 7.12 (d, J=8.7 Hz, 2H), 6.75 (d, J=8.4 Hz, 2H), 4.25~4.50 (m, 3H), 3.69 (s, 3H), 3.50 (s, 3H), 3.22 (d, J=5.4 Hz, 1H), 3.02 (d, J=5.4 Hz, 1H), 2.70 (s, 3H), 2.65 (m, 1H), 1.95 (m, 1H), 1.50~1.85 (m, 7H), 1.40 (s, 3H), 1.00~1.20 (m, 2H), 1.26 (d, J=6.6 Hz, 3H). MS (EI) for $C_{29}H_{38}N_4O_6S$. found 571.2 [M+H]+.

N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)-3-methylisoxazole-5-carboxamide (C-2023): $^1$H NMR (300 MHz, DMSO-d$_6$): δ 8.82 (d, J=7.5 Hz, 1H), 8.32 (d, J=7.2 Hz, 1H), 8.16 (d, J=8.7 Hz, 1H), 7.10 (d, J=8.7 Hz, 2H), 6.96 (s, 1H), 6.75 (d, J=8.1 Hz, 2H), 4.30~4.60 (m, 3H), 3.69 (s, 3H), 3.22 (d, J=5.4 Hz, 1H), 3.02 (d, J=5.4 Hz, 1H), 2.96 (m, 1H), 2.70 (m, 1H), 2.30 (s, 3H), 1.90 (m, 1H), 1.50~1.85 (m, 7H), 1.40 (s, 3H), 1.00~1.20 (m, 2H), 1.26 (d, J=6.6 Hz, 3H). MS (EI) for $C_{29}H_{38}N_4O_7$. found 555.2 [M+H]+.

N—((S)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)-3-hydroxy-3-methylbutanamide (C-2027): $^1$H NMR (CDCl$_3$, 300 MHz): □□ 7.10 (d, J=8.4 Hz, 2H), 6.91~7.00 (m, 1H), 6.81 (d, J=8.4 Hz, 2H), 6.38~6.52 (m, 2H), 4.60~4.67 (m, 1H), 4.4~74.53 (m, 3H), 3.79 (s, 3H), 3.21 (d, J=4.8 Hz, 1H), 2.92~3.01 (m, 2H), 2.90 (d, J=4.8 Hz, 1H), 2.36 (d, J=5.4 Hz, 2H), 1.53~1.90 (m, 9H), 1.52 (s, 3H), 1.39 (d, J=7.5 Hz, 3H), 1.30 (s, 6H), 1.03~1.16 (m, 2H). LC-MS for $C_{29}H_{43}N_3O_7$. found 546.4 [M+H]+.

N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)-3-hydroxy-3-methylbutanamide (C-2028): $^1$H NMR (300 MHz, CDCl3): δ 7.11 (d, J=8.7 Hz, 2H), 6.88 (d, J=7.8 Hz, 1H), 6.83 (d, J=8.7 Hz, 2H), 6.69 (d, J=7.5 Hz, 1H), 6.48 (d, J=8.1 Hz, 1H), 4.62 (m, 1H), 4.47 (m, 2H), 3.79 (s, 3H), 3.25 (d, J=4.8 Hz, 1H), 3.01 (m, 2H), 2.89 (d, J=4.8 Hz, 1H), 2.37 (m, 2H), 1.55 (s, 3H), 1.02-1.78 (m, 20H). LC-MS for $C_{29}H_{43}N_3O_7$. found 546.4 [M+H]+.

N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)-1H-benzo[d]imidazole-2-carboxamide (C-2029): $^1$H NMR (300 MHz, CDCl$^3$): δ 8.27 (br s, 1H), 8.15 (br s, 1H), 7.67 (br s, 2H), 7.36~7.40 (m, 2H), 7.12 (d, J=8.4 Hz, 2H), 6.78 (br s, 1H), 6.70 (d, J=8.4 Hz, 2H), 5.12~5.22 (m, 1H), 4.82~4.88 (m, 1H), 4.48~4.56 (m, 1H), 3.56 (m, 1H), 3.18 (d, J=5.1 Hz, 1H), 3.07 (d, J=6.9 Hz, 1H), 2.82 (d, J=5.1 Hz, 1H), 1.54~1.67 (m, 4H), 1.54 (s, 3H), 1.51 (d, J=6.3 Hz, 3H), 1.26~1.51 (m, 4H), 0.95~1.06 (m, 3H). LC-MS for $C_{32}H_{39}N_5O_6$. found 590.5 [M+H]+.

(S)—N—((S)-3-cyclopentyl-1-((R)-2-methyloxiran-2-yl)-1-oxopropan-2-yl)-3-(4-methoxyphenyl)-2-((S)-2-(3-methoxypropanamido)propanamido)propanamide (C-2019): $^1$H NMR (300 MHz, DMSO-d6): δ 8.17 (d, J=7.2 Hz, 1H), 8.03 (d, J=7.2 Hz, 1H), 7.78 (d, J=8.1 Hz, 1H), 7.11 (d, J=8.4 Hz, 2H), 6.80 (d, J=8.4 Hz, 2H), 4.55 (m, 1H), 4.30 (m, 1H), 4.20 (m, 1H), 3.72 (s, 3H), 3.50 (m, 2H), 3.15~3.30 (m, 4H), 3.05 (m, 1H), 2.95 (m, 1H), 2.70 (m, 1H), 2.30 (m, 2H), 1.50~1.95 (m, 8H), 1.40 (s, 3H), 1.00~1.20 (m, 2H), 1.14 (d, J=6.6 Hz, 3H). LC-MS for C28H41N3O7. found 532.5 [M+H]+.

N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)-3-methyl-1H-indene-2-carboxamide (C-2040): $^1$H NMR (300 MHz, CDCl$_3$): δ 7.50 (m, 2H), 7.48 (m, 2H), 7.39 (m, 2H), 7.15 (m, 2H), 6.80 (d, J=8.4 Hz, 1H), 4.58 (m, 3H), 3.74 (s, 3H), 3.62 (m, 2H), 3.26 (d, J=4.8 Hz, 1H), 3.04 (m, 2H), 2.87 (d, J=5.1 Hz, 1H), 2.54 (s, 3H), 1.73-1.64 (m, 10H), 1.42 (d, J=6.9 Hz, 3H), 1.41-0.91 (m, 3H). LC-MS for $C_{35}H_{43}N_3O_6$. found 602.5 [M+H]$^+$.

(S)—N—((S)-3-cyclopentyl-1-((R)-2-methyloxiran-2-yl)-1-oxopropan-2-yl)-3-(4-methoxyphenyl)-2-((S)-2-(2-(3-methylisoxazol-5-yl)acetamido)propanamido)propanamide (C-2014): $^1$H NMR (400 MHz, CDCl3) δ 7.11 (d, J=8.6 Hz, 2H), 6.81 (d, J=8.6 Hz, 2H), 6.53 (d, J=7.8 Hz, 1H), 6.32 (d, J=7.1 Hz, 1H), 6.19 (d, J=7.9 Hz, 1H), 6.07 (s, 1H), 4.63-4.36 (m, 5H), 3.78 (s, 4H), 3.65 (s, 3H), 3.22 (d, J=5.0 Hz, 1H), 2.98 (qd, J=14.1, 6.9 Hz, 3H), 2.89 (d, J=5.0 Hz, 1H), 2.80 (s, 1H), 2.29 (s, 4H), 1.81-1.42 (m, 10H), 1.33 (d, J=7.0 Hz, 4H), 1.22-0.94 (m, 1H). MS (EI) for $C_{30}H_{40}N_4O_7$. found 569.0 [M+H]+.

N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)isonicotinamide (C-2033): $^1$H NMR (300 MHz, CDCl3): δ 7.28~7.23 (m, 5H), 7.19-7.08 (m, 5H), 7.05 (q, J=3.7 Hz, 2H), 7.00 (dd, J=7.4, 2.0 Hz, 2H), 6.81 (d, J=8.4 Hz, 1H), 6.70 (br s, 1H), 6.55 (d, J=7.2 Hz, 1H), 4.74 (m, 1H), 4.65-4.62 (m, 1H), 4.03 (m, 1H), 3.79 (s, 3H), 3.27 (d, J=4.8 Hz, 1H), 3.11 (d, J=4.5 Hz, 1H), 3.07 (d, J=4.8 Hz, 1H), 2.98 (m, 2H), 2.68 (dd, J=13.8, 8.1 Hz, 1H), 2.30 (m, 1H), 2.22 (m, 2H), 2.20 (m, 3H), 1.48 (s, 3H). LC-MS for $C_{30}H_{38}N_4O_6$. found 551.6 [M+H]+.

N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)-1H-imidazole-2-carboxamide (C-2034): $^1$H NMR (300 MHz, CDCl3): δ 8.00~8.28 (br s, 2H), 7.20 (s, 2H), 7.11 (d, J=8.4 Hz, 2H), 6.73 (d, J=8.4 Hz, 2H), 4.90~5.00 (m, 1H), 4.75~4.83 (m, 1H), 4.45~4.52 (m, 1H), 3.75 (s, 3H), 3.20 (d, J=5.1 Hz, 1H), 3.10 (d, J=6.3 Hz, 1H), 2.88 (d, J=5.1 Hz, 1H), 1.58~1.69 (m, 4H), 1.51 (s, 3H), 1.41 (d, J=6.6 Hz, 3H), 1.26~1.51 (m, 5H), 0.95~1.06 (m, 2H). LC-MS for $C_{28}H_{37}N_5O_6$. found 540.6 [M+H]+.

N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)-1H-indene-2-carboxamide (C-2036): $^1$H NMR (300 MHz, DMSO-d6): δ 8.30 (d, J=6.9 Hz, 1H), 8.20 (d, J=6.9 Hz, 1H), 8.10 (d, J=6.9 Hz, 1H), 7.64 (s, 1H), 7.55 (d, J=4.8 Hz, 2H), 7.33 (d, J=4.8 Hz, 2H), 7.12 (m, 2H), 6.75 (m, 2H), 4.38 (m, 1H), 4.32 (m, 1H), 3.66 (s, 3H), 3.23 (m, 1H), 3.03 (m, 2H), 2.72 (m, 1H), 1.90 (m, 1H), 1.72 (m, 2H), 1.54 (m, 6H), 1.26 (s, 3H), 1.24 (m, 1H), 1.13 (d, J=6.9 Hz, 3H). LC-MS for $C_{34}H_{41}N_3O_6$. found 588.8 [M+H]+.

N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)cyclopent-1-enecarboxamide (C-2037): $^1$H NMR (300 MHz, CDCl3): δ 7.12 (d, J=8.7 Hz, 2H), 6.83 (d, J=8.4 Hz, 3H), 6.76 (d, J=8.4 Hz, 2H), 6.57 (m, 1H), 4.62 (m, 1H), 4.27 (m, 2H), 3.79 (s, 3H), 3.30 (m, 2H), 2.87 (m, 1H), 2.54 (m, 4H), 2.06 (m, 2H), 1.61 (m, 4H), 1.54 (m, 3H), 1.51 (m, 6H), 1.37 (d, J=6.9 Hz, 3H), 1.32 (m, 2H), 1.28 (m, 1H). LC-MS for $C_{30}H_{41}N_3O_6$. found 540.4 [M+H]+.

N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)-4-methylisoxazole-5-carboxamide (C-2024): 1H NMR (300 MHz, DMSO-d$_6$): δ 9.02 (s, 1H), 8.65~8.80 (m, 2H), 8.10~8.30 (m, 3H), 7.55 (m, 1H), 7.12 (d, J=8.4 Hz, 2H), 6.75 (d, J=8.4 Hz, 2H), 4.30~4.60 (m, 3H), 3.69 (s, 3H), 3.23 (d, J=5.1 Hz, 1H), 2.95~3.05 (m, 2H), 2.65 (m, 1H), 1.95 (m, 1H), 1.50~1.85 (m, 10H), 1.40 (s, 3H), 1.00~1.20 (m, 2H), 1.26 (d, J=6.6 Hz, 3H). LC-MS for $C_{29}H_{38}N_4O_7$. found 555.4 [M+H]+.

N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)-1-methyl-1H-benzo[d]imidazole-2-carboxamide (C-2038): $^1$H NMR (300 MHz, CDCl$_3$): δ 8.12 (d, J=6.6 Hz, 1H), 7.80 (d, J=6.9 Hz, 2H), 7.38~7.47 (m, 3H), 7.11 (d, J=8.7 Hz, 2H), 6.70 (d, J=8.7 Hz, 2H), 6.68 (d, J=6.6 Hz, 1H), 6.44 (d, J=6.6 Hz, 1H), 4.50~4.70 (m, 3H), 4.20 (s, 3H), 3.66 (s, 3H), 3.27 (d, J=5.1 Hz, 1H), 2.98~3.15 (m, 2H), 2.88 (d, J=5.1 Hz, 1H), 1.5~02.00 (m, 8H), 1.51 (d, J=7.2 Hz, 3H), 1.49 (s, 3H), 1.06~1.16 (m, 3H). LC-MS for $C_{33}H_{41}N_5O_6$. found 604.5 [M+H]$^+$.

N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)isoxazole-5-carboxamide (C-2041): 1H NMR (300 MHz, DMSO-d$_6$): δ 8.90 (d, J=7.5 Hz, 1H), 8.75 (s, 1H), 8.30 (d, J=6.9 Hz, 1H), 8.19 (d, J=8.4 Hz, 1H), 7.13 (s, 1H), 7.12 (d, J=8.7 Hz, 2H), 6.75 (d, J=8.7 Hz, 2H), 4.50 (m, 1H), 4.40 (m, 1H), 4.30 (m, 1H), 3.69 (s, 3H), 3.23 (d, J=5.4 Hz, 1H), 3.02 (d, J=5.4 Hz, 1H), 2.95 (m, 1H), 2.65 (m, 1H), 1.95 (m, 1H), 1.50~1.85 (m, 7H), 1.40 (s, 3H), 1.00~1.20 (m, 2H), 1.26 (d, J=6.6 Hz, 3H). LC-MS for $C_{28}H_{36}N_4O_7$. found 541.4 [M+H]$^+$.

(R)—N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)-3-hydroxybutanamide (C-2042): $^1$H NMR (300 MHz, DMSO-d$_6$): δ 8.26 (d, J=6.3 Hz, 1H), 8.06 (d, J=8.4 Hz, 1H), 7.97 (d, J=6.6 Hz, 1H), 7.12 (d, J=8.4 Hz, 2H), 6.80 (d, J=8.1 Hz, 2H), 4.66 (d, J=4.8 Hz, 1H), 4.30 (m, 1H), 4.21 (m, 1H), 4.08 (m, 1H), 3.96 (m, 1H), 3.71 (s, 3H), 3.22 (d, J=5.1 Hz, 1H), 3.02 (d, J=5.1 Hz, 1H), 2.94 (m, 2H), 2.52 (m, 1H), 2.18-2.12 (m, 2H), 1.83 (m, 2H), 1.59-1.42 (m, 6H), 1.42 (s, 3H), 1.18 (m, 2H), 1.04 (d, J=6.0 Hz, 3H), 0.96 (d, J=7.2 Hz, 3H). LC-MS for $C_{28}H_{41}N_3O_7$. found 532.4 [M+H]$^+$.

(S)—N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)-3-hydroxybutanamide (C-2043): $^1$H NMR (300 MHz, DMSO-d$_6$): δ 8.23 (d, J=6.9 Hz, 1H), 8.05 (d, J=8.1 Hz, 1H), 7.95 (d, J=7.8 Hz, 1H), 7.11 (d, J=8.4 Hz, 2H), 6.80 (d, J=8.7 Hz, 2H), 4.61 (d, J=4.8 Hz, 1H), 4.30 (m, 1H), 4.20 (m, 1H), 4.08 (m, 1H), 3.96 (m, 1H), 3.71 (s, 3H), 3.23 (d, J=5.1 Hz, 1H), 3.00 (m, 2H), 2.52 (m, 1H), 2.18-2.12 (m, 2H), 1.83 (m, 2H), 1.59-1.42 (m, 6H), 1.39 (s, 3H), 1.18 (m, 2H), 1.04 (d, J=6.3 Hz, 3H), 0.96 (d, J=7.2 Hz, 3H). LC-MS for $C_{28}H_{41}N_3O_7$. found 532.6 [M+H]$^+$.

Synthesis of Select Intermediates

Example 10

Preparation of (R)-2-methyl-5-oxopyrrolidine-2-carboxylic acid (Building block for C-3010)

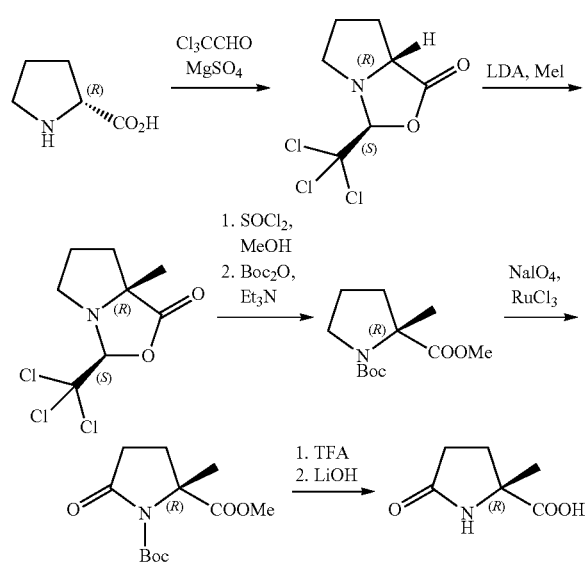

(7aR)-3-(Trichloromethyl)tetrahydropyrrolo[1,2-c]oxazol-1 (3H)-one

Anhydrous MgSO$_4$ (105 g, 0.88 mol) was added to a solution of D-proline (50 g, 0.43 mol) and chloral hydrate (108 g, 0.66 mol) in chloroform (800 mL). The suspension was heated under reflux for 6 h and then cooled to room temperature. The mixture was washed with water (300 mL×3) and the aqueous phase was extracted with chloroform (200 mL×3). The combined organic phases were washed with brine (500 mL×1), dried over Na$_2$SO$_4$ and concentrated. The residue was recrystallized from EtOH to afford compound (7aR)-3-(trichloromethyl)tetrahydropyrrolo[1,2-c]oxazol-1(3H)-one (42 g, 40% yield) as an off-white solid.

(7aR)-7a-Methyl-3-(trichloromethyl)tetrahydropyrrolo[1,2-c]oxazol-1(3H)-one

LDA (2M, 68 mL, 0.136 mol) was added dropwise to a solution of compound (7aR)-3-(trichloromethyl)tetrahydropyrrolo[1,2-c]oxazol-1(3H)-one (22.2 g, 91 mmol) in THF (150 mL) at −78° C. with stirring. The mixture was stirred for 1 h and iodomethane (38.7 g, 0.272 mol) was added dropwise at −78° C. The reaction mixture was stirred for 0.5 h at −78° C. and then allowed to warm to room temperature and stirred overnight. The reaction was quenched with water (200 mL) and the resulting mixture was extracted with CH$_2$Cl$_2$ (200 mL×3). The combined organic phases were washed with brine (500 mL×1), dried over Na$_2$SO$_4$ and concentrated. The residue was purified by flash column chromatography on silica gel (Hexane/EtOAc=4:1) to afford compound (7aR)-7a-methyl-3-(trichloromethyl)tetrahydropyrrolo[1,2-c]oxazol-1(3H)-one (17.8 g, 75% yield).

(R)—N—Boc-2-methylproline methyl ester

SOCl$_2$ (10 mL, 138 mmol) was added dropwise to a solution of compound (7aR)-7a-methyl-3-(trichloromethyl)tetrahydropyrrolo[1,2-c]oxazol-1(3H)-one (17.8 g, 69 mmol) in MeOH (200 mL) at 0° C. with stirring. The reaction mixture was stirred for 1 h and then allowed to warm to room temperature and stirred for 0.5 h. The mixture was further heated under reflux for 5 h. After the mixture was cooled to room temperature, it was concentrated to dryness. The residue was dissolved in CH$_2$Cl$_2$ (200 mL) and Boc$_2$O (18.1 g, 83 mmol) and triethylamine (48 mL, 345 mmol) were added. The reaction mixture was stirred for 5 h at room temperature and then washed with 5% aqueous KHSO$_4$ (100 mL×3), saturated aqueous NaHCO$_3$ (100 mL×3) and brine (100 mL×1), respectively. The organic phase was dried over Na$_2$SO$_4$ and concentrated. The residue was purified by flash column chromatography on silica gel (Hexane/EtOAc=4:1) to afford compound (R)—N—Boc-2-methylproline methyl ester (12.1 g, 72% yield).

(R)—N—Boc-2-methylpyroglutamic acid methyl ester

A solution of NaIO$_4$ (8.2 g, 38 mmol) in water (40 mL) and RuCl$_3$ (20 mg) were added to a solution of compound (R)—N—Boc-2-methylproline methyl ester (2.3 g, 9.6 mmol) in EtOH (40 mL). The reaction mixture was stirred overnight at room temperature. The two layers were separated and the aqueous phase was extracted with EtOAc (50 mL×3). The combined organic phases were washed with brine (50 mL×3), dried over Na$_2$SO$_4$ and concentrated. The residue was purified by flash column chromatography on silica gel (Hexane/EtOAc=4:1) to afford compound (R)—N—Boc-2-methylpyroglutamic acid methyl ester (1.5 g, 61% yield) as a pale yellow solid.

(R)-2-Methylpyroglutamic acid

TFA (10 mL) was added to a solution of compound (R)—N—Boc-2-methylpyroglutamic acid methyl ester (2.0 g, 7.8 mmol) in CH$_2$Cl$_2$ (20 mL) at 0° C. with stirring. The mixture was stirred for further 1 h and concentrated to dryness. And the residue was azeotroped three times with EtOAc (5 mL×3) to remove residual TFA. The crude was dissolved in MeOH (20 mL) and a solution of LiOH (1.3 g, 31 mmol) in water (10 mL) was added at 0° C. with stirring. After the reaction mixture was stirred for 3 h, it was acidified with 2 N aqueous HCl to pH=3. The resulting mixture was concentrated to afford crude (R)-2-methylpyroglutamic acid (~100% yield), which was used in the next step without further purification.

(S)-2-Methylpyroglutamic acid (S)-2-Methylpyroglutamic acid was prepared from L-proline in seven steps following the same procedures for (R)-2-methylpyroglutamic acid.

Example 11

Preparation of (S)-2-(((benzyloxy)carbonyl)amino)-2-(1-((triethylsilyl)oxy)cyclopropyl)acetic acid
(Building block for C-2046)

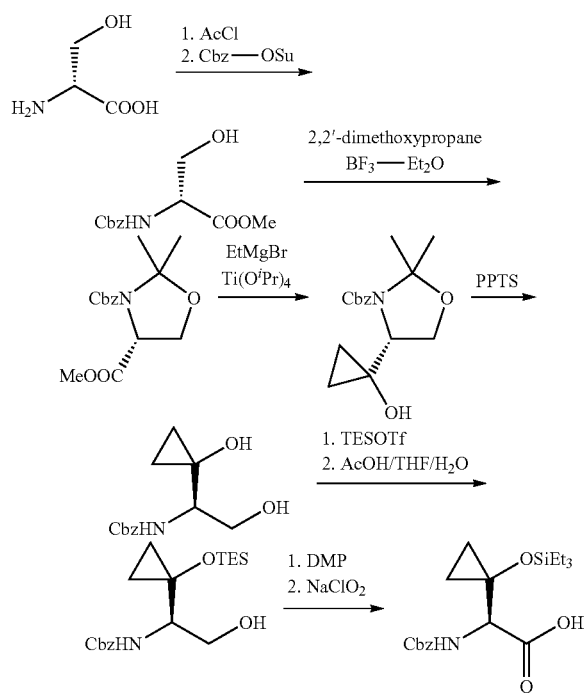

(R)-Methyl 2-(benzyloxycarbonylamino)-3-hydroxypropanoate (4)

Acetyl chloride (40 mL, 0.57 mol) was added to a suspension of D-serine (50.0 g, 0.47 mol) in MeOH (300 mL) at 0° C. with stirring. The reaction mixture was stirred for 12 h and then concentrated to dryness. The residue was dissolved in MeOH (200 mL) followed by addition of triethylamine (50 mL). Cbz-OSu (93.0 g, 0.4 mol) was added at 0° C. and the reaction mixture was stirred for 12 h. The mixture was concentrated to dryness and the residue was dissolved in methylene chloride (500 mL). The resulting solution was washed with brine (200 mL×2), dried over anhydrous sodium sulfate and concentrated to give crude compound (R)-methyl 2-(benzyloxycarbonylamino)-3-hydroxypropanoate (68.0 g, 57% yield) as an oil, which was used directly without further purification.

(R)-3-Benzyl 4-methyl 2,2-dimethyloxazolidine-3,4-dicarboxylate

A mixture of compound (R)-methyl 2-(benzyloxycarbonylamino)-3-hydroxypropanoate (43.0 g, 0.17 mol), 2,2-dimethoxypropane (200 mL, 1.7 mol) and boron trifluoride diethyl etherate (5 mL) was stirred for 2 h at room temperature and then heated under reflux for 4 h. The mixture was cooled to room temperature and then concentrated. The residue was poured into a mixture of water (200 mL) and EtOAc (200 mL). The two phases were separated and the aqueous phase was extracted EtOAc (200 mL×2). The combined organic phases were washed with saturated aqueous NaHCO$_3$ (500 mL×3) and brine (200 mL×1), dried over anhydrous sodium sulfate and concentrated. The residue was purified by flash column chromatography on silica gel (Hexane/EtOAc=3:1) to afford compound (R)-3-benzyl 4-methyl 2,2-dimethyloxazolidine-3,4-dicarboxylate (38.2 g, 77% yield).

(R)-Benzyl 4-(1-hydroxycyclopropyl)-2,2-dimethyl-oxazolidine-3-carboxylate

Titanium(IV) isopropoxide (1.45 g, 5.1 mmol) was added to a solution of compound (R)-3-benzyl 4-methyl 2,2-dimethyloxazolidine-3,4-dicarboxylate (5.0 g, 17.1 mmol) in THF (100 mL) at 0° C. and then EtMgBr (42.7 mmol, a solution in Et$_2$O) was added dropwise over 30 min. The deep dark solution was stirred at room temperature for 18 h. The reaction was quenched by slow addition of water (20 mL) and the resulting mixture was extracted with EtOAc (100 mL×3). The combined organic phases were washed with saturated aqueous NaHCO$_3$ (100 mL×3) and brine (100 mL×1), dried over anhydrous sodium sulfate and concentrated. The residue was purified by flash column chromatography on silica gel (Hexane/EtOAc=2:1) to afford compound (R)-benzyl 4-(1-hydroxycyclopropyl)-2,2-dimethyloxazolidine-3-carboxylate (2.8 g, 56% yield).

(R)-Benzyl 2-hydroxy-1-(1-hydroxycyclopropyl)ethylcarbamate

Pyridinium p-toluenesulfonate (10.0 g, 40 mmol) was added to a solution of compound (R)-benzyl 4-(1-hydroxycyclopropyl)-2,2-dimethyloxazolidine-3-carboxylate (9.0 g, 3.1 mmol) in MeOH (100 mL) at 0° C. The mixture was stirred at room temperature for 18 h and then concentrated. The residue was dissolved in water (200 mL) and the resulting solution was extracted with EtOAc (100 mL×3). The combined organic phases were washed with saturated aqueous NaHCO$_3$ (100 mL×3) and brine (100 mL×1), dried over anhydrous sodium sulfate and concentrated. The residue was purified by flash column chromatography on silica gel (Hexane/EtOAc=1:1) to afford compound (R)-benzyl 2-hydroxy-1-(1-hydroxycyclopropyl)ethylcarbamate (3.8 g, 48% yield).

(R)-Benzyl 1-(1-(triethylsilyloxy)cyclopropyl)-2-hydroxyethylcarbamate

Triethylsilyl triflate (3.2 mL, 12 mmol) was added to a solution of compound (R)-benzyl 2-hydroxy-1-(1-hydroxycyclopropyl)ethylcarbamate (1.2 g, 4.8 mmol) in dichloromethane (10 mL) containing TEA (10 mL) at −78° C. with stirring. The reaction mixture was allowed to warm to room temperature and stirred for 12 h. The reaction was quenched with saturated aqueous NaHCO$_3$ (50 mL) and the resulting mixture was extracted with EtOAc (50 mL×3). The combined organic phases were washed with saturated aqueous NaHCO$_3$ (50 mL×3) and brine (30 mL×1), dried over anhydrous sodium sulfate and concentrated to dryness. The residue was purified by flash column chromatography on silica gel (Hexane/EtOAc=10:1) to afford compound di-TES protected (R)-benzyl (2-hydroxy-1-(1-hydroxycyclopropyl)ethyl)carbamate (780 mg). Di-TES protected (R)-benzyl (2-hydroxy-1-(1-hydroxycyclopropyl)ethyl)carbamate (5.0 g, 10.4 mmol) was added to a mixture of AcOH/THF/H$_2$O (26 mL, 4:8:1) at 0° C. The reaction mixture was stirred for 2 h and then NaHCO$_3$ was added. The mixture was extracted with EtOAc (50 mL×3). The combined organic phases were washed with saturated aqueous NaHCO$_3$ (50 mL×3) and brine (30 mL×1), dried over anhydrous sodium sulfate and concentrated to afford compound (R)-benzyl 1-(1-(triethylsilyloxy)cyclopropyl)-2-hydroxyethylcarbamate (4.8 g, 43% yield), which was used directly without further purification.

(S)-2-(Benzyloxycarbonylamino)-2-(1-(triethylsilyloxy)cyclopropyl)acetic acid

Dess-Martin periodinane (3.2 g, 7.5 mmol) was added to a solution of compound (R)-benzyl 1-(1-(triethylsilyloxy)cyclopropyl)-2-hydroxyethylcarbamate (2.1 g, 5.8 mmol) in dichloromethane (30 mL). The reaction mixture was stirred at room temperature for 12 h and then washed with aqueous sodium hydroxide (1N, 50 mL×3), aqueous sodium thiosulfate (1N, 50 mL×3), saturated aqueous NaHCO$_3$ (50 mL×3) and brine (30 mL×1), respectively. The organic phase was dried over anhydrous sodium sulfate and concentrated to give the corresponding aldehyde.

The crude aldehyde was dissolved in tert-butyl alcohol (20 mL) and THF (20 mL) and a solution of sodium chlorite (80%, 2.5 g, 22 mmol) and sodium dihydrogenphosphate monohydrate (7.9 g, 66 mmol) in water (20 mL) was added dropwise over 1 h at room temperature. The reaction mixture was stirred for 3 h and then diluted with hydrochloric acid (0.1N, 100 mL). The resulting mixture was extracted with EtOAc (50 mL×1). The combined organic layers were washed with 5% aqueous KHSO$_4$ (100 mL×3) and brine (100 mL×1), dried over anhydrous sodium sulfate and concentrated to dryness. The residue was purified by flash column chromatography on silica gel (Hexane/EtOAc=2:1) to afford compound (S)-2-(benzyloxycarbonylamino)-2-(1-(triethylsilyloxy)cyclopropyl)acetic acid (1.3 g, 59% yield).

Example 12

Preparation of tert-Butyl ((S)-3-cyclopentyl-1-((R)-oxiran-2-yl)-1-oxopropan-2-yl)carbamate (Method 1; Intermediate for C-2053 and C-2055)

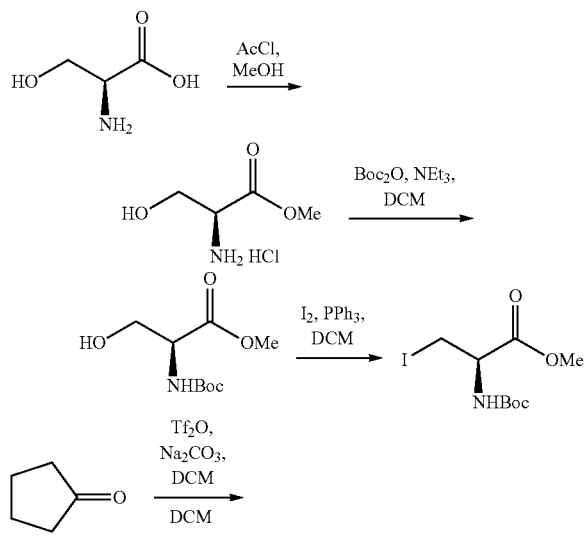

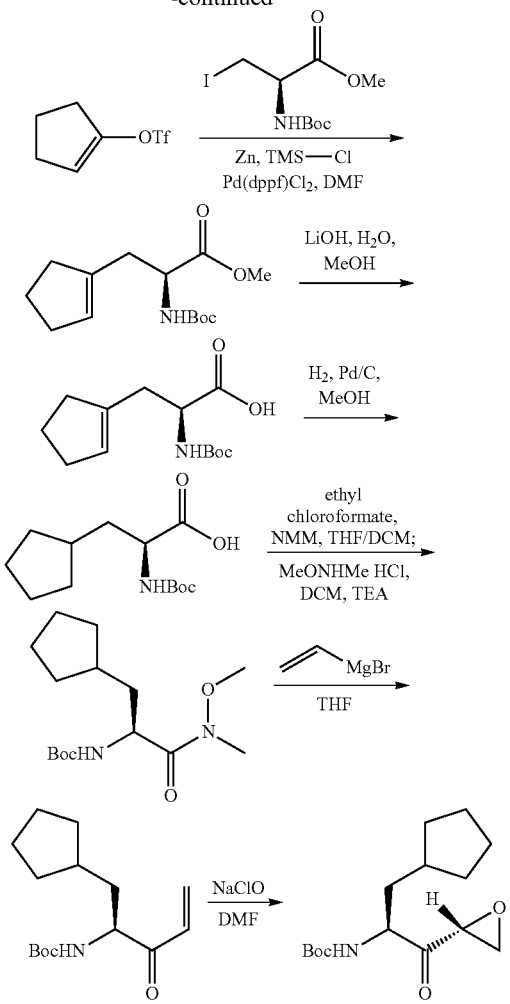

Methanol (450 mL) in a round-bottom flask was cooled to 0° C. and acetyl chloride (55 mL, 0.77 mol) was added dropwise. After completion of the addition, the mixture was stirred at ambient temperature for 10 min and H-Ser-OH (30 g, 0.29 mol) was added in three portions. The reaction mixture was heated at 80° C. for 2 h and then concentrated. The residue was dried under vacuum to afford (S)-methyl 2-amino-3-hydroxypropanoate hydrochloride (quantitative) as a colorless solid, which was used in the next step without further purification.

The crude (S)-methyl 2-amino-3-hydroxypropanoate hydrochloride (0.29 mol) was suspended in DCM (200 mL) and to this mixture was added triethylamine (79 mL, 0.57 mol) and Boc$_2$O (68 g, 0.31 mol) at 0° C. The cooling bath was removed and the reaction mixture was stirred at ambient temperature overnight and then diluted with MTBE (300 mL). The mixture was filtered and the filtrate was concentrated under reduced pressure. The residue was purified by flash column chromatography on silica gel to afford (S)-methyl 2-((tert-butoxycarbonyl)amino)-3-hydroxypropanoate (60 g, 94% yield) as a colorless oil.

A mixture of triphenylphosphine (131 g, 0.500 mol) and imidazole (34 g, 0.50 mol) in DCM (600 mL) was cooled to 0° C. and iodide (127 g, 0.50 mol) was added in small portions over 0.5 h. The cooling bath was removed and the mixture was stirred for 0.5 h. After the mixture was recooled to 0° C., a solution of (5)-methyl 2-((tert-butoxycarbonyl)amino)-3-hydroxypropanoate (73 g, 0.33 mol) in DCM (300 mL) was added dropwise. After the addition, the cooling bath was removed and the mixture was allowed to warm to ambient temperature and stirred for 1.5 h. The mixture was filtered and the filtrate was concentrated to remove most of the solvent. MTBE (400 mL) was added to the residue and the mixture was filtered to remove triphenylphosphine oxide. The filtrate was concentrated and the residue was purified by flash column chromatography on silica gel to afford (R)-methyl 2-((tert-butoxycarbonyl)amino)-3-iodopropanoate (74.0 g, 68% yield) as a colorless solid.

To a solution of cyclopentanone (55 g, 0.66 mol) in DCM (1.3 L) was added Na$_2$CO$_3$ (104 g, 0.98 mol) and the mixture was cooled to −20° C. Trifluoromethanesulfonic anhydride (121 mL, 0.72 mol) was added dropwise. After the addition, the cooling bath was removed and the reaction mixture was stirred at ambient temperature overnight. GC-MS analysis showed the reaction was not complete and more trifluoromethanesulfonic anhydride (33 mL, 0.20 mol) was added. The reaction mixture was stirred for another 4 h and then quenched with water (800 mL). The resulting two phases were separated and the aqueous phase was extracted with DCM (300 mL). The organic layers were combined, washed with brine, and concentrated to afford cyclopent-1-en-1-yl trifluoromethanesulfonate as viscous oil (104 g, 73% yield), which was used in the next step without further purification.

To a suspension of zinc (123 g, 1.90 mol) in DMF (500 mL) was added TMSCl (46 mL) dropwise. The mixture was stirred at ambient temperature for 45 min. The upper clear liquid was drained out and the residue was washed with DMF (2×200 mL). The resulting solid was re-suspended in DMF (200 mL) and the mixture was cooled to 0° C. A solution of (R)-methyl 2-((tert-butoxycarbonyl)amino)-3-iodopropanoate (104 g, 0.32 mol) in DMF (300 mL) was added. The mixture was stirred at 0° C. under nitrogen for 20 min. The upper clear liquid was drained out and added dropwise to a solution of cyclopent-1-en-1-yl trifluoromethanesulfonate (90 g, 0.37 mol) and Pd(dppf)Cl$_2$ (3.9 g, 4.7 mmol) in DMF (500 mL). After addition, the reaction mixture was stirred at 50° C. under nitrogen overnight then cooled to ambient temperature. Brine (500 mL) was added and the resulting mixture was extracted with MTBE (3×300 mL). The organic layers were combined, washed with brine, and concentrated. The residue was purified by flash column chromatography on silica gel (petroleum ether/EtOAc=100:1 to 40:1) to afford (S)-methyl 2-((tert-butoxycarbonyl)amino)-3-(cyclopent-1-en-1-yl)propanoate as a viscous oil (62 g, 72% yield).

To a solution of (5)-methyl 2-((tert-butoxycarbonyl)amino)-3-(cyclopent-1-en-1-yl)propanoate (62 g, 0.23 mol) in water/methanol (900 mL, 2:1) was added lithium hydroxide hydrate (19.3 g, 0.46 mol). The reaction mixture was stirred at ambient temperature overnight and then concentrated to remove most of the methanol. The residue was washed with DCM (400 mL) and the aqueous phase was acidified with dilute HCl to pH=3-4. The resulting mixture was extracted with DCM (3×300 mL). The organic layers were combined and concentrated to afford (S)-2-((tert-butoxycarbonyl)amino)-3-(cyclopent-1-en-1-yl)propanoic acid (56 g, 95% yield) as viscous oil, which was used in the next step without further purification.

To a solution of (S)-2-((tert-butoxycarbonyl)amino)-3-(cyclopent-1-en-1-yl)propanoic acid (56 g, 0.22 mol) in methanol (500 mL) was added Pd/C (23 g, 0.022 mol, 10%). The mixture was stirred under a hydrogen atmosphere (1 atm) at ambient temperature overnight and then filtered through a pad of celite. The filtrate was concentrated under reduced pressure to afford (S)-2-((tert-butoxycarbonyl)amino)-3-cyclopentylpropanoic acid (55 g, 97% yield) as viscous oil, which was used in the next step without further purification.

To a flask charged with compound (S)-2-((tert-butoxycarbonyl)amino)-3-cyclopentylpropanoic acid (55 g, 214 mmol) was added THF/DCM (800 mL, 1:1). The solution was cooled to 0° C. and ethyl chloroformate (24.5 mL, 257 mmol) and NMM (28.4 mL, 257 mmol) was added dropwise sequentially. After addition, the mixture was stirred at 0° C. under nitrogen for 1 h. To the other flask charged with N,O-dimethylhydroxylamine HCl (25 g, 257 mmol) was added DCM (400 mL). The mixture was cooled to 0° C. and TEA (38.7 mL, 278 mmol) was added. The resulting mixture was transferred into the former reaction flask. The reaction mixture was allowed to warm to ambient temperature and stirred overnight. The reaction was then quenched with water (500 mL) and the two phases were separated. The organic phase was washed with water (500 mL), dried over anhydrous sodium sulfate, and concentrated to afford (S)-tert-butyl (3-cyclopentyl-1-(methoxy(methyl)amino)-1-oxopropan-2-yl)carbamate as colorless oil (60 g, 93% yield), which was used in the next step without further purification.

To a solution of (S)-tert-butyl (3-cyclopentyl-1-(methoxy(methyl)amino)-1-oxopropan-2-yl)carbamate (2.5 g, 8.3 mmol) in THF (35 mL) was added vinylmagnesium bromide (16.7 mL, 33.3 mol) at 0° C. dropwise. After completion of the addition, the reaction mixture was stirred at 0° C. for 2 h and then quenched with saturated aqueous ammonium chloride (30 mL). The resulting mixture was extracted with EtOAc (2×40 mL). The organic layers were combined, dried over anhydrous sodium sulfate, and concentrated. The residue was purified by flash column chromatography on silica gel (petroleum ether/EtOAc=100:1) to afford (S)-tert-butyl (1-cyclopentyl-3-oxopent-4-en-2-yl)carbamate as a yellow oil (854 mg, 38% yield).

A solution of (S)-tert-butyl (1-cyclopentyl-3-oxopent-4-en-2-yl)carbamate (854 mg, 3.2 mmol) in DMF (70 mL) was cooled to −20° C. and a bleach solution (9.5 mL, 12.8 mmol, 10% active spice) was added dropwise under nitrogen. The reaction mixture was warmed to 0° C. and stirred for 1.5 h. Water (70 mL) was added and the mixture was extracted with EtOAc (2×50 mL). The organic phases were combined, washed with brine (2×50 mL), dried over anhydrous sodium sulfate, and concentrated. The residue was purified by flash column chromatography on silica gel (petroleum ether/EtOAc=80:1) to afford tert-butyl ((S)-3-cyclopentyl-1-((R)-oxiran-2-yl)-1-oxopropan-2-yl)carbamate as a viscous oil (390 mg, contaminated with some impurities, 43% yield) as a yellow oil.

Example 13

Preparation of tert-butyl ((S)-3-(cyclopent-1-en-1-yl)-1-((R)-2-methyloxiran-2-yl)-1-oxopropan-2-yl) carbamate (Intermediate for: C-3001, C-2060, C-2066, C-2067, C-2068, C-2069, and C-2070)

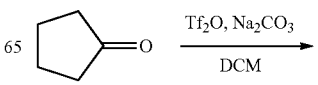

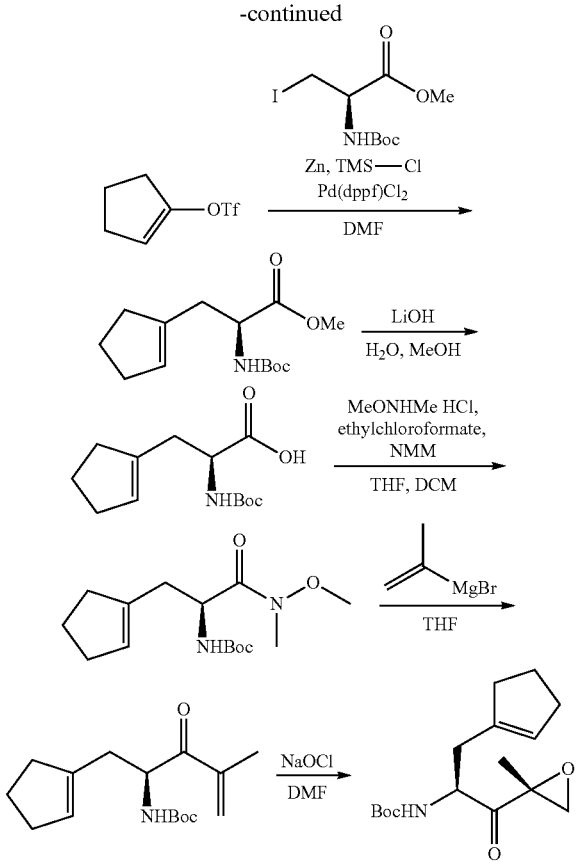

To a solution of cyclopentanone (55 g, 0.66 mol) in DCM (1.3 L) was added Na2CO3 (104 g, 0.980 mol) and the mixture was cooled to −20° C. Trifluoromethanesulfonic anhydride (121 mL, 0.720 mol) was added dropwise. After the addition, the cooling bath was removed and the reaction mixture was stirred at ambient temperature overnight. GC-MS analysis showed the reaction was not complete and additional trifluoromethane sulfonic anhydride (33 mL, 0.20 mol) was added. The reaction mixture was stirred for another 4 h then quenched with water (800 mL). The aqueous phase was extracted with DCM (300 mL). The organics were combined, washed with brine, and concentrated to afford cyclopentenyltrifluoromethanesulfonate as viscous oil (104 g, 73% yield), which was used in the next step without further purification.

To a suspension of zinc (123 g, 1.90 mol) in DMF (500 mL) was added TMSCl (46 mL) dropwise. The mixture was stirred at ambient temperature for 45 min. The upper clear liquid was removed and the residue was washed with DMF (200 mL×2). The resulting solid was re-suspended in DMF (200 mL) and the mixture was cooled to 0° C. A solution of (R)-methyl 2-((tert-butoxycarbonyl)amino)-3-iodopropanoate (104 g, 0.320 mol) in DMF (300 mL) was added. The mixture was stirred at 0° C. under nitrogen for 20 min. The upper clear liquid was removed and added to a solution of cyclopent-1-en-1-yl trifluoromethanesulfonate (90 g, 0.37 mol) and Pd(dppf)Cl2 (3.9 g, 4.7 mmol) in DMF (500 mL) dropwise. After addition, the reaction mixture was stirred at 50° C. under nitrogen overnight then cooled to ambient temperature. Brine (500 mL) was added and the resulting mixture was extracted with MTBE (300 mL×3). The organics were combined, washed with brine, and concentrated.

The residue was purified by flash column chromatography on silica gel (petroleum ether/EtOAc=100:1 to 40:1) to afford (S)-Methyl 2-(tert-butoxycarbonylamino)-3-cyclopentenylpropanoate as viscous oil (62 g, 72% yield). $^1$H NMR (300 MHz, CDCl$_3$): δ □ 5.48 (br s, 1H), 4.97 (d, J=6.6 Hz, 1H), 4.40-4.43 (m, 1H), 3.74 (s, 3H), 2.46-2.63 (m, 2H), 2.23-2.34 (m, 4H), 1.82-1.93 (m, 2H), 1.45 (s, 9H).

To a solution of (S)-Methyl 2-(tert-butoxycarbonylamino)-3-cyclopentenylpropanoate (62 g, 0.23 mol) in water/methanol (900 mL, 2:1) was added lithium hydroxide hydrate (19.3 g, 0.460 mol). The reaction mixture was stirred at ambient temperature overnight and then concentrated to remove the majority of methanol. The residue was washed with DCM (400 mL) and the aqueous phase was acidified with diluted HCl to pH=3-4. The resulting mixture was extracted with DCM (300 mL×3). The organic layers were combined and concentrated to afford (S)-2-(tert-Butoxycarbonylamino)-3-cyclopentenylpropanoic acid (56 g, 95% yield) as viscous oil, which was used in the next step without further purification. $^1$H NMR (300 MHz, CDCl$_3$): δ □ 10.47 (br. s, 1H), 5.52 (br. s, 1H), 4.98 (d, J=8.1 Hz, 1H), 4.40-4.44 (m, 1H), 2.50-2.70 (m, 2H), 2.25-2.34 (m, 4H), 1.79-1.93 (m, 2H), 1.45 (s, 9H).

To a flask charged with (S)-2-(tert-Butoxycarbonylamino)-3-cyclopentenylpropanoic acid (55.0 g, 214 mmol) was added THF/DCM (800 mL, 1:1). The solution was cooled to 0° C. and ethyl chloroformate (24.5 mL, 257 mmol) and NMM (28.4 mL, 257 mmol) were added dropwise sequentially. After addition, the mixture was stirred at 0° C. under nitrogen for 1 h. To the other flask charged with N,O-dimethylhydroxylamine HCl (25 g, 257 mmol) was added DCM (400 mL). The mixture was cooled to 0° C. and TEA (38.7 mL, 278 mmol) was added. The resulting mixture was transferred into the former reaction flask. The reaction mixture was allowed to warm to ambient temperature and stirred overnight. The mixture was quenched with water (500 mL) and the organic phase was washed with water (500 mL), dried over anhydrous sodium sulfate, and concentrated to afford (S)-tert-butyl (3-(cyclopent-1-en-1-yl)-1-(methoxy (methyl)amino)-1-oxopropan-2-yl)carbamate as colorless oil (60 g, 93% yield), which was used in the next step without further purification.

To a solution of (S)-tert-butyl (3-(cyclopent-1-en-1-yl)-1-(methoxy(methyl)amino)-1-oxopropan-2-yl)carbamate (81 g, 0.27 mol) in THF (600 mL) was added freshly prepared prop-1-en-2-ylmagnesium bromide (96.0 mL, 1.08 mol) at 0° C. dropwise. After completion of the addition, the reaction mixture was stirred at 0° C. for 2 h then quenched with saturated aqueous ammonium chloride (500 mL). The resulting mixture was extracted with EtOAc (400 mL×2). The organic phases were combined, dried over anhydrous sodium sulfate, and concentrated. The residue was purified by flash column chromatography on silica gel (petroleum ether/EtOAc=100:1) to afford (S)-tert-butyl (1-(cyclopent-1-en-1-yl)-4-methyl-3-oxopent-4-en-2-yl)carbamate as colorless oil (39.3 g, 52% yield).

A solution of (S)-tert-butyl (1-(cyclopent-1-en-1-yl)-4-methyl-3-oxopent-4-en-2-yl)carbamate (10.0 g, 35.6 mmol) in DMF (180 mL) was cooled to −20° C. and bleach (54.0 mL, 71.2 mmol, 10%) was added dropwise under nitrogen. The reaction mixture was warmed to 0° C. and stirred for 1.5 h. Water (200 mL) was added and the mixture was extracted with EtOAc (200 mL×2). The organic phases were combined, washed with brine (200 mL×2), dried over anhydrous sodium sulfate, and concentrated. The residue was purified by flash column chromatography on silica gel to afford tert-butyl ((S)-3-(cyclopent-1-en-1-yl)-1-((R)-2-methyloxiran-2-yl)-1-oxopropan-2-yl)carbamate as viscous oil (5.6 g, 53% yield). 1H NMR (300 MHz, CDCl3): δ 4.62 (s, 1H), 4.91 (d, J=7.5 Hz, 1H), 4.44-4.37 (m, 1H), 3.29 (d, J=4.8 Hz, 1H), 2.89 (d, J=4.8 Hz, 1H), 2.56-2.52 (m, 1H), 2.29-2.26 (m, 5H), 1.92-1.82 (m, 2H), 1.51 (s, 3H), 1.41 (s, 9H).

Example 14

Preparation of tert-butyl ((S)-3-cyclopentyl-1-((R)-2-methyloxiran-2-yl)-1-oxopropan-2-yl)carbamate (Method 2) (Intermediate for: C-3014, C-3018, C-3019, C-2014, C-2015, C-2018, C-2019, C-2020, C-2021, C-2022, C-2023, C-2025, C-2026, C-2027, C-2028, C-2029, C-2030, C-2031, C-2032, C-2033, C-2034, C-2036, C-2037, C-2038, C-2039, C-2040, C-2041, C-2042, C-2043, C-2044, C-2045, C-2047, C-2050, C-2051, C-2052, C-2054, C-2059, C-2061, C-2062, C-2063, C-2064, and C-2065)

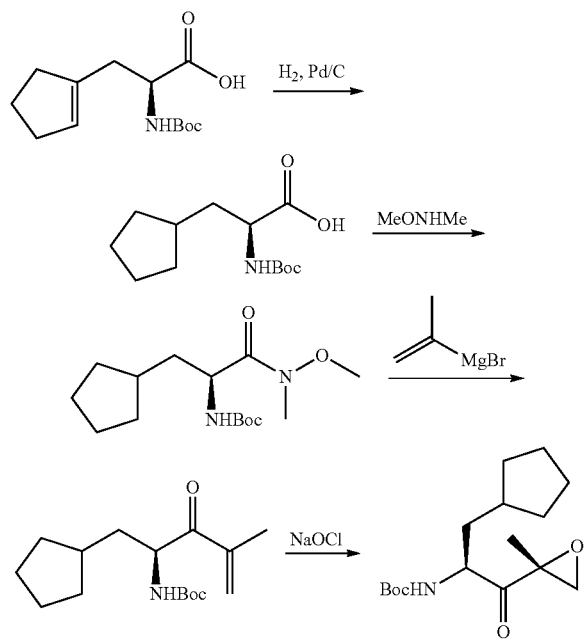

To a solution of (S)-2-(tert-Butoxycarbonylamino)-3-cyclopentenylpropanoic acid (56 g, 0.22 mol) in methanol (500 mL) was added Pd/C (23 g, 0.022 mol, 10%). The mixture was stirred under a hydrogen atmosphere (1 atm) at ambient temperature overnight and then filtered through a pad of celite. The filtrate was concentrated under reduced pressure to afford (S)-2-(tert-Butoxycarbonylamino)-3-cyclopentylpropanoic acid (55 g, 97% yield) as viscous oil, which was used in the next step without further purification.

The remainder of the synthesis of tert-butyl ((S)-3-cyclopentyl-1-((R)-2-methyloxiran-2-yl)-1-oxopropan-2-yl)carbamate was carried out in a similar manner to the synthesis of tert-butyl ((S)-3-(cyclopent-1-en-1-yl)-1-((R)-2-methyloxiran-2-yl)-1-oxopropan-2-yl)carbamate. 1H NMR (300 MHz, CDCl3): δ 4.90 (m, 1H), 4.30 (m, 1H), 3.30 (d, J=5.0 Hz, 1H), 2.90 (d, J=5.0 Hz, 1H), 1.57 (s, 3H), 1.51 (s, 9H), 1.95-1.20 (m, 11H).

Example 15

Preparation of 2-(2-Aminothiazol-5-yl)acetic acid (Intermediate toward C-2066)

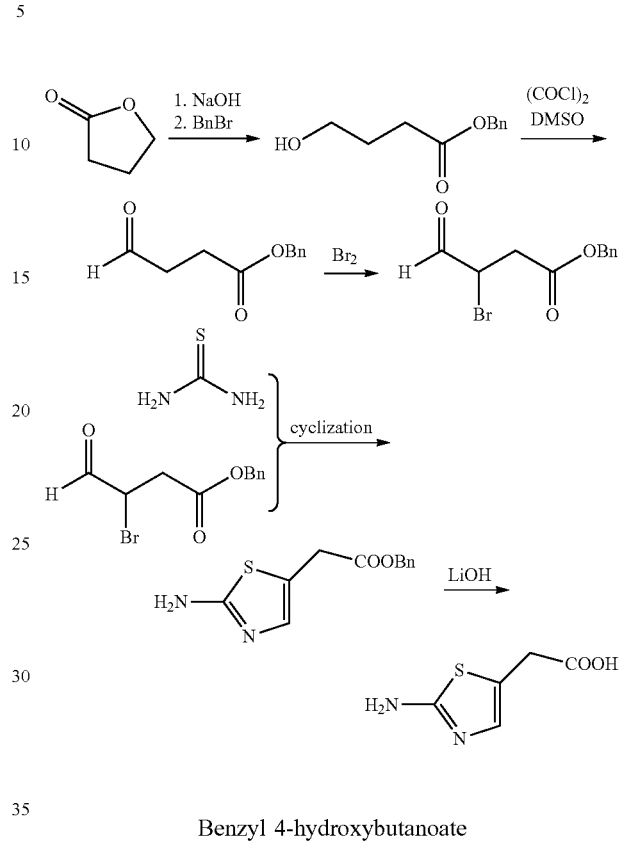

Benzyl 4-hydroxybutanoate

To a solution of dihydrofuran-2(3H)-one (20.0 g, 23.3 mmol) in ethanol (200 mL) were added water (100 ml) and sodium hydroxide (9.3 g, 233 mmol). The reaction mixture was heated under reflux overnight. The mixture was concentrated and the residue was washed with THF/EtOH (1:1, 100 mL) to afford sodium 4-hydroxy butanoate (26.1 g, 89% yield) as a white solid.

A mixture of sodium 4-hydroxybutanoate (26.1 g, 20.7 mmol) and benzyl bromide (42.5 g, 24.9 mmol) in DMF (500 ml) was stirred at room temperature for 1.5 h. Water (300 mL) was added and the resulting mixture was extracted with EtOAc (300 mL×2). The combine organic layers were washed with water (300 mL) and brine (300 mL), dried over anhydrous Na2SO4 and concentrated. The residue was purified by flash column chromatography on silica gel (petroleum ether/EtOAc=5:1 to 2:1) to afford compound benzyl 4-hydroxybutanoate (8.0 g, 19% yield) as an oil.

Benzyl 4-oxobutanoate

A flame-dried flask was charged with DCM (26 mL) and then cooled to −78° C. with dry ice/acetone bath. Oxalyl chloride (2.62 g, 20.6 mmol) was added followed by DMSO (2.41 g, 30.9 mmol). The mixture was kept at −78° C. for 15 min and a solution of compound 16 (2.0 g, 10.3 mmol) in DCM (10 mL) was added. The reaction mixture was stirred at −78° C. for 1 h and triethylamine (7 mL, 51 mmol) was added. The mixture was allowed to warm to room temperature over 30 min and then poured into ice-cold 1N aqueous HCl (100 mL). The resulting mixture was extracted with ethyl acetate (100 mL×2). The combined organic layers were washed with water (100 mL) and brine (100 mL), dried over anhydrous Na2SO4 and concentrated. The residue was purified by flash column chromatography on silica gel (petroleum ether/EtOAc=5:1) to afford compound benzyl 4-oxobutanoate (1.78 g, 89% yield) as a yellow oil.

Benzyl 3-bromo-4-oxobutanoate

Bromine (1.46 g, 9.13 mmol) was added dropwise to a solution of compound 17 (1.75 g, 9.13 mmol) in diethyl ether (8 mL) and dioxane (0.1 mL). The reaction mixture was stirred for 1 h at room temperature and then poured into dichloromethane (10 mL). Calcium carbonate (2.28 g, 22.8 mmol) and sodium bicarbonate (0.76 g, 10 mmol) were added and the mixture was stirred for 12 h at room temperature. The inorganic solids were removed by filtration and the filtrate was concentrated under reduced pressure to afford compound benzyl 3-bromo-4-oxobutanoate (2.44 g, containing 30% of 17 by proton NMR analysis) as a red oil, which was used directly in the next step without further purification.

Benzyl 2-(2-aminothiazol-5-yl)acetate

A suspension of compound 18 (crude, 2.4 g, 8.86 mmol) and thiourea (0.64 g, 8.42 mmol) in methanol (10 mL) was heated under reflux for 4 h. The solvent was evaporated and the residue was diluted with ethyl acetate (30 mL). The solid was collected by filtration and treated with 10% aqueous NaHCO3 (30 mL). The resulting mixture was extracted with ethyl acetate (50 ml×2). The combined organic layers were washed with water (50 mL) and brine (50 mL), dried over anhydrous Na2SO4 and concentrated. The residue was suspended in petroleum ether/EtOAc (2:1, 30 mL) and the yellow solid was collected by filtration to afford compound benzyl 2-(2-aminothiazol-5-yl)acetate (0.93 g, 42% yield).

2-(2-Aminothiazol-5-yl)acetic acid

To a mixture of compound 19 (930 mg, 3.75 mmol) in methanol (12 mL) were added water (6 mL) and lithium hydroxide (236 mg, 5.6 mmol). The reaction mixture was stirred at room temperature for 0.5 h and then diluted with water (50 mL). The resulting mixture was washed with ethyl acetate (25 mL). The aqueous phase was adjusted to pH=4 with 2N aqueous HCl (20 mL) and the precipitate was collected by filtration and dried to afford compound 2-(2-aminothiazol-5-yl)acetic acid (330 mg, 55% yield) as a yellow solid.

2-(2-aminooxazol-5-yl)acetic acid was synthesized in similar fashion utilizing urea instead of thiourea.

Example 16

Preparation of (S)-2-((S)-2-aminopropanamido)-N—((S)-3-(cyclopent-1-en-1-yl)-1-((R)-2-methyl-oxiran-2-yl)-1-oxopropan-2-yl)-3-(4-methoxyphenyl)propanamide (intermediate for: C-2066, C-2067, C-2068, C-2069, and C-2070)

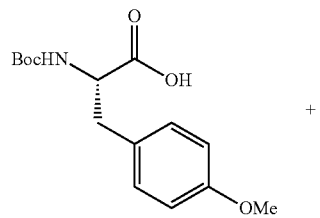

+

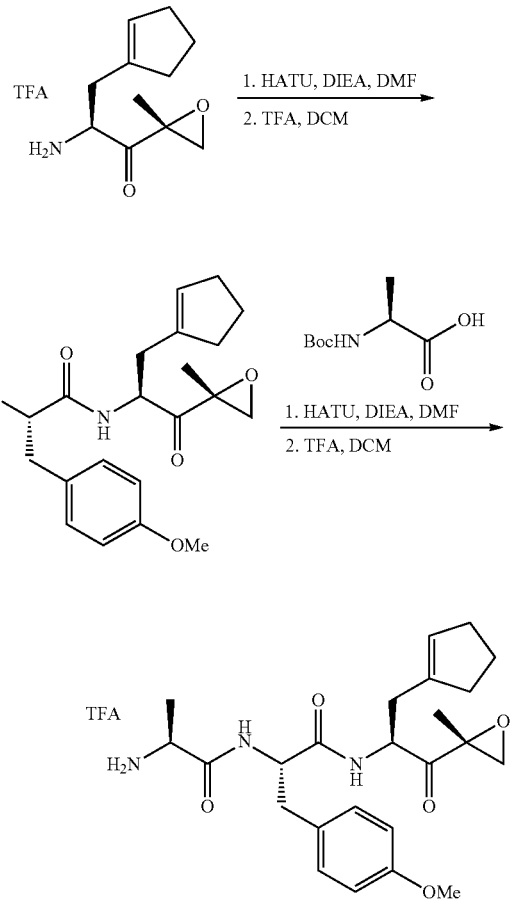

To (S)-2-((tert-butoxycarbonyl)amino)-3-(4-methoxyphenyl)propanoic acid (2.00 g, 6.78 mmol) and (S)-2-amino-3-(cyclopent-1-en-1-yl)-1-((R)-2-methyloxiran-2-yl)propan-1-one (1.98 g, 6.78 mmol) in DMF (10 mL) at 0° C. was added HATU (3.00 g, 8.36 mmol) followed by DIEA (5.90 mL, 33.9 mmol) and the mixture was stirred for 15 min then quenched with NaHCO3 (sat., aq.), extracted with EtOAc (2×), washed with brine, dried with sodium sulfate, filtered, and concentrated. Purification by column chromatography (1:1 hexanes/EtOAc) provided tert-butyl ((S)-1-(((S)-3-(cyclopent-1-en-1-yl)-1-((R)-2-methyloxiran-2-yl)-1-oxopropan-2-yl)amino)-3-(4-methoxyphenyl)-1-oxopropan-2-yl)carbamate (2.62 g, 82%) as a colorless oil. MS(EI) for C26H36N2O6. found 473.3 (MH)+.

To tert-butyl ((S)-1-(((S)-3-(cyclopent-1-en-1-yl)-1-((R)-2-methyloxiran-2-yl)-1-oxopropan-2-yl)amino)-3-(4-methoxyphenyl)-1-oxopropan-2-yl)carbamate (0.99 g, 2.1 mmol) was added DCM (5 mL) and TFA (5 mL). The mixture was allowed to stand at ambient temperature for 30 min then it was concentrated to provide crude (S)-2-amino-N—((S)-3-(cyclopent-1-en-1-yl)-1-((R)-2-methyloxiran-2-yl)-1-oxopropan-2-yl)-3-(4-methoxyphenyl)propanamide (quant.) and carried forward without further purification. MS(EI) for C21H28N2O4. found 373.2 (MH)+.

To (S)-2-amino-N—((S)-3-(cyclopent-1-en-1-yl)-1-((R)-2-methyloxiran-2-yl)-1-oxopropan-2-yl)-3-(4-methoxyphenyl)propanamide (TFA salt, 2.00 g, 4.26 mmol) and (S)-2-((tert-butoxycarbonyl)amino)propanoic acid (805 mg, 4.26 mmol) in DMF (10 mL) at 0° C. was added HATU (1.94 g, 5.11 mmol) followed by DIEA (4.37 mL, 25.6 mmol) and the mixture was stirred for 15 min then quenched with NaHCO3 (sat., aq.), extracted with EtOAc (2×), washed with brine, dried with sodium sulfate, filtered, and concentrated. Purification by column chromatography (1:1 hexanes/EtOAc) provided tert-butyl ((S)-1-(((S)-1-(((S)-3-(cyclopent-1-en-1-yl)-1-((R)-2-methyloxiran-2-yl)-1-oxopropan-2-yl)amino)-3-(4-methoxyphenyl)-1-oxopropan-2-yl)amino)-1-oxopropan-2-yl)carbamate (1.94 g, 84%) as a colorless oil. MS(EI) for C29H41N3O7. found 544.3 (MH)+.

To tert-butyl ((S)-1-(((S)-1-(((S)-3-(cyclopent-1-en-1-yl)-1-((R)-2-methyloxiran-2-yl)-1-oxopropan-2-yl)amino)-3-(4-methoxyphenyl)-1-oxopropan-2-yl)amino)-1-oxopropan-2-yl)carbamate (1.94 g, 2.18 mmol) was added DCM (10 mL) and TFA (10 mL). The mixture was allowed to stand at ambient temperature for 30 min then it was concentrated to provide (S)-2-((S)-2-aminopropanamido)-N—((S)-3-(cyclopent-1-en-1-yl)-1-((R)-2-methyloxiran-2-yl)-1-oxopropan-2-yl)-3-(4-methoxyphenyl)propanamide (quant.) which was carried forward without further purification. MS(EI) for C24H33N3O5. found 444.2 (MH)+.

(S)-2-amino-3-hydroxy-N—((S)-3-(4-methoxyphenyl)-1-(((S)-1-((R)-2-methyloxiran-2-yl)-1-oxo-3-phenylpropan-2-yl)amino)-1-oxopropan-2-yl)propanamide (intermediate for C-2007), (S)-2-((S)-2-aminopropanamido)-3-(4-methoxyphenyl)-N—((S)-1-((R)-2-methyloxiran-2-yl)-1-oxo-3-phenylpropan-2-yl)propanamide (intermediate for C-2012, C-2013, C-2049) and (S)-2-((R)-2-aminopropanamido)-3-(4-methoxyphenyl)-N—((S)-1-((R)-2-methyloxiran-2-yl)-1-oxo-3-phenylpropan-2-yl)propanamide were synthesized in a similar manner.

Example 17

Preparation of 2-(2-(azetidin-1-yl)thiazol-5-yl)acetic acid (intermediate for C-2068)

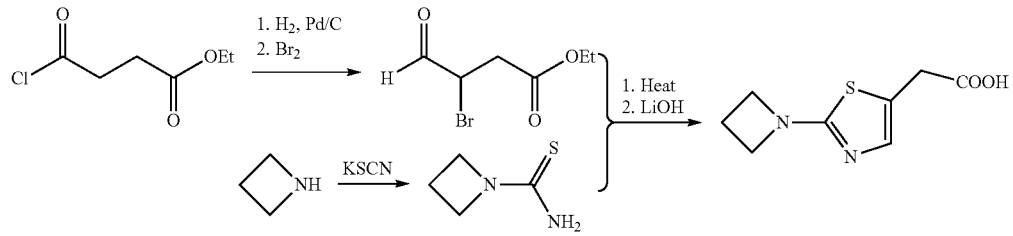

Ethyl 3-bromo-4-oxobutanoate

Pd/C (10%, 4 g) was added to a solution of 3-carbomethoxypropionyl chloride (18.0 g, 0.11 mol) and 2,6-dimethylpyridine (12.5 g, 0.11 mol) in THF (250 ml). The suspension was stirred under hydrogen atmosphere at room temperature for 10 h. Pd/C was filtered off and washed with THF (50 mL). The filtrate and washings were combined and concentrated to dryness. The residue was dissolved in Et2O (200 mL) and the resulting solution was washed with aqueous HCl (1N, 100 mL×3), saturated aqueous NaHCO3 (100 mL×3) and brine (100 mL×1), respectively. The organic solution was dried over anhydrous Na2SO4 and concentrated to dryness.

The residue was dissolved in Et2O (50 mL) and 1,4-dioxane (50 ml) and bromine (18.0 g, 0.11 mmol) was added over 0.5 h. After the addition was complete, the reaction mixture was stirred for 1 h at room temperature. The mixture was diluted with CH2Cl2 (150 ml) and sodium hydrogen carbonate (20.0 g, 0.24 mol) was added. The resulting mixture was stirred overnight. The solids were filtered off and the filtrate was concentrated to afford crude compound ethyl 3-bromo-4-oxobutanoate (23 g, ~100% yield).

Azetidine-1-carbothioamide

A solution of HCl in dioxane (4N, 5.3 ml, 21 mmol) was added to a solution of azetidine hydrochloride (1.9 g, 21 mmol) in THF (10 mL) followed by addition of potassium thiocyanate (2.0 g, 21 mmol). The reaction mixture was heated under reflux for 4 h and then cooled to room temperature. The mixture was filtered and the filtrate was concentrated to dryness to afford crude azetidine-1-carbothioamide (2.0 g, ~100% yield), which was used directly without further purification.

2-(2-(Azetidin-1-yl)thiazol-5-yl)acetic acid

A solution of compounds 5 (2.0 g, crude) and 6 (2.0 g, crude) in EtOH (20 mL) was heated under reflux for 4 h and then cooled to room temperature. The solvent was removed and the residue was dissolved in EtOAc (100 mL) followed by addition of aqueous ammonia (10%, 100 mL). The organic phase was separated, washed with brine (50 mL×1), dried over anhydrous Na2SO4 and concentrated. The residue was purified by flash column chromatography on silica gel (hexane/EtOAc=5:1) to afford 2-(2-(azetidin-1-yl)thiazol-5-yl)acetic acid-ethyl ester (300 mg, ~6% yield).

Compound 2-(2-(azetidin-1-yl)thiazol-5-yl)acetic acid-ethyl ester (300 mg, 1.2 mmol) was treated with a solution of lithium hydroxide-H2O (360 mg, 8.6 mmol) in water/THF (10 mL/4 mL) for 1 h. THF was removed and the aqueous phase was acidified to pH=3-4 with 1N HCl. The mixture was concentrated to dryness to afford crude 2-(2-(azetidin-1-yl)thiazol-5-yl)acetic acid (~100% yield), which was used directly without further purification.

2-(2-(pyrrolidin-1-yl)thiazol-5-yl)acetic acid (intermediate for C-2069), and 2-(2-(dimethylamino)thiazol-5-yl)acetic acid (intermediate for C-2067) were synthesized in similar fashion.

Example 18

Preparation of tert-butyl ((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)carbamate (intermediate for: C-2051, C-2052, C-2061, C-2062, C-2063, C-2026, C-2030, C-2044, and C-2045)

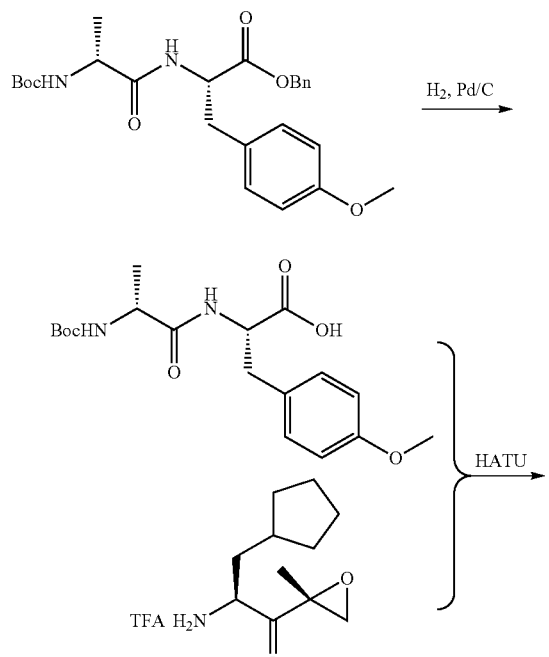

(S)-2-((R)-2-(tert-Butoxycarbonylamino)propanamido)-3-(4-methoxyphenyl)propanoic acid Pd/C (10%, 10 g) was added to a solution of (S)-benzyl 2-((R)-2-((tert-butoxycarbonyl)amino)propanamido)-3-(4-methoxyphenyl)propanoate (4.6 g, 10 mmol) in MeOH (200 mL). The suspension was stirred under hydrogen atmosphere at room temperature for 12 h. Pd/C was filtered off and washed with MeOH (50 mL). The filtrate and washings were combined and concentrated to dryness to afford (S)-2-((R)-2-(tert-Butoxycarbonylamino)propanamido)-3-(4-methoxyphenyl)propanoic acid (4.1 g, ~100% yield) as a white solid.

tert-Butyl ((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)carbamate HATU (3.0 g, 8 mmol) and DIPEA (4.45 mL, 30 mmol) were added to a solution of (S)-2-((R)-2-(tert-Butoxycarbonylamino)propanamido)-3-(4-methoxyphenyl)propanoic acid (2.1 g, 5.5 mmol) and crude (S)-2-amino-3-cyclopentyl-1-((R)-2-methyloxiran-2-yl)propan-1-one (TFA salt, 1.5 g, 5.5 mmol) in DMF (50 mL) at 0° C. The reaction mixture was allowed to warm to room temperature and stirred for 1 h. The mixture was concentrated and the residue was purified by flash column chromatography on silica gel (EtOAc/hexane=1:5) to afford compound tert-Butyl ((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)carbamate (2.3 g, 88% yield).

$^1$H NMR (300 MHz, DMSO-d6): δ 8.20 (m, 1H), 7.93 (m, 1H), 7.09 (m, 2H), 6.80 (m, 2H), 4.49 (m, 1H), 4.33 (m, 1H), 3.90 (m, 1H), 3.71 (s, 3H), 3.20 (m, 1H), 2.90~3.10 (m, 2H), 1.70 (m, 1H), 1.50~2.00 (m, 8H), 1.40 (s, 3H), 1.00~1.20 (m, 4H), 0.95 (d, J=6.6 Hz, 3H). LC-MS for $C_{29}H_{43}N_3O_7$. found 544.24 [M−H]−.

Assays

Example 19

Proteasome Subunit Assays

An ELISA-based technique, the proteasome constitutive/immunoproteasome subunit enzyme-linked immunosorbent (ProCISE) assay, was utilized for quantitative assessment of subunit-specific activity as previously described in Parlati, et al. *Blood* (2009) 114:3439-3447. This assay was used to assess the inhibitory activity against each of LMP2, LMP7, MECL1, β1, β2, and β5. Briefly, test compounds were serially diluted in DMSO at 100× concentration, then diluted to 10× in aqueous hypotonic lysis buffer. Lysate from the human acute lymphoblastic leukemia cell line, MOLT-4, was treated for 1 hour at 25° C. with compound at a final 1× concentration. Treated cell lysate was then incubated with a biotinylated proteasome active-site binding probe for 2 hours at 25° C. Following this, lysate was denatured in guanidine hydrochloride, and subunits bound to probe were isolated with streptavidin-conjugated sepharose beads. Individual subunits were probed with subunit-specific primary antibodies, followed by HRP-conjugated secondary antibodies. A chemiluminescent substrate was used to generate signal associated with HRP binding, which was detected on a plate reader. Luminescent signal was normalized to protein content, then, percent activity calculated relative to DMSO-treated controls to generate $IC_{50}$ curves.

| Compound | LMP2 | LMP7 | MECL1 | β1 | β2 | β5 |
|---|---|---|---|---|---|---|
| 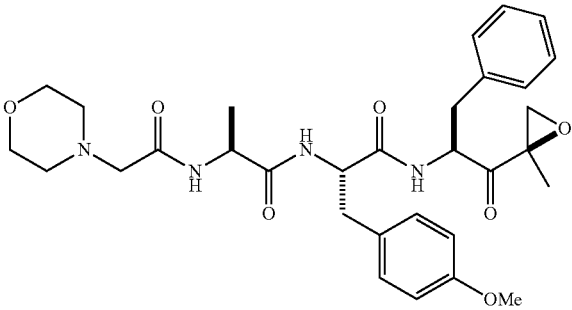 (ONX-0914) | 255 | 41 | 1316 | 4293 | 1070 | 435 |
| 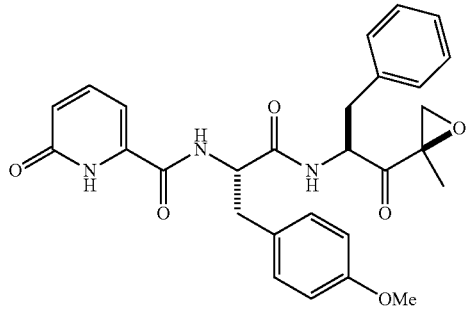 [SMILES: COc1ccc(C[C@H](NC(=O)c2cccc(=O)[nH]2)C(=O)N[C@@H](Cc2ccccc2)C(=O)[C@@]2(C)CO2)cc1] | 109 | 5155 | >250 K | 99,212 | >250 K | 20,582 |

Results for select compounds provided herein are shown in the following table:

| Cmpd | ProCISE beta5 MOLT4 lysate Hu 1 h CONT: IC$_{50}$ (nM) | ProCISE LMP2 MOLT4 lysate Hu 1 h CONT: IC$_{50}$ (nM) | ProCISE LMP7 MOLT4 lysate Hu 1 h CONT: IC$_{50}$ (nM) | Solubility pH 7 (μg/mL) |
|---|---|---|---|---|
| C-2003 | NT | NT | NT | 0.7 |
| C-2004 | NT | NT | NT | 1.9 |
| C-2005 | NT | NT | NT | 735.3 |
| C-2006 | 179.84 | NT | 34.43 | NT |
| C-2007 | 477.98 | NT | 211.44 | 728.5 |
| C-2008 | NT | NT | NT | 2331.1 |
| C-2009 | NT | NT | NT | 162.8 |
| C-2010 | NT | NT | NT | 300.5 |
| C-2011 | 341.5 | NT | 97.08 | NT |
| C-2012 | NT | NT | NT | 3828.4 |
| C-2013 | 358.72 | NT | 66.67 | 725.2 |
| C-2014 | 372.34 | NT | 56.39 | NT |
| C-2015 | 30354.92 | NT | 3063.63 | 169.2 |
| C-2016 | 279.16 | NT | 69.72 | NT |
| C-2017 | 129.43 | NT | 37.17 | NT |
| C-2018 | 34929.21 | NT | 1181.56 | 129.3 |
| C-2019 | NT | NT | NT | 315.6 |
| C-2020 | NT | NT | NT | 59.1 |
| C-2021 | 30811.37 | NT | 1891.13 | 102.8 |
| C-2022 | 429.15 | NT | 194.61 | 84.7 |
| C-2023 | 2690.25 | NT | 318.19 | 100.5 |
| C-2024 | NT | NT | NT | 44.1 |
| C-2025 | NT | NT | NT | 144.2 |
| C-2026 | 3453.13 | NT | 169.63 | 126.1 |
| C-2027 | 3601.4 | NT | 617.59 | 753.1 |
| C-2028 | 1163.98 | NT | 75.69 | 775.7 |
| C-2029 | NT | NT | NT | 1.7 |
| C-2030 | 2127.26 | NT | 314.74 | 286.4 |
| C-2031 | 26730.69 | NT | 1448.56 | 41.7 |
| C-2032 | 4045.94 | NT | 451.59 | 172.1 |
| C-2033 | >250000 | NT | 46736.39 | 164.8 |
| C-2034 | >250000 | 471.02 | 19689.04 | 55.5 |
| C-2035 | 21.06 | NT | 13.21 | 3.1 |
| C-2036 | 4863.52 | NT | 130.28 | 2.1 |
| C-2037 | 9632.93 | NT | 465.76 | 3.6 |
| C-2038 | 2698.61 | NT | 286.46 | 1.8 |
| C-2039 | NT | NT | NT | 1.7 |
| C-2040 | 3753.57 | NT | 74.96 | 0.3 |
| C-2041 | NT | NT | NT | 65.9 |
| C-2042 | 5924.3 | NT | 620.95 | 1834.5 |
| C-2043 | 11007.5 | NT | 593.46 | 2382.9 |
| C-2044 | NT | NT | NT | 130.5 |
| C-2045 | 2943.85 | NT | 219.79 | 159.9 |
| C-2046 | NT | NT | NT | 10.7 |
| C-2047 | 1095.99 | NT | 68.74 | 0.3 |
| C-2048 | 379.14 | NT | 48.64 | 1.4 |
| C-2049 | 57.65 | NT | 45.78 | 0.8 |
| C-2050 | 594.69 | NT | 67.05 | 6157.8 |
| C-2051 | 882.95 | NT | 54.28 | 240.7 |
| C-2052 | 560.31 | NT | 38.5 | 160.2 |
| C-2053 | 5.27 | NT | 1.82 | 1259.3 |
| C-2054 | 670.04 | NT | 74.98 | 122.1 |
| C-2055 | 354.41 | NT | 17.61 | 1972.5 |
| C-2056 | 290.58 | NT | 52.24 | 3725.8 |
| C-2057 | 2364.53 | NT | 57.36 | 0.8 |
| C-2058 | 4291.71 | NT | 539.02 | 45.4 |
| C-2059 | 534.17 | NT | 70.97 | 2447.5 |
| C-2060 | 367.69 | NT | 60.43 | 3014.8 |
| C-2061 | NT | NT | NT | 26.3 |
| C-2062 | NT | NT | NT | 56 |
| C-2063 | NT | NT | NT | 21.4 |
| C-2064 | 6114.85 | 1245.72 | 138.68 | 143.9 |
| C-2065 | 6627.63 | 910.47 | 156.83 | 120.9 |
| C-2066 | NT | NT | NT | 43.6 |
| C-2067 | NT | NT | NT | 61.6 |
| C-2068 | NT | NT | NT | 54.6 |
| C-2069 | NT | NT | NT | 26.6 |
| C-2070 | NT | NT | NT | 1019.1 |
| C-3001 | 5590.24 | 525.56 | 4766.89 | NT |

| Cmpd | ProCISE beta5 MOLT4 lysate Hu 1 h CONT: IC$_{50}$ (nM) | ProCISE LMP2 MOLT4 lysate Hu 1 h CONT: IC$_{50}$ (nM) | ProCISE LMP7 MOLT4 lysate Hu 1 h CONT: IC$_{50}$ (nM) | Solubility pH 7 (μg/mL) |
|---|---|---|---|---|
| C-3002 | 1930 | NT | 934.35 | 1463.1 |
| C-3003 | 1219.79 | NT | 512.78 | 1200 |
| C-3004 | NT | NT | NT | 995.7 |
| C-3005 | NT | NT | NT | 1915 |
| C-3006 | NT | NT | NT | 384.7 |
| C-3007 | 9843.63 | 273.74 | 3456.3 | 86.7 |
| C-3008 | 20581.62 | 109.3 | 5154.72 | NT |
| C-3009 | 8286.07 | 517.46 | 4573.92 | NT |
| C-3010 | 4296.63 | NT | 1164.51 | 1381.1 |
| C-3011 | NT | NT | NT | 1228.9 |
| C-3012 | 6043.13 | NT | 2745.4 | 4408.6 |
| C-3013 | 14177.74 | NT | 3478.43 | 1908.6 |
| C-3014 | NT | 34.85 | NT | 69.4 |
| C-3015 | NT | 37.64 | NT | 143.4 |
| C-3016 | NT | 55.05 | NT | 7524.4 |
| C-3017 | NT | 33.04 | NT | 6639.3 |
| C-3018 | NT | 24.88 | NT | 515.6 |
| C-3019 | NT | 16.81 | NT | 639.2 |

NT = not tested

Example 20

20S Proteasome Assays

Proteasome chymotrypsin-like, caspase-like, and trypsin-like activities for various compounds provided herein were determined using succinyl-Leu-Leu-Val-Tyr-AMC (10 Amol/L), Z-Leu-Leu-Glu-AMC (10 Amol/L), and Boc-Leu-Arg-Arg-AMC (50 Amol/L), respectively, with purified human 20S proteasome (2, 4, and 8.0 nmol/L, respectively) or HT-29 cell lysate (0.125, 0.25, and 0.25 Ag protein/mL, respectively). Assay buffer consisted of TE buffer [20 mmol/L Tris (pH 8.0), 0.5 mmol/L EDTA] with (20S) or without (cell lysate) 0.03% SDS. Reactions were initiated by enzyme or lysate addition and monitored for AMC product formation at 27jC with a plate-based spectofluorometer (Tecan). IC50 values were determined based on the reaction velocity measured between 60 and 75 min. See also Demo, S. D. et al., *Cancer Res.* 2007, 67, 6383-6391.

Results for select compounds provided herein are shown in the following table:

| Structure | LLVY i20S Hu 1 h CONT: IC$_{50}$ (nM) | LLVY c20S Hu 1 h CONT: IC$_5$0 (nM) |
|---|---|---|
| C-2014 | 16.6 | 45.7 |
| C-2018 | 570 | 12800 |
| C-2020 | 560 | 797 |
| C-2021 | 1220 | 99000 |
| C-2015 | 2920 | 18600 |
| C-2022 | 23.5 | 65.3 |
| C-2025 | 569 | 289 |
| C-2023 | 55.3 | 857 |
| C-2026 | 64.6 | 1360 |
| C-2027 | 470 | 2130 |
| C-2028 | 11.9 | 323 |
| C-2029 | 2580 | 3400 |
| C-2030 | 71.7 | 785 |
| C-2031 | 763 | 18300 |
| C-2019 | 332 | 579 |
| C-2032 | 107 | 1890 |
| C-2033 | 1450 | 10100 |
| C-2034 | 19500 | 64400 |
| C-2036 | 1380 | 5140 |
| C-2037 | 891 | 6080 |
| C-2024 | 2270 | 6030 |
| C-2038 | 722 | 3550 |
| C-2039 | 2520 | 3950 |
| C-2040 | 624 | 4610 |
| C-2041 | 1400 | 9800 |
| C-2042 | 336 | 9450 |
| C-2044 | 1604 | 286 |
| C-2043 | 271 | 15100 |
| C-2045 | 102 | 1290 |
| C-2050 | 49.2 | 521 |
| C-2051 | 34.0 | 459 |
| C-2052 | 10.8 | 316 |
| C-2054 | 55.0 | 723 |
| C-2059 | 15.9 | 246 |
| C-2060 | 17.3 | 201 |
| C-2035 | 4.6 | 15.3 |
| C-2046 | 5.2 | 7.9 |
| C-2007 | 118 | 432 |
| C-2008 | 558 | 1590 |
| C-2010 | 414 | 1051 |
| C-2079 | 0.235 | 0.0301 |
| C-2080 | 0.28 | 0.0314 |
| C-2006 | 6.1 | 29.0 |
| C-2011 | 13.5 | 68.6 |
| C-2012 | 86.9 | 262 |
| C-2013 | 40.2 | 117 |
| C-2056 | 28.9 | 191 |
| C-3009 | 9890 | 87800 |
| C-3010 | 1605 | 4080 |
| C-3011 | 4550 | 3320 |
| C-3012 | 4790 | 14500 |
| C-3013 | 4050 | 15900 |
| C-2018 | 570 | 12800 |
| C-2020 | 560 | 797 |
| C-2021 | 1220 | 99000 |
| C-2027 | 470 | 2130 |
| C-2028 | 11.9 | 323 |
| C-2019 | 332 | 579 |
| C-2042 | 336 | 9450 |
| C-2043 | 271 | 15100 |
| C-2050 | 49.2 | 521 |
| C-2051 | 34.0 | 459 |
| C-2052 | 10.8 | 316 |
| C-2054 | 55.0 | 723 |
| C-2059 | 15.9 | 246 |
| C-2060 | 17.3 | 201 |
| C-2004 | 562 | 3610 |
| C-2036 | 199 | 2710 |
| C-2048 | 55.2 | 411 |
| C-2038 | 649 | 7630 |

Other Embodiments

It is to be understood that while the disclosure is read in conjunction with the detailed description thereof, the foregoing description is intended to illustrate and not limit the scope of the disclosure, which is defined by the scope of the appended claims. Other aspects, advantages, and modifications are within the scope of the following claims.

What is claimed is:

1. A compound having a structure selected from the group consisting of:

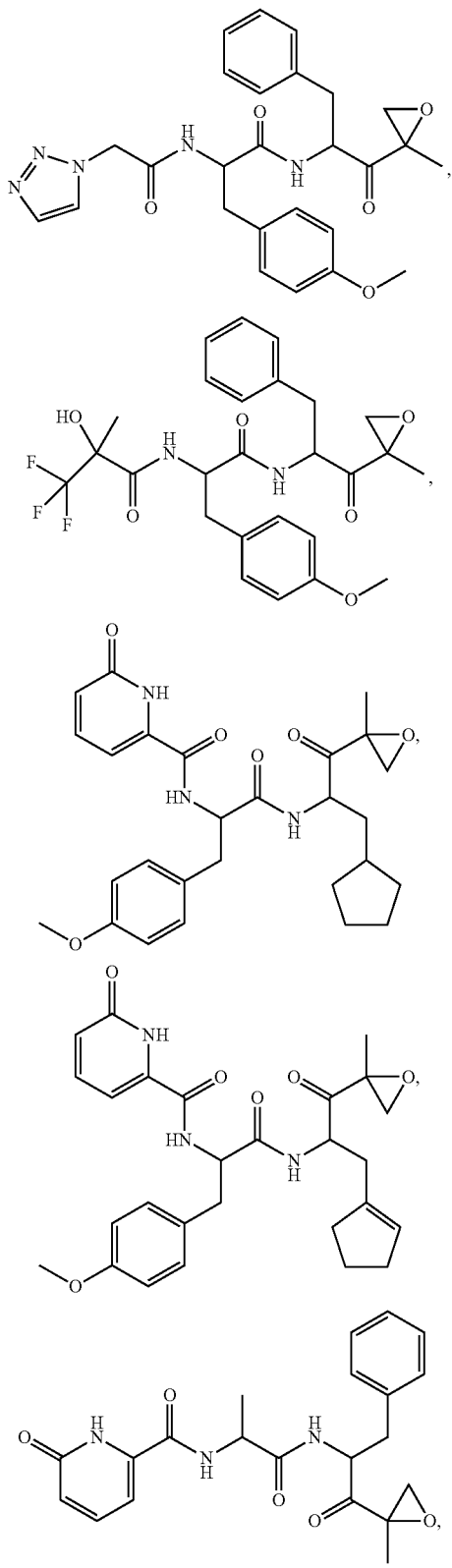

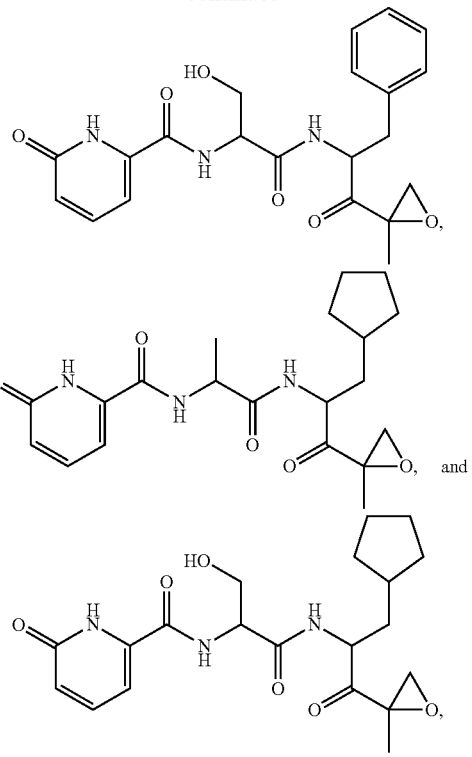

or a pharmaceutically acceptable salt thereof.

2. A compound of Formula (II) or a pharmaceutically acceptable salt thereof,

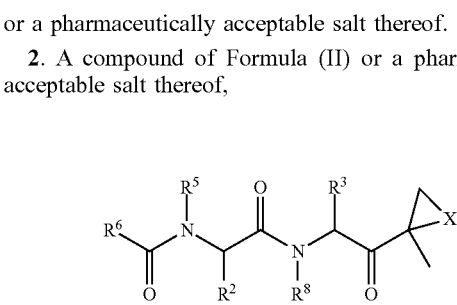

wherein:

X is selected from O, S, NH, and N—$C_{1-6}$alkyl;

$R^2$ and $R^3$ are each independently selected from aryl, $C_{1-6}$aralkyl, heteroaryl, and $C_{1-6}$heteroaralkyl;

$R^5$ is selected from hydrogen, OH, $C_{1-6}$aralkyl, and $C_{1-6}$alkyl;

$R^6$ is heteroaryl, piperidinyl, piperazinyl, morpholinyl, a lactone, a lactam, or

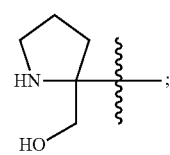

and $R^8$ is selected from hydrogen, $C_{1-6}$alkyl, and $C_{1-6}$aralkyl.

3. A compound having a structure selected from the group consisting of

C-3004
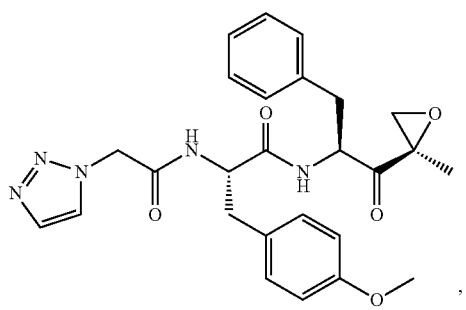

C-3007
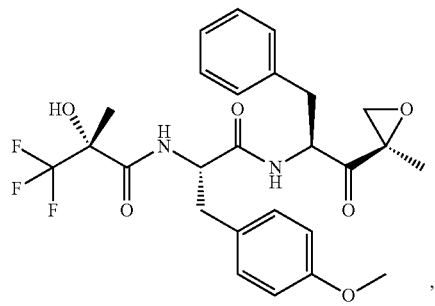

C-3014
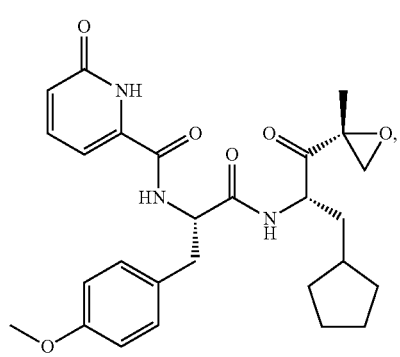

C-3015
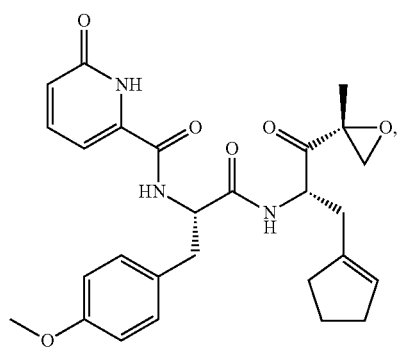

C-3016
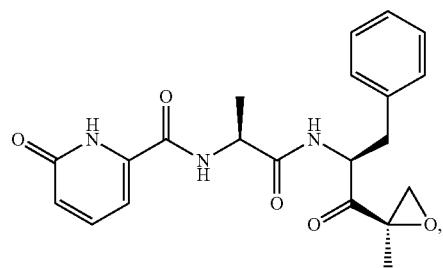

-continued

C-3017
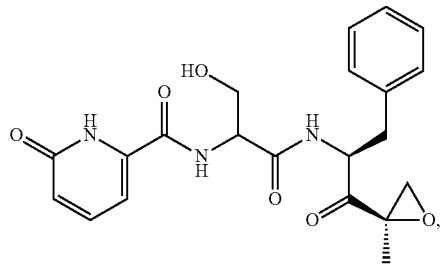

C-3018
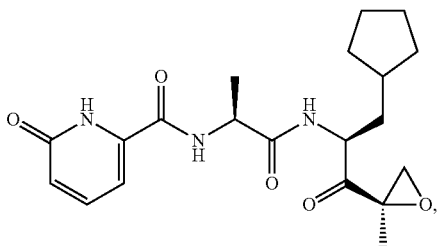

and

C-3019
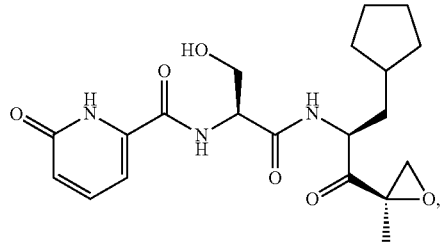

or a pharmaceutically acceptable salt thereof.

4. A pharmaceutical composition comprising the compound of claim 2, or a pharmaceutically acceptable salt thereof, and a pharmaceutically acceptable carrier or diluent.

5. The compound of claim 2, wherein $R^5$ and $R^8$ are each hydrogen.

6. The compound of claim 2, wherein X is O.

7. The compound of claim 2, wherein $R^2$ is selected from $C_{1-6}$aralkyl and $C_{1-6}$heteroaralkyl.

8. The compound of claim 7, wherein $R^2$ is $C_{1-6}$aralkyl.

9. The compound of claim 2, wherein $R^3$ is selected from $C_{1-6}$aralkyl and $C_{1-6}$heteroaralkyl.

10. The compound of claim 9, wherein $R^3$ is $C_{1-6}$aralkyl.

11. The compound of claim 2 having a structure selected from the group consisting of:

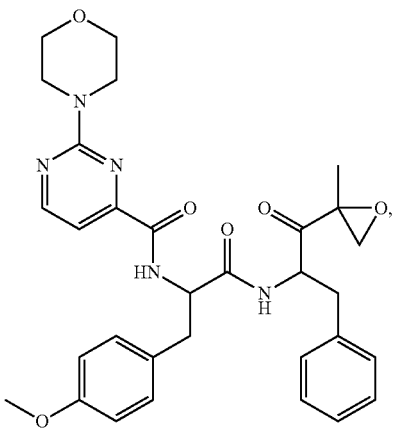

-continued
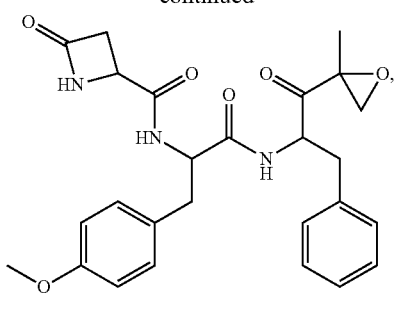
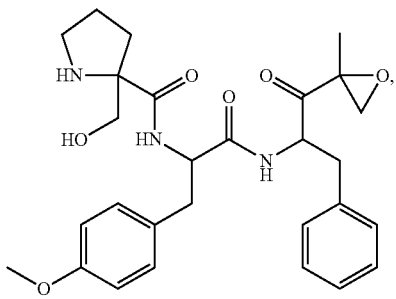
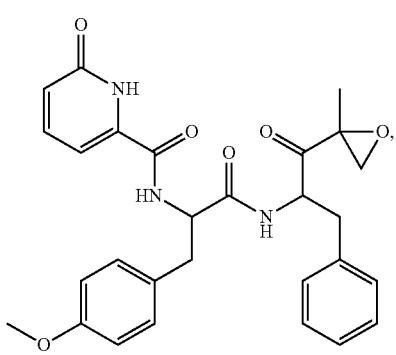
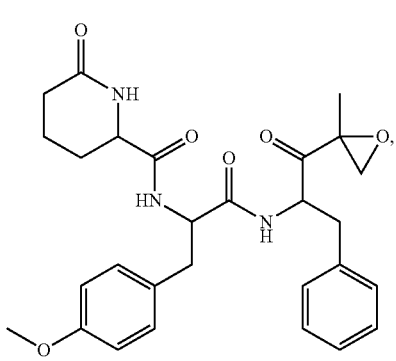
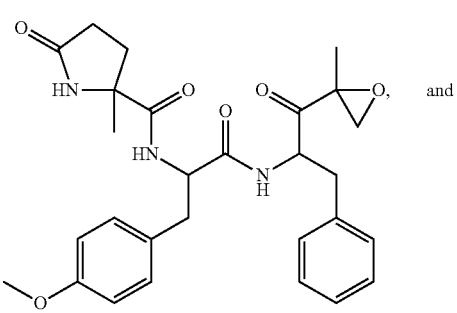
-continued
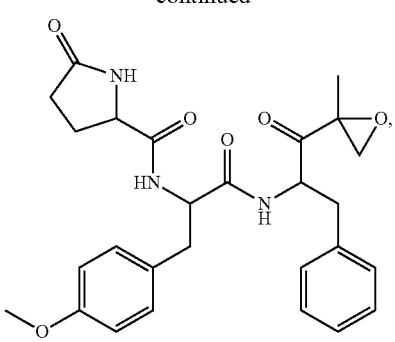
or a pharmaceutically acceptable salt thereof.
12. The compound of claim 11 having a structure selected from the group consisting of
C-3001
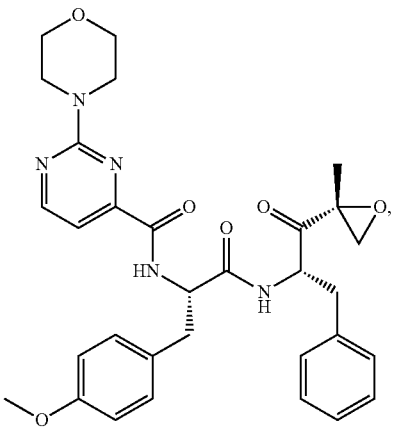
C-3002
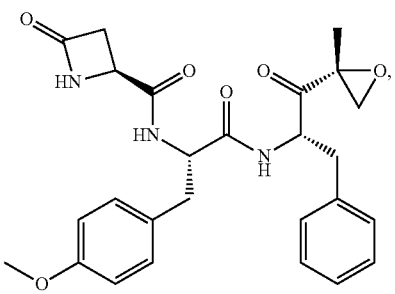
C-3003
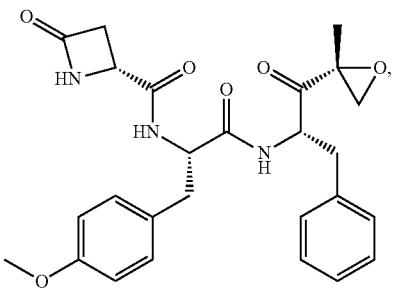

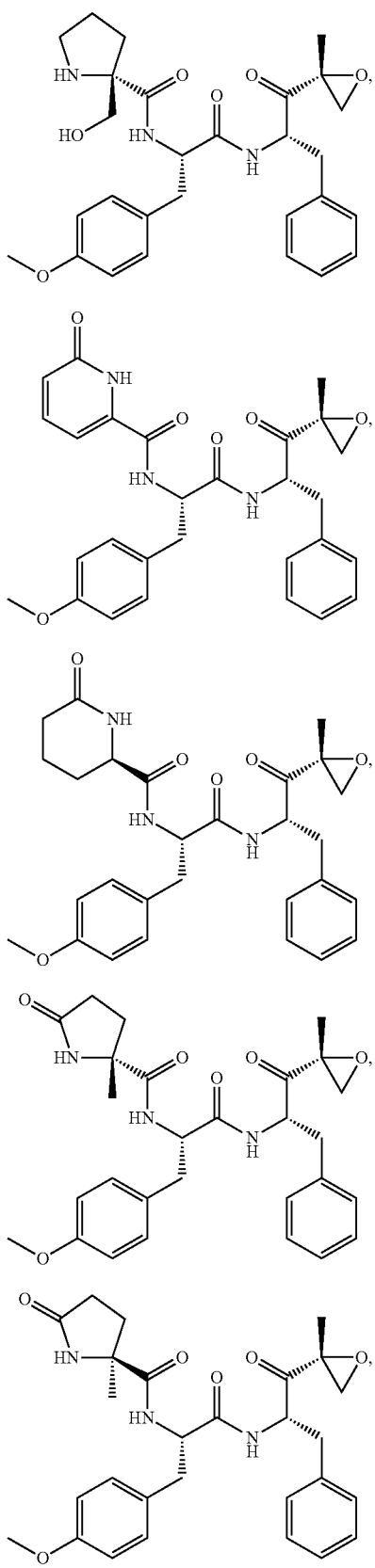

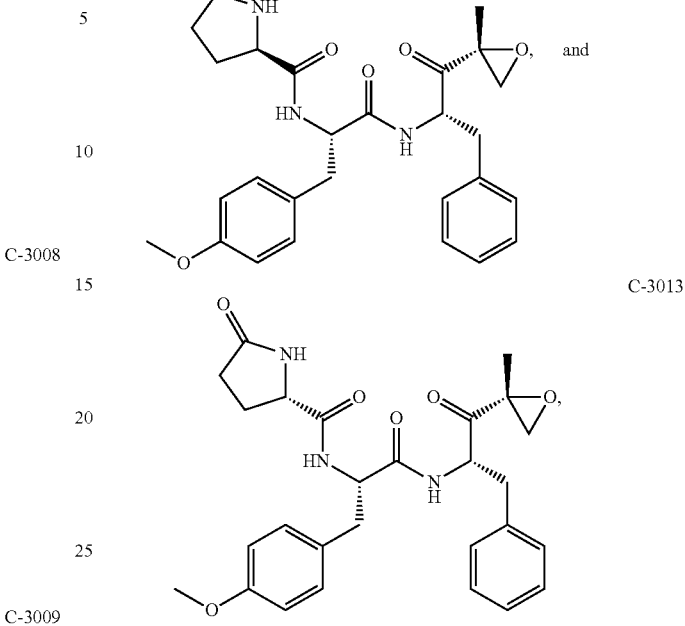

or a pharmaceutically acceptable salt thereof.

13. The compound of claim 2, wherein $R^6$ is heteroaryl.
14. The compound of claim 2, wherein $R^6$ is piperidinyl, piperazinyl, morpholinyl, a lactone, or a lactam.
15. The compound of claim 2, wherein $R^6$ is a lactam.
16. The compound of claim 2, wherein $R^6$ is

17. A method of inhibiting immunoproteasome of a cell comprising contacting the cell with a compound of claim 2 in an effective amount to inhibit the immunoproteasome in the cell, wherein the contacting comprises administering the compound or the composition to a subject.
18. The method of claim 17, wherein the subject suffers from an autoimmune disease.
19. A method for the treatment of an autoimmune disease, comprising administering a therapeutically effective amount of the compound of claim 2 to a subject in need thereof.
20. A method for the treatment of inflammation, comprising administering a therapeutically effective amount of the compound of claim 2 to a subject in need thereof.
21. A method for the treatment of a disease selected from the group consisting of rheumatoid arthritis, systemic lupus erythematosus (SLE), inflammatory bowel disease, multiple sclerosis, or Crohn's disease, comprising administering a therapeutically effective amount of the compound of claim 2 to a subject in need thereof.

* * * * *